United States Patent
Nakagawa et al.

(10) Patent No.: US 6,825,191 B2
(45) Date of Patent: Nov. 30, 2004

(54) BENZODIAZEPINE DERIVATIVES

(75) Inventors: Tadakiyo Nakagawa, Kawasaki (JP); Munetaka Tokumasu, Kawasaki (JP); Kazumi Tashiro, Kawasaki (JP); Mitsuo Takahashi, Kawasaki (JP); Takashi Kayahara, Kawasaki (JP); Shunji Takehana, Kawasaki (JP); Yuki Kajigaya, Kawasaki (JP); Kaoru Yoshida, Kawasaki (JP); Kuniya Sakurai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 73 days.

(21) Appl. No.: 10/397,219

(22) Filed: Mar. 27, 2003

(65) Prior Publication Data
US 2003/0186969 A1 Oct. 2, 2003

Related U.S. Application Data

(63) Continuation of application No. PCT/JP01/08352, filed on Sep. 26, 2001.

(30) Foreign Application Priority Data

Sep. 27, 2000 (JP) ........................................ 2000-294240

(51) Int. Cl.[7] ................... C07D 401/14; C07D 243/24; C07D 409/14; C07D 401/12; A61K 31/551
(52) U.S. Cl. ...................... 514/221; 540/500; 540/501; 540/504; 540/509; 540/510
(58) Field of Search ................... 514/221; 540/500, 540/501, 504, 509, 510

(56) References Cited

FOREIGN PATENT DOCUMENTS

WO    WO 95/04057    2/1995

Primary Examiner—Bruck Kifle
(74) Attorney, Agent, or Firm—Oblon, Spivak, McClelland, Maier & Neustadt, P.C.

(57) ABSTRACT

The present invention provides benzodiazepine derivatives of the following formula, analogs thereof and pharmaceutically acceptable salts thereof. The compounds of the present invention have an excellent effect of inhibiting activated blood-coagulation factor X. These compounds are usable as agents for treating various diseases concerned with the activated blood-coagulation factor X.

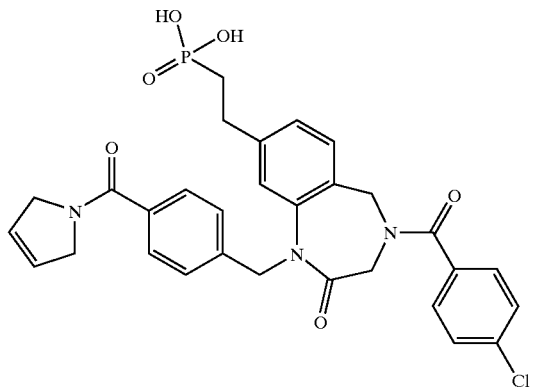

33 Claims, No Drawings

BENZODIAZEPINE DERIVATIVES

The present invention relates to new benzodiazepine derivatives which can be orally administrated to exhibit a strong anticoagulant effect by reversibly inhibiting activated blood-coagulation factor X; anticoagulants containing them as active ingredients; and agents for preventing or treating diseases caused by thrombi or emboli. These diseases include, for example, cerebrovascular disorders such as cerebral infarction, cerebral stroke, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral arterial occlusive disease; deep vein thrombosis; disseminated intravascular coagulation; thrombus formation after an artificial blood vessel-forming operation or an artificial valve substitution; reocclusion and restenosis after a coronary artery bypass grafting; reocclusion and restenosis after a reconstructive operation for the blood circulation such as percutaneous transluminal coronary angioplasty (PTCA) or percutaneous transluminal coronary recanalization (PTCR); and thrombus formation in the course of the extracorporeal circulation.

As the habit of life is being westernized and people of advanced ages are increasing in Japan, thrombotic and embolismic patients such as those suffering from myocardial infarction, cerebral thrombosis and peripheral thrombosis are increasing in number year by year, and the treatment of patients with these diseases is becoming more and more important in the society. Anticoagulation treatment is included in the internal treatments for the remedy and prevention of thrombosis, like fibrinolytic therapy and anti-platelet therapy.

Thrombin inhibitors were developed as thrombus-formation inhibitors in the prior art. However, it has been known that since thrombin not only controls the activation of fibrinogen to form fibrin, which is the last step of the coagulation reaction, but also deeply relates to the activation and aggregation of blood platelets, the inhibition of the action of thrombin causes a danger of causing hemorrhage. In addition, when thrombin inhibitors are orally administered, the bioavailability thereof is low. At present, no thrombin inhibitors which can be orally administered is available on the market.

Since the activated blood coagulation factor X is positioned at the juncture of an extrinsic coagulation cascade reaction and an intrinsic coagulation cascade reaction and in the upstream of thrombin, it is possible to inhibit the coagulation system more efficiently and specifically, than the thrombin inhibition, by inhibiting the factor X (Tidwell, R.; Webster, W. P.; Shaver, S. R.; Geratz, J. D. THROMBOSIS RESEARCH, Vol. 19, pages 339 to 349; 1980).

DISCLOSURE OF THE INVENTION

The object of the present invention is to provide compounds having an excellent effect of inhibiting the effect of activated blood coagulation factor X.

Another object of the present invention is to provide compounds having an effect of specifically inhibiting the effect of activated blood coagulation factor X, which can be orally administered.

Still another object of the present invention is to provide a pharmaceutical composition containing an above-described compound(s).

A further object of the present invention is to provide a blood-coagulation inhibitor or an agent for preventing or treating thrombosis or embolism, which contains one of the above-described compounds.

After intensive investigations made under these circumstances, the inventors have found that specified new benzodiazepine derivatives have an excellent effect of inhibiting activated blood coagulation factor X and are usable for preventing and treating various diseases caused by thrombi and emboli. The present invention has been completed on the basis of this finding.

Namely, the present invention provides benzodiazepine derivatives of following general formula (1) or pharmaceutically acceptable salts thereof:

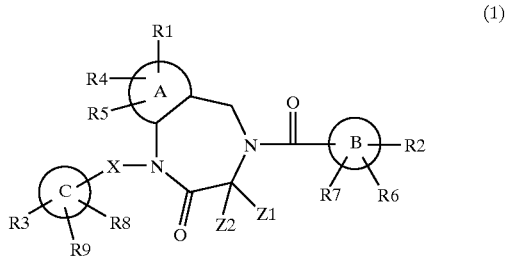

wherein ring A represents an aryl group having 6 to 10 carbon atoms, a heteroaryl group having 3 to 10 carbon atoms or a cycloalkyl group having 4 to 10 carbon atoms, R1 represents hydrogen atom, a halogeno group, hydroxyl group, an alkoxyl group having 1 to 10 carbon atoms, nitro group, formyl group, trifluoromethyl group, trifluoromethoxyl group, trifluoromethanesulfonyloxyl group, methylenedioxyl group, carbamoyl group, thiocarbamoyl group, a mono- or dialkylcarbamoyl group having 2 to 7 carbon atoms, cyano group, a mono- or dialkylamino group having 1 to 6 carbon atoms, carboxyl group, an alkoxycarbonyl group having 2 to 7 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms, a monoalkoxyhydroxyphosphoryl group having 1 to 4 carbon atoms, an alkylsulfonyl group having 1 to 6 carbon atoms, an aminosulfonyl group, a mono- or dialkylaminosulfonyl group having 2 to 8 carbon atoms, an alkyl group having 1 to 6 carbon atoms, which may have a substituent(s), an aryl group having 6 to 10 carbon atoms, which may have a substituent(s), a heteroaryl group having 1 to 10 carbon atoms, which may have a substituent(s), an arylsulfonyl group having 6 to 10 carbon atoms, which may have a substituent(s), a heteroarylsulfonyl group having 4 to 10 carbon atoms, which may have a substituent(s), an acyl group having 1 to 8 carbon atoms, which may have a substituent(s), an alkyl group having 1 to 6 carbon atoms and substituted with an aryl group(s) having 6 to 10 carbon atoms, which may have a substituent(s), an alkyl group having 1 to 6 carbon atoms and substituted with a heteroaryl group(s) having 5 to 10 carbon atoms, which may have a substituent(s), an aryl group having 6 to 10 carbon atoms and substituted with an alkyl group(s) having 1 to 6 carbon atoms, which may have a substituent(s), a heteroaryl group having 5 to 10 carbon atoms and substituted with an alkyl group(s) having 1 to 6 carbon atoms, which may have a substituent(s), an amino group, which may have a substituent(s), an aminoalkyl group having 1 to 7 carbon atoms, which may have a substituent(s), pyrrolidine group, which may have a substituent(s), pyrrolidyloxyl group, which may have a substituent(s), piperidine group, which may have a substituent(s), piperidyloxyl group, which may have a substituent(s), piperazine group, which may have a substituent(s), piperazinecarbonyl group, which may have a substituent(s), amidino group, which may have a substituent(s) or guanidino group, which may have a substituent(s), when R1 has a substituent(s), the substituent is any of alkyl groups having 1 to 6 carbon atoms, halogeno groups, hydroxyl group, alkoxyl groups having 1 to 10 carbon atoms, trifluoromethyl group, trifluoromethoxyl group, carbamoyl group, mono- or dialkylcarbamoyl groups having 2 to 7 carbon atoms, amino group, aminoalkyl groups having 2 to 7 carbon atoms, mono- or dialkylamino groups having 1 to 6 carbon atoms, amidino group, mono- or dialkylamidino groups having 2 to 7 carbon atoms, trialkylamidino groups having 4 to 7 carbon atoms, tetraalkylamidino groups having 5 to 8 carbon atoms, guanidino group, dialkylguanidino groups having 3 to 8 carbon atoms, trialkylguanidino groups having 4 to 9 carbon atoms, aryl groups having 6 to 10 carbon atoms, heteroaryl groups having 1 to 10 carbon atoms, alkyl groups having 1 to 6 carbon atoms and substituted with an aryl group(s) having 6 to 10 carbon atoms, alkyl groups having 1 to 6 carbon atoms and substituted with a heteroaryl group(s) having 5 to 10 carbon atoms, aryl groups having 6 to 10 carbon atoms and substituted with an alkyl group(s) having 1 to 6 carbon atoms, heteroaryl groups having 5 to 10 carbon atoms and substituted with an alkyl group(s) having 1 to 6 carbon atoms, arylsulfonyl groups having 6 to 10 carbon atoms, heteroarylsulfonyl groups having 4 to 10 carbon atoms, carboxyl group, alkoxycarbonyl groups having 2 to 7 carbon atoms, pyrrolidine group, piperidine group, piperazine group, piperazinecarbonyl group, alkylpiperazinecarbonyl groups having 6 to 10 carbon atoms, iminoalkylpiperazinecarbonyl groups having 7 to 10 carbon atoms, piperidyloxyl group, alkylpiperidyloxyl groups having 6 to 10 carbon atoms, iminoalkylpiperidyloxyl groups having 7 to 10 carbon atoms, pyrrolidyloxyl group, alkylpyrrolidyloxyl groups having 6 to 10 carbon atoms, iminoalkylpyrrolidyloxyl groups having 7 to 10 carbon atoms, methylenedioxyl group, cyano group, iminoalkyl groups having 2 to 7 carbon atoms, acyl groups having 1 to 8 carbon atoms, phosphono group, dialkoxyphosphoryl groups having 2 to 9 carbon atoms, monoalkoxyhydroxyphosphoryl groups having 1 to 4 carbon atoms, alkylsulfonyl groups having 1 to 6 carbon atoms, aminosulfonyl group and dialkylaminosulfonyl groups having 2 to 8 carbon atoms, rings B and C may be the same or different from each other, and they each represent an aryl group having 6 to 10 carbon atoms, a heteroaryl group having 3 to 10 carbon atoms, pyrrolidyl group, piperidyl group or piperazinyl group, R2 represents hydrogen atom, an alkyl group having 1 to 6 carbon atoms, a halogeno group, hydroxyl group, a hydroxyalkyl group having 1 to 10 carbon atoms, an alkoxyl group having 1 to 10 carbon atoms, an alkoxyalkyl group having 1 to 10 carbon atoms, nitro group, formyl group, trifluoromethoxyl group, trifluoromethyl group, carbamoyl group, thiocarbamoyl group, a mono- or dialkylcarbamoyl group having 2 to 7 carbon atoms, amino group, a mono- or dialkylamino group having 1 to 6 carbon atoms, an aminoalkyl group having 2 to 9 carbon atoms, a mono- or dialkylaminoalkyl group having 2 to 9 carbon atoms, amidino group, a mono- or dialkylamidino group having 2 to 7 carbon atoms, a trialkylamidino group having 4 to 7 carbon atoms, a tetraalkylamidino group having 5 to 8 carbon atoms, guanidino group, a dialkylguanidino group having 3 to 8 carbon atoms, a trialkylguanidino group having 4 to 9 carbon atoms, methylenedioxyl group, cyano group, an iminoalkyl group having 2 to 7 carbon atoms, an acyl group having 1 to 8 carbon atoms, piperidyloxyl group, an alkylpiperidyloxyl group having 6 to 10 carbon atoms, an iminoalkylpiperidyloxyl group having 6 to 10 carbon atoms, an alkoxycarbonylpiperidyloxyl group having 8 to 14 carbon atoms, pyrrolidyloxyl group, an alkylpyrrolidyloxyl group having 5 to 9 carbon atoms, an iminoalkylpyrrolidyloxyl group having 5 to 9 carbon atoms, an alkoxycarbonylpyrrolidyloxyl group having 7 to 13 carbon atoms, pyrrolidine group, an alkylpyrrolidine group having 5 to 9 carbon atoms, an iminoalkylpyrrolidine group having 5 to 9 carbon atoms, piperidine group, an alkylpiperidine group having 6 to 10 carbon atoms, an iminoalkylpiperidine group having 6 to 10 carbon atoms, piperazine group, an alkylpiperazine group having 5 to 13 carbon atoms, an iminoalkylpiperazine group having 6 to 9 carbon atoms, an aryl group having 6 to 10 carbon atoms, a heteroaryl group having 1 to 10 carbon atoms, an arylsulfonyl group having 6 to 10 carbon atoms, a heteroarylsulfonyl group having 4 to 10 carbon atoms, an iminoalkylpiperazinecarbonyl group having 7 to 10 carbon atoms, an alkylpiperazinecarbonyl group having 6 to 10 carbon atoms, piperazinesulfonyl group, an alkylpiperazinesulfonyl group having 5 to 9 carbon atoms, an iminoalkylpiperazinesulfonyl group having 6 to 9 carbon atoms, an alkylsulfonyl group having 1 to 8 carbon atoms, aminosulfonyl group, a mono- or dialkylaminosulfonyl group having 2 to 8 carbon atoms, a piperidylalkyl group having 6 to 9 carbon atoms or an iminoalkylpiperidylalkyl group having 8 to 12 carbon atoms, R3 represents hydrogen atom, a halogeno group, hydroxyl group, an alkoxyl group having 1 to 10 carbon atoms, nitro group, formyl group, trifluoromethyl group, trifluoromethoxyl group, carbamoyl group, thiocarbamoyl group, a mono- or dialkylcarbamoyl group having 2 to 7 carbon atoms, methylenedioxyl group, cyano group, an iminoalkyl group having 2 to 7 carbon atoms, an acyl group having 1 to 8 carbon atoms, piperidyloxyl group, an iminoalkylpiperidyloxyl group having 6 to 10 carbon atoms, an alkylpiperidyloxyl group having 5 to 10 carbon atoms, an alkoxycarbonylpiperidyloxyl group having 8 to 14 carbon atoms, pyrrolidyloxyl group, an iminoalkylpyrrolidyloxyl group having 5 to 9 carbon atoms, an alkylpyrrolidyloxyl group having 5 to 10 carbon atoms, an alkoxycarbonylpyrrolidyloxyl group having 7 to 13 carbon atoms, an arylsulfonyl group having 6 to 10 carbon atoms, a heteroarylsulfonyl group having 4 to 10 carbon atoms, an iminoalkylpiperazinecarbonyl group having 7 to 10 carbon atoms, piperazinesulfonyl group, an iminoalkylpiperazinesulfonyl group having 6 to 9 carbon atoms, an alkyl group having 1 to 6 carbon atoms, which may have a substituent(s), an amino group, which may have a substituent(s), an aminoalkyl group having 2 to 9 carbon atoms, which may have a substituent(s), pyrrolidine group, which may have a substituent(s), piperidyl group, which may have a substituent(s), a piperazine group, which may have a substituent(s), an aryl group having 6 to 10 carbon atoms, which may have a substituent(s), a heteroaryl group having 1 to 10 carbon atoms, which may have a substituent(s), an aryl group having 6 to 10 carbon atoms, which is substituted with an alkyl group(s) having 1 to 6 carbon atoms, which may have a substituent(s), a heteroaryl group having 5 to 10 carbon atoms, which is substituted with an alkyl group(s) having 1 to 6 carbon atoms, which may have a substituent(s), an alkyl group having 1 to 6 carbon atoms, substituted with an aryl group(s) having 6 to 10 carbon atoms, which may have a substituent(s), an alkyl group having 1 to 6 carbon atoms, substituted with a heteroaryl group(s) having 5 to 10 carbon atoms, which may have a substituent(s), an amidino group, which may have a substituent(s), a guanidino group, which may have a substituent(s), a piperidylalkyl group having 6 to 9 carbon atoms or an iminoalkylpiperidylalkyl group having 8 to 12 carbon atoms, when R3 has a substituent(s), the substituent is any of hydrogen atom, alkyl groups having 1 to 6 carbon atoms, halogeno groups, hydroxyl group, hydroxyalkyl groups having 1 to 10 carbon atoms, alkoxyl groups having 1 to 10 carbon atoms, alkoxyalkyl groups having 1 to 10 carbon atoms, nitro group, formyl group, trifluoromethoxyl group, trifluoromethyl group, carbamoyl group, thiocarbamoyl group, mono- or dialkylcarbamoyl groups having 2 to 7 carbon atoms, amino group, mono- or dialkylamino groups having 1 to 6 carbon atoms, aminoalkyl groups having 2 to 9 carbon atoms, mono- or dialkylaminoalkyl groups having 2 to 9 carbon atoms, amidino group, mono- or dialkylamidino groups having 2 to 7 carbon atoms, trialkylamidino groups having 4 to 7 carbon atoms, tetraalkylamidino groups having 5 to 8 carbon atoms, guanidino group, dialkylguanidino groups having 3 to 8 carbon atoms, trialkylguanidino groups having 4 to 9 carbon atoms, methylenedioxyl group, cyano group, iminoalkyl groups having 2 to 7 carbon atoms, acyl groups having 1 to 8 carbon atoms, piperidyloxyl group, alkylpiperidyloxyl groups having 6 to 10 carbon atoms, iminoalkylpiperidyloxyl groups having 6 to 10 carbon atoms, alkoxycarbonylpiperidyloxyl groups having 8 to 14 carbon atoms, pyrrolidyloxyl group, alkylpyrrolidyloxyl groups having 5 to 9 carbon atoms, iminoalkylpyrrolidyloxyl groups having 5 to 9 carbon atoms, alkoxycarbonylpyrrolidyloxyl groups having 7 to 13 carbon atoms, pyrrolidine group, alkylpyrrolidine groups having 5 to 9 carbon atoms, iminoalkylpyrrolidine groups having 5 to 9 carbon atoms, piperidine group, alkylpiperidine groups having 6 to 10 carbon atoms, iminoalkylpiperidine groups having 6 to 10 carbon atoms, piperazine group, alkylpiperazine groups having 5 to 13 carbon atoms, iminoalkylpiperazine groups having 6 to 9 carbon atoms, aryl groups having 6 to 10 carbon atoms, heteroaryl groups having 1 to 10 carbon atoms, arylsulfonyl groups having 6 to 10 carbon atoms, heteroarylsulfonyl groups having 4 to 10 carbon atoms, iminoalkylpiperazinecarbonyl groups having 7 to 10 carbon atoms, alkylpiperazinecarbonyl groups having 6 to 10 carbon atoms, piperazinesulfonyl group, alkylpiperazinesulfonyl groups having 5 to 9 carbon atoms, iminoalkylpiperazinesulfonyl groups having 6 to 9 carbon atoms, alkylsulfonyl groups having 1 to 8 carbon atoms, aminosulfonyl group and mono- or dialkylaminosulfonyl groups having 2 to 8 carbon atoms, R4, R5, R6, R7, R8 and R9 may be the same or different from one another, and they each represent hydrogen atom, an alkyl group having 1 to 6 carbon atoms, a halogeno group, hydroxyl group, a hydroxyalkyl group having 1 to 10 carbon atoms, an alkoxyl group having 1 to 10 carbon atoms, an alkoxyalkyl group having 1 to 10 carbon atoms, nitro group, trifluoromethoxyl group, trifluoromethyl group, amino group, a mono- or dialkylamino group having 1 to 6 carbon atoms, an aminoalkyl group having 2 to 9 carbon atoms, a mono- or dialkylaminoalkyl group having 2 to 9 carbon atoms, methylenedioxyl group, cyano group, formyl group, carboxyl group, an alkoxycarbonyl group having 2 to 7 carbon atoms, an alkoxycarbonylalkyl group having 3 to 9 carbon atoms, a hydroxycarbonylalkyl group having 3 to 9 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms, a monoalkoxyhydroxyphosphoryl group having 1 to 4 carbon atoms, a phosphorylalkyl group having 1 to 9 carbon atoms, a dialkoxyphosphorylalkyl group having 3 to 9 carbon atoms, a monoalkoxyhydroxyphosphoryl alkyl group having 2 to 9 carbon atoms, 2-carboxy-2-oxoethyl group or a heteroaryl group having 1 to 10 carbon atoms, X represents an alkylene group having 1 to 6 carbon atoms, which may contain —NH—, —C(=O), —NHC(=O)—, —C(=O)NH— or —NHC(=O)NH— in its chain, and Z1 and Z2 may be the same or different from each other, and they each represent hydrogen atom, a halogeno group, an alkyl group having 1 to 6 carbon atoms, hydroxyl group, a hydroxyalkyl group having 1 to 6 carbon atoms, an alkoxyalkyl group having 2 to 6 carbon atoms, a thioalkyl group having 1 to 6 carbon atoms, an alkylthioalkyl group having 2 to 8 carbon atoms, a carbamoylalkyl group having 1 to 6 carbon atoms, an aryl group having 6 to 10 carbon atoms, a heteroaryl group having 1 to 10 carbon atoms, an aryl group having 6 to 10 carbon atoms, which is substituted with an alkyl group(s) having 1 to 6 carbon atoms, a heteroaryl group having 4 to 10 carbon atoms, which is substituted with an alkyl group(s) having 1 to 6 carbon atoms, an aminoalkyl group having 1 to 6 carbon atoms, carboxyl group, an alkoxycarbonyl group having 2 to 6 carbon atoms, a hydroxycarbonylalkyl group having 2 to 8 carbon atoms, an alkoxycarbonylalkyl group having 3 to 8 carbon atoms, an aminoalkyl group having 1 to 6 carbon atoms or a mono- or dialkylaminoalkyl group having 2 to 10 carbon atoms, or Z1 and Z2 together form a ring and in such a case, -Z1-Z2- represents ethylene group, trimethylene group or tetramethylene group.

The present invention also provides benzodiazepine derivatives of the above general formula (1) or pharmaceutically acceptable salts of them, wherein ring A represents an aryl group having 6 to 10 carbon atoms or a heteroaryl group having 4 to 10 carbon atoms, R1 represents hydrogen atom, a halogeno group, an alkyl group having 1 to 6 carbon atoms, hydroxyl group, a hydroxyalkyl group having 1 to 6 carbon atoms, an alkoxyl group having 1 to 10 carbon atoms, nitro group, trifluoromethyl group, trifluoromethoxyl group, carbamoyl group, a mono- or dialkylcarbamoyl group having 2 to 7 carbon atoms, amino group, an aminoalkyl group having 1 to 3 carbon atoms, a mono- or dialkylamino group having 1 to 6 carbon atoms, a mono- or dialkylaminoalkyl group having 2 to 7 carbon atoms, an aryl group having 6 to 10 carbon atoms, a heteroaryl group having 4 to 10 carbon atoms, carboxyl group, an alkoxycarbonyl group having 2 to 7 carbon atoms, a hydroxycarbonylalkyl group having 2 to 7 carbon atoms, an alkoxycarbonylalkyl group having 3 to 8 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms or a monoalkoxyhydroxyphosphoryl group having 1 to 4 carbon atoms, ring B represents an aryl group having 6 to 10 carbon atoms, a heteroaryl group having 4 to 10 carbon atoms, piperidyl group or piperazine group, $R2$ and $R3$ may be the same or different from each other, and they each represent hydrogen atom (only for $R2$), a halogeno group, an alkyl group having 1 to 6 carbon atoms, hydroxyl group, a hydroxyalkyl group having 1 to 6 carbon atoms, an alkoxyl group having 1 to 10 carbon atoms, nitro group, trifluoromethyl group, trifluorometoxyl group, carbamoyl group, a mono- or dialkylcarbamoyl group having 2 to 7 carbon atoms, amino group, an aminoalkyl group having 1 to 3 carbon atoms, a mono- or dialkylamino group having 1 to 6 carbon atoms, a mono- or dialkylaminoalkyl group having 2 to 7 carbon atoms, an aryl group having 6 to 10 carbon atoms, a heteroaryl group having 4 to 10 carbon atoms, amidino group, a mono- or dialkylamidino group having 2 to 7 carbon atoms, guanidino group, a dialkylguanidino group having 3 to 8 carbon atoms, methylenedioxyl group, cyano group, an iminoalkyl group having 2 to 7 carbon atoms, acetyl group, piperidyloxyl group, an iminoalkylpiperidyloxyl group having 6 to 10 carbon atoms, an alkoxycarbonylpiperidyloxyl group having 8 to 14 carbon atoms, pyrrolidyloxyl group, an iminoalkylpyrrolidyloxyl group having 5 to 9 carbon atoms, an alkoxycarbonylpyrrolidyloxyl group having 7 to 13 carbon atoms, an arylsulfonyl group having 6 to 10 carbon atoms, a heteroarylsulfonyl group having 4 to 10 carbon atoms, an arylalkyl group having 5 to 12 carbon atoms, a heteroarylalkyl group having 5 to 12 carbon atoms, an iminoalkylpiperazinecarbonyl group having 7 to 10 carbon atoms, piperazinesulfonyl group, an iminoalkylpiperazinesulfonyl group having 6 to 9 carbon atoms, a piperidylalkyl group having 6 to 9 carbon atoms or an iminoalkylpiperidylalkyl group having 8 to 12 carbon atoms, ring C represents an aryl group having 6 to 10 carbon atoms, a heteroaryl group having 4 to 10 carbon atoms, piperidyl group or piperazine group, $R4$, $R5$, $R6$, $R7$, $R8$ and $R9$ each represent hydrogen atom, X represents an alkyl group having 1 to 6 carbon atoms, which may contain —NH—, —C(=O)—, —NHC(=O)—, —C(=O)NH— or —NHC(=O)NH— in its chain, and $Z1$ and $Z2$ each represent hydrogen atom.

The present invention provides an activated blood coagulation factor X inhibitor containing one of the above-described benzodiazepine derivatives or a pharmaceutically acceptable salt thereof as the active ingredient.

The present invention also provides a pharmaceutical composition containing the above-described benzodiazepine derivatives or a pharmaceutically acceptable salt thereof as the active ingredient.

The present invention further provides a blood coagulation inhibitor or an agent for preventing or treating thrombosis or embolism, which contains one of the above-described benzodiazepine derivatives or a pharmaceutically acceptable salt thereof as the active ingredient.

BEST MODE FOR CARRYING OUT THE INVENTION

In this specification, aryl groups indicate aromatic cyclic hydrocarbon groups having 6 to 10 carbon atoms such as phenyl group, 1-naphthyl group and 2-naphthyl group. Among them, phenyl group is preferred.

Unless otherwise stated, the term "aryl" in the arylsulfonyl groups or the like in this specification will be the same as the "aryl" described above.

The term heteroaryl group indicates aromatic cyclic hydrocarbon group having 1 to 10 carbon atoms and 1 to 3 hetero atoms selected from the group consisting of O, N and S. Concretely, they are pyridyl group, pyrimidyl group, pyridazinyl group, pyrazinyl group, imidazolyl group, pyrrolyl group, thiophene group, pyrazyl group, pyrazolyl group, pyrrolyl group, triazyl group, furyl group, isoxazolyl group, isothiazolyl group, indolyl group, quinolyl group, isoquinolyl group, tetrazole group, etc. Among them, heteroaryl groups having 4 to 10 carbon atoms and 1 or 2 N and/or S as the hetero atom are preferred, and pyridyl group and thiophene group are particularly preferred.

Unless otherwise stated, the term "heteroaryl" in the heteroarylsulfonyl groups or the like in this specification will be the same as the "heteroaryl" described above.

The term alkyl group indicates linear, branched or cyclic alkyl groups having 1 to 6 carbon atoms. In the alkyl groups, those having 1 to 3 carbon atoms are preferred. Concretely, they are methyl group, ethyl group, n-propyl group, i-propyl group, n-butyl group, sec- and tert-butyl groups, n-pentyl group, i-pentyl group, tert-pentyl group, neopentyl group, 2-pentyl group, 3-pentyl group, n-hexyl group, 2-hexyl group, etc. Among them, methyl group, ethyl group, n-propyl group and i-propyl group are preferred.

The cyclic alkyl groups are alkyl groups having 4 to 10 carbon atoms. Those having 5 or 6 carbon atoms are preferred. Concretely, they are cyclobutyl group, cyclopentyl group, cyclohexyl group, cycloheptyl group, cyclooctyl group, etc. Among them, cyclopentyl group and cyclohexyl group are preferred. Cyclohexyl group is particularly preferred.

Unless otherwise stated, the term "alkyl" in the hydroxyalkyl groups and iminoalkyl groups or the like in this specification will be the same as the "alkyl" described above.

The alkenyl groups are linear or branched alkenyl groups having 2 to 6 carbon atoms. Concretely, they are vinyl group, propenyl group, 2-methyl-1-propenyl group, etc.

Unless otherwise stated, the term "alkenyl" in the hydroxycarbonylalkenyl groups, alkoxycarbonylalkenyl groups, etc. in this specification will be the same as the "alkenyl" described above.

The halogeno groups include fluorine atom, chlorine atom, bromine atom and iodine atom. Among them, chlorine atom and bromine atom are preferred.

The alkoxyl groups are linear or branched alkoxyl groups having 1 to 10 carbon atoms, alkoxyl groups having a cycloalkyl groups and 4 to 10 carbon atoms and alkoxyl groups having a fused cyclic carbon chain ring system. Concretely, they are methoxyl group, ethoxyl group, n-propoxyl group, isopropoxyl group, n-butoxyl group, i-butoxyl group, sec-butoxyl group, tert-butoxyl group, benzyloxyl group, 2-phenylethoxyl group, 3-phenylpropyloxyl group, 4-phenylbutoxyl group, 5-phenylpentyloxyl group, 6-phenylhexyloxyl group, cyclopropyloxyl group, cyclobutoxyl group, cyclopentyloxyl group, cyclohexyloxyl group, 1-indanyloxyl group and 2-indanyloxyl group, etc. Among them, methoxyl group, ethoxyl group and n-propoxyl group are preferred.

Unless otherwise stated, the term "alkoxyl" in the alkoxyalkyl groups, alkoxycarbonylpiperidyloxyl groups, etc. in this specification will be the same as the "alkoxyl" described above.

The mono- or dialkylcarbamoyl groups include monoalkylcarbamoyl groups such as methylcarbamoyl group, ethylcarbamoyl group, n-propylcarbamoyl group and i-propylcarbamoyl group, and dialkylcarbamoyl groups such as dimethylcarbamoyl group, diethylcarbamoyl group, di(n-propyl)carbamoyl group and di(i-propyl)carbamoyl group, etc. The chain length of the two alkyl groups in the dialkylcarbamoyl group may be different from each other. The two alkyl groups in the dialkylcarbamoyl group may be bonded together to form a ring or they may form a ring containing an unsaturated hydrocarbon group. In this case, one of —CH$_2$— groups may be replaced with O, NH or S. Concretely, they include 1-pyrrolidinecarbonyl group, 2,5-dihydro-1H-pyrrol-1-ylcarbonyl group, 1-piperidinecarbonyl group, 1-piperazinecarbonyl group, (morpholin-4-yl)carbonyl group and (thiomorpholin-4-yl) carbonyl group, etc. In these groups, dimethylcarbamoyl group, 1-pyrrolidinecarbonyl group, (morpholin-4-yl) carbonyl group, 2,5-dihydro-1H-pyrrol-1-ylcarbonyl group and (thiomorpholin-4-yl)carbonyl group are preferred.

The mono- or dialkylamino groups having 1 to 6 carbon atoms include monoalkylamino groups such as methylamino group, ethylamino group, n-propylamino group and i-propylamino group, etc, and dialkylamino groups such as dimethylamino group, diethylamino group, di(n-propyl) amino group and di(i-propyl)amino group, etc. The chain length of the two alkyl groups in the dialkylamino group may be different from each other. The two alkyl groups in the dialkylamino group may be bonded together to form a ring. In this case, one of —CH$_2$— groups may be replaced with O, NH or S. Concretely, they include pyrrolidinyl group, piperidinyl group, morpholinyl group and thiomorpholinyl group, etc. In these groups, morpholinyl group and thiomorpholinyl group are preferred.

The alkoxycarbonyl groups having 2 to 7 carbon atoms include, for example, methoxycarbonyl group, ethoxycarbonyl group, n-propoxycarbonyl group, isopropoxycarbonyl group, n-butoxycarbonyl group, i-butoxycarbonyl group, sec-butoxycarbonyl group and tert-butoxycarbonyl group, etc. In these groups, methoxycarbonyl group and ethoxycarbonyl group are preferred.

The dialkoxyphosphoryl groups having 2 to 9 carbon atoms include, for example, diethoxyphosphoryl group, di(n-propoxy)phosphoryl group, di(isopropoxy)phosphoryl group, di(n-butoxy)phosphoryl group, di(i-butoxy) phosphoryl group, di(sec-butoxy)phosphoryl group and di(tert-butoxy)phosphoryl group, etc. In these groups, diethoxyphosphoryl group is preferred.

The monoalkoxyhydroxyphosphoryl groups include, for example, monomethoxyhydroxyphosphoryl group, monoethoxyhydroxyphosphoryl group, mono-n-propoxyhydroxyphosphoryl group, monoisopropoxyhydroxyphosphoryl group, mono-n-butoxyhydroxyphosphoryl group, mono-i-butoxyhydroxyphosphoryl group, mono-sec-butoxyhydroxy-phosphoryl group and mono-tert-butoxyhydroxyphosphoryl group, etc. In these groups, monoethoxyhydroxyphosphoryl group is preferred.

The alkylsulfonyl groups include, for example, methylsulfonyl group, ethylsulfonyl group, sulfonyl group, n-propylsulfonyl group and i-propylsulfonyl group, etc. In these groups, methylsulfonyl group is preferred.

The mono- or dialkylaminosulfonyl groups include monoalkylaminosulfonyl groups such as methylaminosulfonyl group, ethylaminosulfonyl group, n-propylaminosulfonyl group and i-propylaminosulfonyl group, etc. and dialkylaminosulfonyl groups such as dimethylaminosulfonyl group, diethylaminosulfonyl group, di(n-propyl)aminosulfonyl group and di(i-propyl) aminosulfonyl group, etc. The chain length of the two alkyl groups in the dialkylaminosulfonyl group may be different from each other. The two alkyl groups in the dialkylaminosulfonyl group may be bonded together to form a ring. In this case, one of —CH$_2$— groups may be replaced with O, NH or S. Concretely, they include (pyrrolidin-1-yl)sulfonyl group, (piperidin-1-yl)sulfonyl group, (morpholin-4-yl) sulfonyl group and (thiomorpholin-4-yl)sulfonyl group, etc. In these groups, (pyrrolidin-1-yl)sulfonyl group is preferred.

The acyl groups include, for example, acetyl group, propionyl group, butyryl group, isobutyryl group, valeryl group, isovaleryl group and pivaloyl group, etc.

The aminoalkyl groups include, for example, aminomethyl group, 2-aminoethyl group, 2-aminopropyl group and 3-aminopropyl group, etc. In these groups, aminoalkyl groups having 1 to 7 carbon atoms, particularly 3-aminopropyl group, is preferred.

The mono- or dialkylamidino groups include monoalkylamidino groups such as methylamidino group and ethylamidino group, and dialkylamidino group such as dimethylamidino group and diethylamidino group. The chain length of the two alkyl groups in the dialkylamidino group may be different from each other. The two alkyl groups in the dialkylamidino group may be bonded together to form a ring or they may form a ring containing an unsaturated hydrocarbon group. In this case, one of —CH$_2$— groups may be replaced with O, NH or S. Concretely, they include (pyrrolidin-1-yl)(imino)methyl group, (piperidin-1-yl) (imino)methyl group, 1,4,5,6-tetrahydro-2-pyrimidinyl group, (morpholin-4-yl)(imino)methyl group, 2,5-dihydro-1 H-pyrrol-1-yl(imino)methyl group and (thiomorpholin-4-yl) (imino) methyl group, etc. In these groups, 2,5-dihydro-1H-pyrrol-1-yl(imino)methyl group, dimethylamidino group, (pyrrolidin-1-yl)(imino)methyl group and (thiomorpholin-4-yl)(imino)methyl group are preferred.

The trialkylamidino groups include trimethylamidino group, triethylamidino group, tri(n-propyl)amidino group and tri(i-propylamidino) group, etc. The chain length of the three alkyl groups in the trialkylamidino group may be different from each other. Two of the three alkyl groups in the trialkylamidino group may be bonded together to form a ring. In this case, one of —CH$_2$— groups may be replaced with O, NH or S. Concretely, they include 1-methyl-1H-imidazol-2-yl group and 1-ethyl-1H-imidazol-2-yl group, etc. In these groups, 1-methyl-1H-imidazol-2-yl group is preferred.

The tetraalkylamidino groups having 5 to 8 carbon atoms include, for example, (dimethylamino)(dimethyl iminio)

methyl group, etc. The chain length of the four alkyl groups in the tetraalkylamidino group may be different from each other. Two of the four alkyl groups in the tetraalkylamidino group may be bonded together to form a ring. In this case, one of —$CH_2$— groups may be replaced with O, NH or S. Concretely, they include 1,3-dimethyl-4,5-dihydro-1H-imidazol-3-ium-2-yl group and 1-ethyl-3-methyl-4,5-dihydro-1H-imidazol-3-ium-2-yl group, etc. In these groups, 1,3-dimethyl-4,5-dihydro-1H-imidazol-3-ium-2-yl group is preferred.

The dialkylguanidino groups include, for example, dimethylguanidino group, diethylguanidino group, di(n-propyl) guanidino group and di(i-propyl)guanidino group, etc. The chain length of the two alkyl groups in the dialkylguanidino groups may be the same or different from each other. Two alkyl groups in the dialkylguanidino group may be bonded together to form a ring. In this case, one of —$CH_2$— groups may be replaced with O, NH or S. Concretely, they include imidazoline-2-amino group, etc.

The trialkylguanidino groups include, for example, trimethylguanidino group, triethylguanidino group, tri(n-propyl) guanidino group and tri(i-propyl)guanidino group, etc. The chain length of the three alkyl groups in the trialkylguanidino groups may be the same or different from each other. Two alkyl groups in the trialkylguanidino group may be bonded together to form a ring. In this case, one of —$CH_2$— groups may be replaced with O, NH or S. Concretely, they include 1-methyl-2-imidazolin-2-yl-amino group, 1-ethyl-2-imidazolin-2-yl-amino group, 1-(n-propyl)-2-imidazolin-2-yl-amino group and 1-(i-propyl)-2-imidazolin-2-yl-amino group, etc. In these groups, 1-methyl-2-imidazolin-2-yl-amino group is preferred.

The alkylpiperazinecarbonyl groups having 6 to 10 carbon atoms include, for example, methylpiperazinecarbonyl group, ethylpiperazinecarbonyl group, n-propylpiperazinecarbonyl group, i-propylpiperazinecarbonyl group, n-butylpiperazinecarbonyl group, i-butylpiperazinecarbonyl group, sec-butylpiperazinecarbonyl group and tert-butylpiperazinecarbonyl group, etc. In these groups, i-propylpiperazinecarbonyl group is preferred.

The mono- or dialkylaminoalkyl groups include monoalkylaminoalkyl groups such as methylaminomethyl group, methylaminoethyl group, methylaminopropyl group, ethylaminomethyl group, ethylaminoethyl group, ethylaminopropyl group, n-propylaminomethyl group, n-propylaminoethyl group, n-propylaminopropyl group, i-propylaminomethyl group, i-propylaminoethyl group and i-propylaminopropyl group, etc. and dialkylaminoalkyl groups such as dimethylaminomethyl group, dimethylaminoethyl group, dimethylaminopropyl group, diethylaminomethyl group, diethylaminoethyl group, diethylaminopropyl group, di(n-propyl)aminomethyl group, di(n-propyl) aminoethyl group, di(n-propyl)aminopropyl group, di(i-propyl)aminomethyl group, di(i-propyl)aminoethyl group and di(i-propyl)aminopropyl group, etc. The chain length of the three alkyl groups in the dialkylaminoalkyl groups may be the same or different from each other. Two alkyl groups in the dialkylaminoalkyl group may be bonded together to form a ring. In this case, one of —$CH_2$— groups may be replaced with O, NH or S. Concretely, they include, for example, (pyrrolidin-1-yl)methyl group, (pyrrolidin-1-yl) ethyl group, (pyrrolidin-1-yl)propyl group, (piperidin-1-yl) methyl group, (piperidin-1-yl)ethyl group, (piperidin-1-yl) propyl group, (morpholin-4-yl)methyl group, (morpholin-4-yl)ethyl group, (morpholin-4-yl)propyl group, (thiomorpholin-1-yl)methyl group, (thiomorpholin-1-yl) ethyl group and (thiomorpholin-1-yl)propyl group, etc.

Ring A in the above general formula (1) is preferably an aryl group having 6 to 10 carbon atoms or a heteroaryl group having 3 to 10 carbon atoms (particularly a heteroaryl group having 4 to 10 carbon atoms, more particularly, a heteroaryl group having 3 to 5 carbon atoms). A cycloalkyl group having 5 or 6 carbon atoms is also preferred. In these groups, phenyl group, pyridyl group, pyrazolyl group and cyclohexyl group are preferred. Phenyl group is particularly preferred.

R1 is preferably hydrogen atom, a halogeno group, hydroxyl group, an alkoxyl group having 1 to 10 carbon atoms, trifluoromethyl group, trifluoromethanesulfonyloxyl group, carbamoyl group, a mono- or dialkylcarbamoyl group having 2 to 7 carbon atoms, cyano group, a mono- or dialkylamino group having 1 to 6 carbon atoms, carboxyl group, an alkoxycarbonyl group having 2 to 7 carbon atoms, an alkyl group having 1 to 6 carbon atoms, which may have a substituent(s), an aminoalkyl group having 2 to 7 carbon atoms, which may have a substituent(s), piperazinecarbonyl group, which may have a substituent(s) and amidino group, which may have a substituent(s). In these groups, hydrogen atom, chloro group, carboxyl group, alkoxycarbonyl groups having 2 to 7 carbon atoms, amino group, which may have a substituent(s), hydroxyl group, which may have a substituent(s) and alkyl groups having 1 to 6 carbon atoms are preferred.

When R1 has a substituent(s), the substituent is preferably an alkyl group having 1 to 6 carbon atoms, hydroxyl group, a mono- or dialkylamino group having 1 to 6 carbon atoms, a heteroaryl group having 1 to 10 carbon atoms, carboxyl group, an alkoxycarbonyl group having 2 to 7 carbon atoms, pyrrolidine group, piperidine group, piperazine group, piperazinecarbonyl group, an alkylpiperazinecarbonyl group having 6 to 10 carbon atoms, phosphono group, a dialkoxyphosphoryl group having 2 to 9 carbon atoms, a monoalkoxyhydroxyphosphoryl group having 1 to 4 carbon atoms, an alkylsulfonyl group having 1 to 6 carbon atoms or dialkylamidino group.

The substituent is more preferably hydroxyl group, phosphono group, carboxyl group, an alkoxycarbonyl group having 2 to 7 carbon atoms, a mono- or dialkylcarbamoyl group having 2 to 7 carbon atoms, a mono- or dialkylamino group having 1 to 6 carbon atoms, piperazinecarbonyl group, an alkylpiperazinecarbonyl group having 6 to 10 carbon atoms or an alkylsulfonyl group having 1 to 6 carbon atoms.

R1 is more preferably hydrogen atom, chloro group, amino group, carboxyl group, ethoxycarbonyl group, carboxyethyl group, ethoxycarbonylethyl group, a morpholinealkyl group, hydroxyl group, methyl group, phosphonoethyl group, morpholinecarbonylethyl group, piperazinecarbonylethyl group, isopropylpiperazinecarbonylethyl group, methanesulfonylaminopropyl group or hydroxypropyl group.

R4 and R5 are each preferably hydrogen atom, a halogeno group, trifluoromethyl group, methoxyl group or hydroxyl group. It is particularly preferred that both R4 and R5 are hydrogen atom.

R1, R4 and R5 may be the same or different from one another. It is particularly preferred that when ring A is phenyl group, R1 is bonded to the phenyl group at the 7- and/or 8-position.

X is preferably an alkylene group having 1 to 6 carbon atoms, more preferably a linear alkylene group having 1 to 3 carbon atoms, and still more preferably methylene group or ethylene group. X is particularly preferably methylene group. The group contained in the chain of the alkylene group X is preferably —C(=O)NH— or —NHC(=O)—. —C(=O)NH— is particularly preferred.

Ring B is preferably an aryl group having 6 to 10 carbon atoms, a heteroaryl group having 3 to 10 carbon atoms (particularly a heteroaryl group having 4 to 10 carbon atoms), piperidyl group or piperazine group. The aryl groups are preferably phenyl group and 2-naphthyl group. The heteroaryl groups are preferably thiophene group and pyridyl group. The aryl groups having 6 to 10 carbon atoms and the heteroaryl groups having 4 to 10 carbon atoms are particularly preferred. Further, phenyl group, naphthyl group, pyridyl group, thiophene group and piperidyl group are preferred. Phenyl group and thiophene group are more preferred.

R2 is preferably a halogeno group, particularly chloro group or bromo group; an alkoxyl group having 1 to 10 carbon atoms, particularly an alkoxyl group having 1 to 3 carbon atoms, and particularly methoxyl group; an alkyl group having 1 to 6 carbon atoms, particularly methyl group or ethyl group; or trifluoromethyl group. The halogeno group, particularly chloro group or bromo group is the most preferred.

R6 and R7 may be the same or different from each other, and preferably, they are each hydrogen atom, a halogeno group, trifluoromethyl group, methoxyl group or hydroxyl group. It is more preferred that both R6 and R7 are hydrogen atoms.

R2, R6 and R7 may be the same or different from one another. Preferably, when ring B is phenyl group, R2 is bonded to the phenyl group at the 3- and/or 4-position; when ring B is thienyl group, R2 is bonded to the thienyl group at the 5-position; when ring B is pyridyl group, R2 is bonded to the thienyl group at the 5-position; and when ring B is piperidyl group, R2 is bonded to the piperidyl group at the 1-position.

It is particularly preferred that ring B is phenyl group, R2 is bonded to the phenyl ring at the 4-position and both R6 and R7 are hydrogen atoms.

Ring C is preferably an aryl group having 6 to 10 carbon atoms or a heteroaryl group having 3 to 6 carbon atoms. Ring C is also preferably piperidyl group. The aryl group is preferably phenyl group. The heteroaryl group is preferably pyridyl group or quinolyl group. Ring C is particularly preferably phenyl group or piperidyl group (particularly 4-piperidyl group).

R3 is preferably a halogeno group, nitro group, an iminoalkyl group having 2 to 7 carbon atoms, piperidyloxyl group, an iminoalkylpiperidyloxyl group having 6 to 10 carbon atoms, an alkylpiperidyloxyl group having 5 to 10 carbon atoms, amino group, which may have a substituent (s), an aminoalkyl group having 2 to 9 carbon atoms, which may have a substituent(s), pyrrolidine group, which may have a substituent(s), piperazine group, which may have a substituent(s), a heteroaryl group having 1 to 10 carbon atoms, which may have a substituent(s) or amidino group, which may have a substituent(s). R3 is more preferably a mono- or dialkylcarbamoyl group having 2 to 7 carbon atoms, an alkyl group having 1 to 6 carbon atoms, which may have a substituent(s) or an amidino group, which may have a substituent(s). R3 is also preferably a heteroaryl group having 1 to 10 carbon atoms, which may have a substituent(s), particularly pyridyl group (particularly 4-pyridyl group). R3 is particularly preferably an alkyl group having 1 to 6 carbon atoms, which may have a substituent(s), a halogeno group, pyridyl group (particularly 4-pyridyl group), nitro group, amino group, dialkylamino group, amidino group, which may have a substituent(s) or piperidyloxyl group, which may have a substituent(s).

When R3 has a substituent(s), the substituent is preferably any of hydrogen atom, alkyl groups having 1 to 6 carbon atoms, mono- or dialkylcarbamoyl groups having 2 to 7 carbon atoms, mono- or dialkylaminoalkyl groups having 2 to 9 carbon atoms, mono- or dialkylamidino groups having 2 to 7 carbon atoms, trialkylamidino groups having 4 to 7 carbon atoms, pyrrolidine group, piperidine group, alkylsulfonyl groups having 1 to 8 carbon atoms and pyridyl group. In these groups, the alkyl groups having 1 to 6 carbon atoms and pyridyl group are more preferred.

R3 is more preferably any of isopropyl group, cyclohexyl group, pyridyl group, 1-methyl-1H-imidazol-2-yl group, 1,3-dimethyl-4,5-dihydro-1H-imidazol-3-ium-2-yl group, 2,5-dihydro-1H-pyrrol-1-ylcarbonyl group, 1-pyrrolidinylcarbonyl group, 2,5-dihydro-1H-pyrrol-1-yl (imino)methyl group and 1-iminoethyl-piperidin-4-yloxyl group.

R8 and R9 may be the same or different from each other, and preferably they are each hydrogen atom, a halogeno group, trifluoromethyl group, methoxyl group or hydroxyl group. It is also preferred that R8 and R9 are each hydrogen atom, a halogeno group or pyridyl group.

The positions of R3, R8 and R9 are not particularly limited. However, it is particularly preferred that when ring C is phenyl group, R3 is bonded to the phenyl group at the 4-position; when ring C is pyridyl group, R3 is bonded to the pyridyl group at the 3-position; and when ring C is piperidyl group, R3 is bonded to the piperidyl group at the 1-position. It is particularly preferred that ring C is piperidyl group, R3 is bonded to the piperidyl group at the 4-position and R8 and R9 are each hydrogen atom.

X is preferably an alkylene group having 1 to 6 carbon atoms. X is also preferably an alkylene group having 1 to 3 carbon atoms, which may contain —C(=O)NH— in its chain. X is more preferably methylene group or ethylene group. X is particularly preferably methylene group.

Z1 and Z2 may be the same or different from each other. It is preferred that they are each hydrogen atom, an alkyl group having 1 to 6 carbon atoms, an aryl group having 6 to 10 carbon atoms or a heteroaryl group having 4 to 10 carbon atoms. It is particularly preferred that both Z1 and Z2 are hydrogen atom.

It is preferred that in general formula (1), ring A represents an aryl group having 6 to 10 carbon atoms, a heteroaryl group having 3 to 10 carbon atoms or a cycloalkyl group having 5 or 6 carbon atoms, R1 represents hydrogen atom, a halogeno group, hydroxyl group, an alkoxyl group having 1 to 10 carbon atoms, trifluoromethyl group, trifluoromethanesulfonyloxyl group, carbamoyl group, a mono- or dialkylcarbamoyl group having 2 to 7 carbon atoms, cyano group, a mono- or dialkylamino group having 1 to 6 carbon atoms, carboxyl group, an alkoxycarbonyl group having 2 to 7 carbon atoms, an alkyl group having 1 to 6 carbon atoms, which may have a substituent(s), an aminoalkyl group having 2 to 7 carbon atoms, which may have a substituent(s), piperazinecarbonyl group, which may have a substituent(s) or amidino group, which may have a substituent(s), when R1 has a substituent(s), the substituent is any of alkyl groups having 1 to 6 carbon atoms, hydroxyl group, mono- or dialkylamino groups having 1 to 6 carbon atoms, heteroaryl groups having 1 to 10 carbon atoms, carboxyl group, alkoxycarbonyl groups having 2 to 7 carbon atoms, pyrrolidine group, piperidine group, piperazine group, piperazinecarbonyl group, alkylpiperazinecarbonyl groups having 6 to 10 carbon atoms, phosphono group, dialkoxyphosphoryl groups having 2 to 9 carbon atoms, monoalkoxyhydroxyphosphoryl groups having 1 to 4 carbon atoms, alkylsulfonyl groups having 1 to 6 carbon atoms and dialkylamidino groups having 1 to 6 carbon atoms, and R4 and R5 are both hydrogen atom.

It is also preferred that in general formula (1), ring A represents phenyl group, R1 represents hydrogen atom, chloro group, carboxyl group, an alkoxycarbonyl group having 2 to 7 carbon atoms, an amino group, which may have a substituent (s), hydroxyl group, which may have a substituent or an alkyl group having 1 to 6 carbon atoms, which may have a substituent(s), when R1 has a substituent(s), the substituent is hydroxyl group, phosphono group, carboxyl group, an alkoxycarbonyl group having 2 to 7 carbon atoms, a mono- or dialkylcarbamoyl group having 2 to 6 carbon atoms, a mono- or dialkylamino group having 1 to 6 carbon atoms, piperazinecarbonyl group, an alkylpiperazinecarbonyl group having 6 to 10 carbon atoms or an alkylsulfonyl group having 1 to 6 carbon atoms, and R4 and R5 may be the same or different from each other and they each represent hydrogen atom, a halogeno group, trifluoromethyl group, methoxyl group or hydroxyl group.

It is also preferred that in general formula (1), ring B represents an aryl group having 6 to 10 carbon atoms or a heteroaryl group having 4 to 10 carbon atoms, R2 represents chloro group or bromo group, and R6 and R7 may be the same or different from each other and they each represent hydrogen atom, a halogeno group, trifluoromethyl group, methoxyl group or hydroxyl group.

It is also preferred that in general formula (1), ring C represents an aryl group having 6 to 10 carbon atoms or piperidyl group, R3 represents a halogeno group, nitro group, an iminoalkyl group having 2 to 7 carbon atoms, a mono- or dialkylcarbamoyl group having 2 to 7 carbon atoms, piperidyloxyl group, an iminoalkylpiperidyloxyl group having 6 to 10 carbon atoms, an alkylpiperidyloxyl group having 5 to 10 carbon atoms, an amino group, which may have a substituent(s), an aminoalkyl group having 2 to 9 carbon atoms, which may have a substituent(s), an alkyl group having 1 to 6 carbon atoms, which may have a substituent(s), pyrrolidine group, which may have a substituent(s), piperazine group, which may have a substituent(s), a heteroaryl group having 1 to 10 carbon atoms, which may have a substituent(s), or an amidino group, which may have a substituent(s), when R3 has a substituent(s), the substituent is hydrogen atom, an alkyl group having 1 to 6 carbon atoms, a mono- or dialkylcarbamoyl group having 2 to 7 carbon atoms, a mono- or dialkylaminoalkyl group having 2 to 9 carbon atoms, a mono- or dialkylamidino group having 2 to 7 carbon atoms, a trialkylamidino group having 4 to 7 carbon atoms, pyrrolidine group, piperidine group, an alkylsulfonyl group having 1 to 8 carbon atoms or pyridyl group, R8 and R9 may be the same or different from each other and each represent hydrogen atom, a halogeno group or pyridyl group, and X represents an alkylene group having 1 to 3 carbon atoms, which may contain —C(=O)NH— in the chain thereof.

It is also preferred that in general formula (1), ring C represents phenyl group or piperidyl group, X represents an alkylene group having 1 to 6 carbon atoms, R3 represents a mono- or dialkylcarbamoyl group having 2 to 7 carbon atoms, an alkyl group having 1 to 6 carbon atoms, which may have a substituent(s) or an amidino group, which may have a substituent(s), when R3 has a substituent(s), the substituent is an alkyl group having 1 to 6 carbon atoms or pyridyl group, and R8 and R9 may be the same or different from each other and they each represent hydrogen atom, a halogeno group, trifluoromethyl group, methoxyl group or hydroxyl group.

It is also preferred that in general formula (1), ring A represents phenyl group, R1 represents hydrogen atom, chloro group, carboxyl group, an alkoxycarbonyl group having 2 to 7 carbon atoms, amino group, which may have a substituent(s), hydroxyl group, which may have a substituent(s) or an alkyl group having 1 to 6 carbon atoms, which may have a substituent(s), when R1 has a substituent(s), the substituent is hydroxyl group, phosphono group, carboxyl group, an alkoxycarbonyl group having 2 to 7 carbon atoms, a mono- or dialkylcarbamoyl group having 2 to 7 carbon atoms, a mono- or dialkylamino group having 1 to 6 carbon atoms, piperazinecarbonyl group, an alkylpiperazinecarbonyl group having 6 to 10 carbon atoms or an alkylsulfonyl group having 1 to 6 carbon atoms, ring B represents an aryl group having 6 to 10 carbon atoms or a heteroaryl group having 4 to 10 carbon atoms, R2 represents chloro group or bromo group, ring C represents phenyl group or piperidyl group, R3 represents a mono- or dialkylcarbamoyl group having 2 to 7 carbon atoms, an alkyl group having 1 to 6 carbon atoms, which may have a substituent(s), or amidino group, which may have a substituent(s), when R3 has a substituent(s), the substituent is an alkyl group having 1 to 6 carbon atoms or pyridyl group, R4, R5, R6, R7, R8 and R9 may be the same or different from one another and they each represent hydrogen atom, a halogeno group, trifluoromethyl group, methoxyl group or hydroxyl group, and X represents an alkylene group having 1 to 6 carbon atoms.

It is also preferred that in general formula (1), ring A represents phenyl group, R1 represents hydrogen atom, chloro group, amino group, carboxyl group, ethoxycarbonyl group, carboxyethyl group, ethoxycarbonylethyl group, a morpholinealkyl group, hydroxyl group, methyl group, phosphonoethyl group, morpholinecarbonylethyl group, piperazinecarbonylethyl group, isopropylpiperazinecarbonylethyl group, methanesulfonylaminoethyl group or hydroxypropyl group, ring B represents phenyl group or thiophene group, R2 represents chloro group or bromo group, ring C represents phenyl group or piperidyl group, R3 represents isopropyl group, cyclohexyl group, pyridyl group, 1-methyl-1H-imidazol-2-yl group, 1, 3-dimethyl-4,5-dihydro-1H-imidazol-3-ium-2-yl group, 2,5-dihydro-1H-pyrrol-1-ylcarbonyl group, 1-pyrrolidinylcarbonyl group, 2,5-dihydro-1H-pyrrol-1-yl(imino)methyl group or 1-iminoethyl-piperidin-4-yloxyl group, R4, R5, R6, R7, R8 and R9 may be the same or different from one another and they each represent hydrogen atom or a halogeno group, X represents methylene group or ethylene group, and Z1 and Z2 each represent hydrogen atom.

It is also preferred that in general formula (1), X represents an alkyl group having 1 to 6 carbon atoms.

It is also preferred that in general formula (1), ring B represents an aryl group having 6 to 10 carbon atoms or a heteroaryl group having 4 to 10 carbon atoms, R2 represents a halogeno group, an alkyl group having 1 to 6 carbon atoms, trifluoromethyl group or an alkoxyl group having 1 to 10 carbon atoms, and R6 and R7 each represent hydrogen atom.

It is also preferred that in general formula (1), ring B represents an aryl group having 6 to 10 carbon atoms and a substituent or a heteroaryl group having 4 to 10 carbon atoms, R2 represents a halogeno group, an alkyl group having 1 or 2 carbon atoms, trifluoromethyl group or an alkoxyl group having 1 to 3 carbon atoms, and R6 and R7 are each hydrogen atom.

It is also preferred that in general formula (1), ring B represents an aryl group having 6 to 10 carbon atoms or a heteroaryl group having 4 to 10 carbon atoms, R2 represents a chloro group or bromo group, and R8 and R9 are each hydrogen atom.

It is also preferred that in general formula (1), ring B represents phenyl group, naphthyl group, pyridyl group or thiophene group.

It is also preferred that in general formula (1), ring C represents an aryl group having 6 to 10 carbon atoms or piperidyl group, R3 represents a halogeno group, an alkyl group having 1 to 6 carbon atoms, which may have a substituent(s), pyridyl group, nitro group, a mono- or dialkylcarbamoyl group having 2 to 7 carbon atoms, amino group, a dialkylamino group, amidino group, which may have a substituent(s) or piperidyloxyl group, which may have a substituent(s), and R8 and R9 are each hydrogen atom It is also preferred that in general formula (1), ring C represents phenyl group or 4-piperidyl group, R3 represents a halogeno group, a mono- or dialkylcarbamoyl group having 2 to 7 carbon atoms, 4-pyridyl group, an alkyl group having 1 to 6 carbon atoms, which may have a substituent(s), nitro group, amino group, dimethylamino group, amidino group, which may have a substituent(s) or a piperidyloxyl group, which may have a substituent(s), and R8 and R9 are each hydrogen atom It is also preferred that in general formula (1), ring A represents phenyl group, ring B represents phenyl group or thiophene group, R2 represents chloro group or bromo group, ring C represents phenyl group or piperidyl group, R3 represents pyridyl group, and X represents methylene group.

It is also preferred that in general formula (1), ring A represents phenyl group, ring B represents phenyl group, pyridyl group, thiophene group or naphthyl group, R2 represents a halogeno group, an alkyl group having 1 to 6 carbon atoms, trifluoromethyl group or an alkoxyl group having 1 to 10 carbon atoms, ring C represents phenyl group or piperidyl group, R3 represents a mono- or dialkylcarbamoyl group having 2 to 7 carbon atoms, a halogeno group, pyridyl group, nitro group, an alkyl group having 1 to 6 carbon atoms, which may have a substituent(s), an amino group, a dialkylamino group, amidino group, which may have a substituent(s) or piperidyloxyl group, which may have a substituent(s), and X represents methylene group.

It is preferred that in general formula (1), ring A represents phenyl group, ring B represents phenyl group or thiophene group, R2 represents chloro group or bromo group, ring C represents phenyl group or piperidyl group, R3 represents pyridyl group, and X represents methylene group.

Typical processes for producing compounds (1) of the present invention will be described below. For example, a compound of general formula (1), wherein ring A represents phenyl group, which may have a substituent(s) and X represents an alkyl group having 1 to 6 carbon atoms, can be produced by a process described below.

Namely, a compound (4) can be obtained by reacting an amino acid ester (2) with, for example, a 2-nitrobenzyl halide (3) in the presence of a base such as sodium hydrogencarbonate in ethanol as the solvent. A compound (6) can be derived from the obtained compound (4) by reacting it with, for example, an acid halide (5) in the presence of a base such as triethylamine in a solvent such as dichloromethane. A compound (7) can be derived from the obtained compound (6) by hydrolyzing it in the presence of a base such as sodium hydroxide in a solvent such as tetrahydrofuran and then reacting the obtained product in the presence of a catalyst such as palladium/carbon in a solvent such as ethanol in, for example, hydrogen atmosphere. A compound (8) can be derived from the obtained compound (7) by reacting it with a condensing agent in the presence of a base such as triethylamine in a solvent such as dimethylformamide to conduct the intramolecular condensation. A benzodiazepine derivative (10) can be derived from the obtained compound (8) by reacting it with a compound (9) in the presence of a base such as sodium hydride in a solvent such as dimethylformamide.

By changing the starting material (3), compounds of general formula (1) wherein ring A is other than phenyl group, such as an aryl group, a heteroaryl group or cycloalkyl group can be synthesized.

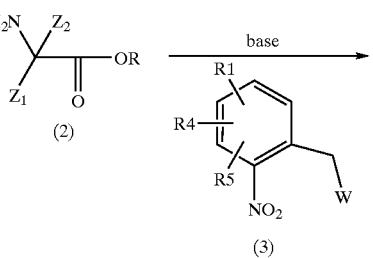

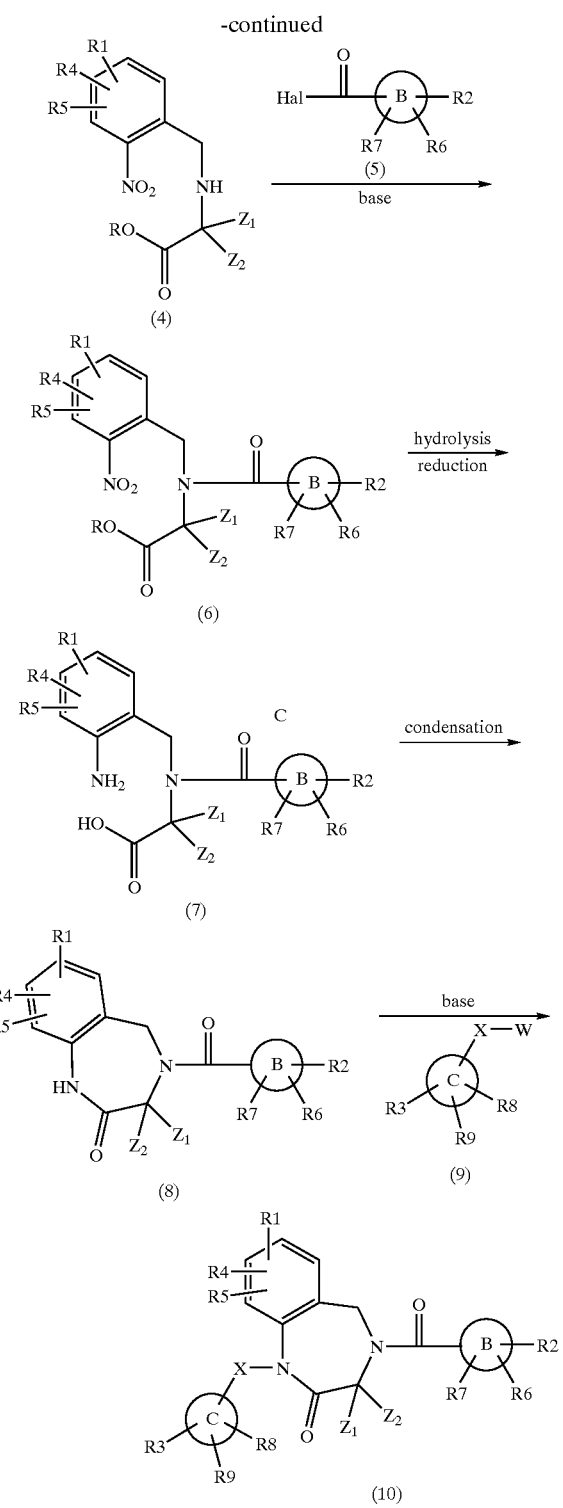

Hal represents a halogen atom.
W represents a leaving group such as a halogen atom.

The compound (6) can be converted to compound (11) by reacting it in the presence of a catalyst such as palladium/carbon in, for example, ethyl acetate in, for example, hydrogen atmosphere. Then a compound (13) can be obtained by reacting the compound (6) with a reducing agent such as sodium triacetoxyborohydride and a compound such as (12) in the presence of an acid such as acetic acid in a solvent such as dichloromethane. The obtained compound (13) can be converted to a benzodiazepine derivative (14) by the hydrolysis in the presence of a base such as sodium hydroxide in a solvent such as tetrahydrofuran followed by the intramolecular condensation with a condensing agent in the presence of a base such as triethylamine in a solvent such as dichloromethane.

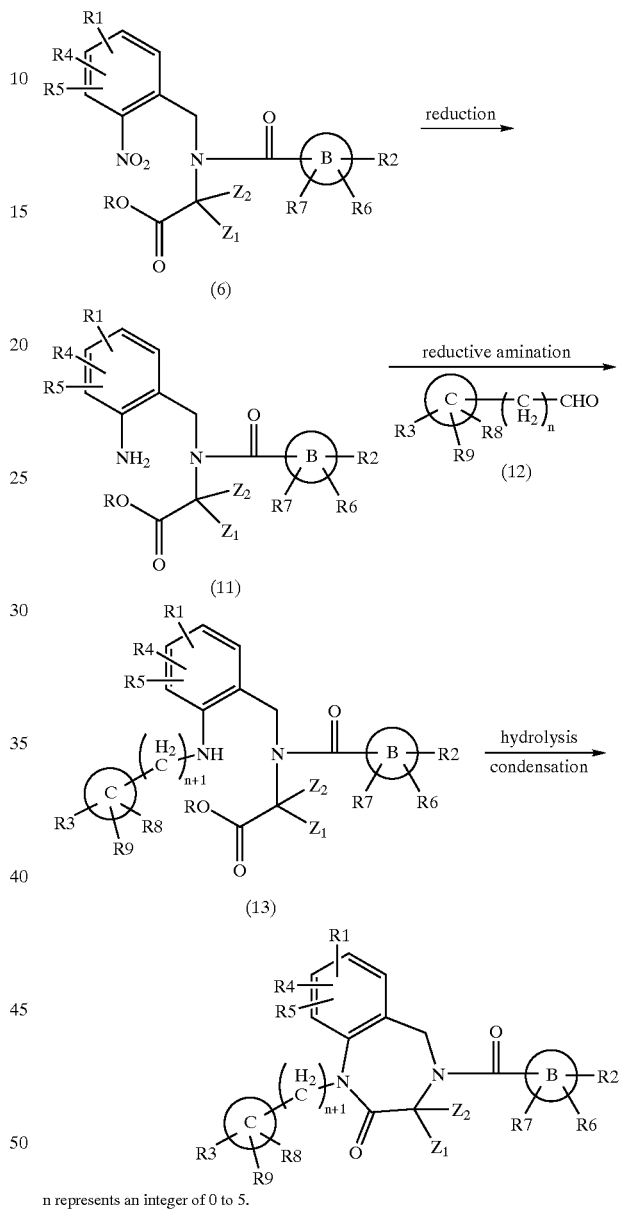

n represents an integer of 0 to 5.

The compounds of general formula (1) produced as described above and salts thereof can be isolated by the purification by a well-known separation/purification method such as extraction, concentration, concentration under reduced pressure, extraction with a solvent, crystallization, recrystallization, redissolution or various chromatographic techniques.

The salts of the benzodiazepine derivatives of general formula (1) are pharmaceutically acceptable ones. When the formula has a basic group, the salts of them are acid addition salts with mineral acids such as hydrochloric acid, hydrobromic acid, sulfuric acid, nitric acid and phosphoric acid, etc.; and organic acids such as formic acid, acetic acid, lactic acid, salicylic acid, mandelic acid, citric acid, oxalic acid, maleic acid, fumaric acid, tartaric acid, tannic acid, malic acid, toluenesulfonic acid, methanesulfonic acid and benzenesulfonic acid, etc. When the formula has an acidic group such as carboxyl group, the salts of them are base addition salts such as ammonium salts, salts with alkali metals such as sodium and potassium, etc., alkaline earth metals such as calcium and magnesium, etc., aluminum, zinc, organic amines such as triethylamine, ethanolamine, morpholine, piperidine and dicyclohexylamine, etc., basic amino acids such as arginine and lysine, etc.

The compounds of general formula (1) in the present invention include their solvates such as hydrates and alcohol adducts thereof.

The compounds of general formula (1) and salts thereof are administered as they are or in the form of various pharmaceutical compositions to patients. The dosage forms of the pharmaceutical compositions are, for example, tablets, powders, pills, granules, capsules, suppositories, solutions, sugar-coated tablets and depots. They can be prepared with ordinary preparation assistants by an ordinary method. For example, the tablets are prepared by mixing the benzodiazepine derivative, the active ingredient of the present invention, with known adjuvants such as inert diluents, e.g. lactose, calcium carbonate and calcium phosphate, binders, e.g. acacia, corn starch and gelatin, extending agents, e.g. alginic acid, corn starch and pre-gelatinized starch, sweetening agents, e.g. sucrose, lactose and saccharin, corrigents, e.g. peppermint and cherry, and lubricants, e.g. magnesium stearate, talc and carboxymethyl cellulose.

The blood-coagulation inhibitor containing one of the benzodiazepine derivatives of general formula (1) and salts thereof is usable for preventing or treating cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral arterial occlusive disease; deep vein thrombosis; disseminated intravascular coagulation; thrombus formation after an artificial blood vessel-forming operation or an artificial valve substitution; reocclusion and restenosis after a coronary artery bypass grafting; reocclusion and restenosis after a reconstructive operation for the blood circulation such as percutaneous transluminal coronary angioplasty (PTCA) or percutaneous transluminal coronary recanalization (PTCR); and thrombus formation in the course of the extracorporeal circulation.

When the benzodiazepine derivatives represented by general formula (1) are used as the anticoagulants, they can be administered either orally or parenterally. The dose which varies depending on the age, body weight and conditions of the patient and the administration method is usually 0.01 to 1,000 mg, preferably 0.1 to 50 mg, a day for adults in the oral administration, and 1 µg to 100 mg, preferably 0.01 to 10 mg, in the parenteral administration.

EXAMPLES

The following Examples will further illustrate the present invention, which are only preferred embodiments of the invention and which by no means limit the invention.

Example 1

Synthesis of 4-(4-methoxybenzoyl)-1-[1-(4-pyridyl)-4-piperidylmethyl]-1,3,4,5-tetrahydrobenzo[e][1,4]diazepin-2-on mono(trifluoroacetate)

Step 1: Synthesis of Ethyl (2-nitrobenzyl)aminoacetate 6.35 g (45.4 mmol) of glycine ethyl ester hydrochloride, 2.45 g (11.3 mmol) of 2-nitrobenzyl bromide and 4.75 g (56.5 mmol) of sodium hydrogencarbonate were dissolved in ethanol, and the obtained solution was stirred at 70° C. overnight. The reaction solution was filtered, and the obtained filtrate was treated with ethyl acetate as the extracting solvent by an ordinary method to obtain the crude product. After the purification by the silica gel column chromatography, the title compound was obtained.

Yield: 2.2 g (9.24 mmol) (81%)

H-NMR (CDCl3) δ 1.25 (3H, t), 3.41 (2H, s), 4.08 (2H, s), 4.15 (2H, q), 7.40 (1H, dd), 7.57 (1H, dd), 7.62 (1H, dd), 7.93 (1H, dd)

Step 2: Synthesis of 4-t-butoxycarbonyl-1,3,4,5-tetrahydrobenzo-[e][1,4]diazepin-2-on 2.2 g (9.24 mmol) of ethyl (2-nitrobenzyl)aminoacetate was dissolved in 20 ml of dichloromethane. 3.0 g (13.9 mmol) of di-t-butyl dicarbonate and 2.6 ml (18.5 mmol) of triethylamine were added to the obtained solution, and they were stirred at room temperature for 5 hours. After the treatment with dichloromethane as the extracting solvent by an ordinary method, the obtained crude product was dissolved in a mixture of 20 ml of THF (hereinafter referred to as THF), 20 ml of ethanol and 10 ml of 1 mol/l sodium hydroxide. The obtained solution was stirred at room temperature for 3 hours. After the treatment with ethyl acetate as the extracting solvent by an ordinary method, the obtained crude product was dissolved in 20 ml of methanol. 220 mg of 10% palladium/carbon was added to the obtained solution and they were stirred in the presence of hydrogen at room temperature overnight. The reaction solution was filtered through Celite. The solvent was evaporated and the obtained crude product was dissolved in 20 ml of DMF. 1.87 g (11.1 mmol) of 2-chloro-1,3-dimethylimidazonium chloride and 3.86 ml (27.7 mmol) of triethylamine were added to the obtained solution, and they were stirred overnight. After the treatment with ethyl acetate as the extracting solvent by an ordinary method, the obtained crude product was washed with hexane/ethyl acetate (1:1) to obtain the title compound.

Yield: 670 mg (2.56 mmol) (28%)

H-NMR (CDCl3) δ 1.44 (9H, br), 4.22–4.58 (4H, m), 6.89 (1H, d),7.00–7.26 (2H, m), 7.63–7.86 (1H, m)

Step 3: Synthesis of 1-[1-(4-pyridyl)-4-piperidylmethyl]-1,3,4,5-tetrahydrobenzo[e][1,4]diazepin-2-on bistrifluoroacetate 982 mg (5.1 mmol) of 1-(4-pyridyl)piperidin-4-ylmethanol was dissolved in a mixture of 50 ml of dichloromethane and 1.25 ml (9.0 mmol) of triethylamine. 0.60 ml (7.7 mmol) of methanesulfonyl chloride was added to the obtained solution under cooling with ice, and they were stirred at that temperature for 3 hours. After the treatment with dichloromethane as the extracting solvent by an ordinary method, the crude product was obtained.

670 mg (2.56 mmol) of 4-t-butoxycarbonyl-1,3,4,5-tetrahydrobenzo-[e][1,4]diazepin-2-on was dissolved in 40 ml of N,N-dimethylformamide (hereinafter referred to as DMF). 113 mg (2.82 mmol) of sodium hydride was added to the obtained solution at room temperature. After stirring for 30 minutes, the crude product obtained as described above was added thereto, and they were stirred at 70° C. overnight. The solvent was evaporated, and 5 ml of 4N solution of hydrogen chloride in dioxane was added to the obtained crude product, and they were stirred at room temperature for 3 hours. The solvent was evaporated, and the obtained crude product was treated by the reversed-phase high-performance liquid chromatography with column of silica gel of chemically bonded with octadodecyl group as the filler and eluted with a solvent mixture of water and acetonitrile containing 0.1% (v/v) of trifluoroacetic acid. The intended fraction was freeze-dried to obtain the title compound.

Yield: 320 mg (0.567 mmol) (22%)

H-NMR (DMSO-d6) δ 1.08–1.25 (2H, m), 1.62–1.71 (2H, m), 1.92–2.00 (1H, m), 3.01–3.18 (2H, m), 3.77–3.95 (4H, m), 4.08–4.22 (4H, m), 7.14 (2H, d), 7.31–7.40 (1H, m), 7.50 (1H, d), 7.57 (2H, d), 8.17 (2H, d),8.20 (1H, br)

Step 4: Synthesis of 4-(4-methoxybenzoyl)-1-[1-(4-pyridyl)-4-piperidylmethyl]-1,3,4,5-tetrahydrobenzo[e][1,4]diazepin-2-on mono(trifluoroacetate)

16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 7 mg (0.043 mmol) of 4-methoxybenzoyl chloride were added to the obtained solution, and they were stirred overnight. The solvent was evaporated, and the obtained crude product was treated in the same manner as in step 3 in Example 1 to obtain the title compound.

Yield: 2.4 mg (0.0041 mmol) (15%)

MS (ESI, m/z) 471 (MH+)

H-NMR (DMSO-d6) δ 1.08–1.24 (2H, m), 1.60–1.77 (2H, m), 1.91–2.05 (1H, m), 3.03–3.19 (2H, m), 3.81 (3H, s), 3.82–3.94 (4H, m), 4.09–4.21 (2H, m), 4.57 (2H, br), 6.99 (2H, d), 7.12 (2H, d), 7.22–7.38 (1H, m), 7.42–7.66 (5H, m), 8.15 (2H, d)

Example 2

Synthesis of 4-(4-chlorobenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 7 mg (0.043 mmol) of 4-chlorobenzoyl chloride were added to the obtained solution, and they were stirred overnight. The solvent was evaporated and the obtained crude product was treated in the same manner as in step 3 in Example 1 to obtain the title compound.

Yield: 9.2 mg (0.015 mmol) (56%)

MS (ESI, m/z) 475 (MH+)

H-NMR (DMSO-d6) δ 1.06–1.24 (2H, m), 1.57–1.75 (2H, m), 1.93–2.04 (1H, m), 3.01–3.19 (2H, m), 3.82–4.17 (4H, m), 4.43–4.66 (4H, m), 7.12 (2H, d), 7.18–7.38 (1H, m), 7.42–7.63 (7H, m), 8.15 (2H, d)

Example 3

Synthesis of 4-(naphthalene-2-carbonyl)-1-[1-(4-pyridyl)-4-piperidylmethyl]-1,3,4,5-tetrahydrobenzo[e][1,4]diazepin-2-on tri-fluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 8 mg (0.043 mmol) of 2-naphthoyl chloride were added to the obtained solution, and they were stirred overnight. The solvent was evaporated and the obtained crude product was treated in the same manner as in step 3 in Example 1 to obtain the title compound.

Yield: 4.6 mg (0.0076 mmol) (27%)

MS (ESI, m/z) 491 (MH+)

H-NMR (DMSO-d6) δ 1.08–1.26 (2H, m), 1.60–1.78 (2H, in), 1.89–2.10 (1H, m), 3.03–3.19 (2H, m), 3.82–4.22 (4H, m), 4.52–4.73 (4H, m), 7.13 (2H, d), 7.24–7.38 (1H, m), 7.42–7.63 (6H, m), 7.89–8.14 (4H, m), 8.16 (2H, d)

Example 4

Synthesis of 4-(4-fluorobenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 6 mg (0.043 mmol) of 4-fluorobenzoyl chloride were added to the obtained solution, and they were stirred overnight. The solvent was evaporated and the obtained crude product was treated in the same manner as in step 3 in Example 1 to obtain the title compound.

Yield: 4.6 mg (0.008 mmol) (28%)

MS (ESI, m/z) 459(MH+)

H-NMR (DMSO-d6) δ 1.08–1.23 (2H, m), 1.60–1.76 (2H, m), 1.84–2.08 (1H, m), 3.01–3.17 (2H, m), 3.78–4.26 (4H, m), 4.44–4.73 (4H, m), 7.12 (2H, d), 7.18–7.62 (8H, m), 8.15 (2H, d)

Example 5

Synthesis of 4-(4-methylbenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 6 mg (0.043 mmol) of 4-toluoyl chloride were added to the obtained solution, and they were stirred overnight. The solvent was evaporated and the obtained crude product was treated in the same manner as in step 3 in Example 1 to obtain the title compound.

Yield: 7.4 mg (0.013 mmol) (47%)

MS (ESI, m/z) 455(MH+)

H-NMR (DMSO-d6) δ 1.04–1.23 (2H, m), 1.59–1.70 (2H, m), 1.83–2.03 (1H, m), 2.34 (3H, s), 3.01–3.17 (2H, m), 3.78–3.85 (4H, m), 4.09–4.21 (2H, m), 4.32–4.62 (2H, m), 7.12 (2H, d), 7.21–7.62 (8H, m), 8.15 (2H, d)

Example 6

Synthesis of 4-(3-methoxybenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 6 mg (0.043 mmol) of 3-methoxybenzoyl chloride were added to the obtained solution, and they were stirred overnight. The solvent was evaporated and the obtained crude product was treated in the same manner as in step 3 in Example 1 to obtain the title compound.

Yield: 7.1 mg (0.012 mmol) (43%)

MS (ESI, m/z) 455(MH+)

H-NMR (DMSO-d6) δ 1.06–1.24 (2H, m), 1.60–1.77 (2H, m), 1.87–2.03 (1H, m), 3.03–3.19 (2H, m), 3.75 (3H, s), 3.82–3.94 (4H, m), 4.09–4.21 (2H, m) 4.60 (2H, br), 6.86–7.10 (4H, m), 7.12 (2H, d), 7.26–7.63 (4H, m), 8.15 (2H, d)

Example 7
Synthesis of 4-(4-trifluoromethylbenzoyl)-1-[1-(4-pyridyl)-4-piperidyl-methyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 8 mg (0.043 mmol) of 4-trifluorometylbenzoyl chloride were added to the obtained solution, and they were stirred overnight. The solvent was evaporated and the obtained crude product was treated in the same manner as in step 3 in Example 1 to obtain the title compound.

Yield: 12.2 mg (0.02 mmol) (70%)
MS (ESI, m/z) 509(MH+)
H-NMR (DMSO-d6) δ 1.06–1.24 (2H, m), 1.58–1.72 (2H, m), 1.85–2.09 (1H, m), 3.04–3.17 (2H, m), 3.78 (2H, br), 3.83 (2H, br), 4.09–4.16 (2H, m), 4. 60 (2H, br), 7.12 (2H, d), 7.19–7.38 (2H, m), 7.44–7.61 (3H, m), 7.62–7.92 (2H, m), 8.15 (2H, d)

Example 8
Synthesis of 4-benzoyl-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 6 mg (0.043 mmol) of benzoyl chloride were added to the obtained solution, and they were stirred overnight. The solvent was evaporated and the obtained crude product was treated in the same manner as in step 3 in Example 1 to obtain the title compound.

Yield: 12.6 mg (0.022 mmol) (81%)
MS (ESI, m/z) 441(MH+)
H-NMR (DMSO-d6) δ 1.04–1.22 (2H, m), 1.58–1.74 (2H, m), 1.85–2.08 (1H, m), 3.01–3.18 (2H, m), 3.84 (4H, br), 4.06–4.21 (2H, m), 4.60 (2H, br), 7. 12 (2H, d), 7.19–7.38 (2H, m), 7.41–7.63 (9H, m), 8.15 (2H, d)

Example 9
Synthesis of 4-(4-bromobenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 8 mg (0.043 mmol) of 4-bromobenzoyl chloride were added to the obtained solution, and they were stirred overnight. The solvent was evaporated and the obtained crude product was treated in the same manner as in step 3 in Example 1 to obtain the title compound.

Yield: 12.4 mg (0.02 mmol) (70%)
MS (ESI, m/z) 520(MH+)
H-NMR (DMSO-d6) δ 1.08–1.22 (2H, m), 1.58–1.76 (2H, m), 1.83–2.04 (1H, m), 3.00–3.18 (2H, m), 3.63–3.88 (4H, m), 4.06–4.21 (2H, m), 4.60 (2H, b r), 7.12 (2H, d), 7.19–7.78 (8H, m), 8.15 (2H, d)

Example 10
Synthesis of 4-(4-ethylbenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 6 mg (0.043 mmol) of 4-ethylbenzoyl chloride were added to the obtained solution, and they were stirred overnight. The solvent was evaporated and the obtained crude product was treated in the same manner as in step 3 in Example 1 to obtain the title compound.

Yield: 11.0 mg (0.019 mmol) (68%)
MS (ESI, m/z) 469(MH+)
H-NMR (DMSO-d6) δ 1.03–1.22 (5H, m), 1.58–1.73 (2H, m), 1.83–2.04 (1H, m), 2.63–2.76 (2H, m), 2.98–3.17 (2H, m), 3.86 (4H, br), 4.08–4.21 (2H, m), 4.56 (2H, br), 7.12 (2H, d), 7.19–7.83 (8H, m), 8.15 (2H, d)

Example 11
Synthesis of 4-(3,4-dichlorobenzoyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 0.016 ml (0.084 mmol) of triethylamine and 8 mg (0.043 mmol) of 3,4-dichlorobenzoyl chloride were added to the obtained solution, and they were stirred overnight. The solvent was evaporated and the obtained crude product was treated in the same manner as in step 3 in Example 1 to obtain the title compound.

Yield: 16 mg (0.027 mmol) (98%)
MS (ESI, m/z) 509(MH+)
H-NMR (DMSO-d6) δ 1.05–1.23 (2H, m), 1.56–1.75 (2H, m), 1.83–2.06 (1H, m), 2.98–3.19 (2H, m), 3.78–3.96 (4H, m), 4.08–4.21 (2H, m), 4.56 (2H, br), 7.12 (2H, d), 7.19–7.83 (8H, m), 8.16 (2H, d)

Example 12
Synthesis of 4-(4-chlorobenzoyl)-1-(4-fluorobenzyl)-1,3,4,5-tetrahydrobenzo[e][1,4]diazepin-2-on Step 1 Synthesis of 4-(4-chlorobenzoyl)-1,3,4,5-tetrahydrobenzo[e][1,4](diazepin-2-on 2.1 g (8.8 mmol) of ethyl (2-nitrobenzyl)aminoacetate was dissolved in 50 ml of dichloromethane. 1.8 g (10.6 mmol) of 4-chlorobenzoyl chloride and 1.6 ml (11.4 mmol) of triethylamine were added to the obtained solution, and they were stirred at room temperature overnight. After the treatment with dichloromethane as the extracting solvent by an ordinary method, the obtained crude product was dissolved in a mixture of 20 ml of THF, 20 ml of ethanol and 10 ml of 1 mol/l sodium hydroxide. The obtained solution was stirred at room temperature for 3 hours. After the treatment with ethyl acetate as the extracting solvent by an ordinary method, the obtained crude product was dissolved in 20 ml of methanol. 220 mg of 10% palladium/carbon was added to the obtained solution and they were stirred in the presence of hydrogen at room temperature overnight. The reaction solution was filtered through Celite. The solvent was evaporated and the obtained crude product was dissolved in 20 ml of DMF. 1.8 g (10.6 mmol) of 2-chloro-1,3-dimethylimidazonium chloride and 2.4 ml (17.6 mmol) of triethylamine were added to the obtained solution, and they were stirred overnight. After the treatment with ethyl acetate as the extracting solvent by an ordinary method, the obtained crude product was washed with hexane/ethyl acetate (5:1) to obtain the title compound.

Yield: 1.2 g (4.0 mmol) (45%)
H-NMR (CDCl3) δ 4.16 (2H, br), 4.53 (2H, br), 7.02 (2H, d), 7.42 (6H, br)

Step 2 Synthesis of 4-(4-chlorobenzoyl)-1-(4-fluorobenzyl)-1,3,4,5-tetrahydrobenzo[e][1,4]diazepin-2-on 20 mg (0.067 mmol) of 4-(4-chlorobenzoyl)-1,3,4,5-tetrahydrobenzo[e][1,4]diazepin-2-on was dissolved in 5 ml of DMF. 3 mg (0.08 mmol) of sodium hydride was added to the obtained solution, and they were stirred at room temperature for 30 minutes. 12 mg (0.08 mmol) of 4-fluorobenzyl chloride was added to the obtained mixture and they were stirred at 60° C. overnight. The reaction mixture was treated with ethyl acetate as the extracting solvent by an ordinary method to obtain the crude product. After the purification by the silica gel column chromatography, the title compound was obtained.

Yield: 13.2 mg (0.032 mmol) (48%)
MS (FAB, m/z) 409(MH+)
H-NMR (DMSO-d6) δ 3.85 (2H, br), 4.38 (2H, br), 5.05 (2H, br), 7.03–7.60 (12H, m)

Example 13

Synthesis of 4-(4-chlorobenzoyl)-1-(3,4-dichlorobenzyl)-1,3,4,5-tetrahydrobenzo[e][1,4]diazepin-2-on 20 mg (0.067 mmol) of 4-(4-chlorobenzoyl)-1,3,4,5-tetrahydrobenzo[e][1,4]diazepin-2-on was dissolved in 5 ml of DMF. 3 mg (0.08 mmol) of sodium hydride was added to the obtained solution, and they were stirred at room temperature for 30 minutes. 16 mg (0.08 mmol) of 3,4-dichlorobenzyl chloride was added to the obtained mixture and they were stirred at 60° C. overnight. The reaction mixture was treated with ethyl acetate as the extracting solvent by an ordinary method to obtain the crude product. After the purification by the silica gel column chromatography, the title compound was obtained.

Yield: 15.9 mg (0.035 mmol) (52%)
MS (FAB, m/z) 459(MH+)
H-NMR (DMSO-d6) δ 3.85 (2H, br), 4.42 (2H, br), 5.03 (2H, br), 7.18–7.63 (12H, m)

Example 14

Synthesis of 1-(4-bromobenzyl)-4-(4-chlorobenzoyl)-1,3,4,5-tetrahydrobenzo[e][1,4]diazepin-2-on 20 mg (0.067 mmol) of 4-(4-chlorobenzoyl)-1,3,4,5-tetrahydrobenzo[e][1,4]diazepin-2-on was dissolved in 5 ml of DMF. 3 mg (0.8 mmol) of sodium hydride was added to the obtained solution, and they were stirred at room temperature for 30 minutes. 20 mg (0.08 mmol) of 4-bromobenzyl bromide was added to the obtained mixture and they were stirred at 60° C. overnight. The reaction mixture was treated with ethyl acetate as the extracting solvent by an ordinary method to obtain the crude product. After the purification by the silica gel column chromatography, the title compound was obtained.

Yield: 15.3 mg (0.033 mmol) (49%)
MS (FAB, m/z) 470(MH+)
H-NMR (DMSO-d6) δ 3.85 (2H, br), 4.44 (2H, br), 5.05 (2H, br), 7.06–7.60 (12H, m)

Example 15

Synthesis of 4-(4-chlorobenzoyl)-1-(4-nitrobenzyl)-1,3,4,5-tetrahydrobenzo[e][1,4]diazepin-2-on 110 mg (0.37 mmol) of 4-(4-chlorobenzoyl)-1,3,4,5-tetrahydrobenzo[e][1,4]diazepin-2-on was dissolved in 5 ml of DMF. 17 mg (0.44 mmol) of sodium hydride was added to the obtained solution, and they were stirred at room temperature for 30 minutes. 76 mg (0.44 mmol) of 4-nitrobenzyl chloride was added to the obtained mixture and they were stirred at 60° C. overnight. The reaction mixture was treated with ethyl acetate as the extracting solvent by an ordinary method to obtain the crude product. After the purification by the silica gel column chromatography, the title compound was obtained.

Yield: 50 mg (0.11 mmol) (31%)
MS (FAB, m/z) 436(MH+)
H-NMR (DMSO-d6) δ 3.91 (2H, br), 4.45 (2H, br), 5.20 (2H, br), 7.18–7.63 (10H, m), 8.09–8.18 (2H, m)

Example 16

Synthesis of 1-(4-aminobenzyl)-4-(4-chlorobenzoyl)-1,3,4,5-tetrahydrobenzo[e][1,4]diazepin-2-on trifluoroacetate 50 mg (0.11 mmol) of 4-(4-chlorobenzoyl)-1-(4-nitrobenzyl)-1,3,4,5-tetrahydrobenzo[e][1,4]diazepin-2-on was dissolved in a mixture of 5 ml of N-methylpyrrolidone and 0.5 ml of ethanol. 91 mg (0.4 mmol) of tin chloride was added to the obtained solution, and they were stirred at room temperature overnight. The solvent was evaporated and the obtained crude product was treated in the same manner as in step 3 in Example 1 to obtain the title compound.

Yield: 40 mg (0.077 mmol) (70%)
MS (ESI, m/z) 406(MH+)
H-NMR (DMSO-d6) δ 3.91 (2H, br), 4.38 (2H, br), 5.04 (2H, br), 6.97 (2H, d), 7.20 (3H, br), 7.51 (7H, br), Example 17

Synthesis of 1-(4-dimethylaminobenzene)-4-(4-chlorobenzoyl)-1,3,4,5-tetrahydrobenzo[e][14]diazepin-2-on trifluoro-acetate 30 mg (0.0578 mmol) of 1-(4-aminobenzyl)-4-(4-chlorobenzoyl)-1,3,4,5-tetrahydrobenzo[e][1,4]diazepin-2-on trifluoroacetate was dissolved in 5 ml of acetonitrile. 0.047 ml (0.578 mmol) of 37% solutions of formaldehyde in water was added to the obtained solution, and they were stirred at room temperature for 1 hour. 6 mg (0.0867 mmol) of sodium cyanoborohydride was added to the obtained mixture. After stirring for 30 minutes, 0.5 ml of acetic acid was added to the obtained mixture, and they were stirred overnight. The product was treated by an ordinary method and the solvent was evaporated. The obtained crude product was treated in the same manner as in step 3 in Example 1 to obtain the title compound.

Yield: 10 mg (0.018 mmol) (31%)
MS (ESI, m/z) 434(MH+)
H-NMR (DMSO-d6) δ 3.85 (2H, br), 4.37 (2H, br), 4.99 (2H, br), 6.72 (2H, d), 7.08 (3H, br), 7.52 (7H, br), Example 18

Synthesis of 1-(4-amidinobenzyl)-4-(4-chlorobenzoyl)-1,3,4,5-tetrahydrobenzo[e][1,4]diazepin-2-on trifluoroacetate 110 mg (0.067 mmol) of 4-(4-chlorobenzoyl)-1,3,4,5-tetrahydrobenzo[e][1,4]diazepin-2-on was dissolved in 5 ml of DMF. 17 mg (0.44 mmol) of sodium hydride was added to the obtained solution, and they were stirred at room temperature for 30 minutes. 86 mg (0.44 mmol) of 4-cyanobenzyl bromide was added to the obtained mixture and they were stirred at 60° C. overnight. The reaction mixture was treated with ethyl acetate as the extracting solvent by an ordinary method to obtain the crude product. After the purification by the silica gel column chromatography, the obtained compound was dissolved in a mixture of 5 ml of 4 N solution of hydrogen chloride in dioxane and 1 ml of ethanol. The obtained solution was stirred at room temperature for 2 days. The solvent was evaporated and the obtained residue was dissolved in 5 ml of ethanol. 16 mg of ammonium carbonate was added to the obtained solution, and they were stirred at room temperature overnight. The solvent was evaporated, and the obtained crude product was treated in the same manner as in step 3 in Example 1 to obtain the title compound.

Yield: 10 mg (0.018 mmol) (27%)
MS (ESI, m/z) 433(MH+)
H-NMR (DMSO-d6) δ 3.85 (2H, br), 4.42 (2H, br), 5.20 (2H, br), 7.18–7.63 (10H, m), 7.70 (2H, d), 9.05 (2H, br), 9.22 (2H, br),

Example 19
Synthesis of 4-(pyridine-3-carbonyl)-1-[1-(4-pyridyl)-4-piperidylmethyl]-1,3,4,5-tetrahydrobenzo[e][1,4]diazepin-2-on bistrifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of nicotinic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound Yield: 16.4 mg (0.024 mmol) (88%)

MS (ESI, m/z) 442(MH+)

H-NMR (DMSO-d6) δ 1.03–1.22 (2H, m), 1.58–1.76 (2H, m), 1.83–2.08 (1H, m), 3.03–3.17 (2H, m), 3.84 (4H, br), 4.12–4.21 (2H, m), 4.58 (2H, br), 7.12 (2H, d), 7.21–7.41 (1H, m), 7.55 (4H, br), 7.93 (1H, br), 8.16 (2H, br), 8.70 (2H, br)

Example 20
Synthesis of 4-(pyridine-4-carbonyl)-1-[1-(4-pyridyl)-4-piperidylmethyl]-1,3,4,5-tetrahydrobenzo[e][1,4]diazepin-2-on bistrifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of isonicotinic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 8.3 mg (0.012 mmol) (44%)

MS ESI, m/z) 442(MH+)

H-NMR (DMSO-d6) δ 1.03–1.22 (2H, m), 1.58–1.76 (2H, m), 1.83–2.08 (1H, m), 3.03–3.17 (2H, m), 3.86 (4H, br), 4.12–4.21 (2H, m), 4.62 (2H, br), 7.12 (2H, d), 7.21–7.38 (2H, m), 7.42–7.63 (4H, m), 8.15 (2H, br), 8.66 (2H, br)

Example 21
Synthesis of 4-(pyridine-2-carbonyl)-1-[1-(4-pyridyl)-4-piperidylmethyl]-1,3,4,5-tetrahydrobenzo[e][1,4]diazepin-2-on bistrifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of picolinic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 11.7 mg (0.017 mmol) (62%)

MS (ESI, m/z) 442(MH+)

H-NMR (DMSO-d6) δ 1.03–1.22 (2H, m), 1.58–1.76 (2H, m), 1.83–2.03 (1H, m), 3.03–3.17 (2H, m), 3.79–3.92 (4H, m), 4.12–4.21 (2H, m), 4.53–4.67 (2H, m), 7.12 (2H, d), 7.21–7.38 (2H, m), 7.42–7.61 (3H, m), 7.63–7.78 (1H, m), 7.91–8.02 (1H, m), 8.15 (2H, d), 8.63 (1H, dd)

Example 22
Synthesis of 4-(2-chloropyridine-5-carbonyl)-1-[1-(4-pyridyl)-4-piperidylmethyl]-1,3,4,5-tetrahydrobenzo[e][1,4]diazepin-2-on bistrifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of 6-chloronicotinic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 8.5 mg (0.012 mmol) (43%)

MS (ESI, m/z) 476(MH+)

H-NMR (DMSO-d6) δ 1.03–1.23 (2H, m), 1.58–1.76 (2H, m), 1.83–2.03 (1H, m), 2.96–3.17 (2H, m), 3.79–3.92 (4H, m), 4.12–4.21 (2H, m), 4.53–4.67 (2H, m), 7.12 (2H, d), 7.17–7.38 (2H, m), 7.42–7.61 (4H, m), 7.94–8.03 (1H, m), 8.15 (2H, d), 8.55 (1H, br)

Example 23
Synthesis of 4-(5-methylthiophene-2-carbonyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of 5-methylthiophene-2-carboxylic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 2.8 mg (0.0049 mmol) (18%)

MS (ESI, m/z) 461(MH+)

H-NMR (DMSO-d6) δ 1.03–1.22 (2H, m), 1.57–1.76 (2H, m), 1.83–2.05 (1H, m), 2.49 (3H, s), 3.03–3.17 (2H, m), 3.87 (2H, d), 3.88–4.21 (4H, m), 4.83 (2H, br), 7.12 (2H, d), 7.21–7.39 (2H, m), 7.42–7.64 (4H, m), 8.15 (2H, d)

Example 24
Synthesis of 4-(5-chlorothiophene-2-carbonyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of 5-chlorothiophene-2-carboxylic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 8.5 mg (0.022 mmol) (78%)

MS (ESI, m/z) 481(MH+)

H-NMR (DMSO-d6) δ 1.03–1.22 (2H, m), 1.57–1.76 (2H, m), 1.83–2.05 (1H, m), 3.03–3.17 (2H, m), 3.87 (2H, br), 3.88–4.21 (4H, m), 4.83 (2H, br), 7.12 (2H, d), 7.21 (1H, d), 7.32 (1H, d), 7.42–7.64 (2H, m), 8.15 (2H, d)

Example 25

Synthesis of 4-(5-bromothiophene-2-carbonyl)-1-[1-(4-pyridyl)-4-piperidylmethyl]-1,3,4,5-tetrahydrobenzo[e][1,4]diazepin-2-on trifluoroacetate 16 mg (0.028 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 7 mg (0.042 mmol) of 2-chloro-1,3-dimethylimidazonium chloride, 5 mg (0.043 mmol) of 5-bromothiophene-2-carboxylic acid and 0.016 ml (0.084 mmol) of triethylamine were added to the obtained solution, and they were stirred overnight. The solvent was evaporated and the obtained crude product was treated in the same manner as in step 3 in Example 1 to obtain the title compound.

Yield: 18 mg (0.028 mmol) (quantitative yield)

MS (ESI, m/z) 524(MH+)

H-NMR (DMSO-d6) δ 1.03–1.22 (2H, m), 1.60–1.76 (2H, m), 1.83–2.02 (1H, m), 3.03–3.17 (2H, m), 3.87 (2H, br), 4.02–4.21 (4H, m), 4.83 (2H, br), 7.12 (2H, d), 7.32 (2H, br), 7.42–7.63 (4H, m), 8.15 (2H, br)

Example 26

Synthesis of 4-(4-chlorobenzoyl)-1-[4-(4-piperidyl-oxy)benzyl]-1,3,4,5-tetrahydrobenzo[e][1,4]diazepin-2-on trifluoro4acetate Step 1: Synthesis of [4-(1-t-butoxycarbonyl-4-piperidyloxy)-phenyl]methanol 2.67 g (8.3 mmol) of 4-(1-t-butoxycarbonyl-4-piperidyloxy)benzoic acid and 1.73 ml (12.5 mmol) of triethylamine were dissolved in 50 ml of THF. 0.95 ml (9.9 mmol) of ethyl chloroformate was added to the obtained solution, and they were stirred for 15 minutes. The obtained precipitate was removed by the suction filtration. 1 g of ice and 0.47 g (12.5 mmol) of sodium borohydride were added to the filtrate under cooling with ice, and they were stirred overnight. The reaction mixture was treated with ethyl acetate as the extracting solvent by an ordinary method to obtain the crude product. After the purification by the silica gel column chromatography, the title compound was obtained.

Yield: 2.3 mg (7.49 mmol) (90%)

H-NMR (CDCl3) δ 1.46 (9H, s), 1.73–1.99 (4H, m), 3.23–3.41 (2H, m), 3.63-3.78 (2H, m), 3.38–3.49 (2H, m), 4.61 (2H, br), 6.88 (1H, d), 6.96 (1H, d), 7.27 (1H, d), 8.07 (1H, d)

Step 2: Synthesis of 4-(4-chlorobenzoyl)-1-[4-(4-piperidyloxy)benzyl]1,3,4,5-tetrahydrobenzo[e][1,4]diazepin-2-on trifluoroacetate 310 mg (1.1 mmol) of [4-(1-t-butoxycarbonyl-4-piperidyloxy)phenyl]methanol was dissolved in a mixture of 10 ml of dichloromethane and 0.24 ml (1.7 mmol) of triethylamine. 0.1 ml (1.3 mmol) of methanesulfonyl chloride was added to the obtained solution under cooling with ice, and they were stirred at that temperature for 3 hours. The reaction mixture was treated with dichloromethane as the extracting solvent by an ordinary method to obtain the crude product.

252 mg (0.84 mmol) of 4-t-butoxycarbonyl-1,3,4,5-tetrahydrobenzo[e][1,4]diazepin-2-on was dissolved in 10 ml of DMF. 34 mg (1.1 mmol) of sodium hydride was added to the obtained solution at room temperature, and they were stirred for 30 minutes. The crude product obtained as described above was added to the obtained mixture and they were stirred at 70° C. overnight. The solvent was evaporated and the obtained crude product was dissolved in 5 ml of 4 N solution of hydrogen chloride in dioxane, and the obtained solution was stirred at room temperature for 2 hours. The solvent was evaporated, and the obtained crude product was treated in the same manner as in Step 3 in Example 1 to obtain the title compound.

Yield: 85 mg (0.14 mmol) (17%)

MS (ESI, m/z) 490(MH+)

H-NMR (DMSO-d6) δ 1.63–1.81 (2H, m), 1.96–2.06 (2H, m), 2.97–3.24 (4H, m), 3.81–4.05 (2H, m), 4.28–4.42 (2H, br), 4.56 (1H, br), 5.03 (2H, br), 6.86 (2H, d), 7.13 (4H, br), 7.51 (6H, br), 8.51 (1H, br)

Example 27

Synthesis of 4-(4-chlorobenzoyl)-1-[4-(1-acetoimidoyl)-4-piperidyloxy]benzyl]-1,3,4,5-tetrahydrobenzo[e][1,4]diazepin-2-on trifluoroacetate 10 mg (0.017 mmol) of 4-(4-chlorobenzoyl)-1-[4-(4-piperidyloxy)-benzyl]-1,3,4,5-tetrahydrobenzo[e][1,4]diazepin-2-on trifluoro-acetate was dissolved in 1 ml of ethanol. 23 mg (0.17 mmol) of ethyl acetoimidate hydrochloride and 0.051 mg (0.34 mmol) of triethylamine were added to the obtained solution, and they were stirred overnight. The solvent was evaporated and the obtained crude product was treated in the same manner as in step 3 in Example 1 to obtain the title compound.

Yield: 2.4 mg (0.004 mmol) (23%)

MS (ESI, m/z) 490(MH+)

H-NMR (DMSO-d6) δ 1.61–1.82 (2H, m), 1.97–2.08 (2H, m), 2.25 (3H, s), 3.31–3.50 (4H, m), 3.62–4.05 (2H, m), 4.28–4.42 (2H, br), 4.59 (1H, br), 5.03 (2H, br), 6.86 (2H, d), 7.13 (3H, br), 8.53 (6H, br), 9.08 (1H, br)

Example 28

Synthesis of 4-(4-chlorobenzoyl)-1-[4-(1-isopropyl)-4-piperidyloxy)benzyl]-1,3,4,5-tetrahydrobenzo[e][1,4]diazepin-2-on trifluoroacetate 25 mg (0.041 mmol) of 4-(4-chlorobenzoyl)-1-[4-(4-piperidyloxy)-benzyl]-1,3,4,5-tetrahydrobenzo[e][1,4]diazepin-2-on trifluoro-acetate was dissolved in a mixture of 1 ml of dichloromethane, 0.6 ml of acetone and 0.011 ml (0.19 mmol) of acetic acid. After stirring for 30 minutes, 40 mg (0.19 mmol) of triacetoxy borohydride was added to the obtained solution, and they were stirred overnight. The solvent was evaporated and the obtained crude product was treated in the same manner as in step 3 in Example 1 to obtain the title compound.

Yield: 10 mg (0.017 mmol) (40%)

MS (ESI, m/z) 491(MH+)

H-NMR (DMSO-d6) δ 1.23 (6H, dd), 1.63–1.81 (2H, m), 1.96–2.06 (2H, m), 2.12–2.24 (2H, m), 2.97–3.20 (4H, m), 3.82 (1H, br), 4.31–4.58 (3H, br), 5.03 (2H, br), 6.86 (2H, dd), 7.13 (4H, br), 7.52 (6H, br).

Example 29

Synthesis of 4-(4-aminomethyl)benzoyl-1-[1-(4-pyridyl)-4-piperidylmethyl]-1,3,4,5-tetrahydrobenzo[e][1,4]diazepin-2-on di(tri-fluoroacetate)

40 mg (0.071 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 18 mg (0.11 mmol) of 2-chloro-1,3-dimethylimidazonium chloride, 28 mg (0.11 mmol) of 4-t-butoxycarbonylaminomethylbenzoic acid and 0.03 2 mg (0.213 mmol) of triethylamine were added to the obtained solution, and they were stirred overnight. The solvent was evaporated and the obtained crude product was dissolved in 2 ml of 4N solution of hydrogen chloride in dioxane and the obtained solution was stirred for 3 hours. The solvent was evaporated and the obtained crude product was treated in the same manner as in step 3 in Example 1 to obtain the title compound.

Yield: 19 mg (0.027 mmol) (38%)

MS (ESI, m/z) 470(MH+)

H-NMR (DMSO-d6) δ 1.04–1.22 (2H, m), 1.58–1.74 (2H, m), 1.85–2.08 (1H, m), 3.01–3.18 (2H, m), 3.84 (4H, br), 4.06–4.21 (2H, m), 4.60 (2H, br), 7.12 (2H, d), 7.19–7.38 (2H, m), 7.41–7.63 (9H, m), 8.15 (2H, d)

Example 30

Synthesis of 4-(3-aminomethyl)benzoyl-1-[1-(4-pyridyl)4-piperidylmethyl]-1,3,4,5-tetrahydrobenzo[e][1,4]diazepin-2-on di(tri-floroacetate)

40 mg (0.071 mmol) of 1-[1-(4-pyridyl)-4-piperidylmethyl]-1,3,4,5-tetrahydrobenzo[e][1,4]diazepin-2-on bistrifluoroacetate was dissolved in 2 ml of DMF. 18 mg (0.11 mmol) of 2-chloro-1,3-dimethylimidazonium chloride, 28 mg (0.11 mmol) of 3-t-butoxycarbonylaminomethylbenzoic acid and 0.032 mg (0.213 mmol) of triethylamine were added to the obtained solution, and they were stirred overnight. The solvent was evaporated and the obtained crude product was dissolved in 2 ml of 4N solution of hydrogen chloride in dioxane and the obtained solution was stirred for 3 hours. The solvent was evaporated and the obtained crude product was treated in the same manner as in step 3 in Example 1 to obtain the title compound.

Yield: 15 mg (0.021 mmol) (30%)

MS (ESI, m/z) 470(MH+)

H-NMR (DMSO-d6) δ 1.04–1.22 (2H, m), 1.58–1.74 (2H, m), 1.85–2.08 (1H, m), 3.01–3.18 (2H, m), 3.84 (4H, br), 4.06–4.21 (2H, m), 4.60 (2H, br), 7.12 (2H, 7.19–7.38 (2H, m), 7.41–7.63 (9H, m), 8.15 (2H, d)

Example 31

Synthesis of 8-chloro-4-(4-chlorobenzoyl-1-[4-(4-piperidyloxy)benzyl]-1,3,4,5-tetrahydrobenzo[e][1,4]diazepin-2-on trifluoroacetate Step 1: Synthesis of ethyl (4-chloro-2-nitrobenzyl)aminoacetate 4.84 g (28.3 mmol) of 4-chloro-2-nitrotoluene was dissolved in 50 ml of benzene. 50 mg of perbenzoic acid and 6.0 g (34 mmol) of N-bromosuccinimide were added to the obtained solution, and the obtained solution was stirred at 80° C. overnight. The reaction solution was treated with ethyl acetate as the extracting solvent by an ordinary method to obtain the crude product. The crude product was dissolved in 100 ml of ethanol. 11.9 g (84.9 mmol) of glycine ethyl ester hydrochloride and 8.9 g (106 mmol) of sodium hydrogencarbonate were added to the obtained solution, and they were stirred at 80° C. for 4 hours. The insoluble matter was removed by the filtration, and the solvent was evaporated. After the extraction with ethyl acetate followed by washing with 1 N hydrochloric acid, the obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 4.8 g (17.6 mmol) (62%)

H-NMR (CDCl3) δ 1.27 (3H, t), 3.41 (2H, s), 4.97 (2H, s), 4.18 (2H, q), 7.55 (1H, dd), 7.64 (1H, d), 7.95 (1H, d)

Step 2: Synthesis of 8-chloro-4-t-butoxycarbonyl-1,3,4,5-tetrahydrobenzo[e][1,4]diazepin-2-on 2.6 g (9.6 mmol) of ethyl (4-chloro-2-nitrobenzyl) aminoacetate was dissolved in 50 ml of dichloromethane. 3.2 g (14.4 mmol) of di-t-butyl dicarbonate and 2.7 ml (19.1 mmol) of triethylamine were added to the obtained solution, and they were stirred at room temperature for 5 hours. After the treatment with dichloromethane as the extracting solvent by an ordinary method, the obtained crude product was dissolved in 20 ml of ethanol. 810 mg (19.1 mmol) of lithium hydroxide was added to the obtained solution, and they were stirred at room temperature for 3 hours. After the treatment with ethyl acetate as the extracting solvent by an ordinary method, the obtained crude product was dissolved in 20 ml of ethyl acetate. 260 mg of 10% palladium/carbon was added to the obtained solution and they were stirred in the presence of hydrogen at room temperature for 4 hours. The reaction solution was filtered through Celite. The solvent was evaporated and the obtained crude product was dissolved in 20 ml of DMF. 1.9 g (11.1 mmol) of 2-chloro-1,3-dimethylimidazonium chloride and 4.0 ml (28.7 mmol) of triethylamine were added to the obtained solution, and they were stirred overnight. After the treatment with ethyl acetate as the extracting solvent by an ordinary method, the obtained crude product was purified by the silica gel column chromatography to obtain the title compound.

Yield: 165 mg (0.56 mmol) (6%)

H-NMR (CDCl3) δ 1.44 (9H, br), 4.22–4.58 (4H, m), 7.00–7.18 (2H, m), 7.73–7.94 (1H, m)

Step 3: Synthesis of 8-chloro-4-(4-chlorobenzoyl)-1,3,4,5-tetrahydrobenzo[e][1,4]diazepin-2-on 165 mg (0.56 mmol) of 8-chloro-4-t-butoxycarbonyl-1,3,4,5-tetrahydrobenzo[e][1,4]diazepin-2-on was dissolved in 5 ml of trifluoroacetic acid, and the obtained solution was stirred at room temperature for 2 hours. The solvent was evaporated and the obtained crude product was dissolved in dichloromethane. 0.24 ml (1.68 mmol) of triethylamine and 0.085 ml (0.67 mmol) of 4-chlorobenzoyl chloride were added to the obtained solution, and they were stirred overnight. After the treatment with ethyl acetate as the extracting solvent by an ordinary method, the obtained crude product was washed with hexane/ethyl acetate (1/1) to obtain the title compound.

Yield: 100 mg (0.30 mmol) (53%)

H-NMR (CDCl3) δ 4.12–4.83 (4H, m), 7.11 (2H, br), 7.39 (4H, br), 8.48 (1H, br)

Step 4: Synthesis of 8-chloro-4-(4-chlorobenzoyl)-1-[4-(4-piperidyloxy)benzyl]-1,3,4,5-tetrahydrobenzo[e][1,4]diazepin-2-on trifluoroacetate 49 mg (0.16 mmol) of [4-(1-t-butoxycarbonyl-4-piperidyloxy)phenyl]methanol was dissolved in a mixture of 5 ml of dichloromethane and 0.039 ml (0.028 mmol) of triethylamine. 0.016 ml (0.021 mmol) of methanesulfonyl chloride was added to the obtained solution under cooling with ice, and they were stirred at that temperature for 3 hours. After the treatment with dichloromethane as the extracting solvent by an ordinary method, the crude product was obtained.

47 mg (0.14 mmol) of 8-chloro-4-(4-chlorobenzoyl)-1,3,4,5-tetrahydrobenzo[e][1,4]diazepin-2-on was dissolved in 10 ml of DMF. 7 mg (0.16 mmol) of sodium hydride was added to the obtained solution at room temperature. After stirring for 30 minutes, the crude product obtained as described above was added thereto, and they were stirred at 70° C. overnight. The solvent was evaporated, and the obtained crude product was dissolved in 5 ml of 4 N solution of hydrogen chloride in dioxane, and they were stirred at room temperature for 2 hours. The solvent was evaporated, and the obtained crude product was treated in the same manner as in step 3 in Example 1 to obtain the title compound.

Yield: 15 mg (0.024 mmol) (17%)

MS (ESI, m/z) 524(MH+)

H-NMR (DMSO-d6) δ 1.63–1.84 (2H, m), 1.96–2.15 (2H, m), 2.97–3.28 (4H, m), 3.81–4.05 (2H, m), 4.28–4.42

(2H, br), 4.56 (1H, br), 5.03 (2H, br), 6.88 (2H, d), 7.13–7.64 (9H, m), 8.41 (1H, br)

Example 32

Synthesis of 8-chloro-4-(4-chlorobenzoyl)-1-[4-(1-(1-acetimidoyl)-4-piperidyloxy)benzyl]-1,3,4,5-tetrahydrobenzo[e][1,4]diazepin-2-on trifluoroacetate 10 mg (0.016 mmol) of 8-chloro-4-(4-chlorobenzoyl)-1-[1-(4-piperidyloxy)benzyl]-1,3,4,5-tetrahydrobenzo[e][1,4]diazepin-2-on trifluorocetate was dissolved in 1 ml of ethanol. 23 mg (0.17 mmol) of ethyl acetimidate hydrochloride and 0.051 ml (0.34 mmol) of triethylamine were added to the obtained solution, and they were stirred overnight. The solvent was evaporated, and the obtained crude product was treated in the same manner as in step 3 in Example 1 to obtain the title compound.

Yield: 2.4 mg (0.005 mmol) (31%)
MS (ESI, m/z) 565(MH+)

Example 33

Synthesis of 2-[4-(4-chlorobenzoyl)-2-oxo-2,3,4,5-tetrahydrobenzo[e][1,4]diazepin-1-yl]-N-pyridin-3-ylacetamide trifluoroacetate Step 1: Synthesis of t-butyl [4-(4-chlorobenzoyl)-2-oxo-2,3,4,5-tetrahydrobenzo[e][1,4]diazepin-1-yl]acetate 400 mg (1.3 mmol) of [4-(4-chlorobenzoyl)-1,3,4,5-tetrahydrobenzo[e][1,4]diazepin-2-on was dissolved in 10 ml of DMF. 59 mg (1.4 mmol) of sodium hydride was added to the obtained solution, and they were stirred at room temperature for 30 minutes. 380 mg (2.0 mmol) of t-butyl bromoacetate was added to the obtained mixture, and they were stirred at room temperature for 4 hours. After the treatment with ethyl acetate as the extracting solvent by an ordinary method, the crude product was obtained. The crude product was purified by the silica gel column chromatography to obtain the title compound.

Yield: 400 mg (0.97 mmol) (74%)
H-NMR (CDCl3) δ 1.43 (9H, br), 3.98 (2H, br), 4.47 (2H, br), 4.88 (2H, br), 7.20 (2H, d), 7.38–7.52 (6H, m)

Step 2: Synthesis of [4-(4-chlorobenzoyl)-2-oxo-2,3,4,5-tetrahydrobenzo[e][1,4]diazepin-1-yl]acetic acid trifluoroacetate 400 mg (0.97 mmol) of t-butyl [4-(4-chlorobenzoyl)-2-oxo-2,3,4,5-tetrahydrobenzo[e][1,4]diazepin-1-yl]acetate was dissolved in a mixture of 2 ml of dichloromethane and 2 ml of trifluoroacetic acid, and the obtained solution was stirred at room temperature for 1 hour. The solvent was evaporated to obtain the crude title compound.

Step 3: Synthesis of 2-[4-(4-chlorobenzoyl)-2-oxo-2,3,4,5-tetrahydrobenzo[e][1,4]diazepin-1-yl]-N-pyridin-3-ylacetamide trifluoroacetate 20 mg (0.042 mmol) of [4-(4-chlorobenzoyl)-2-oxo-2,3,4,5-tetrahydrobenzo[e][1,4]diazepin-1-yl]acetic acid trifluoroacetate was dissolved in 2 ml of dichloroethane. 5 mg (0.055 mmol) of 3-aminopyridine, 11 mg (0.055 mmol) of 2-chloro-1,3-dimethylimidazonium chloride and 0.018 ml (0.126 mmol) of triethylamine were added to the obtained solution, and they were stirred overnight. The solvent was evaporated, and the obtained crude product was treated in the same manner as in step 3 in Example 1 to obtain the title compound.

Yield: 19 mg (0.035 mmol) (83%)
MS (ESI, m/z) 435(MH+)
H-NMR (DMSO-d6) δ 3.84 (4H, br), 4.60 (2H, br), 7.19–7.63 (6H, m), 8.18 (2H, d), 8.41 (2H, d), 8.92 (2H, br)

Example 34

Synthesis of 2-[4-(4-chlorobenzoyl)-2-oxo-2,3,4,5-tetrahydrobenzo[e][1,4]diazepin-1-yl]-N-pyridin-4-ylacetamide trifluoroacetate 20 mg (0.042 mmol) of [4-(4-chlorobenzoyl)-2-oxo-2,3,4,5-tetrahydrobenzo[e][1,4]diazepin-1-yl]acetic acid trifluoroacetate was dissolved in 2 ml of dichloromethane. 5 mg (0.055 mmol) of 4-aminopyridine, 11 mg (0.055 mmol) of 2-chloro-1,3-dimethylimidazonium chloride and 0.018 ml (0.126 mmol) of triethylamine were added to the obtained solution, and they were stirred overnight. The solvent was evaporated, and the obtained crude product was treated in the same manner as in step 3 in Example 1 to obtain the title compound.

Yield: 16 mg (0.029 mmol) (69%)
MS (ESI, m/z) 435(MH+)
H-NMR (DMSO-d6) δ 3.84 (4H, br), 4.60 (2H, br), 7.18–7.61 (6H, m), 7.96 (2H, d), 8.66 (2H, d)

Example 35

Synthesis of 2-[4-(4-chlorobenzoyl)-2-oxo-2,3,4,5-tetrahydrobenzo[e][1,4]diazepin-1-yl]-N-(2-pyridin-2-ylethyl)acetamide trifluoroacetate 20 mg (0.042 mmol) of [4-(4-chlorobenzoyl)-2-oxo-2,3,4,5-tetrahydrobenzo[e][1,4]diazepin-1-yl]acetic acid trifluoroacetate was dissolved in 2 ml of dichloromethane. 7 mg (0.05 5 mmol) of 2-aminoethylpyridine, 11 mg (0.05 5 mmol) of 2-chloro-1,3-dimethylimidazonium chloride and 0.018 ml (0.126 mmol) of triethylamine were added to the obtained solution, and they were stirred overnight. The solvent was evaporated, and the obtained crude product was treated in the same manner as in step 3 in Example 1 to obtain the title compound.

Yield: 8 mg (0.013 mmol) (31%)
MS (ESI, m/z) 463(MH+)
H-NMR (DMSO-d6) δ 3.02–3.09 (2H, m), 3.40–3.48 (2H, m), 3.81 (2H, br), 4.36 (2H, br), 4.60 (2H, br), 7.29 (2H, d), 7.38–7.61 (6H, m), 7.65 (2H, d) 8.23 (2H, d), 8.62 (1H, d)

Example 36

Synthesis of 2-[4-(4-chlorobenzoyl)-2-oxo-2,3,4,5-tetrahydrobenzo[e][1,4]diazepin-1-yl]-N-(2-pyridin-3-ylethyl)acetamide trifluoroacetate 20 mg (0.042 mmol) of [4-(4-chlorobenzoyl)-2-oxo-2,3,4,5-tetrahydrobenzo[e][1,4]diazepin-1-yl]acetic acid trifluoroacetate was dissolved in 2 ml of dichloromethane. 7 mg (0.055 mmol) of 3-aminoethylpyridine, 11 mg (0.055 mmol) of 2-chloro-1,3-dimethylimidazonium chloride and 0.018 ml (0.126 mmol) of triethylamine were added to the obtained solution, and they were stirred overnight The solvent was evaporated, and the obtained crude product was treated in the same manner as in step 3 in Example 1 to obtain the title compound.

Yield: 22 mg (0.039 mmol) (93%)
MS (ESI, m/z) 463(MH+)
H-NMR (DMSO-d6) δ 2.82–2.95 (2H, m), 3.28–3.43 (2H, m), 3.81 (2H, br), 4.36 (2H, br), 4.72 (2H, br), 7.29 (2H, d), 7.39–7.61 (6H, m), 7.81 (1H, d), 8.26 (2H, d), 8.72 (2H, d)

Example 37

Synthesis of 2-[4-(4-chlorobenzoyl)-2-oxo-2,3,4,5-tetrahydrobenzo[e][1,4]diazepin-1-yl]-N-(2-pyridin-4-ylethyl)acetamide trifluoroacetate 20 mg (0.042 mmol) of [4-(4-chlorobenzoyl)-2-oxo-2,3,4,5-tetrahydrobenzo[e][1,4]diazepin-1-yl]acetic acid trifluoroacetate was dissolved in 2 ml of dichloromethane. 7 mg (0.055 mmol) of 4-aminoethylpyridine, 11 mg (0.055 mmol) of 2-chloro-1,3-dimethylimidazonium chloride and 0.018 ml (0.126 mmol) of triethylamine were added to the obtained solution, and they were stirred overnight. The solvent was evaporated, and the obtained crude product was treated in the same manner as in step 3 in Example 1 to obtain the title compound.

Yield: 14 mg (0.025 mmol) (60%)

MS (ESI, m/z) 463(MH+)

H-NMR (DMSO-d6) δ 2.82–2.98 (2H, m), 3.33–3.43 (2H, m), 3.83 (2H, br), 4.37 (2H, br), 4.72 (2H, br), 7.29 (2H, d), 7.39–7.61 (6H, m), 7.81 (2H, d), 8.26 (1H, d), 8.74 (2H, d)

Example 38

Synthesis of 6-chloro-4-(4-chlorobenzoyl)-1-[4-(4-piperidyloxy)benzyl]-1,3,4,5-tetrahydrobenzo[e][1,4]diazepin-2-on trifluoroacetate Step 1: Synthesis of ethyl (2-chloro-6-nitrobenzyl)aminoacetate 4.84 g (28.3 mmol) of 2-chloro-6-nitrotoluene was dissolved in 50 ml of benzene. 50 mg of perbenzoic acid and 6.0 g (34 mmol) of N-bromosuccinimide were added to the obtained solution, and the obtained solution was stirred at 80° C. overnight. The reaction solution was treated with ethyl acetate as the extracting solvent by an ordinary method to obtain the crude product. The crude product was dissolved in 100 ml of ethanol. 11.9 g (84.9 mmol) of glycine ethyl ester hydrochloride and 8.9 g (106 mmol) of sodium hydrogencarbonate were added to the obtained solution, and they were stirred at 80° C. for 4 hours. The insoluble matter was removed by the filtration, and the solvent was evaporated. After the extraction with ethyl acetate followed by washing with 1 N hydrochloric acid, the obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 4.8 g (17.6 mmol) (62%)

H-NMR (CDCl3) δ 1.27 (3H, t), 3.47 (2H, s), 4.13 (2H, s), 4.18 (2H, q), 7.36 (1H, dd), 7.63 (1H, d), 7.71 (1H, d)

Step 2: Synthesis of ethyl [(2-amino-6-chlorobenzyl)-(4-chloro-benzoylamino)acetate 1.14 g (4.2 mmol) of ethyl (2-chloro-6-nitrobenzyl)aminoacetate was dissolved in 10 ml of dichloromethane. 0.64 ml (14.4 mmol) of 4-chlorobenzoyl chloride and 0.88 ml (19.1 mmol) of triethylamine were added to the obtained solution, and they were stirred at room temperature for 4 hours. After the treatment with dichloromethane as the extracting solvent by an ordinary method, the obtained crude product was dissolved in 20 ml of ethyl acetate. 100 mg of 10% palladium/carbon was added to the obtained solution and they were stirred in the presence of hydrogen at room temperature for 4 hours. The reaction solution was filtered through Celite. The solvent was evaporated and the obtained crude product was purified by the silica gel column chromatography to obtain the title compound.

Yield: 820 mg (2.16 mmol) (51%)

H-NMR (CDCl3) δ 1.24 (3H, t), 3.86 (2H, s), 4.17 (2H, q), 5.02 (2H, s), 6.55 (1H, d), 6.70 (1H, d), 7.01 (1H, dd), 7.36 (4H, br)

Step 3: Synthesis of 4-(1-t-butoxycarbonyl-4-piperidyloxy)benzaldehyde 770 mg (3.83 mmol) of 1-t-butoxycarbonyl-4-hydroxypiperidine and 467 mg (3.83 mmol) of 4-hydroxybenzaldehyde were dissolved in 20 ml of THF. 1.2 g (4.6 mmol) of triphenylphosphine and 790 mg (4.6 mmol) of N,N,N',N'-tetramethylazodicarboxyamide were added to the obtained solution, and they were stirred overnight. After the treatment with ethyl acetate as the extracting solvent by an ordinary method, the obtained crude product was purified by the silica gel column chromatography to obtain the title compound.

Yield: 240 mg (0.79 mmol) (21%)

H-NMR (CDCl3) δ 1.47 (9H, t), 1.70–2.03 (4H, m), 3.31–3.42 (2H, m), 3.62–3.71 (2H, m), 4.58–4.63 (1H, m), 6.99 (2H, d), 7.83 (2H, d), 9.88 (1H, s)

Step 4: Synthesis of ethyl [(4-chlorobenzoyl)-(2-chloro-6-(4-(1-t-butoxycarbonyl-4-piperidyloxy)benzylamino)benzyl)amino]acetate 40 mg (0.125 mmol) of ethyl [(2-amino-6-chlorobenzyl)-(4-chlorobenzoyl)aminoacetate and 80 mg (0.25 mmol) of 4-(1-t-butoxycarbonyl-4-piperidyloxy)benzaldehyde were dissolved in 5 ml of dichloromethane. 0.017 ml (0.29 mmol) of acetic acid was added to the obtained solution. They were stirred at room temperature for 30 minutes. 66 mg (0.31 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 60 mg (0.08 mmol) (64%)

H-NMR (CDCl3) δ 1.23 (3H, t), 1.47 (9H, t), 1.83–2.03 (4H, m), 3.24–3.43 (2H, m), 3.62–3.78 (2H, m), 3.85 (2H, br), 4.17 (2H, q), 4.35 (3H, br), 5.06 (2H, br), 6.82–7.18 (4H, m), 7.27.42 (6H, m), 7.78–7.95 (4H, m)

Step 5: Synthesis of 6-chloro-4-(4-chlorobenzoyl)-1-[4-(4-piperidyloxy)benzyl]-1,3,4,5-tetrahydrobenzo[e][1,4]diazepin-2-on trifluoroacetate 60 mg (0.08 mmol) of ethyl [(4-chlorobenzoyl)-(2-chloro-6-(4-(1-t-butoxycarbonyl-4-piperidyloxy)benzylamino)benzyl)amino]acetate was dissolved in a mixture of 1 ml of 1 N sodium hydroxide and 2 ml of ethanol. The obtained solution was stirred at room temperature for 4 hours. After the treatment with ethyl acetate as the extraction solvent, the obtained crude product was dissolved in 5 ml of dichloromethane. 16 mg (0.096 mmol) of 2-chloro-1,3-dimethylimidazonium chloride and 0.022 ml (0.016 mmol) of triethylamine were added to the obtained solution, and they were stirred overnight. The solvent was evaporated, and the obtained crude product was dissolved in 5 ml of 4N solution of hydrogen chloride in dioxane. The obtained solution was stirred at room temperature for 3 hours. The solvent was evaporated, and the obtained crude product was treated in the same manner as in step 3 in Example 1 to obtain the title compound.

Yield: 4 mg (0.0062 mmol) (8%)

MS (ESI, m/z) 524(MH+)

H-NMR (DMSO-d6) δ 1.62–1.81 (2H, m), 1.95–2.09 (2H, m), 2.98–3.30 (4H, m), 3.83–4.04 (2H, m), 4.55 (3H, br), 5.05 (2H, br), 6.87 (2H, d), 7.16 (2H, br), 7.53 (6H, br), 8.42 (2H, br)

Example 39

Synthesis of 6-chloro-4-(4-chlorobenzoyl)-1-[4-(1-(1-acetimidoyl)-4-piperidyloxy)benzyl]-1,3,4,5-tetrahydrobenzo[e][1,4]diazepin-2-on trifluoroacetate 30 mg (0.016 mmol) of 6-chloro-4-(4-chlorobenzoyl)-1-[4-(4-piperidyloxy)benzyl]-1,3,4,5-tetrahydrobenzo[e][1,4]diazepin-2-on trifluoroacetate was dissolved in 1 ml of ethanol. 12 mg (0.17 mmol) of ethyl acetimidate hydrochloride and 0.020 ml (0.141 mmol) of triethylamine were added to the obtained solution, and they were stirred overnight. The solvent was evaporated, and the obtained crude product was treated in the same manner as in step 3 in Example 1 to obtain the title compound.

Yield: 4 mg (0.006 mmol) (37%)

MS (ESI, m/z) 565(MH+)

H-NMR (DMSO-d6) δ 1.60–1.81 (2H, m), 1.97–2.11 (2H, m), 2.25 (3H, s), 3.41–3.56 (4H, m), 3.82–4.04 (2H, m), 4.55 (3H, br), 5.05 (2H, br), 6.87 (2 H, d), 7.19 (2H, br), 7.53 (6H, br), 8.55 (1H, br), 9.10 (1H, br)

Example 40

Synthesis of 7-chloro-4-(4-chlorobenzoyl)-1-[4-(4-piperidyloxy)benzyl]-1,3,4,5-tetrahydrobenzo[e][1,4]diazepin-2-on trifluoroacetate 1.52 g (8.09 mmol) of 5-chloro-2-nitrobenzyl alcohol was dissolved in 20 ml of dichloromethane. 0.76 ml (9.7 mmol) of methanesulfonyl chloride and 1.7 ml (12.2 mmol) of triethylamine were added to the obtained solution, and they were stirred at room temperature for 2 hours. The reaction mixture was treated with dichloromethane as the extracting solvent by an ordinary method to obtain the crude product. The crude product was dissolved in 50 ml of THF. 4.5 g (32.4 mmol) of glycine ethyl ester hydrochloride and 3.4 g (40 mmol) of sodium hydrogencarbonate were added to the obtained solution, and they were stirred at 70° C. for 6 hours. The insoluble matter was removed by the filtration, and the solvent was evaporated. After the extraction with ethyl acetate followed by washing with 1 N hydrochloric acid, the obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 1.15 g (4.2 mmol) (52%)

H-NMR (CDCl3) δ 1.28 (3H, t), 3.44 (2H, s), 4.11 (2H, s), 4.20 (2H, q), 7.38 (1H, dd), 7.73 (1H, d), 7.95 (1H, d)

Step 2: Synthesis of ethyl [(2-amino-5-chlorobenzyl)-(4-chlorobenzoyl)amino]acetate 1.15 g (4.2 mmol) of ethyl (5-chloro-2-nitrobenzyl)aminoacetate was dissolved in 20 ml of dichloromethane. 0.64 ml (5.1 mmol) of 4-chlorobenzoyl chloride and 0.88 ml (6.3 mmol) of triethylamine were added to the obtained solution, and they were stirred at room temperature for 2 hours. After the treatment with dichloromethane as the extracting solvent by an ordinary method, the obtained crude product was dissolved in 20 ml of ethyl acetate. 120 mg of 10% palladium/carbon was added to the obtained solution and they were stirred in the presence of hydrogen at room temperature for 4 hours. The reaction solution was filtered through Celite. The solvent was evaporated and the obtained crude product was purified by the silica gel column chromatography to obtain the title compound.

Yield: 780 mg (2.05 mmol) (49%)

H-NMR (CDCl3) δ 1.26 (3H, t), 3.83 (2H, s), 4.12 (2H, q), 4.67 (2H, s), 6.60 (1H, d), 6.99 (1H, br), 7.08 (1H, dd), 7.37 (4H, br)

Step 3: Synthesis of ethyl [(4-chlorobenzoyl)-(5-chloro-2-(4-(1-t-butoxycarbonyl-4-piperidyloxy)benzylamino)benzyl)amino]acetate 190 mg (0.5 mmol) of ethyl [(2-amino-5-chlorobenzyl)-(4-chlorobenzoyl)aminoacetate and 183 mg (0.6 mmol) of 4-(1-t-butoxycarbonyl-4-piperidyloxy)benzaldehyde were dissolved in 10 ml of dichloromethane. 0.057 ml (1.0 mmol) of acetic acid was added to the obtained solution. They were stirred at room temperature for 30 minutes. 528 mg (0.13 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 200 mg (0.30 mmol) (60%)

H-NMR (CDCl3) δ 1.26 (3H, t), 1.46 (9H, t), 1.83–2.00 (4H, m), 3.24–3.41 (2H, m), 3.63–3.78 (2H, m), 3.82 (2H, br), 4.13 (2H, q), 4.31 (3H, br), 4.77 (2H, br), 6.84–7.18 (4H, m), 7.27–7.42 (10H, m)

Step 4: Synthesis of 7-chloro-4-(4-chlorobenzoyl-1-[4-(4-piperidyloxy)benzyl]-1,3,4,5-tetrahydrobenzo[e][1,4]diazepin-2-on trifluoroacetate 200 mg (0.30 mmol) of ethyl [(4-chlorobenzoyl)-(2-chloro-6-(4-(1-t-butoxycarbonyl-4-piperidyloxy)benzylamino)benzyl)amino]acetate was dissolved in a mixture of 1 ml of 1 N sodium hydroxide and 2 ml of ethanol. The obtained solution was stirred at room temperature for 4 hours. After the treatment with ethyl acetate as the extracting solvent by an ordinary method, the obtained crude product was dissolved in 5 ml of dichloromethane. 61 mg (0.36 mmol) of 2-chloro-1,3-dimethylimidazonium chloride and 0.083 ml (0.6 mmol) of triethylamine were added to the obtained solution, and they were stirred overnight. The solvent was evaporated, and the obtained crude product was dissolved in 5 ml of 4N solution of hydrogen chloride in dioxane. The obtained solution was stirred at room temperature for 3 hours. The solvent was evaporated, and the obtained crude product was treated in the same manner as in step 3 in Example 1 to obtain the title compound.

Yield: 17.2 mg (0.027 mmol) (9%)

MS (ESI, m/z) 524(MH+)

H-NMR (DMSO-d6) δ 1.62–1.81 (2H, m), 1.99–2.08 (2H, m), 2.96–3.29 (4H, m), 3.83–4.08 (2H, m), 4.38 (1H, br), 4.47–4.51 (1H, m), 5.02 (2H, br), 6.87 (2H, d), 7.16 (2H, br), 7.52 (6H, br), 8.44 (2H, br)

Example 41

Synthesis of 7-chloro-4-(4-chlorobenzoyl)-1-[4-(1-(1-acetimidoyl)-4-piperidyloxy)benzyl]-1,3,4,5-tetrahydrobenzo[e][1,4]diazepin-2-on trifluoroacetate 20 mg (0.03 1 mmol) of 7-chloro-4-(4-chlorobenzoyl)-1-[4-(4-piperidyloxy)benzyl]-1,3,4,5-tetrahydrobenzo[e][1,4]diazepin-2-on trifluoroacetate was dissolved in 1 ml of ethanol. 12 mg (0.17 mmol) of ethyl acetimidate hydrochloride and 0.020 ml (0.141 mmol) of triethylamine were added to the obtained solution, and they were stirred overnight. The solvent was evaporated, and the obtained crude product was treated in the same manner as in step 3 in Example 1 to obtain the title compound.

Yield: 4.2 mg (0.006 mmol) (19%)

MS (ESI, m/z) 565(MH+)

H-NMR (DMSO-d6) δ 1.60–1.80 (2H, m), 1.96–2.08 (2H, m), 2.25 (3H, s), 3.41–3.78 (2H, m), 3.84–4.06 (2H, m), 4.38 (2H, br), 4.57–4.64 (1H, m), 5.02 (2H, br), 6.87 (2H, d), 7.16 (2H, br), 7.52 (6H, br), 8.57 (1H, br), 9.08 (1H, br)

Example 42

Synthesis of 4-(4-chlorobenzoyl)-2-oxo-1-[4-(4-piperidyloxy)benzyl]-2,3,4,5-tetrahydro-1H-benzo[e][1,4]diazepine-8-carboxylic acid trifluoroacetate Step 1: Synthesis of methyl 4-[(ethoxycarbonylmethylamino)methyl]-3-nitrobenzoate 2.5 g (9.6 mmol) of 3-nitro-4-bromomethylbenzoic acid was dissolved in 100 ml of dichloromethane. 0.78 ml (19.2 mmol) of methanol, 2.2 g (11.5 mmol) of 1-ethyl-3-(3-dimethylaminopropyl)-3-carbodiimide hydrochloride and 30 mg of dimethylaminopyridine were added to the obtained solution, and they were stirred at room temperature for 3 hours. The reaction mixture was treated with dichloromethane as the extracting solvent by an ordinary method to obtain the crude product. The crude product was dissolved in 50 ml of THF. 2.0 g (14.6 mmol) of glycine ethyl ester hydrochloride and 1.8 g (21.9 mmol) of sodium hydrogencarbonate were added to the obtained solution, and they were stirred at 80° C. for 4 hours. The insoluble matter was removed by the filtration, and the solvent was evaporated.

After the extraction with ethyl acetate followed by the treatment by an ordinary method, the crude title compound was obtained.

Yield: 1.38 g (3.86 mmol) (40%)

H-NMR (CDCl3) δ 1.27 (3H, t), 3.43 (2H, s), 3.97 (3H, s), 4.16 (2H, s), 4.17 (2H, q), 7.79 (1H, d), 8.23 (1H, dd), 8.59 (1H, d)

Step 2: Synthesis of methyl 4-[((4–5-chlorobenzoyl) ethoxycarbonylmethylamino)methyl]-3-aminobenzoate 1.38 g (3.86 mmol) of methyl 4-[(ethoxycarbonylmethylamino)methyl]-3-nitrobenzoate was dissolved in 20 ml of dichloromethane. 0.81 ml (5.8 mmol) of triethylamine and 0.59 ml (4.6 mmol) of 4-chlorobenzoyl chloride were added to the obtained solution, and they were stirred overnight. After the treatment with ethyl acetate as the extracting solvent by an ordinary method, the obtained crude product was crystallized in hexane:ethyl acetate (1/1). The obtained crystals were separated by the filtration. The solvent in the filtrate was evaporated. The obtained crude product was washed with hexane/ethyl acetate (3/1), and the obtained residue was dissolved in 20 ml of ethyl acetate. 200 mg of 10% palladium/carbon was added to the obtained solution and they were stirred in the presence of hydrogen at room temperature for 5 hours. The reaction solution was filtered through Celite. The solvent was evaporated to obtain the crude product.

Yield: 1.56 g (3.86 mmol)

H-NMR (CDCl3) δ 1.24 (3H, t), 3.86 (2H, br), 3.89 (3H, s), 4.17 (2H, q), 4.78 (2H, br), 7.00–7.18 (2H, m), 7.37 (5H, br)

Step 3: Synthesis of methyl [((4-chlorobenzoyl) ethoxycarbonylmethylamino)methyl]-3-[4-(1-t-butoxycarbonyl-4-piperidyloxy)benzylamino]benzoate 304 mg (0.75 mmol) of methyl 4-[((4-chlorobenzoyl) ethoxycarbonylmethylamino)methyl]-3-aminoacetate and 230 mg (0.75 mmol) of 4-(1-t-butoxycarbonyl-4-piperidyloxy)benzaldehyde were dissolved in 10 ml of dichloromethane. 0.090 ml (1.5 mmol) of acetic acid was added to the obtained solution. They were stirred at room temperature for 30 minutes. 396 mg (1.88 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 200 mg (0.30 mmol) (40%)

H-NMR (CDCl3) δ 1.26 (3H, t), 1.46 (9H, t), 1.63–2.00 (4H, m), 3.24–3.38 (2H, m), 3.63–3.78 (2H, m), 3.80 (2H, br), 3.89 (3H, s), 4.12 (2H, q), 4.31 (2H, br), 4.61 (1H, d), 4.78 (2H, br), 6.81–6.89 (2H, m), 7.05–7.40 (9H, m)

Step 4: Synthesis of 4-(4-chlorobenzoyl)-2-oxo-1-[4-(4-piperidyloxy)-benzyl]-2,3,4,5-tetrahydro-1H-benzo[e][1,4] diazepine-8-carboxylic acid trifluoroacetate 200 mg (0.30 mmol) of methyl 4-[((4-chlorobenzoyl) ethoxy-carbonylmethylamino)methyl]-3-(4-(1-t-butoxycarbonyl-4-piperidyloxy)-benzylamino]benzoate was dissolved in a mixture of 1 ml of 1 N sodium hydroxide and 2 ml of ethanol. The obtained solution was stirred at room temperature for 4 hours. After the treatment with ethyl acetate as the extracting solvent, the obtained crude product was dissolved in 5 ml of dichloromethane. 61 mg (0.36 mmol) of 2-chloro-1,3-dimethyl-imidazonium chloride and 0.083 ml (0.6 mmol) of triethylamine were added to the obtained solution, and they were stirred overnight. The solvent was evaporated, and the obtained crude product was dissolved in 5 ml of 4N solution of hydrogen chloride in dioxane solution. The obtained solution was stirred at room temperature for 3 hours. The solvent was evaporated, and the obtained crude product was treated in the same manner as in step 3 in Example 1 to obtain the title compound.

Yield: 30 mg (0.046 mmol) (15%)

MS (ESI, m/z) 534(MH+)

H-NMR (DMSO-d6) δ 1.62–1.81 (2H, m), 1.97–2.08 (2H, m), 2.96–3.27 (4H, m), 3.83–4.13 (2H, m), 4.41 (2H, br), 4.47–4.51 (1H, m), 5.06 (2H, br), 6.87 (2H, d), 7.09–7.18 (4H, m), 7.52 (3H, br), 7.98 (2H, br), 8.44 (2H, br)

Example 43

Synthesis of 4-(4-chlorobenzoyl)-2-oxo-1-[4-(1-(1-acetimidoyl)-4-piperidyloxy)benzyl]-2,3,4,5-tetrahydro-1H-benzo[e][1,4]-diazepine-8-carboxylic acid trifluoroacetate 21 mg (0.032 mmol) of 4-(4-chlorobenzoyl)-2-oxo-1-[4-(4-piperidyloxy)benzyl]-2,3,4,5-tetrahydro-1H-benzo[e][1, 4-diazepine-8-carboxylic acid trifluoroacetate was dissolved in 1 ml of ethanol. 8 mg (0.060 mmol) of ethyl acetimidate hydrochloride and 0.013 ml (0.090 mmol) of triethylamine were added to the obtained solution, and they were stirred overnight. The solvent was evaporated, and the obtained crude product was treated in the same manner as in step 3 in Example 1 to obtain the title compound.

Yield: 5.4 mg (0.008 mmol) (25%)

MS (ESI, m/z) 575(MH+)

H-NMR (DMSO-d6) δ 1.60–1.80 (2H, m), 1.96–2.08 (2H, m), 2.25 (3H, s), 3.41–3.5 (2H, m), 3.84–4.02 (2H, m), 4.44 (2H, br), 4.58–4.65 (1H, m), 5.0 (2H, br), 6.88 (2H, d), 7.11–7.38 (3H, m), 7.56 (3H, br), 7.78–7.98 (2H, m), 8.54 (1H, br), 9.09 (1H, br)

Example 44

Synthesis of ethyl 4-(4-chlorobenzoyl)-2-oxo-1-[4-(4-piperidyloxy)benzyl]-2,3,4,5-tetrahydro-1H-benzo[e][1,4]-diazepine-8-carboxylate trifluoroacetate 500 mg (0.72 mmol) of methyl 4-[((4chlorobenzoyl) ethoxycarbonylmethylamino)methyl]-3-[4-(1-t-butoxycarbonyl-4-piperidyloxy)benzylamino)]benzoate was dissolved in a mixture of 1 ml of 1 N sodium hydroxide and 2 ml of ethanol. The obtained solution was stirred at room temperature for 4 hours. After the treatment with ethyl acetate as the extracting solvent by an ordinary method, the obtained crude product was dissolved in 5 ml of dichloromethane. 146 mg (0.87 mmol) of 2-chloro-1,3-dimethylimidazonium chloride and 0.15 ml (1.08 mmol) of triethylamine were added to the obtained solution, and they were stirred overnight. The solvent was evaporated, and the obtained crude product was dissolved in 5 ml of 4N solution of hydrogen chloride in dioxane. The obtained solution was stirred at room temperature for 3 hours. The solvent was evaporated, and the obtained crude product was dissolved in 5 ml of dichloromethane. 146 mg (0.87 mmol) of 2-chloro-1,3-dimethylimidazonium chloride, 0.15 ml (1.08 mmol) of triethylamine and 0.051 ml (0.87 mmol) of ethanol were added to the obtained solution, and they were stirred overnight. The solvent was evaporated and the obtained crude product was treated in the same manner as in step 3 in Example 1 to obtain the title compound.

Yield: 50 mg (0.074 mmol) (10%)

MS (ESI, m/z) 562(MH+)

H-NMR (DMSO-d6) δ 1.28 (3H, t), 1.62–1.81 (2H, m), 1.93–2.08 (2H, m), 2.96–3.25 (4H, m), 3.83–4.07 (2H, m), 4.29 (2H, q), 4.41 (1 μl, br), 4.47–4.61 (1H, m), 5.06 (2H, br), 6.88 (2H, d), 7.09–8.03 (9H, m), 8.46 (2H, br)

Example 45

Synthesis of ethyl 4-(4-chlorobenzoyl)-2-oxo-1-[4-(1-(1-acetimidoyl)-4-piperidyloxy)benzyl]-2,3,4,5-tetrahydro-1H-benzo[e][1,4]-diazepine-8-carboxylate trifluoroacetate 20 mg (0.030 mmol) of ethyl 4-(4-chlorobenzoyl)-2-oxo-1-[4-(4-piperidyloxy)benzyl]-2,3,4,5-tetrahydro-1H-benzo[e][1,4]-diazepine-8-carboxylate mono(trifluoroacetate) was dissolved in 1 ml of ethanol. 7 mg (0.059 mmol) of ethyl acetimidate hydrochloride and 0.013 ml (0.090 mmol) of triethylamine were added to the obtained solution, and they were stirred overnight. The solvent was evaporated, and the obtained crude product was treated in the same manner as in step 3 in Example 1 to obtain the title compound.

Yield: 3.6 mg (0.005 mmol) (17%)

MS (ESI, m/z) 603(MH+)

H-NMR (DMSO-d6) δ 1.29 (3H, t), 1.60–1.80 (2H, m), 1.96–2.08 (2H, m), 2.25 (3H, s), 3.41–3.56 (2H, m), 3.84–4.08 (4H, m), 4.31 (2H, q), 4.44 (2H, br), 4.58–4.65 (1H, m), 5.04 (2H, br), 6.89 (2H, d), 7.11–7.22 (2H, m), 7.53 (5H, br), 7.78–7.98 (1H, m),8.54 (1H, br), 9.09 (1H, br)

Example 46

Synthesis of 4-(4-chlorobenzoyl)-2-oxo-1-[4-(4-piperidyloxy)benzyl]-2,3,4,5-tetrahydro-1H-benzo[e][1,4]-diazepine-8-carboxylic acid dimethylamide trifluoroacetate 5 mg (0.008 mmol) of 4-(4-chlorobenzoyl)-2-oxo-1-[4-(4-piperidyloxy)benzyl]-2,3,4,5-tetrahydro-1H-benzo[e][1,4]diazepine-8-carboxylic acid trifluoroacetate was dissolved in 5 ml of dichloromethane. 2 mg (0.018 mmol) of dimethylamine hydrochloride, 3 mg (0.018 mmol) of 2-chloro-1,3-dimethylimidazonium chloride and 0.005 ml (0.036 mmol) of triethylamine were added to the obtained solution, and they were stirred overnight. The solvent was evaporated, and the obtained crude product was treated in the same manner as in step 3 in Example 1 to obtain the title compound.

MS (ESI, m/z) 561(MH+)

H-NMR (DMSO-d6) δ 1.62–1.81 (2H, m), 1.97–2.08 (2H, m), 2.96–3.27 (10H, m), 3.83–4.13 (2H, m), 4.41 (1H, br), 4.47–4.51 (1H, m), 5.06 (2H, br), 6.83 (2H, d), 7.09–7.18 (4H, m), 7.54 (5H, br), 8.44 (2H, br)

Example 47

Synthesis of 4-(4-chlorobenzoyl)-1-[4-(4-piperidyloxy)benzyl]-8-(1-pyrrolidinecarbonyl)-1,3,4,5-tetrahydrobenzo[e][1,4]diazepin-2-on trifluoroacetate 5 mg (0.008 mmol) of 4-(4-chlorobenzoyl)-2-oxo-1-[4-(4-piperidyloxy)benzyl]-2,3,4,5-tetrahydro-1H-benzo[e][1,4]diazepine-8-carboxylic acid trifluoroacetate was dissolved in 5 ml of dichloromethane. 1 mg (0.018 mmol) of pyrrolidine, 3 mg (0.018 mmol) of 2-chloro-1,3-dimethylimidazonium chloride and 0.005 ml (0.036 mmol) of triethylamine were added to the obtained solution, and they were stirred overnight. The solvent was evaporated, and the obtained crude product was treated in the same manner as in step 3 in Example 1 to obtain the title compound.

Yield: 3.7 mg (0.005 mmol) (66%)

MS (ESI, m/z) 587(MH+)

H-NMR (DMSO-d6) δ 1.62–1.87 (6H, m), 1.97–2.08 (2H, m), 2.96–3.27 (4H, m), 3.38–3.44 (2H, m), 3.83–4.13 (2H, m), 4.35–4.60 (5H, m), 5.06 (2H, br), 6.83 (2H, d), 7.09–7.29 (4H, m), 7.52 (5H, br), 8.42 (2H, br)

Example 48

Synthesis of 1-[4-(1-pyrrolidinecarbonyl)benzyl]-4-(4-chlorobenzoyl)-1,3,4,5-tetrahydrobenzo[e][1,4]-diazepin-2-on Step 1 Synthesis of 1-(4-carboxybenzyl)-4-(4-chlorobenzoyl)-1,3,4,5-tetrahydrobenzo[e][1,4]diazepin-2-on 300 mg (1.0 mmol) of 4-(4-chlorobenzoyl)-1,3,4,5-tetrahydrobenzo[e][1,4]diazepin-2-on was dissolved in 10 ml of DMF. 48 mg (1.2 mmol) of sodium hydride was added to the obtained solution, and they were stirred at room temperature for 30 minutes. 300 mg (1.3 mmol) of methyl 4-bromomethylbenzoate was added to the obtained mixture, and they were stirred at 60° C. overnight. After the treatment with ethyl acetate as the extracting solvent, the obtained crude product was stirred together with 2 ml of THF, 2 ml of ethanol and 2 ml of 1 N aqueous sodium hydroxide solution at room temperature overnight. The obtained product was treated with ethyl acetate as the extracting solvent by an ordinary method to obtain the crude product.

Yield: 210 mg (0.48 mmol) (48%)

Step 2 Synthesis of 1-[4-(1-pyrrolidinecarbonyl)benzyl]-4-(4-chlorobenzoyl)-1,3,4,5-tetrahydrobenzo[e][1,4]diazepin-2-on 23 mg (0.053 mmol) of 1-(4-carboxybenzyl)-4-(4-chlorobenzoyl)-1,3,4,5-tetrahydrobenzo[e][1,4]diazepin-2-on was dissolved in 5 ml of dichloromethane. 6 mg (0.079 mmol) of pyrrolidine, 13 mg (0.079 mmol) of 2-chloro-1,3-dimethylimidazonium chloride and 0.022 ml (0.159 mmol) of triethylamine were added to the obtained solution, and they were stirred overnight. The solvent was evaporated, and the obtained crude product was treated in the same manner as in step 3 in Example 1 to obtain the title compound.

Yield: 7.7 mg (0.016 mmol) (30%)

MS (ESI, m/z) 488(MH+)

H-NMR (DMSO-d6) δ 1.69–1.90 (4H, m), 3.30 (2H, dd), 3.41 (2H, dd), 3.83–4.12 (2H, m), 4.41 (2H, br), 5.18 (2H, br), 7.17–7.61 (12H, m)

Example 49

Synthesis of 1-[4-(2,5-dihydro-1H-pyrrol-1-ylcarbonyl)benzyl]-4-(4-chlorobenzoyl)-1,3,4,5-tetrahydrobenzo[e][1,4]-diazepin-2-on 23 mg (0.053 mmol) of 1-(4-carboxybenzyl)-4-(4-chlorobenzoyl)-1,3,4,5-tetrahydrobenzo[e][1,4]diazepin-2-on was dissolved in 5 ml of dichloromethane. 6 mg (0.079 mmol) of 3-pyrroline, 13 mg (0.079 mmol) of 2-chloro-1,3-dimethylimidazonium chloride and 0.022 ml (0.159 mmol) of triethylamine were added to the obtained solution, and they were stirred overnight. The solvent was evaporated, and the obtained crude product was treated in the same manner as in step 3 in Example 1 to obtain the title compound.

Yield: 4.1 mg (0.085 mmol) (16%)

MS (ESI, m/z) 486(MH+)

H-NMR (DMSO-d6) δ 3.83–4.12 (2H, m), 4.12 (2H, br), 4.24 (2H, br), 4.39–4.57 (2H, m), 5.12 (2H, br), 5.80 (1H, br), 5.90 (2H, br), 7.17–7.64 (12H, m)

Example 50

Synthesis of 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylic acid Step 1: Synthesis of 4-(1-pyrrolidinecarbonyl)benzaldehyde 1.0 g (6.7 mmol) of 4-formylbenzoic acid was dissolved in 20 ml of dichloromethane. 0.67 ml (8.0 mmol) of pyrrolidine, 1.35 g (8.0 mmol) of 2-chloro-1,3- dimethylimidazonium chloride and 2.8 ml (20.5 mmol) of triethylamine were added to the obtained solution, and they were stirred at room temperature for 5 hours. After the treatment with dichloromethane as the extracting solvent by an ordinary method, the crude product was obtained.

Yield: 605 mg (2.98 mmol) (44%)

H-NMR (CDCl3) δ 1.83–2.01 (4H, m), 3.38 (2H, dd), 3.67 (2H, dd), 7.66 (2H, d), 7.92 (2H, dd)

Step 2 Synthesis of methyl 4-[((4-chlorobenzoyl) ethoxycarbonylmethylamino)methyl]-3-[4-(1-pyrrolidinecarbonyl)benzylamino]-benzoate 120 mg (0.30 mmol) of methyl 4-[((4-chlorobenzoyl)ethoxycarbonylmethylamino)methyl]-3-aminobenzoate and 66 mg (0.33 mmol) of 4-(1-pyrrolidinecarbonyl)benzaldehyde were dissolved in 10 ml of dichloromethane. 0.034 ml (0.6 mmol) of acetic acid was added to the solution, and they were stirred at room temperature for 30 minutes. 158 mg (0.75 mmol) of sodium triacetoxyborohydride was added to the obtained mixture, and they were stirred at room temperature overnight. After the treatment with dichloromethane as the extracting solvent by an ordinary method, the obtained crude product was purified by the silica gel column chromatography to obtain the title compound Yield: 140 mg (0.23 mmol) (80%)

H-NMR (CDCl3) δ 1.25 (3H, t), 1.81–2.03 (4H, m), 3.42 (2H, dd), 3.63 (2H, dd), 3.83 (2H, br), 3.86 (3H, s), 4.13 (2H, q), 4.46 (2H, br), 4.78 (2H, br), 7.05–7.51 (11H, m)

Step 3 Synthesis of 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylic acid 140 mg (0.23 mmol) of methyl 4-[((4-chlorobenzoyl)ethoxycarbonylmethylamino)methyl]-3-[4-(1-pyrrolidinecarbonyl)benzylamino]-benzoate was dissolved in a mixture of 2 ml of 1 N sodium hydroxide and 4 ml of ethanol. The obtained solution was stirred at room temperature for 4 hours. After the treatment with ethyl acetate as the extracting solvent by an ordinary method, the obtained crude product was dissolved in 10 ml of dichloromethane. 47 mg (0.27 mmol) of 2-chloro-1,3-dimethylimidazonium chloride and 0.064 ml (0.46 mmol) of triethylamine were added to the obtained solution, and they were stirred overnight. The solvent was evaporated, and the obtained crude product was treated in the same manner as in step 3 in Example 1 to obtain the title compound.

Yield: 2.1 mg (0.004 mmol) (2%)

MS (ESI, m/z) 532(MH+)

H-NMR (DMSO-d6) δ 1.66–1.89 (4H, m), 3.30 (2H, dd), 3.42 (2H, dd), 3.83–4.16 (2H, m), 4.48 (2H, br), 5.16 (2H, br), 7.25–7.93 (11H, m)

Example 51

Synthesis of Ethyl 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylate 5 mg (0.009 mmol) of 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylic acid was dissolved in 5 ml of dichloromethane. 0.001 ml (0.018 mmol) of ethanol, 2 mg (0.011 mmol) of 2-chloro-1,3-dimethylimidazonium chloride and 0.003 ml (0.018 mmol) of triethylamine were added to the obtained solution, and they were stirred overnight. The solvent was evaporated and the obtained crude product was treated in the same manner as in step 3 in Example 1 to obtain the title compound.

Yield: 0.5 mg (0.001 mmol) (10%)

MS (ESI, m/z) 560(MH+)

H-NMR (DMSO-d6) δ 1.26 (3H, t), 1.66–1.91 (4H, m), 3.30 (2H, dd), 3.42 (2H, dd), 3.83–4.16 (2H, m), 4.27 (2H, q), 4.53 (2H, br), 5.13 (2H, br), 7.22–7.93 (11H, m)

Example 52

Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-8-carboxylic acid Step 1: Synthesis of 4-(2,5-dihydro-1H-pyrrol-1-ylcarbonyl)benzo-aldehyde 5.2 g (35 mmol) of 4-formylbenzoic acid was dissolved in 100 ml of dichloromethane. 2.0 g (29 mmol) of pyrroline, 5.9 g (35 mmol) of 2-chloro-1,3-dimethylimidazonium chloride and 6.1 ml (43 mmol) of triethylamine were added to the obtained solution, and they were stirred at room temperature for 5 hours. After the treatment with dichloromethane as the extracting solvent by an ordinary method, the crude product was obtained.

Yield: 4.6 g (22.7 mmol) (65%)

H-NMR (CDCl3) δ 4.15–4.22 (2H, m), 4.43–4.49 (2H, m), 5.71–5.80 (1H, m), 5.88–5.97 (1H, m), 7.68 (2H, d), 7.94 (2H, d)

Step 2 Synthesis of methyl 4-[((4-chlorobenzoyl)ethoxycarbonylamino]benzoate 430 mg (1.06 mmol) of methyl 4-[((4-chlorobenzoyl)ethoxycarbonylmethylamino)methyl]-3-aminobenzoate and 257 mg (1.38 mmol) of 4-(2,5-dihydro-1H-pyrrol-1-ylcarbonyl)benzaldehyde were dissolved in 10 ml of dichloromethane. 0.121 ml (2.12 mmol) of acetic acid was added to the solution, and they were stirred at room temperature for 30 minutes. 844 mg (4 mmol) of sodium triacetoxyborohydride was added to the obtained mixture, and they were stirred at room temperature overnight. After the treatment with dichloromethane as the extracting solvent by an ordinary method, the obtained crude product was purified by the silica gel column chromatography to obtain the title compound.

Yield: 220 mg (0.37 mmol) (35%)

H-NMR (CDCl3) δ 1.23 (3H, t), 3.86 (5H, br), 4.12–4.23 (4H, m), 4.46 (4H, br), 4.78 (2H, br), 5.73 (1H, br), 5.91 (1H, br), 7.05–7.51 (11H, m)

Step 3 Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-8-carboxylic acid 220 mg (0.37 mmol) of methyl 4-[((4-chlorobenzoyl)ethoxycarbonylmethylamino)methyl]-3-[4-(2,5-dihydro-1H-pyrrol-1-yl-carbonyl)benzylamino]benzoate was dissolved in a mixture of 2 ml of 1 N sodium hydroxide and 4 ml of ethanol. The obtained solution was stirred at room temperature overnight. After the treatment with ethyl acetate as the extracting solvent by an ordinary method, the obtained crude product was dissolved in 5 ml of dichloromethane. 75 mg (0.44 mmol) of 2-chloro-1,3-dimethylimidazonium chloride and 0.108 ml (0.74 mmol) of triethylamine were added to the obtained solution, and they were stirred overnight. The solvent was evaporated, and the obtained crude product was treated in the same manner as in step 3 in Example 1 to obtain the title compound.

MS (ESI, m/z) 530(MH+)

Example 53

Synthesis of ethyl 4-(4-chlorobenzoyl)-2-oxo-1-[4-(2,5-dihydro-1H-pyrrol-1-ylcarbonyl)benzyl]-2,3,4,5-tetrahydro-1H-benzo-[e][1,4]-diazepine-8-carboxylate 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-8-carboxylate 10 mg (0.019 mmol) of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-8-carboxylic acid was dissolved in 2 ml of dichloromethane. 0.022 ml (0.38 mmol) of ethanol, 4 mg (0.023 mmol) of 2-chloro-1,3- dimethylimidazonium chloride and 0.005 ml (0.038 mmol) of triethylamine were added to the obtained solution, and they were stirred overnight. The solvent was evaporated and the obtained crude product was treated in the same manner as in step 3 in Example 1 to obtain the title compound.

Yield: 6.4 mg (0.012 mmol) (63%)
MS (ESI, m/z) 558(MH+)
H-NMR (DMSO-d6) δ 1.26 (3H, t), 3.83–4.37 (8H, m), 4.56 (2H, br), 5.14 (2H, br), 5.79 (1H, br), 5.91 (1H, br), 7.22–7.97 (1H, m)

Example 54

Synthesis of 4-(4-chlorobenzoyl)-2-oxo-1-[4-(4-piperidyloxy)benzyl]-2,3,4,5-tetrahydro-1H-benzo[e][1,4]-diazepine-7-carboxylic acid trifluoroacetate 3-Methyl-4-nitrobenzoic acid was dissolved in 100 ml of dichloromethane. 6.8 ml (167 mmol) of methanol, 12.8 g (67 mmol) of 1-(3-dimethylaminopropyl)-3-carbodiimide hydrochloride and 100 mg of 4-dimethylaminopyridine were added to the obtained solution, and they were stirred at room temperature for 2 hours. After the treatment with dichloromethane as the extracting solvent by an ordinary method, the obtained crude product was dissolved in 200 ml of benzene. 50 mg of perbenzoic acid and 10.5 g (60 mmol) of N-bromosuccinimide were added to the obtained solution, and they were stirred at 80° C. for 2 days. After the treatment with ethyl acetate as the extracting solvent by an ordinary method, the obtained crude product was dissolved in 100 ml of ethanol. 4.7 g (33 mmol) of glycine ethyl ester hydrochloride and 4.2 g (50 mmol) of sodium hydrogencarbonate were added to the obtained solution, and they were stirred at 80° C. for 4 hours. The insoluble matter was filtered out, and the solvent was evaporated. After the extraction with ethyl acetate, the obtained product was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 2.2 g (6.14 mmol) (11%)
H-NMR (CDCl3) δ 1.27 (3H, t), 3.43 (2H, s), 3.96 (3H, s), 4.11 (2H, s), 4.20 (2H, q), 7.95 (1H, d), 8.06 (1H, dd), 8.30 (1H, d)

Step 2 Synthesis of methyl 3-[((4-chlorobenzoyl)ethoxycarbonylmethylamino)-methyl]-4-aminobenzoate 2.2 g (6.14 mmol) of methyl 3-[(ethoxycarbonylmethylamino)-methyl]-4-nitrobenzoate was dissolved in 50 ml of dichloromethane. 4 mg (0.023 mmol) of 2-chloro-1,3-dimethylimidazonium chloride, 1.29 ml (9.2 mmol) of triethylamine and 1.16 g (7.3 mmol) of 4-chlorobenzoic acid were added to the obtained solution, and they were stirred overnight. After the treatment with dichloromethane as the extracting solvent by an ordinary method, the obtained crude product was dissolved in 20 ml of ethyl acetate. 200 mg of 10% palladium/carbon was added to the obtained solution and they were stirred in the presence of hydrogen at room temperature for 5 hours. The reaction mixture was filtered through Celite and the solvent was evaporated to obtain the crude product.

Yield: 2.4 g
H-NMR (CDCl3) δ 1.24 (3H, t), 3.85 (5H, br), 4.17 (2H, q), 4.72 (2H, br), 6.62 (1H, d), 7.70 (1H, br), 7.80 (1H, dd)

Step 3: Synthesis of methyl 3-[((4-chlorobenzoyl)ethoxycarbonylmethylamino)methyl]-4-[4-(1-t-butoxycarbonyl-4-piperidyloxy)benzylamino]benzoate 523 mg (1.29 mmol) of methyl 3-[((4-chlorobenzoyl)ethoxycarbonylmethylamino)methyl]-4-aminoacetate and 474 mg (1.55 mmol) of 4-(1-t-butoxycarbonyl-4-piperidyloxy)benzaldehyde were dissolved in 10 ml of dichloromethane. 0.147 ml (2.58 mmol) of acetic acid was added to the obtained solution. They were stirred at room temperature for 30 minutes. 680 mg (3.23 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 500 mg (0.72 mmol) (56%)
H-NMR (CDCl3) δ 1.26 (3H, t), 1.46 (9H, t), 1.64–1.98 (4H, m), 3.25–3.37 (2H, m), 3.62–3.77 (3H, m), 3.84 (3H, s), 4.12 (2H, q), 4.37–4.49 (2H, m), 4.62 (1H, br), 4.78 (2H, br), 6.90 (2H, d), 7.11–7.37 (9H, m)

Step 4: Synthesis of 4-(4-chlorobenzoyl)-2-oxo-1-[4-(4-piperidyloxy)benzyl]-2,3,4,5-tetrahydrobenzo-1H-benzo[e][1,4]diazepine-7-carboxylic acid trifluoroacetate 500 mg (0.72 mmol) of methyl 3-[((4-chlorobenzoyl)ethoxy-carbonylmethylamino)methyl]-4-[4-(1-t-butoxycarbonyl-4-piperidyloxy)-benzylamino]benzoate was dissolved in a mixture of 2 ml of 1 N sodium hydroxide and 4 ml of ethanol. The obtained solution was stirred at room temperature for 4 hours. After the treatment with ethyl acetate as the extracting solvent by an ordinary method, the obtained crude product was dissolved in 10 ml of dichloromethane. 148 mg (0.86 mmol) of 2-chloro-1,3-dimethylimidazonium chloride and 0.207 ml (1.44 mmol) of triethylamine were added to the obtained solution, and they were stirred overnight. The solvent was evaporated, and the obtained crude product was dissolved in 5 ml of 4N solution of hydrogen chloride indioxane. The obtained solution was stirred at room temperature for 3 hours. The solvent was evaporated, and the obtained crude product was treated in the same manner as in step 3 in Example 1 to obtain the title compound.

Yield: 35 mg (0.054 mmol) (8%)
MS (ESI, m/z) 534(MH+)
H-NMR (DMSO-d6) δ 1.62–1.81 (2H, m), 1.97–2.08 (2H, m), 2.96–3.29 (4H, m), 3.83–4.13 (2H, m), 4.46 (2H, br), 4.47–4.56 (1H, m), 5.06 (2H, br), 6.86 (2H, d), 7.16 (2H, m), 7.52 (3H, br), 7.98 (2H, br), 8.41 (2H, br)

Example 55

Synthesis of 4-(4-chlorobenzoyl)-2-oxo-1-[4-(1-(1-acetimidoyl)-4-piperidyloxy)benzyl]-2,3,4,5-tetrahydro-1H-benzo[e][1,4]-diazepine-7-carboxylic acid trifluoroacetate 35 mg (0.054 mmol) of 4-(4-chlorobenzoyl)-2-oxo-1-[4-(4-piperidyloxy)benzyl]-2,3,4,5-tetrahydro-1H-benzo[e][1,4]diazepine-7-carboxylic acid trifluoroacetate was dissolved in 1 ml of ethanol. 14 mg (0.12 mmol) of ethyl acetimidate hydrochloride and 0.026 ml (0.18 mmol) of triethylamine were added to the obtained solution, and they were stirred overnight. The solvent was evaporated, and the obtained crude product was treated in the same manner as in step 3 in Example 1 to obtain the title compound.

Yield: 15 mg (0.022 mmol) (41%)
MS (ESI, m/z) 575(MH+)
H-NMR (DMSO-d6) δ 1.60–1.80 (2H, m), 1.92–2.06 (2H, m), 2.25 (3H, s), 3.41–3.56 (2H, m), 3.81–4.08 (4H, m), 4.42 (2H, br), 4.58–4.63 (1H, m), 5.04 (2H, br), 6.87 (2H, d), 7.08–7.35 (2H, m), 7.42–7.69 (5H, br), 7.97–8.03 (1H, m), 8.57 (1H, br), 9.08 (1H, br)

Example 56

Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-7-carboxylic acid Step 1: Synthesis of Methyl 3-[((4-chlorobenzoyl) ethoxycarbonylmethylamino)methyl]-4-[4-(2,5-dihydro-1H-pyrrol-1-ylcarbonyl)benzylamino]benzoate 660 mg (1.63 mmol) of methyl 3-[((4-chlorobenzoyl) ethoxycarbonylmethylamino)methyl]-4-aminobenzoate and 431 mg (2.1 mmol) of 4-(2,5-dihydro-1H-pyrrol-1-ylcarbonyl)benzaldehyde were dissolved in 10 ml of dichloromethane. 0.185 ml (3.26 mmol) of acetic acid was added to the solution, and they were stirred at room temperature for 30 minutes. 860 mg (4.1 mmol) of sodium triacetoxyborohydride was added to the obtained mixture, and they were stirred at room temperature overnight. After the treatment with dichloromethane as the extracting solvent by an ordinary method, the obtained crude product was purified by the silica gel column chromatography to obtain the title compound.

Yield: 530 mg (0.90 mmol) (55%)

H-NMR (CDCl3) δ 1.23 (3H, t), 3.84 (5H, br), 4.08–4.21 (4H, m), 4.40–4.56 (4H, m), 4.78 (2H, br), 5.74 (1H, br), 5.90 (1H, br), 6.49 (2H, br), 7.21–7.82 (9H, m)

Step 2 Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-7-carboxylic acid 530 mg (0.90 mmol) of methyl 3-[((4-chlorobenzoyl) ethoxycarbonylmethylamino)methyl]-4-[4-(2,5-dihydro-1H-pyrrol-1-yl-carbonyl)benzylamino]benzoate was dissolved in a mixture of 5 ml of 1 N sodium hydroxide and 5 ml of ethanol. The obtained solution was stirred at room temperature for 5 hours. After the treatment with ethyl acetate as the extracting solvent by an ordinary method, the obtained crude product was dissolved in 10 ml of dichloromethane. 182 mg (0.44 mmol) of 2-chloro-1,3-dimethylimidazonium chloride and 0.257 ml (1.8 mmol) of triethylamine were added to the obtained solution, and they were stirred overnight. The solvent was evaporated, and a half of the obtained crude product was treated in the same manner as in step 3 in Example 1 to obtain the title compound.

Yield: 25 mg (0.047 mmol) (11%)

MS (ESI, m/z) 530(MH+)

H-NMR (DMSO-d6) δ 3.95 (2H, br), 4.12 (2H, br), 4.24 (2H, br),4.51 (2H, br), 5.16 (2H, br), 5.77 (1H, br), 5.89 (1H, br), 7.22–8.03 (11H, m)

Example 57

Synthesis of ethyl 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]diazepine-7-carboxylate 10 mg (0.019 mmol) of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-7-carboxylic acid was dissolved in 2 ml of dichloromethane. 0.022 ml (0.38 mmol) of ethanol, 4 mg (0.023 mmol) of 2-chloro-1,3-dimethylimidazonium chloride and 0.005 ml (0.038 mmol) of triethylamine were added to the obtained solution, and they were stirred overnight. The solvent was evaporated and the obtained crude product was treated in the same manner as in step 3 in Example 1 to obtain the title compound.

Yield: 8 mg (0.015 mmol) (79%)

MS (ESI, m/z) 558(MH+)

H-NMR (DMSO-d6) δ 1.23 (3H, br), 3.95 (2H, br), 4.10 (2H, br), 4.23 (4H, br), 4.51 (2H, br), 5.16 (2H, br), 5.79 (1H, br), 5.86 (1H, br), 7.22–8.11 (11H, m)

Example 58

Synthesis of 4-(4-chlorobenzoyl)-7-(1-pyrrolidinecarbonyl)-1-[4-(2,5-dihydro-1H-pyrrol-1-ylcarbonyl)benzyl]-1, 3,4,5-tetrahydrobenzo[e][1,4] diazepin-2-on 40 mg of the crude product obtained in step 2 in Example 56 was dissolved in 2 ml of dichloromethane. 3 mg (0.38 mmol) of pyrrolidine, 4 mg (0.023 mmol) of 2-chloro-1,3-dimethylimidazonium chloride and 0.013 ml (0.092 mmol) of triethylamine were added to the obtained solution, and they were stirred overnight. The solvent was evaporated and the obtained crude product was treated in the same manner as in step 3 in Example 1 to obtain the title compound.

Yield: 6.9 mg (0.012 mmol)

MS (ESI, m/z) 583(MH+)

H-NMR (DMSO-d6) δ 1.81 (4H, br), 3.41 (6H, br), 4.10 (2H, br), 4.23 (2H, br), 4.51 (2H, br), 5.16 (2H, br), 5.79 (1H, br), 5.86 (1H, br), 7.22–7.77 (11H, m)

Example 59

Synthesis of 4-(4-chlorobenzoyl)-7-(4-morpholinecarbonyl)-1-[4-(2,5-dihydro-1H-pyrrol-1-ylcarbonyl)benzyl]-1,3,4,5-tetrahydro-benzo[e][1,4] diazepin-2-on 40 mg of the crude product obtained in step 2 in Example 56 was dissolved in 2 ml of dichloromethane. 3 mg (0.38 mmol) of morpholine, 4 mg (0.023 mmol) of 2-chloro-1,3-dimethylimidazonium chloride and 0.013 ml (0.092 mmol) of triethylamine were added to the obtained solution, and they were stirred overnight. The solvent was evaporated and the obtained crude product was treated in the same manner as in step 3 in Example 1 to obtain the title compound.

Yield: 6.5 mg(0.011 mmol)

MS (ESI, m/z) 599(MH+)

H-NMR (DMSO-d6) 63.56 (8H, br), 3.95 (2H, br), 4.13 (2H, br), 4.25 (2H, br), 4.51 (2H, br), 5.16 (2H, br), 5.79 (1H, br), 5.86 (1H, br), 7.22–7.63 (11H, m)

Example 60

Synthesis of 4-(4-chlorobenzoyl)-1-[4-(2,5-dihydro-1H-pyrrol-1-ylcarbonyl)benzyl]-7-(1-thiomorpholinecarbonyl)-1,3,4,5-tetrahydrobenzo[e][1,4]diazepin-2-on 40 mg of the crude product obtained in step 2 in Example 56 was dissolved in 2 ml of dichloromethane. 3 mg (0.38 mmol) of thiomorpholine, 4 mg (0.023 mmol) of 2-chloro-1,3-dimethylimidazonium chloride and 0.013 ml (0.092 mmol) of triethylamine were added to the obtained solution, and they were stirred overnight. The solvent was evaporated and the obtained crude product was treated in the same manner as in step 3 in Example 1 to obtain the title compound.

Yield: 6.5 mg (0.011 mmol)

MS (ESI, m/z) 599(MH+)

H-NMR (DMSO-d6) δ 2.61 (8H, br), 3.95 (2H, br), 4.10 (2H, br), 4.22 (2H, br), 4.47 (2H, br), 5.16 (2H, br), 5.81 (1H, br), 5.86 (1H, br), 7.22–7.62 (11H, m)

Example 61

Synthesis of 3-[4-(4-chlorobenzoyl)-2-oxo-1-(4-(4-piperidyloxy)benzyl)-2,3,4,5-tetrahydro-1H-benzo[e][1,4] diazepin-8-yl]-propionic acid trifluoroacetate Step 1 Synthesis of ethyl (4-bromo-2-nitrobenzyl) aminoacetate 19.8 g (91 mmol) of 4-bromo-2-nitrotoluene was dissolved in 150 ml of benzene. 50 mg of perbenzoic acid and 19.6 g (91 mmol) of N-bromosuccinimide were added to the obtained solution, and they were stirred at 80° C. for 2 days. After the treatment with ethyl acetate as the extracting solvent by an ordinary method, the obtained crude product was dissolved in 100 ml of ethanol. 12.9 g (91 mmol) of glycine ethyl ester hydrochloride and 15.3 g (182 mmol) of sodium hydrogencarbonate were added to the obtained solution, and they were stirred at 80° C. for 4 hours. The insoluble matter was filtered out, and the solvent was evaporated. After the extraction with ethyl acetate, the obtained product was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 8.25 g (26 mmol) (29%)

H-NMR (CDCl3) δ 1.27 (3H, t), 3.41 (2H, s), 4.06 (2H, s), 4.17 (2H, q), 7.57 (1H, d), 7.71 (1H, dd), 8.10 (1H, d)

Step 2 Synthesis of ethyl [(2-nitro-4-bromobenzyl)-(4-chlorobenzoyl)amino]acetate 4.2 g (13.1 mmol) of ethyl (4-bromo-2-nitrobenzyl)aminoacetate was dissolved in 30 ml of dichloromethane. 2.2 ml (17.7 mmol) of 4-chlorobenzoyl chloride and 2.9 ml (19.6 mmol) of triethylamine were added to the obtained solution, and they were stirred overnight. After the treatment with dichloromethane as the extracting solvent by an ordinary method, the obtained crude product was purified by the silica gel column chromatography to obtain the crude product.

Yield: 2.86 g (6.29 mmol)(48%)

H-NMR (CDCl3) δ 1.25 (3H, t), 3.97–4.22 (4H, m), 4.82 (2H, br), 7.38 (4H, br), 7.58 (1H, d), 7.58 (1H, br), 7.81 (1H, br), 8.22 (1H, br)

Step 3: Synthesis of methyl 3-[3-nitro-4-(((4-chlorobenzoyl)ethoxycarbonylmethylamino)methyl)phenyl]acrylate 1.4 g (3.08 mmol) of ethyl [(2-nitro-4-bromobenzyl)-(4-chlorobenzoyl)amino]acetate, 67 mg (0.03 mmol) of palladium acetate, 0.74 ml (7.7 mmol) of methyl acrylate, 560 mg (2.2 mmol) of triphenylphosphine and 1.3 ml (9.24 mmol) of triethylamine were dissolved in 20 ml of DMF. The obtained solution was stirred at 100° C. overnight. After the treatment with ethyl acetate as the extracting solvent by an ordinary method, the crude product was obtained. The crude product was purified by the silica gel column chromatography to obtain the title compound.

Yield: 1.3 g (2.82 mmol) (92%)

H-NMR (CDCl3) δ 1.25 (3H, t), 3.83 (3H, br), 3.97–4.24 (4H, m), 4.99 (2H

Step 4: Synthesis of Methyl 3-[3-amino-4-(((4-chlorobenzoyl)ethoxycarbonylmethylamino)methyl)phenyl]propionate 1.3 g (2.82 mmol) of methyl 3-[3-nitro-4-((4-chlorobenzoyl)ethoxy-carbonylmethylamino)methyl)phenyl]acrylate was dissolved in 20 ml of ethyl acetate. 200 mg of 10% palladium/carbon was added to the obtained solution and they Were stirred in the presence of hydrogen at room temperature for 5 hours. The reaction solution was filtered through Celite. The solvent was evaporated to obtain the title compound.

Yield: 1.2 g (2.78 mmol)

Step 5: Synthesis of Methyl 3-[((4-chlorobenzoyl)ethoxycarbonylmethylamino)methyl]-3-(4-(1-t-butoxycarbonyl-4-piperidyloxy)benzylamino)phenyl]propionate 630 mg (1.46 mmol) of methyl 3-[3-amino-4-(((4-chlorobenzoyl)ethoxycarbonylmethylamino)methyl)phenyl]propionate and 534 mg (1.75 mmol) of 4-(1-t-butoxycarbonyl-4-piperidyloxy)-benzaldehyde were dissolved in 10 ml of dichloromethane. 0.166 ml (2.9 mmol) of acetic acid was added to the obtained solution. They were stirred at room temperature for 30 minutes. 770 mg (3.23 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 550 mg (0.76 mmol) (52%)

H-NMR (CDCl3) δ 1.26 (3H, t), 1.47 (9H, t), 1.64–1.98 (4H, m), 2.51–2.63 (2H, m), 2.78–2.85 (2H, m), 3.25–3.37 (2H, m), 3.62–3.77 (5H, m), 4.08–4.18 (4H, m), 4.34–4.53 (2H, m), 4.58–4.67 (3H, m),6.89 (2H, d), 7.18–7.30 (9H, m)

Step 6: Synthesis of 3-[4-(4-chlorobenzoyl)-2-oxo-1-(4-(4-piperidyloxy)benzyl)-2,3,4,5-tetrahydro-1H-benzo[e][1,4]diazepin-8-yl]propionic acid Mono(trifluoroacetate)

550 mg (0.76 mmol) of methyl 3-[((4-chlorobenzoyl)ethoxy-carbonylmethylamino)methyl]-3-(4-(1-t-butoxycarbonyl-4-piperidyloxy)-benzylamino)phenyl]propionate was dissolved in a mixture of 2 ml of 1 N sodium hydroxide and 4 ml of ethanol. The obtained solution was stirred at room temperature for 4 hours. After the treatment with ethyl acetate as the extracting solvent by an ordinary method, the obtained crude product was dissolved in 10 ml of dichloromethane. 154 mg (0.91 mmol) of 2-chloro-1,3-dimethylimidazonium chloride and 0.159 ml (1.14 mmol) of triethylamine were added to the obtained solution, and they were stirred overnight. The solvent was evaporated, and the obtained crude product was dissolved in 5 ml of 4N solution of hydrogen chloride in dioxane. The obtained solution was stirred at room temperature for 3 hours. The solvent was evaporated, and the obtained crude product was treated in the same manner as in step 3 in Example 1 to obtain the title compound.

Yield: 35 mg (0.049 mmol) (6%)

MS (ESI, m/z) 562(MH+)

H-NMR (DMSO-d6) δ 1.62–1.80 (2H, m), 1.93–2.05 (2H, m), 2.50–2.59 (2H, m), 2.72–2.84 (2H, m), 2.91–3.23 (4H, m), 3.89–4.01 (2H, m), 4.23 (2H, br), 4.47–4.57 (1H, m), 5.03 (2H, br), 6.86 (2H, d), 7.16 (2H, br), 7.52 (3H, br), 7.88 (2H, d), 8.45 (2H, br)

Example 62

Synthesis of 3-[4-(4-chlorobenzoyl)-2-oxo-1-(4-(1-(1-acetimidoyl)-4-piperidyloxy)benzyl)-2,3,4,5-tetrahydro-1H-benzo[e][1,4]-diazepin-8-yl]propionic acid trifluoroacetate 33 mg (0.049 mmol) of 3-[4-(4-chlorobenzoyl)-2-oxo-1-(4-(4-piperidyloxy)benzyl)-2,3,4,5-tetrahydro-1H-benzo[e][1,4]diazepin-8-yl]propionic acid trifluoroacetate was dissolved in 1 ml of ethanol. 14 mg (0.12 mmol) of ethyl acetimidate hydrochloride and 0.026 ml (0.18 mmol) of triethylamine were added to the obtained solution, and they were stirred overnight. The solvent was evaporated, and the obtained crude product was treated in the same manner as in step 3 in Example 1 to obtain the title compound.

Yield: 7 mg (0.003 mmol) (6%)

MS (ESI, m/z) 603(MH+)

H-NMR (DMSO-d6) δ 1.58–1.78 (2H, m), 1.93–2.04 (2H, m), 2.25 (3H, s), 2.49–2.58 (2H, m), 2.77–2.83 (2H, m), 3.40–3.57 (4H, m), 3.81–3.85 (2H, m), 4.23 (1H, br), 4.56–4.63 (1H, m), 5.04 (2H, br), 6.87 (2H, d), 6.99–7.21 (2H, m), 7.37–7.69 (5H, br), 8.57 (1H, br), 9.08 (1H, br)

Example 63

Synthesis of Methyl 3-[4-(4-chlorobenzoyl)-2-oxo-1-(4-(1-pyrrolidinecarbonyl)benzyl)-2,3,4,5-tetrahydro-1H-benzo[e][1,4]-diazepin-8-yl]propionate Step 1: Synthesis of Methyl 3-[((4-chlorobenzoyl)ethoxycarbonylmethylamino)methyl-3-(4-(1-pyrrolidinecarbonyl)benzylamino)phenyl]-propionate 130 mg (0.37 mmol) of methyl 3-[3-amino-4-(((4-chlorobenzoyl)ethoxycarbonylmethylamino)methyl)phenyl]propionate and 67 mg (0.39 mmol) of 4-(1- pyrrolidinecarbonyl)benzaldehyde were dissolved in 10 ml of dichloromethane. 0.042 ml (0.72 mmol) of acetic acid was added to the obtained solution. They were stirred at room temperature for 30 minutes. 195 mg (0.93 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 115 mg (0.19 mmol) (51%)

H-NMR (CDCl3) δ 1.22 (3H, t), 1.78–1.97 (2H, m), 2.48 (2H, dd), 2.75 (2H, dd), 3.38 (2H, dd), 3.60 (2H, dd) 3.62 (3H, s) 3.81 (2H, br), 4.12 (2H, q), 4.40 (2H, br), 4.72 (2H, br), 6.37–6.63 (2H, m), 6.84–7.11 (2H, m), 7.21–7.48 (7H, m)

Step 2: Synthesis of methyl 3-[4-(4-chlorobenzoyl)-2-oxo-1-(4-(1-pyrrolidinecarbonyl)benzyl)-2,3,4,5-tetrahydro-1H-benzo[e][1,4]diazepin-8-yl]propionate 115 mg (0.19 mmol) of methyl 3-[((4-chlorobenzoyl) ethoxycarbonylmethylamino)methyl-3-(4-(1-pyrrolidinecarbonyl)benzylamino)phenyl]propionate was dissolved in a mixture of 5 ml of 1 N sodium hydroxide and 5 ml of ethanol. The obtained solution was stirred at room temperature for 5 hours. After the treatment with ethyl acetate as the extracting solvent by an ordinary method, the obtained crude product was dissolved in 5 ml of dichloromethane. 39 mg (0.23 mmol) of 2-chloro-1,3-dimethylimidazonium chloride and 0.040 ml (0.29 mmol) of triethylamine were added to the obtained solution, and they were stirred overnight. The solvent was evaporated, and the obtained crude product was treated in the same manner as in step 3 in Example 1 to obtain the title compound.

Yield: 14 mg (0.024 mmol) (13%)

MS (ESI, m/z) 574(MH+)

H-NMR (DMSO-d6) δ 1.68–1.87 (4H, m), 2.42 (2H, br), 2.82 (2H, br), 3.29 (2H, dd), 3.41 (2H, dd), 3.55 (3H, s), 3.97 (2H, br), 4.33 (2H, br), 5.13 (2H, br), 7.01–7.59 (11H, m)

Example 64

Synthesis of 3-[4-(4-chlorobenzoyl)-2-oxo-1-(4-(1-pyrrolidinecarbonyl)benzyl)-2,3,4,5-tetrahydro-1H-benzo[e][1,4]-diazepin-8-yl]propionic acid 10 mg (0.017 mmol) of methyl 3-[4-(4-chlorobenzoyl)-2-oxo-1-(4-(1-pyrrolidinecarbonyl)benzyl)-2,3,4,5-tetrahydro-1H-benzo[e][1,4]diazepin-8-yl]propionate was dissolved in a mixture of 5 ml of 1 N sodium hydroxide and 5 ml of ethanol. The obtained solution was stirred at room temperature for 5 hours. The solvent was evaporated, and the obtained crude product was treated in the same manner as in step 3 in Example 1 to obtain the title compound.

Yield: 4 mg (0.007 mmol) (42%)

MS (ESI, m/z) 560(MH+)

H-NMR (DMSO-d6) δ 1.68–1.87 (4H, m), 2.48 (2H, br), 2.80 (2H, br), 3.29 (2H, dd), 3.41 (2H, dd), 3.97 (2H, br), 4.33 (2H, br), 5.13 (2H, br), 6.98–7.59 (11H, m)

Example 65

Synthesis of 3-[4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepin-8-yl]propionic acid Step 1: Synthesis of methyl 3-[((4-chlorobenzoyl) ethoxycarbonylmethylamino)methyl-3-(4-(2,5-dihydro-1H-pyrrol-1-ylcarbonyl)benzylamino)phenyl]-propionate 656 mg (1.52 mmol) of methyl 3-[3-amino-4-(((4-chlorobenzoyl)ethoxycarbonylmethylamino)methyl) phenyl]propionate and 408 mg (1.97 mmol) of 4-(2,5-dihydro-1H-pyrrol-1-ylcarbonyl)benzaldehyde were dissolved in 20 ml of dichloromethane. 0.18 ml (3.0 mmol) of acetic acid was added to the obtained solution. They were stirred at room temperature for 30 minutes. 791 mg (3.75 mmol) of sodium triacetoxyborohydride was added to the obtained mixture and they were stirred at room temperature overnight. After the treatment with dichloromethane as the extracting solvent by an ordinary method, the crude product was obtained. The crude product was purified by the silica gel column chromatography to obtain the title compound.

Yield: 430 mg (0.73 mmol) (49%)

H-NMR (CDCl3) δ 1.23 (3H, t), 2.52 (2H, dd), 2.81 (2H, dd), 3.64 (3H, br), 3.81 (2H, br), 4.08–4.21 (4H, m), 4.43 (4H, br), 4.76 (2H, br), 5.74 (1H, br), 5.90 (1H, br), 6.38 (2H, br), 7.21–7.557 (9H, m)

Step 2: Synthesis of 3-[4-(4-chlorobenzoyl)-2-oxo-1-[4-(2.5-dihydro-1H-pyrrol-1-ylcarbonyl)benzyl]-2,3,4,5-tetrahydro-1H-benzo[e][1,4]-diazepin-8-yl]propionic acid 430 mg (0.73 mmol) of methyl 3-[((4-chlorobenzoyl) ethoxycarbonylmethylamino)methyl-3-(4-(2,5-dihydro-1H-pyrrol-1-ylcarbonyl)benzylamino)phenyl]propionate was dissolved in a mixture of 5 ml of 1 N sodium hydroxide and 5 ml of ethanol. The obtained solution was stirred at room temperature for 5 hours. After the treatment with ethyl acetate as the extracting solvent by an ordinary method, the obtained crude product was dissolved in 10 ml of dichloromethane. 149 mg (0.88 mmol) of 2-chloro-1,3-dimethylimidazonium chloride and 0.20 ml (1.46 mmol) of triethylamine were added to the obtained solution, and they were stirred overnight. The solvent was evaporated, and a half of the obtained crude product was treated in the same manner as in step 3 in Example 1 to obtain the title compound.

Yield: 24 mg (0.043 mmol) (6%)

MS (ESI, m/z) 558(MH+)

H-NMR (DMSO-d6) δ 2.51 (2H, br), 2.89 (2H, br), 3.94 (2H, br),4.11 (2H, br), 4.23 (4H, br), 5.16 (2H, br), 5.80 (1H, br), 5.91 (1H, br), 7.00–7.62 (11H, m)

Example 66

Synthesis of ethyl 3-[4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]diazepin-8-yl]propionate 10 mg (0.018 mmol) of 3[4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepin-8-propionic acid was dissolved in 2 ml of dichloro-methane. 4 mg (0.02 1 mmol) of 2-chloro-1,3-dimethylimidazonium chloride and 0.005 nil (0.036 mmol) of triethylamine were added to the obtained solution, and they were stirred overnight. The solvent was evaporated and the obtained crude product was treated in the same manner as in step 3 in Example 1 to obtain the title compound.

Yield: 8 mg (0.013 mmol) (72%)

MS (ESI, m/z) 586(MH+)

H-NMR (DMSO-d6) δ 1.11 (3H, t), 2.60 (2H, br), 2.82 (2H, br), 3.96 (2H, br), 4.02 (2H, q), 4.12 (2H, br), 4.23 (4H, br), 5.16 (2H, br), 5.78 (1H, br), 5.91 (1H, br), 7.00–7.62 (11H, m)

Example 67

Synthesis of 4-(4-chlorobenzoyl)-8-(3-pyrrolidin-4-yl-3-oxopropyl)-1-[4-(2,5-dihydro-1H-pyrrol-1-ylcarbonyl) benzyl]-1,3,4,5-tetrahydrobenzo[e][1,4]diazepin-2-on 35 mg of the crude product obtained in step 2 in Example 65 was dissolved in 2 ml of dichloromethane. 3 mg (0.38 mmol) of pyrrolidine, 4 mg (0.023 mmol) of 2-chloro-1,3-dimethylimidazonium chloride and 0.013 ml (0.092 mmol) of triethylamine were added to the obtained solution, and they were stirred overnight. The solvent was evaporated and the obtained crude product was treated in the same manner as in step 3 in Example 1 to obtain the title compound.

Yield: 6.6 mg (0.011 mmol)
MS (ESI, m/z) 611(MH+)
H-NMR (DMSO-d6) δ 1.83–1.94 (4H, m), 2.51 (2H, br), 2.82 (2H, br), 3.18–3.33 (4H, br), 3.97 (2H, br), 4.18 (2H, br), 4.23 (2H, br), 4.40 (2H, br), 5.16 (2H, br), 5.79 (1H, br), 5.83 (1H, br), 6.98–7.60 (11H, m)

Example 68

Synthesis of 4-(4-chlorobenzoyl)-8-(3-morpholine-4-yl-3-oxopropyl)-1-[4-(2,5-dihydro-1H-pyrrol-1-ylcarbonyl)benzyl]-1,3,4,5-tetrahydrobenzo[e][1,4]diazepin-2-on 35 mg of the crude product obtained in step 2 in Example 65 was dissolved in 2 ml of dichloromethane. 3 mg (0.38 mmol) of morpholine, 4 mg (0.023 mmol) of 2-chloro-1,3-dimethylimidazonium chloride and 0.013 ml (0.092 mmol) of triethylamine were added to the obtained solution, and they were stirred overnight. The solvent was evaporated and the obtained crude product was treated in the same manner as in step 3 in Example 1 to obtain the title compound.

Yield: 2.7 mg (0.004 mmol)
MS (ESI, m/z) 627(MH+)
H-NMR (DMSO-d6) δ 2.59 (2H, br), 2.83 (2H, br), 3.39 (8H, br), 3.83 (2H, br), 4.11 (2H, br), 4.21 (2H, br), 4.37 (2H, br), 5.16 (2H, br), 5.79 (1H, br), 5.82 (1H, br), 6.98–7.61 (11H, m)

Example 69

Synthesis of 4-(4-chlorobenzoyl)-8-(3-thiomorpholin-4-yl-3-oxopropyl)-1-[4-(2,5-dihydro-1H-pyrrol-1-ylcarbonyl)benzyl]-1,3,4,5-tetrahydrobenzo[e][1,4]diazepin-2-on 70 mg of the crude product obtained in step 2 in Example 65 was dissolved in 2 ml of dichloromethane. 10 mg (1.03 mmol) of thiomorpholine, 12 mg (0.069 mmol) of 2-chloro-1,3-dimethylimidazonium chloride and 0.039 ml (0.276 mmol) of triethylamine were added to the obtained solution, and they were stirred overnight. The solvent was evaporated and the obtained crude product was treated in the same manner as in step 3 in Example 1 to obtain the title compound.

Yield: 21.5 mg (0.033 mmol)
MS (ESI, m/z) 583(MH+)
H-NMR (DMSO-d6) δ 2.57 (2H, br), 2.82 (2H, br), 3.63 (4H, br), 3.88 (2H, br), 4.12 (2H, br), 4.24 (2H, br), 4.62 (6H, br), 5.16 (2H, br), 5.78 (1H, br), 5.83 (1H, br), 6.98–7.60 (11H, m)

Example 70

Synthesis of diethyl [2-(4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]diazepin-8-yl)ethyl]phosphonate Step 1: Synthesis of Ethyl ((4-chlorobenzoyl)-(4-(2-(diethoxyphosphoryl)vinyl)-2-nitrobenzyl)amino)acetate 580 mg (1.27 mmol) of ethyl [(2-nitro-4-bromobenzyl)-(4-chlorobenzoyl)amino]acetate, 28 mg (0.13 mmol) of palladium acetate, 0.23 ml (1.6 mmol) of diethylvinyl phosphonate, 233 mg (0.89 mmol) of triphenylphosphine and 0.35 ml (2.5 mmol) of triethylamine were dissolved in 10 ml of DMF. They were stirred at 100° C. for 4 hours. After the treatment with ethyl acetate as the extracting solvent by an ordinary method, the crude product was obtained. The crude product was purified by the silica gel column chromatography to obtain the title compound.

Yield: 505 mg (0.94 mmol) (74%)
H-NMR (CDCl3) δ 1.21–1.41 (9H, m), 4.03–4.23 (8H, br), 5.01 (2H, br), 6.02 (1H, dd), 7.18–7.70 (8H, m)

Step 2: Synthesis of Ethyl ((4-chlorobenzoyl)-(4-(2-(diethoxyphosphoryl)ethyl-2-aminobenzyl)amino)acetate 505 mg (0.94 mmol) of ethyl ((4-chlorobenzoyl)-(4-(2-(diethoxyphosphoryl)vinyl)-2-nitrobenzyl)amino)acetate was dissolved in 10 ml of ethyl acetate. 100 mg of 10% palladium/carbon was added to the obtained solution and they were stirred in the presence of hydrogen at room temperature for 5 hours. The reaction solution was filtered through Celite. The solvent was evaporated to obtain the title compound.

Yield: 480 mg (0.94 mmol) (100%)

Step 3: Synthesis of Diethyl [2-(4-(4-chlorobenzoyl)-2-oxo-1-(4-(1-pyrrolidinecarbonyl)benzyl)-2,3,4,5-tetrahydro-1H-benzo[e][1,4]-diazepin-8-yl)ethyl]phosphonate 240 mg (0.47 mmol) of ethyl ((4-chlorobenzoyl)-(4-(2-(diethoxyphosphoryl)ethyl)-2-aminobenzyl)amino)acetate and 105 mg (0.52 mmol) of 4-(1-pyrrolidinecarbonyl)benzaldehyde were dissolved in 10 ml of dichloromethane. 0.054 ml (0.94 mmol) of acetic acid was added to the obtained solution. They were stirred at room temperature for 30 minutes. 248 mg (1.18 mmol) of sodium triacetoxyborohydride was added to the obtained mixture and they were stirred at room temperature overnight. After the treatment with dichloromethane as the extracting solvent by an ordinary method, the obtained crude product was dissolved in a mixture of 4 ml of 1 N sodium hydroxide and 2 ml of ethanol, and the solution was stirred at room temperature for 5 hours. After the treatment with ethyl acetate by an ordinary method, the obtained crude product was dissolved in 10 ml of dichloromethane. 95 mg (0.56 mmol) of 2-chloro-1,3-dimethylimidazonium chloride and 0.14 ml (0.94 mmol) of triethylamine were added to the obtained solution, and they were stirred overnight. The solvent was evaporated and the obtained crude product was treated in the same manner as in step 3 in Example 1 to obtain the title compound.

Yield: 40 mg (0.051 mmol) (13%)
MS (ESI, m/z) 652(MH+)
H-NMR (DMSO-d6) δ 1.18 (6H, t), 1.73–1.82 (4H, m), 1.96–2.09 (2H, m), 2.70–2.83 (2H, m), 3.25 (2H, dd), 3.49 (2H, dd), 3.81–4.00 (6H, m), 4.31 (2H, br), 5.16 (2H, br), 6.98–7.61 (11H, m)

Example 71-1

Synthesis of [2-(4-(4-chlorobenzoyl)-2-oxo-1-(4-(1-pyrrolidinecarbonyl)benzyl)-2,3,4,5-tetrahydro-1H-benzo[e][1,4]-diazepin-8-yl)ethyl]phosphonic acid Example 71-2

Synthesis of Monoethyl [2-(4-(4-chlorobenzoyl)-2-oxo-1-(4-(1-pyrrolidinecarbonyl)benzyl)-2,3,4,5-tetrahydro-1H-benzo[e][1,4]-diazepin-8-yl)ethyl]phosphonate 40 mg (0.051 mmol) of diethyl [2-(4-(4-chlorobenzoyl)-2-oxo-1-(4-(1-pyrrolidinecarbonyl)benzyl)-2,3,4,5-tetrahydro-1H-benzo[e][1,4]-diazepin-8-yl)ethyl]phosphonate was dissolved in 10 ml of acetonitrile. 0.15 ml of trimethylsilyl bromide was added to the obtained solution, and they were stirred at room temperature overnight. The solvent was evaporated and the obtained crude product was treated in the same manner as in step 3 in Example 1 to obtain the title compound.

Example 71-1

Yield: 3.5 mg (0.006 mmol) (12%)
MS (ESI, m/z) 596(MH+)
H-NMR (DMSO-d6) δ 1.73–1.82 (4H, m), 1.96–2.09 (2H, m), 2.70–2.83 (2H, m), 3.25 (2H, dd), 3.49 (2H, dd), 3.81–4.00 (2H, m), 4.31 (2H, br), 5.16 (2H, br), 6.98–7.61 (11H, m)

Example 71-2

Yield: 3.5 mg (0.006 mmol) (12%)

MS (ESI, m/z) 624(MH+)

H-NMR (DMSO-d6) δ 1.18 (3H, t), 1.73–1.82 (4H, m), 1.96–2.09 (2H, m), 2.70–2.83 (2H, m), 3.25 (2H, dd), 3.49 (2H, dd), 3.81–4.00 (4H, m), 4.31 (2H, br), 5.16 (2H, br), 6.98–7.61 (11H, m)

Example 72

Synthesis of diethyl [2-(4-(4-chlorobenzoyl)-2-oxo-1-[4-(2, 5-dihydro-1H-pyrrol-1-ylcarbonyl)benzyl]-2,3,4,5-tetrahydro-1H-benzo[e][4,1]-diazepin-8-yl)ethyl] phosphonate 180 mg (0.35 mmol) of ethyl ((4-chlorobenzoyl)-(4-(2-(diethoxyphosphoryl)ethyl)-2-aminobenzyl)amino)acetate and 92 mg (0.46 mmol) of 4-(2,5-dihydro-1H-pyrrol-1-ylcarbonyl)benzaldehyde were dissolved in 10 ml of dichloromethane. 0.040 ml (0.7 mmol) of acetic acid was added to the obtained solution. They were stirred at room temperature for 30 minutes. 185 mg (0.88 mmol) of sodium triacetoxyborohydride was added to the obtained mixture and they were stirred at room temperature overnight. After the treatment with dichloromethane as the extracting solvent by an ordinary method, the obtained crude product was dissolved in a mixture of 2 ml of 1 N sodium hydroxide and 4 ml of ethanol, and the obtained solution was stirred at room temperature for 5 hours. After the treatment with ethyl acetate as the extracting solvent by an ordinary method, the obtained crude product was dissolved in 10 ml of dichloromethane. 78 mg (0.46 mmol) of 2-chloro-1,3-dimethylimidazonium chloride and 0.15 ml (1.05 mmol) of triethylamine were added to the obtained solution, and they were stirred overnight. The solvent was evaporated and the obtained crude product was treated in the same manner as in step 3 in Example 1 to obtain the title compound.

Yield: 46 mg (0.071 mmol) (20%)

MS (ESI, m/z) 650(MH+)

H-NMR (DMSO-d6) δ 1.18 (6H, t), 1.96–2.09 (2H, m), 2.70–2.83 (2H, m), 3.81–4.00 (6H, m), 4.11 (2H, br), 4.22 (2H, br), 4.22 (2H, br), 5.16 (2H, br), 6.98–7.61 (11H, m)

Example 73

Synthesis of [2-(4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepin-8-yl)ethyl] phosphonic acid 40 mg (0.051 mmol) of diethyl [2-(4-(4-chlorobenzoyl)-2-oxo-1-[4-(2,5-dihydro-1H-pyrrol-1-ylcarbonyl)-benzyl]-2,3,4,5-tetrahydro-1H-benzo[e][1,4]diazepin-8-yl)ethyl] phosphonate was dissolved in 10 ml of acetonitrile. 0.15 ml of trimethylsilyl bromide was added to the obtained solution, and they were stirred overnight. The solvent was evaporated, and the obtained crude product was treated in the same manner as in step 3 in Example 1 to obtain the title compound.

Yield: 10 mg (0.017 mmol) (33%)

MS (ESI, m/z) 594(MH+)

H-NMR (DMSO-d6) δ 1.73–1.84 (2H, m), 2.68–2.84 (2H, m), 3.97 (2H, br), 4.11 (2H, br), 4.23 (2H, br), 4.42 (2H, br), 5.16 (2H, br), 5.79 (1H, br), 5.87 (2H, br), 6.98–7.61 (11H, m)

Example 74

Synthesis of 4-(4-chloro-2-fluorobenzoyl)-1-[1-(4-pyridyl)-4-piperidylmethyl]-1,3,4,5-tetrahydrobenzo[e][1,4]diazepin-2-on trifluoroacetate 20 mg (0.035 mmol) of 1-[1-(4-pyridyl)-4-piperidylmethyl]-1,3,4,5-tetrahydrobenzo[e][1,4]diazepin-2-on bistrifluoroacetate was dissolved in 2 ml of dichloromethane. 7 mg (0.042 mmol) of 2-chloro-1,3-dimethylimidazonium chloride and 8 mg (0.043 mmol) of 4-chloro-2-fluorobenzoic acid and then 0.012 ml (0.084 mmol) of triethylamine were added to the obtained solution, and they were stirred overnight. The solvent was evaporated, and the obtained crude product was treated in the same manner as in step 3 in Example 1 to obtain the title compound.

Yield: 18 mg (0.030 mmol) (84%)

MS (ESI, m/z) 493(MH+)

H-NMR (DMSO-d6) δ 1.05–1.23 (2H, m), 1.59–1.75 (2H, m), 1.83–2.06 (1H, m), 3.03–3.17 (2H, m), 3.78–3.91 (2H, m), 4.08–4.21 (2H, m), 4.38 (2H, br), 4.61 (2H, br), 7.12 (2H, d), 7.23–7.83 (7H, m), 8.16 (2H, d)

Example 75

Synthesis of 4-(2,4-dichlorobenzoyl)-1-[1-(4-pyridyl)-4-piperidylmethyl]-1,3,4,5-tetrahydrobenzo[e][1,4]diazepin-2-on trifluoroacetate 20 mg (0.035 mmol) of 1-[1-(4-pyridyl)-4-piperidylmethyl]-1,3,4,5-tetrahydrobenzo[e][1,4]diazepin-2-on bistrifluoroacetate was dissolved in 2 ml of dichloromethane. 7 mg (0.042 mmol) of 2-chloro-1,3-dimethylimidazonium chloride and 8 mg (0.043 mmol) of 2,4-dichlorobenzoic acid and then 0.012 ml (0.084 mmol) of triethylamine were added to the obtained solution, and they were stirred overnight. The solvent was evaporated, and the obtained crude product was treated in the same manner as in step 3 in Example 1 to obtain the title compound.

Yield: 16 mg (0.026 mmol) (73%)

MS (ESI, m/z) 509(MH+)

H-NMR (DMSO-d6) δ 1.02–1.23 (2H, m), 1.58–1.72 (2H, m), 1.83–2.02 (1H, m), 3.00–3.17 (2H, m), 3.78–3.93 (2H, m), 4.01–4.18 (2H, m), 4.21 (2H, br), 4.58 (2H, br), 7.12 (2H, d), 7.22–7.81 (7H, m), 8.16 (2H, d)

Example 76

Synthesis of 4-(4-chloro-2-hydroxybenzoyl)-1-[1-(4-pyridyl)-4-piperidylmethyl]-1,3,4,5-tetrahydrobenzo[e][1,4]diazepin-2-on trifluoroacetate 20 mg (0.035 mmol) of 1-[1-(4-pyridyl)-4-piperidylmethyl]-1,3,4,5-tetrahydrobenzo[e][1,4]diazepin-2-on bistrifluoroacetate was dissolved in 2 ml of dichloromethane. 7 mg (0.042 mmol) of 2-chloro-1,3-dimethylimidazonium chloride and 8 mg (0.043 mmol) of 4-chloro-2-hydroxybenzoic acid and then 0.012 ml (0.084 mmol) of triethylamine were added to the obtained solution, and they were stirred overnight. The solvent was evaporated, and the obtained crude product was treated in the same manner as in step 3 in Example 1 to obtain the title compound.

Yield: 16 mg (0.013 mmol) (35%)

MS (ESI, m/z) 491(MH+)

H-NMR (DMSO-d6) δ 1.02–1.23 (2H, m), 1.59–1.71 (2H, m), 1.83–2.00 (1H, m), 2.98–3.17 (2H, m), 3.78–3.96 (2H, m), 4.01–4.21 (4H, m), 4.56 (2H, br), 6.84–7.60 (7H, m), 7.12 (2H, d), 8.15 (2H, d)

Example 77

Synthesis of 4-(4-chloro-2-methoxybenzoyl)-1-[1-(4-pyridyl)-4-piperidylmethyl]-1,3,4,5-tetrahydrobenzo[e][1,4]diazepin-2-on trifluoroacetate 20 mg (0.035 mmol) of 1-[1-(4-pyridyl)-4-piperidylmethyl]-1,3,4,5-tetrahydrobenzo[e][1,4]diazepin-2-on bistrifluoroacetate was dissolved in 2 ml of dichloromethane. 7 mg (0.042 mmol) of 2-chloro-1,3-dimethylimidazonium chloride and 8 mg (0.043 mmol) of 4-chloro-2-methoxybenzoic acid and then 0.012 ml (0.084 mmol) of triethylamine were added to the obtained solution, and they were stirred overnight. The solvent was evaporated, and the obtained crude product was treated in the same manner as in step 3 in Example 1 to obtain the title compound.

Yield: 4.9 mg (0.008 mmol) (23%)
MS (ESI, m/z) 505(MH+)
H-NMR (DMSO-d6) δ 1.05–1.23 (2H, m), 1.58–1.71 (2H, m), 1.83–2.02 (1H, m), 2.99–3.17 (2H, m), 3.88 (3H, s), 3.98–4.56 (8H, m), 7.11–7.60 (9H, m), 8.16 (2H, d)

Example 78

Synthesis of 4-(4-chloro-2-nitrobenzoyl)-1-[1-(4-pyridyl)-4-piperidylmethyl]-1,3,4,5-tetrahydrobenzo[e][1,4]diazepin-2-on trifluoroacetate 20 mg (0.035 mmol) of 1-[1-(4-pyridyl)-4-piperidylmethyl]-1,3,4,5-tetrahydrobenzo[e][1,4]diazepin-2-on bistrifluoroacetate was dissolved in 2 ml of dichloromethane. 7 mg (0.042 mmol) of 2-chloro-1,3-dimethylimidazonium chloride and 8 mg (0.043 mmol) of 4-chloro-2-nitrobenzoic acid and then 0.012 ml (0.084 mmol) of triethylamine were added to the obtained solution, and they were stirred overnight. The solvent was evaporated, and the obtained crude product was treated in the same manner as in step 3 in Example 1 to obtain the title compound.

Yield: 17 mg (0.027 mmol) (77%)
MS (ESI, m/z) 520(MH+)
H-NMR (DMSO-d6) δ 1.03–1.24 (2H, m), 1.58–1.78 (2H, m), 1.85–2.03 (1H, m), 2.98–3.19 (2H, m), 3.78–4.37 (6H, m), 4.63 (2H, br), 7.12 (2H, d), 7.19–7.62 (4H, m), 7.93–8.03 (1H, m), 8.16 (2H, d), 8.36 (1H, d)

Example 79

Synthesis of 4-(4-chloro-2-aminobenzoyl)-1-[1-(4-pyridyl)-4-piperidylmethyl]-1,3,4,5-tetrahydrobenzo[e][1,4]diazepin-2-on di(tri-fluoroacetate)

10 mg (0.016 mmol) of 4-(4-chloro-2-aminobenzoyl)-1-[1-(4-pyridyl)-4-piperidylmethyl -1,3,4,5-tetrahydrobenzo[e][1,4]diazepin-2-on trifluoroacetate was dissolved in 5 ml of ethanol. 10 mg of palladium/carbon was added to the obtained solution, and they were stirred in the presence of hydrogen at room temperature for 5 hours. The reaction solution was filtered through Celite. The solvent was evaporated and the obtained crude product was treated in the same manner as in step 3 in Example 1 to obtain the title compound.

Yield: 1.5 mg (0.002 mmol) (16%)
MS (ESI, m/z) 490(MH+)
H-NMR (DMSO-d6) δ 1.03–1.23 (2H, m), 1.59–1.71 (2H, m), 1.83–2.06 (1H, m), 2.98–3.18 (2H, m), 3.84 (4H, br), 4.08–4.21 (2H, m), 4.53 (2H, br), 6.58 (1H, d), 6.79 (1H, br), 7.09 (1H, br), 7.12 (2H, d), 7.23 (1H, br), 7.38–7.59 (3H, m), 8.16 (2H, d)

Example 80

Synthesis of 1-[4-(2,5-dihydro-1H-pyrrol-1-ylcarbonyl)benzyl]-4-(4-aminobenzoyl)-1,3,4,5-tetrahydrobenzo[e][1,4]-diazepin-2-on trifluoroacetate Step 1: Synthesis of 1-[4-(2,5-dihydro-1H-pyrrol-1-ylcarbonyl)benzyl]-1,3,4,5-tetrahydrobenzo[e][1,4]diazepin-2-on hydrochloride 2.0 g (8.47 mmol) of ethyl (2-nitrobenzyl)aminoacetate was dissolved in 20 ml of dichloromethane. 2.7 g (12.6 mmol) of di-t-butyl dicarbonate and 2.4 ml (16.9 mmol) of triethylamine were added to the obtained solution, and they were stirred at room temperature overnight. After the treatment with dichloromethane as the extracting solvent by an ordinary method, 200 mg of 10% palladium/carbon was added to the obtained crude product and they were stirred in the presence of hydrogen at room temperature for 5 hours. The reaction solution was filtered through Celite. The solvent was evaporated and the obtained crude product was dissolved in 20 ml of dichloromethane. 670 mg (3.29 mmol) of 4-(2,5-dihydro-1H-pyrrol-1-ylcarbonyl)benzaldehyde and 0.29 ml (5.1 mmol) of acetic acid were added to the obtained solution, and they were stirred at room temperature for 30 minutes. 1.3 g (6.3 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 2 ml of 1 N sodium hydroxide and 4 ml of ethanol, and the obtained solution was stirred at room temperature for 5 hours. After the treatment with ethyl acetate as the extracting solvent by an ordinary method, the obtained crude product was dissolved in 10 ml of dichloromethane. 78 mg (3.29 mmol) of 2-chloro-1,3-dimethylimidazonium chloride and 0.71 ml (5.1 mmol) of triethylamine were added to the obtained solution, and they were stirred overnight. After the treatment with dichloromethane as the extracting solvent by an ordinary method, the obtained crude product was dissolved in 5 ml of 4N solution of hydrogen chloride in dioxane, and the obtained solution was stirred at room temperature for 3 hours. The solvent was evaporated to obtain the crude title compound.

Yield: 60 mg

Step 2: Synthesis of 1-[4-(2,5-dihydro-1H-pyrrol-1-ylcarbonyl)benzyl]-4-(4-aminobenzoyl)-1,3,4,5-tetrahydrobenzo[e][1,4]diazepin-2-on trifluoroacetate 8 mg (0.021 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 4 mg (0.025 mmol) of 2-chloro-1,3-dimethylimidazonium chloride and 3 mg (0.025 mmol) of 4-aminobenzoic acid and then 0.006 ml (0.042 mmol) of triethylamine were added to the obtained solution, and they were stirred overnight. The solvent was evaporated, and the obtained crude product was treated in the same manner as in step 3 in Example 1 to obtain the title compound.

Yield: 3 mg (0.005 mmol) (25%)
MS (ESI, m/z) 467(MH+)
H-NMR (DMSO-d6) δ 3.88 (2H, br), 4.11 (2H, br), 4.22 (2H, br), 4.44 (2H, br), 5.13 (2H, br), 5.81 (1H, br), 5.92 (1H, br), 7.18–7.63 (12H, m)

Example 81

Synthesis of 1-[4-(2.5-dihydro-1H-pyrrol-1-ylcarbonyl)benzyl]-4-(4-methylaminobenzoyl]-1,3,4,5-tetrahydrobenzo[e][1,4]diazepin-2-on trifluoroacetate 8 mg (0.02 1 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 4 mg (0.025 mmol) of 2-chloro-1,3-dimethylimidazonium chloride and 4 mg (0.025 mmol) of 4-methylaminobenzoic acid and then 0.006 ml (0.042 mmol) of triethylamine were added to the obtained solution, and they were stirred overnight. The solvent was evaporated, and the obtained crude product was treated in the same manner as in step 3 in Example 1 to obtain the title compound.

Yield: 3.4 mg (0.006 mmol) (29%)
MS (ESI, m/z) 481(MH+)
H-NMR (DMSO-d6) δ 3.58 (3H, s), 4.11 (2H, br), 4.22 (2H, br), 4.62 (2H, br), 5.13 (2H, br), 5.79 (1H, br), 5.91 (1H, br), 7.22–7.58 (12H, m), 8.23 (1H, br)

Example 82

Synthesis of 1-[4-(2,5-dihydro-1H-pyrrol-1-ylcarbonyl)benzyl]-4-(1H-benzimidazol-5-ylcarbonyl)-1,3,4,5-tetrahydro-benzo[e][1,4]diazepin-2-on trifluoroacetate 8 mg (0.021 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 4 mg (0.02 5 mmol) of 2-chloro-1,3-dimethylimidazonium chloride and 4 mg (0.025 mmol) of benzimidazole-5-carboxylic acid and then 0.006 ml (0.042 mmol) of triethylamine were added to the obtained solution, and they were stirred overnight. The solvent was evaporated, and the obtained crude product was treated in the same manner as in step 3 in Example 1 to obtain the title compound.

Yield: 5.3 mg (0.009 mmol) (36%)

MS (ESI, m/z) 492(MH+)

H-NMR (DMSO-d6) δ 3.98 (2H, br), 4.12 (2H, br), 4.24 (2H, br), 4.58 (2H, br), 5.14 (2H, br), 5.79 (1H, br), 5.91 (1H, br), 7.22–8.00 (11H, m), 9.27 (1H, s)

Example 83

Synthesis of 1-[4-(2,5-dihydro-1H-pyrrol-1-ylcarbonyl)benzyl]-4-(3-aminobenzoyl)-1,3,4,5-tetrahydrobenzo-[e][1,4-diazepin-2-on trifluoroacetate 24 mg (0.063 mmol) of 1-4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 12 mg (0.075 mmol) of 2-chloro-1,3-dimethylimidazonium chloride and 12 mg (0.075 mmol) of 3-aminobenzoic acid and then 0.018 ml (0.146 mmol) of triethylamine were added to the obtained solution, and they were stirred overnight. The solvent was evaporated, and the obtained crude product was treated in the same manner as in step 3 in Example 1 to obtain the title compound.

Yield: 20 mg (0.034 mmol) (55%)

MS (ESI, m/z) 467(MH+)

H-NMR (DMSO-d6) δ 3.88 (2H, br), 4.11 (2H, br), 4.22 (2H, br), 4.44 (2H, br), 5.13 (2H, br), 5.81 (1H, br), 5.92 (1H, br), 7.22–7.63 (12H, m)

Example 84

Synthesis of 1-[4-(2,5-dihydro-1H-pyrrol-1-ylcarbonyl)benzyl]-4-(3-aminomethylbenzoyl)-1,3,4,5-tetrahydrobenzo[e][1,4-diazepin-2-on trifluoroacetate 16 mg (0.042 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 8 mg (0.050 mmol) of 2-chloro-1,3-dimethylimidazonium chloride and 10 mg (0.050 mmol) of 3-t-butoxycarbonylaminomethylbenzoic acid and then 0.012 ml (0.084 mmol) of triethylamine were added to the obtained solution, and they were stirred overnight. The solvent was evaporated, and 5 ml of 4N solution of hydrogen chloride in dioxane was added to the obtained crude product, and they were stirred at room temperature for 2 hours. The solvent was evaporated and the obtained crude product was treated in the same maimer as in step 3 in Example 1 to obtain the title compound.

Yield: 8.2 mg (0.014 mmol) (33%)

MS (ESI, m/z) 481(MH+)

H-NMR (DMSO-d6) δ 3.98 (2H, br), 4.12 (4H, br), 4.24 (2H, br), 4.44 (2H, br), 5.16 (2H, br), 5.80 (1H, br), 5.92 (1H, br), 7.18–7.63 (12H, m), 8.18 (2H, br)

Example 85

Synthesis of 1-[4-(2,5-dihydro-1H-pyrrol-1-ylcarbonyl)benzyl]-4-(4-aminomethylbenzoyl)-1,3,4,5-tetrahydrobenzo[e][1,4]-diazepin-2-on trifluoroacetate 16 mg (0.042 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 8 mg (0.050 mmol) of 2-chloro-1,3-dimethylimidazonium chloride and 10 mg (0.050 mmol) of 4-t-butoxycarbonylaminomethylbenzoic acid and then 0.012 ml (0.084 mmol) of triethylamine were added to the obtained solution, and they were stirred overnight. The solvent was evaporated, and 5 ml of 4N solution of hydrogen chloride in dioxane was added to the obtained crude product, and they were stirred at room temperature for 2 hours. The solvent was evaporated and the obtained crude product was treated in the same manner as in step 3 in Example 1 to obtain the title compound.

Yield: 8.2 mg (0.014 mmol) (33%)

MS (ESI, m/z) 481(MH+)

H-NMR (DMSO-d6) δ 3.91 (2H, br), 4.12 (4H, br), 4.24 (2H, br), 4.41 (2H, br), 5.16 (2H, br), 5.80 (1H, br), 5.92 (1H, br), 7.18–7.63 (12H, m), 8.21 (2H, br)

Example 86

Synthesis of 1-[4-(2,5-dihydro-1H-pyrrol-1-ylcarbonyl)benzyl]-4-(1H-indol-5-ylcarbonyl)-1,3,4,5-tetrahydrobenzo[e][1,4]diazepin-2-on trifluoroacetate 8 mg (0.021 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 4 mg (0.025 mmol) of 2-chloro-1,3-dimethylimidazonium chloride and 5 mg (0.025 mmol) of 5-indolecarboxylic acid and then 0.006 ml (0.042 mmol) of triethylamine were added to the obtained solution, and they were stirred overnight. The solvent was evaporated and the obtained crude product was treated in the same manner as in step 3 in Example 1 to obtain the title compound.

Yield: 6.2 mg (0.011 mmol) (52%)

MS (ESI, m/z) 491(MH+)

H-NMR (DMSO-d6) δ 4.05 (2H, br), 4.13 (2H, br), 4.24 (2H, br), 4.47 (2H, br), 5.13 (2H, br), 5.80 (1H, br), 5.92 (1H, br), 7.18–7.63 (12H, m)

Example 87

Synthesis of 1-[4-(2,5-dihydro-1H-pyrrol-1-ylcarbonyl)benzyl]-4-(1H-indol-6-ylcarbonyl)-1,3,4,5-tetrahydrobenzo[e][1,4]diazepin-2-on trifluoroacetate 8 mg (0.021 mmol) of 1-[4-(2,5-dihydro-1H-pyrrol-1-ylcarbonyl)benzyl]-1,3,4,5-tetrahydrobenzo[e][1,4]diazepin-2-on hydrochloride was dissolved in 2 ml of dichloromethane. 4 mg (0.025 mmol) of 2-chloro-1,3-dimethylimidazonium chloride and 5 mg (0.025 mmol) of 6-indolecarboxylic acid and then 0.006 ml (0.042 mmol) of triethylamine were added to the obtained solution, and they were stirred overnight. The solvent was evaporated and the obtained crude product was treated in the same manner as in step 3 in Example 1 to obtain the title compound.

Yield: 5.5 mg (0.011 mmol) (52%)

MS (ESI, m/z) 491(MH+)

H-NMR (DMSO-d6) δ 3.98 (2H, br), 4.12 (2H, br), 4.24 (2H, br), 4.47 (2H, br), 5.13 (2H, br), 5.80 (1H, br), 5.92 (1H, br), 7.08–7.88 (12H, m)

Example 88
Synthesis of 1-[4-(2,5-dihydro-1H-pyrrol-1-ylcarbonyl)benzyl]-4-(3-amino-4-chlorobenzoyl)-1,3,4,5-tetrahydrobenzo[e][1,4]-diazepin-2-on trifluoroacetate 8 mg (0.021 mmol) of 1-[4-(2,5-dihydro-1H-pyrrol-1-ylcarbonyl)benzyl]-1,3,4,5-tetrahydrobenzo-[e][1,4]diazepin-2-on monohydrochloride was dissolved in 2 ml of dichloromethane. 4 mg (0.025 mmol) of 2-chloro-1,3-dimethylimidazonium chloride and 5 mg (0.025 mmol) of 3-amino-4-chlorobenzoic acid and then 0.006 ml (0.042 mmol) of triethylamine were added to the obtained solution, and they were stirred overnight. The solvent was evaporated and the obtained crude product was treated in the same manner as in step 3 in Example 1 to obtain the title compound.

Yield: 4.3 mg (0.007 mmol) (33%)
MS (ESI, m/z) 501(MH+)
H-NMR (DMSO-d6) δ 3.93 (2H, br), 4.12 (2H, br), 4.24 (2H, br), 4.48 (2H, br), 5.12 (2H, br), 5.80 (1H, br), 5.91 (1H, br), 7.21–7.83 (13H, m)

Example 89
Synthesis of ethyl 3-[4-(4-chlorobenzoyl)-2-oxo-1-(4-(1-(1-acetimidoyl)-4-piperidyloxy)benzyl)-2,3,4,5-tetrahydro-1H-benzo[e][1,4]-diazepin-8-yl]propionate mono(trifluoroacetate)

7 mg (0.010 mmol) of 3-[4-(4-chlorobenzoyl)-2-oxo-1-(4-(1-(1-acetimidoyl)-4-piperidyloxy)benzyl)-2,3,4,5-tetrahydro-1H-benzo[e][1,4]-diazepin-8-yl]propionic acid trifluoroacetate was dissolved in 2 ml of dichloromethane. 4 mg (0.025 mmol) of 2-chloro-1,3-dimethylimidazonium chloride and 5 mg (0.025 mmol) of ethanol and then 0.006 ml (0.042 mmol) of triethylamine were added to the obtained solution, and they were stirred overnight. The solvent was evaporated and the obtained crude product was treated in the same manner as in step 3 in Example 1 to obtain the title compound.

Yield: 3.4 mg (0.005 mmol) (50%)
MS (ESI, m/z) 631(MH+)
H-NMR (DMSO-d6) δ 1.13 (3H, t), 1.58–1.78 (2H, m), 1.87–2.04 (2H, m), 2.10 (3H, s), 2.57–2.66 (2H, m), 2.80–2.93 (2H, m), 3.68 (2H, br), 3.78–4.04 (4H, m), 4.19–4.37 (2H, m), 4.56–4.63 (1H, m), 5.03 (2H, br), 6.87 (2H, d), 7.03–7.60 (10H, m)

Example 90
Synthesis of 8-(3-hydroxypropyl)-1-[4-(2,5-dihydro-1H-pyrrol-1-ylcarbonyl)benzyl]-4-4-chlorobenzoyl)-1,3,4,5-tetrahydrobenzo[e][1,4]-diazepin-2-on 160 mg (0.297 mmol) of 3-[4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]diazepin-8-yl]propionic acid was dissolved in 10 ml of THF. 0.062 ml (0.045 mmol) of triethylamine and 0.033 ml (0.34 mmol) of ethyl chloroformate were added to the obtained solution under cooling with ice, and they were stirred for 30 minutes. A piece of ice was added to the obtained mixture, and then 24 mg (0.6 mmol) of sodium borohydride was added thereto. The temperature was elevated to room temperature, and the obtained mixture was stirred overnight. The solvent was evaporated and the obtained crude product was treated in the same manner as in step 3 in Example 1 to obtain the title compound.

Yield: 19 mg (0.035 mmol) (11%)
MS (ESI, m/z) 544(MH+)
H-NMR (DMSO-d6) δ 1.64 (2H, br), 2.60 (2H, br), 3.35 (2H, br), 3.83 (2H, br), 4.11 (2H, br), 4.23 (2H, br), 4.40 (2H, br), 5.16 (2H, br), 5.80 (1H, br), 5.92 (1H, br), 6.98–7.63 (1H, m)

Example 91
Synthesis of 8-(3-dimethylaminopropyl)-1-[4-(2,5-dihydro-1H-pyrrol-1-ylcarbonyl)benzyl[-4-(4-chlorobenzoyl)-1,3,4,5-tetrahydro-benzo[e][1,4]diazepin-2-on trifluoroacetate Step 1: Synthesis of 8-methanesulfonyloxypropyl-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on 150 mg (0.27 mmol) of 8-hydroxypropyl-1-[4-(2,5-dihydro-1H-pyrrol-1-ylcarbonyl)benzyl]-4-(4-chlorobenzoyl)-1,3,4,5-tetrahydro-benzo[e][1,4]diazepin-5-on was dissolved in 5 ml of dichloromethane. 0.056 ml (0.41 mmol) of triethylamine and 0.026 ml (0.33 mmol) of methanesulfonyl chloride were added to the obtained solution under cooling with ice, and they were stirred for 2 hours. After the treatment with dichloromethane as the extracting solvent by an ordinary method, the crude product was obtained.

Step 2 Synthesis of 8-(3-dimethylaminopropyl)-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on trifluoroacetate ⅓ of the crude product obtained in step 1 was dissolved in 5 ml of acetonitrile. 25 mg (0.18 mmol) of potassium carbonate and 0.007 ml (0.014 mmol) of 1 mol/l dimethylamine were added to the obtained solution, and they were stirred at 60° C. overnight. The solvent was evaporated and the obtained crude product was treated in the same manner as in step 3 in Example 1 to obtain the title compound.

Yield: 6 mg (0.009 mmol) (10%)
MS (ESI, m/z) 571(MH+)
H-NMR (DMSO-d6) δ 1.84 (2H, br), 2.60 (2H, br), 2.74 (3H, s), 2.75 (3H, s), 3.01 (2H, br), 3.87 (2H, br), 4.11 (2H, br), 4.23 (2H, br), 4.40 (2H, br), 5.17 (2H, br), 5.80 (1H, br), 5.92 (1H, br), 7.02–7.63 (11H, m)

Example 92
Synthesis of 8-(3-pyrrolidin-1-ylpropyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on trifluoroacetate 40 mg (0.09 mmol) of 8-(3-hydroxypropyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on was dissolved in 5 ml of dichloromethane. 0.019 ml (0.135 mmol) of triethylamine and 0.01 ml (0.11 mmol) of methanesulfonyl chloride were added to the obtained solution under cooling with ice, and they were stirred for 2 hours. After the treatment with dichloromethane as the extracting solvent by an ordinary method, the obtained crude product was dissolved in 5 ml of acetonitrile. 25 mg (0.18 mmol) of potassium carbonate and 0.011 ml (0.14 mmol) of pyrrolidine were added to the obtained solution, and they were stirred at 60° C. overnight. The solvent was evaporated, an the obtained crude product was treated in the same manner as in step 3 in Example 1 to obtain the title compound.

Yield: 4 mg (0.059 mmol) (6%)
MS (ESI, m/z) 597(MH+)
H-NMR (DMSO-d6) δ 1.78–2.01 (6H, m), 2.63 (2H, br), 2.84–3.07 (6H, m), 3.87 (2H, br), 4.12 (2H, br), 4.24 (2H, br), 4.41 (2H, br), 5.14 (2H, br), 5.81 (1H, br), 5.92 (1H, br), 7.00–7.63 (11H, m)

Example 93
Synthesis of 8-(3-piperidin-1-yl-propyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on trifluoroacetate ⅓ of the crude product obtained in step 1 in Example 91 was dissolved in 5 ml of acetonitrile. 25 mg (0.18 mmol) of potassium carbonate and 0.01 ml (0.011 mmol) of piperidine were added to the obtained solution, and they were stirred at 60° C. overnight. The solvent was evaporated and the obtained crude product was treated in the same manner as in step 3 in Example 1 to obtain the title compound.

Yield: 4 mg (0.006 mmol) (7%)
MS (ESI, m/z) 611(MH+)
H-NMR (DMSO-d6) δ 1.78–2.01 (8H, m), 2.61 (2H, br), 2.71–3.01 (6H, m), 3.87 (2H, br), 4.12 (2H, br), 4.24 (2H, br), 4.42 (2H, br), 5.17 (2H, br), 5.81 (1H, br), 5.92 (1H, br), 7.00–7.63 (11H, m)

Example 94

Synthesis of 8-(3-(morpholin-4-yl)-propyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on trifluoroacetate ⅓ of the crude product obtained in step 1 in Example 91 was dissolved in 5 ml of acetonitrile. 25 mg (0.18 mmol) of potassium carbonate and 0.01 ml (0.011 mmol) of morpholine were added to the obtained solution, and they were stirred at 60° C. overnight. The solvent was evaporated and the obtained crude product was treated in the same manner as in step 3 in Example 1 to obtain the title compound.

Yield: 4 mg (0.006 mmol) (7%)
MS (ESI, m/z) 611(MH+)
H-NMR (DMSO-d6) δ 1.88 (2H, br), 2.61 (2H, br), 3.03 (6H, m), 3.61 (2H, br), 3.95 (4H, br), 4.12 (2H, br), 4.23 (2H, br), 4.42 (2H, br), 5.14 (2H, br), 5.81 (1H, br), 5.92 (1H, br), 7.02–7.63 (11H, m)

Example 95

Synthesis of 8-hydroxymethyl-1-[4-(2,5-dihydro-1H-pyrrol-1-ylcarbonyl)benzyl]-4-(4-chlorobenzoyl)-1,3,4,5-tetrahydrobenzo[e][1,4]-diazepin-2-on trifluoroacetate 280 mg (0.53 mmol) of 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylic acid was dissolved in 5 ml of THF. 0.12 ml (0.80 mmol) of triethylamine and 0.06 ml (0.63 mmol) of ethyl chloroformate were added to the obtained solution under cooling with ice, and they were stirred for 30 minutes. A piece of ice was added to the obtained mixture, and then 40 mg (1.1 mmol) of sodium borohydride was added thereto. The temperature was elevated to room temperature, and the obtained mixture was stirred overnight. The solvent was evaporated and the obtained crude product was treated in the same manner as in step 3 in Example 1 to obtain the title compound.

Yield: 7 mg (0.013 mmol) (2%)
MS (ESI, m/z) 516(MH+)
H-NMR (DMSO-d6) δ 3.83 (2H, br), 4.13 (2H, br), 4.24 (2H, br), 4.42 (2H, br), 4.49 (2H, br), 5.11 (2H, br), 5.81 (1H, br), 5.92 (1H, br), 7.05–7.63 (11H, m)

Example 96

Synthesis of 8-dimethylaminomethyl-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on trifluoroacetate Step 1: Synthesis of 8-hydroxymethyl-1-[4-(2,5-dihydro-1H-pyrrol-1-ylcarbonyl)benzyl]-4-(4-chlorobenzoyl)-1,3,4,5-tetrahydrobenzo[e][1,4]-diazepin-2-on 650 mg (1.22 mmol) of 4-(4-chlorobenzoyl)-2-oxo-1-[4-(1-pyrrolidinecarbonyl)benzyl]-2,3,4,5-tetrahydro-1H-benzo[e][1,4]-diazepine-8-carboxylic acid was dissolved in 50 ml of THF. 0.42 ml (2.4 mmol) of triethylamine and 0.15 ml (0.63 mmol) of ethyl chloroformate were added to the obtained solution under cooling with ice, and they were stirred for 30 minutes. A piece of ice was added to the obtained mixture, and then 92 mg (1.1 mmol) of sodium borohydride was added thereto. The temperature was elevated to room temperature, and the obtained mixture was stirred overnight. After the treatment with ethyl acetate as the extracting solvent, the title compound was obtained.

Yield: 450 mg (0.87 mmol)

Step 2: Synthesis of 8-methanesulfonyloxymethyl-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on 450 mg (0.87 mmol) of 8-hydroxymethyl-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on was dissolved in 5 ml of dichloromethane. 0.18 ml (1.31 mmol) of triethylamine and 0.08 1 ml (1.05 mmol) of methanesulfonyl chloride were added to the obtained solution under cooling with ice, and the obtained mixture was stirred for 2 hours. After the treatment with dichloromethane as the extracting solvent by an ordinary method, the crude product was obtained.

Step 3: Synthesis of 8-dimethylaminomethyl-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on trifluoroacetate ⅐ of the crude product obtained in step 2 was dissolved in 5 ml of acetonitrile. 50 mg (0.36 mmol) of potassium carbonate and 0.14 ml (0.14 mmol) of 1 mol/l dimethylamine were added to the obtained solution, and they were stirred at room temperature overnight. The solvent was evaporated and the obtained crude product was treated in the same manner as in step 3 in Example 1 to obtain the title compound.

Yield: 5.7 mg (0.0087 mmol) (5%)
MS (ESI, m/z) 543(MH+)
H-NMR (DMSO-d6) δ 2.48 (3H, s), 2.49 (3H, br), 3.83 (2H, r) 4.13 (2H, br), 4.24 (2H, br), 4.27 (2H, br), 4.45 (2H, br), 5.15 (2H, br), 5.81 (1H, br), 5.92 (1H, br), 7.18–7.63 (11H, m)

Example 97

Synthesis of 8-(pyrrolidin-1-yl-methyl)-1-[4-(2,5-dihydro-1H-pyrrol-1-ylcarbonyl)benzyl]-4-(4-chlorobenzoyl-1,3,4,5-tetrahydro-benzo[e][1,4]diazepin-2-on trifluoroacetate ⅐ of the crude product obtained in step 2 in Example 96 was dissolved in 5 ml of acetonitrile. 50 mg (0.36 mmol) of potassium carbonate and 0.011 ml (0.14 mmol) of pyrrolidine were added to the obtained solution, and they were stirred at room temperature overnight. The solvent was evaporated and the obtained crude product was treated in the same manner as in step 3 in Example 1 to obtain the title compound.

Yield: 25 mg (0.037 mmol) (21%)
MS (ESI, m/z) 569(MH+)
H-NMR (DMSO-d6) δ 1.82 (2H, br), 2.03 (2H, br), 3.04 (2H, br),3.23 (2H, br), 3.87 (2H, br), 4.11 (2H, br), 4.23 (2H, br), 4.26 (2H, br), 4.42 (2H, br), 5.17 (2H, br), 5.81 (1H, br), 5.92 (1H, br), 7.21–7.66 (11H, m)

Example 98

Synthesis of 8-(piperidin-1-yl-methyl)-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on trifluoroacetate ⅐ of the crude product obtained in step 2 in Example 96 was dissolved in 5 ml of acetonitrile. 50 mg (0.36 mmol) of potassium carbonate and 0.1 ml (0.11 mmol) of piperidine were added to the obtained solution, and they were stirred at room temperature overnight. The solvent was evaporated and the obtained crude product was treated in the same manner as in step 3 in Example 1 to obtain the title compound.

Yield: 27 mg (0.039 mmol) (22%)

MS (ESI, m/z) 583(MH+)

H-NMR (DMSO-d6) δ 1.53–1.81 (4H, br), 3.00 (4H, br), 3.21 (2H, br), 3.87 (2H, br), 4.10 (2H, br), 4.23 (2H, br), 4.26 (2H, br), 4.44 (2H, br), 5.17 (2H, br), 5.81 (1H, br), 5.92 (1H, br), 7.21–7.69 (11H, m)

Example 99

Synthesis of 8-(morpholine-1-yl-methyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on mono (trifluoroacetate)

⅓ of the crude product obtained in step 2 in Example 96 was dissolved in 5 ml of acetonitrile. 50 mg (0.36 mmol) of potassium carbonate and 0.1 ml (0.11 mmol) of morpholine were added to the obtained solution, and they were stirred at room temperature overnight. The solvent was evaporated and the obtained crude product was treated in the same manner as in step 3 in Example 1 to obtain the title compound.

Yield: 16 mg (0.023 mmol) (13%)

MS (ESI, m/z) 585(MH+)

H-NMR (DMSO-d6) δ 2.73 (2H, br), 3.16 (2H, br), 3.81 (2H, br), 4.11 (2H, br), 4.24 (2H, br), 4.40 (2H, br), 4.44 (2H, br), 5.17 (2H, br), 5.81 (1H, br), 5.92 (1H, br), 7.17–7.61 (11H, m)

Example 100

Synthesis of 8-(4-piperazin-1-yl-methyl)-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on di(trifluoroacetate)

⅔ of the crude product obtained in step 2 in Example 96 was dissolved in 5 ml of acetonitrile. 50 mg (0.36 mmol) of potassium carbonate and 22 mg (0.11 mmol) of tert-butylpiperazine carboxylate were added to the obtained solution, and they were stirred at room temperature overnight. The solvent was evaporated and the obtained crude product was dissolved in 5 ml of 4N solution of hydrogen chloride in dioxane and the obtained solution was stirred at room temperature for 3 hours. The solvent was evaporated) and the obtained crude product was treated in the same manner as in step 3 in Example 1 to obtain the title compound.

Yield: 36 mg (0.043 mmol) (12%)

MS (ESI, m/z) 584(MH+)

H-NMR (DMSO-d6) δ 2.77 (4H, br), 3.16 (4H, br), 3.82 (2H, br), 4.11 (2H, br), 4.24 (2H, br), 4.43 (2H, br), 5.18 (2H, br), 5.80 (1H, br), 5.91 (1H, br), 7.18–7.61 (11H, br), 8.82 (1H, br)

Example 101

Synthesis of 8-[(4-methyl-1-piperazinyl)methyl]-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on di(trifluoroacetate)

10 mg (0.014 mmol) of 8-(4-piperazin-1-yl-methyl)-1-[4-(2,5-dihydro-1H-pyrrol-1-ylcarbonyl)benzyl]4-(4-chlorobenzoyl)-1,3,4,5-tetra-hydrobenzo[e][1,4]diazepin-2-on di(trifluoroacetate) was dissolved in 5 ml of dichloromethane. 5 mg of paraformaldehyde and 0.005 ml (0.09 mmol) of acetic acid were added to the obtained solution, and they were stirred at room temperature for 30 minutes. 24 mg (0.12 mmol) of sodium triacetoxyborohydride was added to the obtained mixture, and they were stirred at room temperature overnight. The solvent was evaporated, and the obtained crude product was treated in the same manner as in step 3 in Example 1 to obtain the title compound.

Yield: 3 mg (0.004 mmol) (26%)

MS (ESI, m/z) 598(MH+)

H-NMR (DMSO-d6) δ 2.32 (2H, br), 2.77 (3H, s), 2.88 (2H, br), 3.38 (2H, br), 3.60 (2H, br), 3.88 (2H, br), 4.12 (2H, br), 4.24 (2H, br), 4.43 (2H, br), 5.17 (2H, br), 5.82 (1H, br), 5.91 (1H, br), 7.18–7.61 (11H, m)

Example 102

Synthesis of 8-[(4-isopropyl-1-piperazinyl)methyl]-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on bistrifluoroacetate 10 mg (0.014 mmol) of 8-(4-piperazin-1-yl-methyl)-1-[4-(2,5-dihydro-1H-pyrrol-1-ylcarbonyl)benzyl]-4-(4-chlorobenzoyl)-1,3,4,5-tetrahydrobenzo[e][1,4]diazepin-2-on di(trifluoroacetate) was dissolved in 5 ml of dichloromethane. 0.01 ml of acetone and 0.005 ml (0.09 mmol) of acetic acid were added to the obtained solution, and they were stirred at room temperature for 30 minutes. 24 mg (0.12 mmol) of sodium triacetoxyborohydride was added to the obtained mixture, and they were stirred at room temperature overnight. The solvent was evaporated, and the obtained crude product was treated in the same manner as in step 3 in Example 1 to obtain the title compound.

Yield: 3 mg (0.003 mmol) (25%)

MS (ESI, m/z) 626(MH+)

H-NMR (DMSO-d6) δ 1.21 (3H, s), 1.23 (3H, s), 2.32 (2H, br), 2.88 (5H, br), 3.37 (2H, br), 3.60 (2H, br), 3.88 (2H, br), 4.12 (2H, br), 4.24 (2H, br), 4.43 (2H, br), 5.17 (2H, br), 5.82 (1H, br), 5.91 (1H, br), 7.18–7.51 (11H, m)

Example 104

Synthesis of 4-[(5-chloro-2-pyridinyl)carbonyl]-1-[4-(2,5-dihydro-1H-pyrrol-1-ylcarbonyl)benzyl]-1,3,4,5-tetrahydrobenzo[e][1,4]-diazepin-2-on trifluoroacetate Step 1: Synthesis of ethyl 5-chloropyridin-2-carboxylate 1.2 g (8.2 mmol) of 2,5-dichloropyridine was dissolved in 50 ml of acetonitrile. 1.46 g (9.7 mmol) of sodium iodide and 0.7 ml (9.7 mmol) of acetyl chloride were added to the obtained solution, and they were stirred at 50° C. overnight. After the treatment with ethyl acetate as the extracting solvent by an ordinary method, the obtained crude product was dissolved in 15 ml of DMF. 182 mg (0.8 mmol) of palladium acetate, 147 mg (0.56 mmol) of triphenylphosphine, 2.3 ml of ethanol and 1.3 ml (9.7 mmol) of triethylamine were added to the obtained solution, and they were stirred in the presence of carbon monoxide at 70° C. overnight. After the treatment with ethyl acetate as the extracting solvent by an ordinary method, the obtained crude product was purified by the silica gel column chromatography to obtain the title compound.

Yield: 250 mg (1.35 mmol) (16%)

H-NMR (CD3Cl) δ 1.44 (3H, t), 4.47 (2H, d), 7.82 (1H, dd), 8.09 (1H, d), 8.69 (1H, d)

Step 2: Synthesis of 5-chloropyridin-2-carboxylic acid hydrochloride 250 mg (1.35 mmol) of ethyl 5-chloropyridin-2-carboxylate was dissolved in 6 N hydrochloric acid, and the obtained solution was stirred at 70° C. for 2 hours. The solvent was evaporated to obtain the crude product.

Step 3: Synthesis of 4-[(5-chloro-2-pyridinyl)carbonyl]-1-[4-(2,5-dihydro-1H-pyrrol-1-ylcarbonyl)benzyl]-1,3,4,5-tetrahydrobenzo[e][1,4]-diazepin-2-on trifluoroacetate 20 mg (0.058 mmol) of 1-(4-(2,5-dihydro-1H-pyrrol-1-ylcarbonyl)benzyl]-1,3,4,5-tetrahydrobenzo[e][1,4]diazepin-2-on hydrochloride was dissolved in 5 ml of dichloromethane. 12 g (0.069 mmol) of 2-chloro-1,3-dimethylimidazonium chloride and 12 mg (0.069 mmol) of 5-chloropyridin-2-carboxylic acid hydrochloride and then 0.024 ml (0.174 mmol) of triethylamine were added to the obtained solution, and they were stirred overnight. The solvent was evaporated and the obtained crude product was treated in the same manner as in step 3 in Example 1 to obtain the title compound.

Yield: 4.3 mg (0.007 mmol) (10%)
MS (ESI, m/z) 487(MH+)
H-NMR (DMSO-d6) δ 4.02 (2H, br), 4.13 (2H, br), 4.24 (2H, br), 4.47 (2H, d), 5.13 (2H, d), 5.80 (1H, br), 5.92 (1H, br), 7.18–7.56 (7H, m), 7.76 (1H, dd), 8.11 (1H, dd), 8.63 (1H, dd)

Example 105
Synthesis of 4-(4-chlorobenzoyl)-1-[4-(N,N-dimethylamidino)benzyl]-1,3,4,5-tetrahydrobenzo[e][1,4]diazepin-2-on trifluoroacetate Step 1: Synthesis of 4-(4-chlorobenzoyl)-1-(4-cyanobenzyl)-1,3,4,5-tetrahydrobenzo[e][1,4]diazepin-2-on 230 mg (0.77 mmol) of 4-(4-chlorobenzoyl)-1,3,4,5-tetrahydrobenzo[e][1,4]diazepin-2-on was dissolved in 5 ml of DMF. 37 mg (0.92 mmol) of sodium hydride was added to the obtained solution, and they were stirred at room temperature for 30 minutes. 196 mg (1.00 mmol) of 4-cyanobenzyl bromide was added to the obtained mixture, and they were stirred at room temperature for 4 hours. After the treatment with ethyl acetate as the extracting solvent by an ordinary method, the obtained crude product was purified by the silica gel column chromatography to obtain the title compound.

Yield: 250 mg (0.60 mmol) (78%)

Step 2: Synthesis of 4-(4-chlorobenzoyl)-1-[4-(ethoxy(imino)methyl)-benzyl]-1,3,4,5-tetrahydrobenzo[e][1,4]diazepin-2-on hydrochloride 250 mg (0.60 mmol) of 4-(4-chlorobenzoyl)-1-[4-(cyanobenzyl)]-1,3,4,5-tetrahydrobenzo[e][1,4]diazepin-2-on was dissolved in a mixture of 5 ml of 4N solution of hydrogen chloride in dioxane and 1 ml of ethanol, and the obtained solution was stirred at room temperature for 2 days. The solvent was evaporated to obtain the crude product.

Step 3: Synthesis of 4-(4-chlorobenzoyl)-1-[4-(N,N-dimethylamidino)-benzyl]-1,3,4,5-tetrahydrobenzo[e][1,4]diazepin-2-on trifluoroacetate ⅕ of the crude product obtained in step 2 was dissolved in 1 ml of ethanol. 0.010 ml of dimethylamine was added to the obtained solution and they were stirred overnight. The solvent was evaporated and the obtained crude product was treated in the same manner as in step 3 in Example 1 to obtain the title compound.

Yield: 3.6 mg (0.006 mmol) (5%)
MS (ESI, m/z) 461(MH+)
H-NMR (DMSO-d6) δ 2.92 (3H, s), 3.17 (3H, s), 3.92 (2H, br), 4.47 (2H, br), 5.20 (2H, br), 7.16–7.63 (1H, m), 8.83 (1H, br), 9.22 (1H, br)

Example 106
Synthesis of 4-(4-chlorobenzoyl)-1-[4-(imino(1-pyrrolidinyl)methyl)benzyl]-1,3,4,5-tetrahydrobenzo[e][1,4]diazepin-2-on trifluoroacetate ⅕ of the crude product obtained in step 2 in Example 105 was dissolved in 1 ml of ethanol. 0.010 ml of pyrrolidine was added to the obtained solution and they were stirred overnight. The solvent was evaporated and the obtained crude product was treated in the same manner as in step 3 in Example 1 to obtain the title compound.

Yield: 8.2 mg (0.014 mmol) (11%)
MS (ESI, m/z) 487(MH+)
H-NMR (DMSO-d6) δ 1.83 (2H, dd), 2.00 (2H, dd), 3.31 (2H, dd), 3.48 (2H, dd), 3.92 (2H, br), 4.47 (2H, br), 5.18 (2H, br), 7.16–7.63 (1H, m), 8.72 (1H, br), 9.18 (1H, br)

Example 107
Synthesis of 4-(4-chlorobenzoyl)-1-[4-(2,5-dihydro-1H-pyrrol-1-yl(imino)methyl)benzyl]-1,3,4,5-tetrahydrobenzo[e][1,4]-diazepin-2-on trifluoroacetate ⅕ of the crude product obtained in step 2 in Example 105 was dissolved in 1 ml of ethanol. 0.010 ml of 3-pyrroline was added to the obtained solution and they were stirred overnight. The solvent was evaporated and the obtained crude product was treated in the same manner as in step 3 in Example 1 to obtain the title compound.

Yield: 6.2 mg (0.010 mmol) (9%)
MS (ESI, m/z) 485(MH+)
H-NMR (DMSO-d6) δ 3.92 (2H, br), 4.12 (2H, br), 4.33 (2H, br), 4.47 (2H, br), 5.19 (2H, br), 5.88 (1H, br), 6.03 (2H, br), 7.16–7.62 (1H, m), 8.90 (1H, br), 9.42 (1H, br)

Example 108
Synthesis of 4-(4-chlorobenzoyl)-1-[4-(imino(1-piperidinyl)methyl)benzyl]-1,3,4,5-tetrahydrobenzo[e][1,4]diazepin-2-on trifluoroacetate ⅕ of the crude product obtained in step 2 in Example 105 was dissolved in 1 ml of ethanol. 0.010 ml of piperidine was added to the obtained solution and they were stirred overnight. The solvent was evaporated and the obtained crude product was treated in the same manner as in step 3 in Example 1 to obtain the title compound.

Yield: 10.7 mg (0.017 mmol) (14%)
MS (ESI, m/z) 501(MH+)
H-NMR (DMSO-d6) δ 1.51 (2H, br), 1.63 (2H, br), 1.69 (2H, br), 3.22 (2H, br), 3.67 (2H, br), 3.91 (2H, br), 4.47 (2H, br), 5.18 (2H, br), 7.08–7.62 (11H, m), 9.03 (1H, br), 9.29 (1H, br)

Example 109
Synthesis of 4-(4-chlorobenzoyl)-1-[4-(imino(4-morpholinyl)methyl)benzyl]-1,3,4,5-tetrahydrobenzo[e][1,4]diazepin-2-on trifluoroacetate ⅕ of the crude product obtained in step 2 in Example 105 was dissolved in 1 ml of ethanol. 0.010 ml of morpholine was added to the obtained solution and they were stirred overnight. The solvent was evaporated and the obtained crude product was treated in the same manner as in step 3 in Example 1 to obtain the title compound.

Yield: 8.5 mg (0.014 mmol) (11%)
MS (ESI, m/z) 503(MH+)

Example 110
Synthesis of 8-amino-4-(4-chlorobenzoyl)-1-[4-(2,5-dihydro-1H-pyrrol-1-ylcarbonyl)benzyl]-1,3,4,5-tetrahydrobenzo[e][1,4]-diazepin-2-on trifluoroacetate 46 mg (0.10 mmol) of 4-(4-chlorobenzoyl)-2-oxo-1-4-(2,5-dihydro-1H-pyrrol-1-ylcarbonyl)benzyl]-2,3,4,5-tetrahydro-1H-benzo[e][1,4]-diazepine-8-carboxylic acid was dissolved in 5 ml of t-butyl alcohol. 29 mg (0.11 mmol) of diphenylphosphono azide and 0.028 ml (0.15 mmol) of triethylamine were added to the obtained solution and they were stirred at 70° C. overnight. The crude product obtained by the treatment with ethyl acetate as the extracting solvent was dissolved in 5 ml of 4N solution of hydrogen chloride in dioxane and the obtained solution was stirred at room temperature for 2 hours. The solvent was evaporated and the obtained crude product was treated in the same manner as in step 3 in Example 1 to obtain the title compound.

Yield: 15 mg (0.024 mmol) (24%)
MS (ESI, m/z) 501(MH+)
H-NMR (DMSO-d6) δ 3.98 (2H, br), 4.15 (2H, br), 4.25 (2H, br), 4.41 (2H, br), 5.03 (2H, br), 5.80 (1H, br), 5.92 (1H, br), 7.08–7.62 (11H, m)

Example 111
Synthesis of 8-(3-aminopropyl-4-(4-chlorobenzoyl-1-[4-(2,5-dihydro-1H-pyrrol-1-ylcarbonyl)benzyl]-1,3,4,5-tetrahydrobenzo[e][1,4]-diazepin-2-on trifluoroacetate 120 mg (0.22 mmol) of 8-(3-hydroxypropyl)-4-(4-chlorobenzoyl)-1-[4-(2,5-dihydro-1H-pyrrol-1-ylcarbonyl)benzyl]-1,3,4,5-tetrahydrobenzo[e][1,4]diazepin-2-on was dissolved in 10 ml of dichloromethane. 232 mg (0.88 mmol) of triphenylphosphine, 129 mg (0.88 mmol) of phthalimide and 382 mg (0.88 mmol) of diethylazo dicarboxylate were added to the obtained solution and they were stirred at room temperature overnight. The crude product obtained by the treatment with ethyl acetate as the extracting solvent was dissolved in a mixture of 0.1 ml of hydrazine and 5 ml of ethanol, and the obtained solution was stirred at 70° C. for 2 hours. The solvent was evaporated and the obtained crude product was treated in the same manner as in step 3 in Example 1 to obtain the title compound.

Yield: 23 mg (0.035 mmol) (16%)
MS (ESI, m/z) 543(MH+)
H-NMR (DMSO-d6) δ 1.82 (2H, br), 2.66 (2H, br), 3.86 (2H, br), 4.12 (2H, br), 4.23 (2H, br), 4.41 (2H, br), 5.16 (2H, br), 5.80 (1H, br), 5.91 (1H, br), 6.98–7.86 (11H, m)

Example 112
Synthesis of 4-(4-chlorobenzoyl)-1-[4-(2,5-dihydro-1H-pyrrol-1-ylcarbonyl)benzyl]-8-[3-oxo-3-(1-piperidinyl)propyl]-1,3,4,5-tetrahydrobenzo[e][1,4]diazepin-2-on 10 mg (0.018 mmol) of 3-[4-(4-chlorobenzoyl)-2-oxo-1-[4-(2,5-dihydro-1H-pyrrol-1-ylcarbonyl)benzyl]-2,3,4,5-tetrahydrobenzo-1H-benzo[e][1,4]diazepin-8-yl]propionic acid was dissolved in 2 ml of dichloromethane. 0.010 ml of piperidine, 4 mg (0.022 mmol) of 2-chloro-1,3-dimethylimidazonium chloride and 0.009 ml (0.066 mmol) of triethylamine were added to the obtained solution and they were stirred overnight. The solvent was evaporated and the obtained crude product was treated in the same manner as in step 3 in Example 1 to obtain the title compound.

Yield: 2.0 mg (0.0032 mmol) (20%)
MS (ESI, m/z) 625(MH+)
H-NMR (DMSO-d6) δ 1.41 (4H, br), 1.57 (2H, br), 2.58 (2H, br), 2.61 (4H, br), 3.31 (2H, br), 3.37 (2H, br), 3.84 (2H, br), 4.11 (2H, br), 4.23 (2H, br), 4.41 (2H, br), 5.16 (2H, br), 5.79 (1H, br), 5.91 (1H, br), 6.98–7.60 (11H, m)

Example 113
Synthesis of 4-(4-chlorobenzoyl)-1-4-(2,5-dihydro-1H-pyrrol-1-ylcarbonyl)benzyl]-8-[3-oxo-3-(1-piperazinyl)propyl]-1,3,4,5-tetrahydrobenzo[e][1,4]diazepin-2-on trifluoroacetate 60 mg (0.108 mmol) of 3-(4-(4-chlorobenzoyl)-2-oxo-1-[4-(2,5-dihydro-1H-pyrrol-ylcarbonyl)benzyl]-2,3,4,5-tetrahydrobenzo-1H-benzo[e][1,4]diazepin-8-yl]propionic acid was dissolved in 2 ml of dichloromethane. 13 mg (0.132 mmol) of t-butylpiperazine carboxylate, 24 mg (0.132 mmol) of 2-chloro-1,3-dimethylimidazonium chloride and 0.056 ml (0.264 mmol) of triethylamine were added to the obtained solution and they were stirred overnight. The solvent was evaporated and the obtained crude product was dissolved in 5 ml of 4N solution of hydrogen chloride in dioxane. The obtained solution was stirred for 2 hours. The solvent was evaporated and the obtained crude product was treated in the same manner as in step 3 in Example 1 to obtain the title compound.

Yield: 26 mg (0.036 mmol) (33%)
MS (ESI, m/z) 625(MH+)
H-NMR (DMSO-d6) δ 2.64 (2H, br), 2.82 (2H, br), 3.03 (2H, br), 3.97 (2H, br), 4.12 (2H, br), 4.24 (2H, br), 4.38 (2H, br), 5.13 (2H, br), 5.80 (1H, br), 5.91 (1H, br), 6.98–7.66 (11H, m), 8.88 (2H, br)

Example 114
Synthesis of 4-(4-chlorobenzoyl)-1-[4-(2,5-dihydro-1H-pyrrol-1-ylcarbonyl)benzyl]-8-[3-(4-methyl-1-piperazinyl)-3-oxopropyl]-1,3,4,5-tetrahydrobenzo[e][1,4]diazepin-2-on trifluoroacetate 10 mg (0.014 mmol) of 4-(4-chlorobenzoyl)-1-[4-(2,5-dihydro-1H-pyrrol-1-ylcarbonyl)benzyl]-8-[3-oxo-3-(1-piperazinyl)propyl]-1,3,4,5-tetrahydrobenzo[e][1,4]diazepin-2-on trifluoroacetate was dissolved in 2 ml of dichloromethane. 5 mg of paraformaldehyde and 0.005 ml (0.09 mmol) of acetic acid were added to the obtained solution and they were stirred at room temperature for 30 minutes. 24 mg (0.12 mmol) of sodium triacetoxyborohydride was added to the obtained mixture and they were stirred at room temperature overnight. The solvent was evaporated and the obtained crude product was treated in the same manner as in step 3 in Example 1 to obtain the title compound.

Yield: 1.2 mg (0.016 mmol) (11%)
MS (ESI, m/z) 641(MH+)
H-NMR (DMSO-d6) δ 2.61 (2H, br), 2.79 (2H, br), 3.23–3.60 (8H, br), 3.88 (2H, br), 4.18 (2H, br), 4.23 (2H, br), 4.40 (2H, br), 5.16 (2H, br), 5.79 (1H, br), 5.91 (1H, br), 6.98–7.60 (1111, m)

Example 115
Synthesis of 4-(4-chlorobenzoyl)-1-[4-(2,5-dihydro-1H-pyrrol-1-ylcarbonyl)benzyl]-8-[3-(4-isopropyl-1-piperazinyl)-3-oxo-propyl]-1,3,4,5-tetrahydrobenzo[e][1,4]diazepin-2-on trifluoroacetate 10 mg (0.014 mmol) of 4-(4-chlorobenzoyl)-1-[4-(2,5-dihydro-1H-pyrrol-1-ylcarbonyl)benzyl]-8-[3-oxo-3-(1-piperazinyl)propyl]-1,3,4,5-tetrahydrobenzobenzo[e][1,4]diazepin-2-on trifluoroacetate was dissolved in 2 ml of dichloromethane. 5 mg of acetone and 0.005 ml (0.09 mmol) of acetic acid were added to the obtained solution and they were stirred at room temperature for 30 minutes. 24 mg (0.12 mmol) of sodium triacetoxyborohydride was added to the obtained mixture and they were stirred at room temperature overnight. The solvent was evaporated and the obtained crude product was treated in the seine manner as in step 3 in Example 1 to obtain the title compound.

Yield: 5.1 mg (0.065 mmol) (47%)
MS (ESI, m/z) 668(MH+)
H-NMR (DMSO-d6) δ 1.20 (3H, s), 1.23 (3H, s), 2.62 (2H, br), 2.82 (5H, br), 3.21–3.67 (6H, br), 3.97 (2H, br), 4.14 (2H, br), 4.23 (2H, br), 4.43 (2H, br), 5.16 (2H, br), 5.79 (1H, br), 5.91 (1H, br), 6.98–7.61 (11H, m)

Example 116
Synthesis of 4-(4-chlorobenzoyl)-1-[4-(2.5-dihydro-1H-pyrrol-1-ylcarbonyl)benzyl]-7-(dimethylamino)-1,3,4,5-tetrahydrobenzo[e][1,4]diazepin-2-on trifluoroacetate Step 1: Synthesis of ethyl (5-fluoro-2-nitrobenzyl) aminoacetate 1.8 g (10.7 mmol) of 5-fluoro-2-nitrobenzyl alcohol was dissolved in 20 ml of dichloromethane. 0.9 ml (12.8 mmol) of methanesulfonyl chloride and 2.2 ml (16.1 mmol) of triethylamine were added to the obtained solution, and they were stirred at room temperature for 2 hours. After the treatment with dichloromethane as the extracting solvent by an ordinary method, the obtained crude product was dissolved in 20 ml of ethanol. 1.79 g (12.8 mmol) of glycine ethyl ester hydrochloride and 1.35 g (16.1 mmol) of sodium hydrogencarbonate were added to the obtained solution, and they were stirred at 70° C. for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 1.05 g (3.95 mmol) (37%)

Step 2 Synthesis of ethyl [(5-fluoro-2-nitrobenzyl)-(4-chlorobenzoyl)-amino]acetate 1.15 g (3.95 mmol) of ethyl (5-fluoro-2-nitrobenzyl) aminoacetate was dissolved in 20 ml of dichloromethane. 0.61 ml (4.7 mmol) of 4-chlorobenzoyl chloride and 0.82 ml (5.9 mmol) of triethylamine were added to the obtained solution, and they were stirred at room temperature for 2 hours. After the treatment with dichloromethane as the extracting solvent by an ordinary method, the crude product was obtained.

Step 3 Synthesis of 4-(4-chlorobenzoyl)-1-[4-(2,5-dihydro-1H-pyrrol-1-ylcarbonyl)benzyl]-7-(dimethylamino)-1,3,4,5-tetrahydrobenzo[e][1,4]-diazepin-2-on trifluoroacetate 210 mg (0.53 mmol) of ethyl [(5-fluoro-2-nitrobenzyl)-(4-chlorobenzoyl)amino]acetate was dissolved in 5 ml of ethanol. 0.5 ml (1.06 mmol) of 2.0 M solution of dimethylamine in THF and 0.22 ml (1.59 mmol) of triethylamine were added to the obtained solution, and they were stirred at room temperature overnight. After the treatment with ethyl acetate as the extracting solvent by an ordinary method, the obtained crude product was dissolved in 10 ml of ethyl acetate. 210 mg of 10% palladium/carbon was added to the obtained solution and they were stirred in the presence of hydrogen at room temperature for 4 hours. The reaction solution was filtered through Celite. The solvent was evaporated and the obtained crude product was dissolved in 5 ml of dichloromethane. 107 mg (0.53 mmol) of 4-(2,5-dihydro-1H-pyrrol-1-ylcarbonyl)benzaldehyde and 0.06 ml (1.06 mmol) of acetic acid were added to the obtained solution, and they were stirred at room temperature for 30 minutes. 280 mg (1.3 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and they were stirred at room temperature for 5 hours. After the treatment with ethyl acetate as the extracting solvent by an ordinary method, the obtained crude product was dissolved in 5 ml of dichloromethane. 90 mg (0.53 mmol) of 2-chloro-1,3-dimethylimidazonium chloride and 0.22 ml (1.6 mmol) of triethylamine were added to the obtained solution, and they were stirred overnight. The solvent was evaporated and the obtained crude product was treated in the same manner as in Step 3 in Example 1 to obtain the title compound.

Yield: 5 mg (0.0078 mmol) (1%)

MS (ESI, m/z) 529(MH+)

H-NMR (DMSO-d6) δ 2.90 (6H, br), 3.83 (2H, br), 4.13 (2H, br), 4.24 (2H, br), 4.41 (2H, br), 5.03 (2H, br), 5.80 (1H, br), 5.91 (1H, br), 7.21–7.62 (11H, m)

Example 117

Synthesis of 4-(4-chlorobenzoyl)-1-[4-(2,5-dihydro-1H-pyrrol-1-ylcarbonyl)benzyl]-7-methyl-1,3,4,5-tetrahydrobenzo[e][1,4]-diazepin-2-on Step 1: Synthesis of ethyl (5-methyl-2-nitrobenzyl) aminoacetate 5.0 g (27 mmol) of 5-methyl-2-nitrobenzyl chloride was dissolved in 100 ml of ethanol. 7.5 g (54 mmol) of glycine ethyl ester hydrochloride and 6.8 g (81 mmol) of sodium hydrogencarbonate were added to the obtained solution, and they were stirred at 70° C. for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 5.5 g (21.9 mmol) (81%)

Step 2 Synthesis of 4-(4-chlorobenzoyl)-1-[4-(2,5-dihydro-1H-pyrrol-1-ylcarbonyl) benzyl]-7-methyl-1,3,4,5-tetrahydrobenzo[e][1,4]-diazepin-2-on trifluoroacetate 5.5 g (21.9 mmol) of ethyl (5-methyl-2-nitrobenzyl) aminoacetate was dissolved in 100 ml of dichloromethane. 3.2 ml (25 mmol) of 4-chlorobenzoyl chloride and 4.0 ml (5.9 mmol) of triethylamine were added to the obtained solution, and they were stirred at room temperature for 2 hours. After the treatment with dichloromethane as the extracting solvent by an ordinary method, the crude product was obtained. The crude product was dissolved in 50 ml of ethyl acetate. 550 mg of 10% palladium/carbon was added to the obtained solution and they were stirred in the presence of hydrogen at room temperature for 4 hours. The reaction mixture was filtered through Celite. The solvent was evaporated and 620 mg (1.7 mmol) of the obtained crude product was dissolved in 20 ml of dichloromethane. 415 mg (2.1 mmol) of 4-(2,5-dihydro-1H-pyrrol-1-ylcarbonyl) benzaldehyde and 0.91 ml (3.4 mmol) of acetic acid were added to the obtained solution, and they were stirred at room temperature for 30 minutes. 900 mg (4.3 mmol) of sodium triacetoxyborohydride was added to the reaction mixture, and they were stirred overnight. After the treatment with dichloromethane as the extracting solvent by an ordinary method, the obtained crude product was dissolved in a mixture of 5 ml of 1 N sodium hydroxide and 5 ml of ethanol, and they were stirred at room temperature for 5 hours. After the treatment with ethyl acetate as the extracting solvent by an ordinary method, the obtained crude product was dissolved in 5 ml of dichloromethane. 390 mg (2.0 mmol) of 2-chloro-1,3-dimethylimidazonium chloride and 0.47 ml (3.4 mmol) of triethylamine were added to the obtained solution, and they were stirred overnight. The solvent was evaporated and the obtained crude product was treated in the same manner as in Step 3 in Example 1 to obtain the title compound.

Yield: 70 mg (0.14 mmol) (0.6%)

MS (ESI, m/z) 500(MH+)

H-NMR (DMSO-d6) δ 2.23 (3H, br), 3.84 (2H br) 4.12 (2H, br), 4.23 (2H, br), 4.41 (2H, br), 5.12 (2H, br), 5.80 (1H, br), 5.91 (1H, br), 7.21–7.62 (11H, m)

Example 118

Synthesis of 6-chloro-4-(4-chlorobenzoyl)-1-[4-(2,5-dihydro-1H-pyrrol-1-ylcarbonyl)benzyl]-7-methyl-1,3,4,5-tetrahydro-benzo[e][1,4]-diazepin-2-on 140 mg (0.37 mmol) of ethyl [(2-amino-6-chlorobenzyl)-(4-chlorobenzoyl)amino]acetate and 89 mg (0.44 mmol) of 4-(2,5-dihydro-1H-pyrrol-1-ylcarbonyl)benzaldehyde were dissolved in 5 ml of dichloromethane. 0.042 ml (0.74 mmol) of acetic acid was added to the obtained solution, and they were stirred at room temperature for 30 minutes. 195 mg (0.93 mmol) of sodium triacetoxyborohydride was added to the obtained solution, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and they were stirred at room temperature for 4 hours. After the treatment with ethyl acetate as the extracting solvent by an ordinary method, the obtained crude product was dissolved in 5 ml of dichloromethane. 74 mg (0.44 mmol) of 2-chloro-1,3-dimethylimidazonium chloride and 0.1 ml (0.74 mmol) of triethylamine were added to the obtained solution, and they were stirred overnight. The solvent was evaporated and the obtained crude product was dissolved in 5 ml of 4N solution of hydrogen chloride in dioxane. The obtained solution was stirred at room temperature for 3 hours. The solvent was evaporated and the obtained crude product was treated in the same manner as in Step 3 in Example 1 to obtain the title compound.

Yield: 20 mg (0.038 mmol) (9%)

MS (ESI, m/z) 520(MH+)

H-NMR (DMSO-d6) δ 3.96 (2H, br), 4.13 (2H, br), 4.24 (2H, br), 4.61 (2H, br), 5.13 (2H, br), 5.80 (1H, br), 5.91 (1H, br), 7.24–7.61 (11H, m)

Example 119

Synthesis of 6-chloro-4-(4-chlorobenzoyl)-1-[4-(4,5-dihydro-1H-imidazol-2-yl)benzyl]-1,3,4,5-tetrahydrobenzo[e][1,4]-diazepin-2-on trifluoroacetate Step 1 Synthesis of 6-chloro-4-(4-chlorobenzoyl)-1-(cyanobenzyl)-1,3,4,5-tetrahydrobenzo[e][1,4]diazepin-2-on 600 mg (1.58 mmol) of ethyl (2-amino-6-chlorobenzyl)-(4-chlorobenzoyl)amino]acetate and 249 mg (1.9 mmol) of 4-cyanobenzaldehyde were dissolved in 10 ml of dichloromethane. 0.19 ml (3.16 mmol) of acetic acid was added to the obtained solution, and they were stirred at room temperature for 30 minutes. 833 mg (3.95 mmol) of sodium triacetoxyborohydride was added to the obtained solution, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and they were stirred at room temperature for 4 hours. After the treatment with ethyl acetate as the extracting solvent by an ordinary method, the obtained crude product was dissolved in 10 ml of dichloromethane. 363 mg (1.9 mmol) of 2-chloro-1,3-dimethylimidazonium chloride and 0.43 ml (3.2 mmol) of triethylamine were added to the obtained solution, and they were stirred overnight. After the treatment with dichloromethane as the extracting solvent by an ordinary method, the crude title compound was obtained.

Step 2: Synthesis of 6-chloro-4-(4-chlorobenzoyl)-1-[4-(4,5-dihydro-1H-imidazol-2-yl)benzyl]-1,3,4,5-tetrahydrobenzo[e][1,4]-diazepin-2-on trifluoroacetate The crude product obtained in step 1 was dissolved in a mixture of 5 ml of 4N solution of hydrogen chloride in dioxane hind 1 ml of ethanol, and the obtained solution was stirred at room temperature for 2 days. The solvent was evaporated, and ⅓ of the obtained crude product was dissolved in 5 ml of ethanol. 95 mg (1.58 mmol) of ethylenediamine was added to the obtained solution, and they were stirred at 70° C. for 4 hours. The solvent was evaporated, and the obtained crude product was treated in the same manner as in Step 3 in Example 1 to obtain the title compound.

Yield: 9.8 mg (0.016 mmol) (5%)

MS (ESI, m/z) 493(MH+)

H-NMR (DMSO-d6) δ 3.09 (2H, dd), 3.82 (2H, br), 4.14 (2H, m), 4.61 (2H, m), 5.21 (2H, br), 7.20–7.63 (11H, br)

Example 120

Synthesis of 6-chloro-4-(4-chlorobenzoyl)-1-[4-(1,4,5,6-tetrahydro-2-pyrimidinyl)benzyl]-1,3,4,5-tetrahydrobenzo[e][1,4]-diazepin-2-on trifluoroacetate The crude product obtained in step 1 in Example 119 was dissolved in a mixture of 5 ml of 4N solution of hydrogen chloride in dioxane and 1 ml of ethanol, and the obtained solution was stirred at room temperature for 2 days. The solvent was evaporated, and ⅓ of the obtained crude product was dissolved in 5 ml of ethanol. 117 mg (1.58 mmol) of propylenediamine was added to the obtained solution, and they were stirred at 70° C. for 4 hours. The solvent was evaporated, and the obtained crude product was treated in the same manner as in Step 3 in Example 1 to obtain the title compound.

Yield: 8.4 mg (0.014 mmol) (4%)

MS (ESI, m/z). 507(MH+)

H-NMR (DMSO-d6) δ 1.31 (2H, br), 3.51 (2H, dd), 4.08 (2H, dd), 4.41 (2H, br), 4.63 (2H, br), 5.22 (2H, br), 7.27–7.84 (11H, m)

Example 121

Synthesis of 6-chloro-4-(4-chlorobenzoyl)-1-[4-(2,5-dihydro-1H-pyrrol-1-yl-(imino)methyl)benzyl]-1,3,4,5-tetrahydrobenzo[e][1,4]diazepin-2-on trifluoroacetate The crude product obtained in step 1 in Example 119 was dissolved in a mixture of 5 ml of 4N solution of hydrogen chloride in dioxane and 1 ml of ethanol, and the obtained solution was stirred at room temperature for 2 days. The solvent was evaporated, and ⅓ of the obtained crude product was dissolved in 5 ml of ethanol. 117 mg (1.58 mmol) of 3-pyrroline was added to the obtained solution, and they were stirred at 70° C. for 4 hours. The solvent was evaporated, and tile obtained crude product was treated in the same manner as in Step 3 in Example 1 to obtain the title compound.

Yield: 7.6 mg (0.012 mmol) (4%)

MS (ESI, m/z) 519(MH+)

H-NMR (DMSO-d6) δ 3.94 (2H, br), 4.13 (2H, br), 4.34 (2H, br), 4.63 (2H, br), 5.11 (2H, br), 5.85 (1H, br), 6.05 (1H, br), 7.33–7.77 (11H, d), 8.91 (1H, br), 9.22 (1H, br)

Example 122

Synthesis of 6-chloro-4-(4-chlorobenzoyl)-1-[4-(1-methyl-4,5-dihydro-1H-imidazol-2-yl)benzyl]-1,3,4,5-tetrahydrobenzo[e][1,4]-diazepin-2-on trifluoroacetate The crude product obtained in step 1 in Example 119 was dissolved in a mixture of 5 ml of 4N solution of hydrogen chloride in dioxane and 1 ml of ethanol, and the obtained solution was stirred at room temperature for 2 days. The solvent was evaporated, and ⅓ of the obtained crude product was dissolved in 5 ml of ethanol. 117 mg (1.58 mmol) of N-methylethylenediamine was added to the obtained solution, and they were stirred at 70° C. for 4 hours. The solvent was evaporated, and the obtained crude product was treated in the same manner as in Step 3 in Example 1 to obtain the title compound.

Yield: 7.5 mg (0.012 mmol) (4%)

MS (ESI, m/z) 507(MH+)

H-NMR (DMSO-d6) δ 2.48–2.61 (2H, m), 3.01 (5H, br), 3.82–4.03 (2H, m), 4.62 (2H, br), 5.12 (2H, br), 7.20–7.63 (11H, m)

Example 123

Synthesis of 1-(1,1'-biphenyl-4-ylmethyl)-4-(4-chlorobenzoyl)-1,3,4,5-tetrahydrobenzo[e][1,4]diazepin-2-on 300 mg (1.0 mmol) of 4-(4-chlorobenzoyl)-1,3,4,5-tetrahydrobenzo[e][1,4]diazepin-2-on was dissolved in 10 ml of DMF. 50 mg (1.25 mmol) of sodium hydride was added to the obtained solution, and they were stirred at room temperature for 30 minutes. 300 mg (1.0 mmol) of 4-iodobenzyl bromide was added to the obtained mixture, and they were stirred at room temperature overnight. After the treatment with ethyl acetate as the extracting solvent by an ordinary method, the solvent was evaporated, and the obtained crude product was washed with hexane. 30 mg (0.058 mmol) of the obtained product was mixed with 7 mg (0.058 mmol) of phenyl boronic acid, 5 mg of [1,1'-bis (diphenylphosphino)ferrocene]dichloropalladium, 3 mg of 1,1'-bisdiphenylphosphinoferrocene, 265 mg (2.5 mmol) of sodium carbonate, 1 ml of water and 3 ml of toluene, and the obtained mixture was stirred at 80° C. overnight. After the treatment with ethyl acetate as the extracting solvent by an ordinary method, the solvent was evaporated, and the obtained crude product was treated in the same manner as in Step 3 in Example 1 to obtain the title compound.

Yield: 4.0 mg (0.009 mmol) (14.8%)

MS (ESI, m/z) 507(MH+)

H-NMR (DMSO-d6) δ 2.48–2.61 (2H, m), 3.01 (5H, br), 3.82–4.03 (2H, m), 4.62 (2H, br), 5.12 (2H, br), 7.20–7.63 (11H, m)

Example 124

Synthesis of 4-(4-chlorobenzoyl)-1-[(2'-(methylsulfonyl)-1,1'-biphenyl-4-yl)methyl]-1,3,4,5-tetrahydrobenzo[e][1,4]diazepin-2-on 300 mg (1.0 mmol) of 4-(4-chlorobenzoyl)-1,3,4,5-tetrahydrobenzo[e][1,4]diazepin-2-on was dissolved in 10 ml of DMF. 50 mg (1.25 mmol) of sodium hydride was added to the obtained solution, and they were stirred at room temperature for 30 minutes. 300 mg (1.00 mmol) of 4-iodobenzyl bromide was added to the obtained mixture, and they were stirred at room temperature overnight. After the treatment with ethyl acetate as the extracting solvent by an ordinary method, the solvent was evaporated, and the obtained crude product was washed with hexane. 30 mg (0.058 mmol) of the obtained product was mixed with 7 mg (0.058 mmol) of 2-methylthioethyl boronic acid, 5 mg of [1,1-bis(diphenylphosphino)ferrocene]dichloropalladium, 3 mg of 1,1-bisdiphenylphosphinoferrocene, 265 mg (2.5 mmol) of sodium carbonate, 1 ml of water and 3 ml of toluene, and the obtained mixture was stirred at 80° C. overnight. After the treatment with ethyl acetate as the extracting solvent by an ordinary method, the solvent was evaporated, and the obtained crude product was dissolved in 3 ml of dichloromethane. 40 mg (0.23 mmol) of metachloroperbenzoic acid was added to the obtained solution, and they were stirred at room temperature for 4 hours. After the treatment with ethyl acetate as the extracting solvent by an ordinary method, the solvent was evaporated and the obtained crude product was treated in the same manner as in Step 3 in Example 1 to obtain the title compound.

Yield: 9.0 mg (0.017 mmol) (28.5%)

H-NMR (DMSO-d6) δ 2.65 (3H, s), 3.90–4.10 (2H, m), 4.30–4.50 (2H, m), 5.15 (2H, br), 7.28–7.39 (4H, m), 7.37 (1H, dd), 7.44–7.60 (8H, m), 7.65 (1H, dt), 7.73 (1H, dt), 8.07 (1H, dd)

Example 125

Synthesis of 4-(4-chlorobenzoyl)-1-[4-(1-methyl-4,5-dihydro-1H-imidazol-2-yl)benzyl]-1,3,4,5-tetrahydrobenzo[e][1,4]-diazepin-2-on trifluoroacetate Step 1: Synthesis of 4-(4-chlorobenzoyl)-1-(4-cyanobenzyl)-1,3,4,5-tetrahydrobenzo[e][1,4]-diazepin-2-on 200 mg (0.67 mmol) of 4-(4-chlorobenzoyl)-1,3,4,5-tetrahydrobenzo[e][1,4]diazepin-2-on was dissolved in 10 ml of DMF. 30 mg (0.75 mmol) of sodium hydride was added to the obtained solution, and they were stirred at room temperature for 30 minutes. 147 mg (0.75 mmol) of 4-cyanobenzyl bromide was added to the obtained mixture, and they were stirred at room temperature overnight. After the treatment with ethyl acetate as the extracting solvent by an ordinary method, the obtained crude product was purified by the silica gel column chromatography to obtain the title compound.

Yield: 270 mg (0.65 mmol) (97%)

MS (ESI, m/z) 416(MH+)

H-NMR (CDCl3) δ 4.01 (2H, br), 4.10–4.40 (2H, br), 5.13 (2H, s), 7.23–7.50 (10H, m), 7.58 (2H, d)

Step 2 Synthesis of 4-(4-chlorobenzoyl)-1-[4-(1-methyl-4,5-dihydro-1H-imidazol-2-yl)benzyl]-1,3,4,5-tetrahydrobenzo[e][1,4]diazepin-2-on trifluoroacetate 4-(4-Chlorobenzoyl)-1-(4-cyanobenzyl)-1,3,4,5-tetrahydrobenzo[e][1,4]diazepin-2-on obtained in step 1 was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 80 mg (1.08 mmol) of N-methyletylenediamine was added to the obtained solution, and they were stirred at 60° C. overnight. The solvent was evaporated, and the obtained crude product was treated in the same manner as in Step 3 in Example 1 to obtain the title compound.

Yield: 64 mg (0.11 mmol) (17%)

MS (ESI, m/z) 473(MH+)

H-NMR (DMSO-d6) δ 3.02 (3H, s), 3.84–4.18 (6H, m), 4.50 (2H, br), 5.21 (2H, br), 7.12–7.77 (12H, m)

Example 126

Synthesis of 4-(4-chlorobenzoyl)-1-[4-(1-pyrrolidinylmethyl)benzyl]-1,3,4,5-tetrahydrobenzo[e][1,4]diazepin-2-on trifluoroacetate Step 1: Synthesis of 4-(4-chlorobenzoyl)-1-(4-chloromethylbenzyl)-1,3,4,5-tetrahydrobenzo[e][1,4]diazepin-2-on 80 mg (0.18 mmol) of 1-(4-carboxybenzyl)-4-(4-chlorobenzoyl)-1,3,4,5-tetrabenzo[e][1,4]diazepin-2-on obtained in Step 1 in Example 48 was dissolved in 5 ml of THF. 0.06 ml (0.043 mmol) of triethylamine and 0.03 ml (0.31 mmol) of ethyl chloroformate were added to the obtained solution under cooling with ice, and they were stirred for 30 minutes. A piece of ice and 50 mg (1.4 mmol) of sodium borohydride were added thereto. The temperature was elevated to room temperature, and the obtained mixture was stirred for 1 hour. The solvent was evaporated and the obtained crude product was dissolved in 5 ml of dichloromethane. 0.03 ml (0.22 mmol) of triethylamine and 0.014 ml (0.18 mmol) of methanesulfonyl chloride were added to the obtained solution, and they were stirred overnight. After the treatment with dichloromethane as the extracting solvent, the product was treated by an ordinary method to obtain the crude product.

MS (ESI, m/z) 4,39(MH+)

H-NMR (CDCl3) δ 3.98 (2H, br), 4.08–4.35 (2H, br), 4.53 (2H, s), 5.07 (2H, s), 7.17–7.50 (12H, m)

Step 2 Synthesis of 4-(4-chlorobenzoyl)-1-[4-(1-pyrrolidinylmethyl)-benzyl]-1,3,4,5-tetrahydrobenzo[e][1,4]diazepin-2-on trifluoroacetate 0.04 mmol of 4-(4-chlorobenzoyl)-1-(4-chloromethylbenzyl)-1,3,4,5-tetrahydrobenzo[e][1,4]diazepin-2-on obtained in step 1 was dissolved in 4 ml of acetonitrile. 20 mg (0.15 mmol) of potassium carbonate and 7.1 mg (0.1 mmol) of pyrrolidine were added to the solution,

Example 127

Synthesis of 4-(4-chlorobenzoyl)-1-[4-(2,5-dihydro-1H-pyrrol-1-ylmethyl)benzyl]-1,3,4,5-tetrahydrobenzo[e][1,4]diazepin-2-on trifluoroacetate 0.04 mmol of 4-(4-chlorobenzoyl)-1-(4-chloromethylbenzyl)-1,3,4,5-tetrahydrobenzo[e][1,4]diazepin-2-on obtained in Step 1 in Example 126 was dissolved in 4 ml of acetonitrile. 20 mg (0.15 mmol) of potassium carbonate and 6.9 mg (0.1 mmol) of 3-pyrroline were added to the solution, and they were stirred at room temperature overnight. The solvent was evaporated and the obtained crude product was treated in the same manner as in Step 3 in Example 1 to obtain the title compound.

Yield: 16 mg (0.028 mmol) (70%)
MS (ESI, m/z) 472(MH+)
H-NMR (DMSO-d6) δ 3.86–4.12 (6H, br), 4.35–4.50 (4H, br), 5.12 (2H, br), 5.89 (2H, s), 7.10–7.64 (12H, m)

Example 128

Synthesis of 4-(4-chlorobenzoyl)-1-[4-((4-methyl-1-piperazinyl)methyl)benzyl]-1,3,4,5-tetrahydrobenzo[e][1,4]diazepin-2-on bistrifluoroacetate 0.04 mmol of 4-(4-chlorobenzoyl)-1-(4-chloromethylbenzyl)-1,3,4,5-tetrahydrobenzo[e][1,4]diazepin-2-on obtained in Step 1 in Example 126 was dissolved in 4 ml of acetonitrile. 20 mg (0.15 mmol) of potassium carbonate and 10.0 mg (0.1 mmol) of 1-methylpiperazine were added to the solution, and they were stirred at room temperature overnight. The solvent was evaporated and the obtained crude product was treated in the same manner as in Step 3 in Example 1 to obtain the title compound.

Yield: 5.5 mg (0.008 mmol) (19%)
MS (ESI, m/z) 503(MH+)
H-NMR (DMSO-d6) δ 2.76 (3H, s), 3.60–4.20 (12H, br), 4.43 (2H, br), 5.09 (2H, br), 7.10–7.33 (5H, m), 7.40–7.63 (7H, m)

Example 129

Synthesis of 4-(4-chlorobenzoyl)-1-[4-(((2-(dimethylamino)ethyl)(methyl)amino)methyl)benzyl]-1,3,4,5-tetrahydrobenzo[e][1,4]diazepin-2-on bistrifluoroacetate 0.04 mmol of 4-(4-chlorobenzoyl)-(4-chloromethylbenzyl)-1,3,4,5-tetrahydrobenzo[e][1,4]diazepin-2-on obtained in Step 1 in Example 126 was dissolved in 4 ml of acetonitrile. 20 mg (0.15 mmol) of potassium carbonate and 10.2 mg (0.1 mmol) of N,N,N'-trimethylethylenediamine were added to the solution, and they were stirred at room temperature overnight. The solvent was evaporated and the obtained crude product was treated in the same manner as in Step 3 in Example 1 to obtain the title compound.

Yield: 18.0 mg (0.025 mmol) (62%)
MS (ESI, m/z) 505(MH+)
H-NMR (DMSO-d6) δ 2.49 (6H, s), 2.76 (3H, s), 3.30–4.20 (8H, br), 4.41 (2H, br), 5.12 (2H, br), 7.10–7.63 (12H, m)

and they were stirred at room temperature overnight. The solvent was evaporated, and the obtained crude product was treated in the same manner as in Step 3 in Example 1 to obtain the title compound.

Yield: 15 mg (0.025 mmol) (63%)
MS (ESI, m/z) 474(MH+)
H-NMR (DMSO-d6) δ 1.82 (2H, br), 1.99 (2H, br), 3.04 (2H, br), 3.31 (2H, br), 3.91–4.10 (2H, br), 4.27 (2H, br), 4.45 (2H, br), 5.12 (2H, br), 7.10–7.64 (12H, m)

Example 130

Synthesis of ethyl 3-[4-4-chlorobenzoyl)-2-oxo-(4-(imino(1-pyrrolidinyl)methyl)benzyl)-2,3,4,5-tetrahydro-1H-benzo[e][1,4]-diazepin-8-yl]propionate trifluoroacetate Step 1: Synthesis of 3–14-(4-chlorobenzoyl)-2-oxo-1-(4-(cyano)benzyl)-2,3,4,5-tetrahydro-1H-benzo[e][1,4]diazepin-8-yl]propionic acid 1.02 g (2.4 mmol) of methyl 3-[3-amino-4-(((4-chlorobenzoyl)ethoxycarbonylmethylamino)methyl)phenyl]propionate and 371 mg (2.8 mmol) of 4-cyanobenzaldehyde were dissolved in 100 ml of dichloromethane. 0.27 ml (4.8 mmol) of acetic acid was added to the obtained solution, and they were stirred at room temperature for 30 minutes. 1.3 g (6.0 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 4 hours. After the treatment with ethyl acetate as the extracting solvent by an ordinary method, the obtained crude product was dissolved in 5 ml of dichloromethane. 74 mg (0.44 mmol) of 2-chloro-1,3-dimethylimidazonium chloride and 0.1 ml (0.74 mmol) of triethylamine were added to the obtained solution, and they were stirred overnight. After the treatment with ethyl acetate as the extracting solvent by an ordinary method, the crude title compound was obtained.

Yield: 1.5 g (3.08 mmol)

Step 2: Synthesis of ethyl 3-[4-(4-chlorobenzoyl)-2-oxo-1-(4-(imino(1-pyrrolidinyl)methyl)benzyl)-2,3,4,5-tetrahydro-1H-benzo[e][1,4]-diazepin-8-yl ]propionate trifluoroacetate 150 mg of the crude product obtained in Step 1 was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 17 mg (0.24 mmol) of pyrrolidine was added to the obtained solution, and they were stirred at 70° C. for 4 hours. The solvent was evaporated and the obtained crude product was treated in the same manner as in step 3 in Example 1 to obtain the title compound.

Yield: 4.1 mg (0.006 mmol) (3%)
MS (ESI, m/z) 587(MH+)

Example 131

Synthesis of 3-[4-(4-chlorobenzoyl)-2-oxo-1-(4-(imino(1-pyrrolidinyl)methyl)benzyl)-2,3,4,5-tetrahydro-1H-benzo[e][1,4]-diazepin-8-yl]propionic acid trifluoroacetate 4.1 mg (0.006 mmol) of ethyl 3-[4-(4-chlorobenzoyl)-2-oxo-1-(4-(imino(1-pyrrolidinyl)methyl)benzyl)-2, 3,4,5-tetrahydro-1H-benzo-[e][1,4]diazepin-8-yl]propionate was dissolved in a mixture of 5 ml of 1 N sodium hydroxide and 5 ml of ethanol, and the obtained solution was stirred at room temperature for 4 hours. The solvent was evaporated, and the obtained crude product was treated in the same manner as in step 3 in Example 1 to obtain the title compound.

Yield: 3.0 mg (0.004 mmol) (74%)
MS (ESI, m/z) 559(MH+)
H-NMR (DMSO-d6) δ 1.97–2.09 (4H, m), 2.41 (2H, br), 2.62 (2H, br), 3.88–4.05 (4H, m), 4.41 (4H, br), 5.09 (2H, br), 7.27–7.65 (1H, m)

Example 132

Synthesis of 4-(4-chlorobenzoyl)-1-[4-(2,5-dihydro-1H-pyrrol-1-ylcarbonyl)benzyl]-6-(trifluoromethyl)-1,3,4,5-tetrahydrobenzo[e][1,4]diazepin-2-on Step 1: Synthesis of ethyl [2-nitro-6-(trifluoromethyl)benzyl]-aminoacetate 5.0 g (24.3 mmol) of 2-methyl-1-nitro-3-(trifluoromethyl)benzene was added to a mixture of 100 ml of benzene, 50 ml of perbenzoic acid and 5.6 g (32 mmol) of N-bromosuccinimide, and they were stirred at 80° C. for 2 days. After the treatment with ethyl acetate as the extracting solvent by an ordinary method, the obtained crude product was dissolved in 50 ml of ethanol. 6.8 g (48.6 mmol) of glycine ethyl ester hydrochloride and 6.1 g (72.9 mmol) of sodium hydrogencarbonate were added to the obtained solution, and they were stirred at 70° C. for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 3.2 g (10.5 mmol) (43%)

Step 2: Synthesis of 4-(4-chlorobenzoyl)-1-[4-(2,5-dihydro-1H-pyrrol-1-ylcarbonyl)benzyl]-6-(trifluoromethyl)-1,3,4,5-tetrahydrobenzo[e][1,4]-diazepin-2-on 3.2 g (10.5 mmol) of ethyl [2-nitro-6-(trifluoromethyl)benzyl]-aminoacetate was dissolved in 50 ml of dichloromethane. 1.6 ml (12.6 mmol) of 4-chlorobenzoyl chloride and 1.9 ml (13.7 mmol) of triethylamine were added to the obtained solution under cooling with ice, and they were stirred under cooling with ice for 2 hours. After the treatment with dichloromethane as the extracting solvent by an ordinary method, the crude product was obtained. The crude product was dissolved in 20 ml of ethyl acetate. 320 mg of 10% palladium/carbon was added to the obtained solution and they were stirred in the presence of hydrogen at room temperature for 4 hours. The reaction solution was filtered through Celite. The solvent was evaporated and 210 mg (0.58 mmol) of the obtained crude product was dissolved in 5 ml of dichloromethane. 122 mg (0.68 mmol) of 4-(2,5-dihydro-1H-pyrrol-1-ylcarbonyl)benzaldehyde and 0.06 ml (1.2 mmol) of acetic acid were added to the obtained solution, and they were stirred at room temperature for 30 minutes. 310 mg (1.45 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 5 ml of dichloromethane. 118 mg (0.70 mmol) of 2-chloro-1,3-dimethyl-imidazonium chloride and 0.12 ml (0.87 mmol) of triethylamine were added to the obtained solution, and they were stirred overnight. The solvent was evaporated, and the obtained crude product was treated in the same manner as in step 3 in Example 1 to obtain the title compound.

Yield: 19 mg (0.034 mmol) (6%)

MS (ESI, m/z) 554(MH+)

H-NMR (DMSO-d6) δ 3.91 (2H, br), 4.12 (2H, br), 4.24 (2H, br), 4.42 (2H, br), 5.19 (2H, br), 5.80 (1H, br), 5.91 (1H, br), 7.24–7.81 (11H, m)

Example 133

Synthesis of 4(4-chlorobenzoyl)-1-[4-(2,5-dihydro-1H-pyrrol-1-ylcarbonyl)benzyl]-8-(trifluoromethyl)-1,3,4,5-tetrahydrobenzo[e][1,4]diazepin-2-on Step 1: Synthesis of ethyl[2-nitro-4-(trifluoromethyl)benzyl]-aminoacetate 5.0 g (21 mmol) of 4-trifluoromethyl-2-nitrobenzoic acid was dissolved in a mixture of 200 ml of THF and 4.4 ml (31.5 mmol) of triethylamine. 2.6 ml (28 mmol) of ethyl chloroformate was added to the obtained solution under cooling with ice, and they were stirred for 15 minutes. Precipitates thus formed were removed by the suction filtration. A piece of ice was added to the obtained filtrate, and then 1.6 g (42 mmol) of sodium borohydride was added thereto under cooling with ice. The temperature was elevated to room temperature, and the obtained mixture was stirred overnight. After the treatment with ethyl acetate as the extracting solvent by an ordinary method, the obtained crude product was dissolved in 100 ml of dichloromethane. 1.96 ml (25.2 mmol) of methanesulfonyl chloride and 4.4 ml (31.5 mmol) of triethylamine were added to the obtained solution, and they were stirred under cooling with ice for 2 hours. After the treatment with dichloromethane as the extracting solvent, the obtained crude product was dissolved in 100 ml of ethanol. 5.9 g (42 mmol) of glycine ethyl ester hydrochloride and 5.3 g (16.1 mmol) of sodium hydrogencarbonate were added to the obtained solution, and they were stirred at 70□ for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 1.6 g (5.2 mmol) (25%)

H-NMR (CDCl3) δ 1.28 (3H, t), 3.44 (2H, s), 4.18 (2H, s), 4.20 (2H, q), 7.78–7.91 (2H, m), 8.22 (1H, br)

Step 2: Synthesis of 4-(4-chlorobenzoyl)-1-[4-(2,5-dihydro-1H-pyrrol-1-ylcarbonyl)benzyl]-8-(trifluoromethyl)-1,3,4,5-tetrahydrobenzo[e][1,4]-diazepin-2-on 1.6 g (5.2 mmol) of ethyl [2-nitro-4-(trifluoromethyl)benzyl]-aminoacetate was dissolved in 50 ml of dichloromethane. 0.8 ml (6.3 mmol) of 4-chlorobenzoyl chloride and 1.1 ml (7.8 mmol) of triethylamine were added to the obtained solution under cooling with ice, and they were stirred under cooling with ice for 2 hours. After the treatment with dichloromethane as the extracting solvent by an ordinary method, the crude product was obtained. The crude product was dissolved in a mixture of 10 ml of ethyl acetate and 10 ml of ethanol. 160 mg of 10% palladium/carbon was added to the obtained solution and they were stirred in the presence of hydrogen at room temperature for 4 hours. The reaction mixture was filtered through Celite. The solvent was evaporated and 87 mg (0.21 mmol) of the obtained crude product was dissolved in 10 ml of dichloromethane. 50 mg (0.25 mmol) of 4-(2,5-dihydro-1H-pyrrol-1-ylcarbonyl)benzaldehyde and 0.25 ml (0.42 mmol) of acetic acid were added to the obtained solution, and they were stirred at room temperature for 30 minutes. 110 mg (0.53 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 5 ml of dichloromethane. 42 mg (0.25 mmol) of 2-chloro-1,3-dimethylimidazonium chloride and 0.04 ml (0.42 mmol) of triethylamine were added to the obtained solution, and they were stirred overnight. The solvent was evaporated, and the obtained crude product was treated in the same manner as in step 3 in Example 1 to obtain the title compound.

Yield: 6.6 mg (0.012 mmol) (6%)
MS (ESI, m/z) 554(MH+)
H-NMR (DMSO-d6) δ 3.98 (2H, br), 4.09 (2H, br), 4.23 (2H, br), 4.42 (2H, br), 5.21 (2H, br), 5.80 (1H, br), 5.91 (1H, br), 7.23–7.62 (11H, m)

Example 134

Synthesis of 4-(4-chlorobenzoyl)-1-[4-(2,5-dihydro-1H-pyrrol-1-ylcarbonyl)benzyl]-6-methoxy-1,3,4,5-tetrahydrobenzo[e][1,4]-diazepin-2-on Step 1: Synthesis of ethyl (6-methoxy-2-nitrobenzyl) aminoacetate 5.0 g (29 mmol) of 1-methoxy-2-methyl-3-nitrobenzene was added to a mixture of 50 ml of benzene, 50 ml of perbenzoic acid and 8 g (45 mmol) of N-bromosuccinimide, and they were stirred at 80° C. for one day. After the treatment with ethyl acetate as the extracting solvent by an ordinary method, the obtained crude product was dissolved in 50 ml of ethanol. 8.4 g (60 mmol) of glycine ethyl ester hydrochloride and 5.0 g (60 mmol) of sodium hydrogencarbonate were added to the obtained solution, and they were stirred at 70° C. overnight. The solvent was evaporated. After the extraction with ethyl acetate, the obtained extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 5.6 g (21.3 mmol) (73%)
H-NMR (CDCl3) δ 1.26 (3H, t), 3.79 (3H, s), 3.98 (2H, br), 4.18 (2H, q), 4.20 (2H, s), 7.01 (1H, dd), 7.21–7.28 (2H, m)

Step 2: Synthesis of ethyl [(2-amino-6-methoxybenzyl)-(4-chlorobenzoyl)amino]acetate 5.6 g (21.3 mmol) of ethyl (6-methoxy-2-nitrobenzyl) aminoacetate was dissolved in 50 ml of dichloromethane. 3.3 ml (25.2 mmol) of 4-chlorobenzoyl chloride and 4.4 ml (32 mmol) of triethylamine were added to the obtained solution under cooling with ice, and they were stirred under cooling with ice for 2 hours. After the treatment with dichloromethane as the extracting solvent by an ordinary method, the crude product was obtained. The crude product was dissolved in 50 ml of ethyl acetate. 520 mg of 10% palladium/carbon was added to the obtained solution and they were stirred in the presence of hydrogen at room temperature for 4 hours. The reaction mixture was filtered through Celite. The solvent was evaporated to obtain the crude product, which was then purified by the silica gel column chromatography to obtain the title compound.

Yield: 3.2 g (8.5 mmol) (40%)
H-NMR (CD3Cl) δ 1.25 (3H, t), 3.74 (3H, s), 3.88 (2H, br), 4.16 (2H, q), 4.83 (2H, br), 6.23 (2H, dd), 7.07 (1H, dd), 7.35 (4H, br)

Step 3: Synthesis of 4-(4-chlorobenzoyl)-1-[4-(2,5-dihydro-1H-pyrrol-1-ylcarbonyl)benzyl]-6-methoxy-1,3,4,5-tetrahydrobenzo[e][1,4]-diazepin-2-on 243 mg (0.65 mmol) of ethyl [(2-amino-6-methoxybenzyl)-(4-chlorobenzoyl)amino]acetate was dissolved in 5 ml of dichloromethane. 156 mg (0.78 mmol) of 4-(2,5-dihydro-1H-pyrrol-1-ylcarbonyl)-benzaldehyde and 0.074 ml (1.3 mmol) of acetic acid were added to the obtained solution, and they were stirred at room temperature for 30 minutes. 340 mg (1.6 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 2 ml of 1 N sodium hydroxide and 10 ml of ethanol, and the obtained solution was stirred at room temperature for 5 hours. After the treatment with ethyl acetate as the extracting solvent by an ordinary method, the obtained crude product was dissolved in 5 ml of dichloromethane. 131 mg (0.78 mmol) of 2-chloro-1,3-dimethylimidazonium chloride and 0.19 ml (1.3 mmol) of triethylamine were added to the obtained solution, and they were stirred overnight. The solvent was evaporated, and the obtained crude product was treated in the same manner as in step 3 in Example 1 to obtain the title compound.

Yield: 85 mg (0.17 mmol) (27%)
H-NMR (DMSO-d6) δ 3.62 (3H, br), 3.84 (2H, br), 4.14 (2H, br), 4.25 (4H, br), 5.14 (2H, br), 5.82 (1H, br), 5.92 (1H, br), 7.23–7.62 (11H, m)

Example 135

Synthesis of 4-(4-chlorobenzoyl)-1-[4-(2,5-dihydro-1H-pyrrol-1-ylcarbonyl)benzyl]-6-hydroxy-1,3,4,5-tetrahydrobenzo[e][1,4]-diazepin-2-on 75 mg (0.15 mmol) of 4-(4-chlorobenzoyl)-1-[4-(2,5-dihydro-1H-pyrrol-1-ylcarbonyl)benzyl]-6-methoxy-1,3,4,5-tetrahydrobenzo[e][1,4]-diazepin-2-on was dissolved in 10 ml of dichloromethane. 1.3 ml of borane tribromide was added to the obtained solution, and they were stirred at room temperature overnight. After the treatment with dichloromethane as the extracting solvent by an ordinary method, the obtained crude product was treated in the same manner as in step 3 in Example 1 to obtain the title compound.

Yield: 35 mg (0.07 mmol) (47%)
MS (ESI, m/z) 502(MH+)
H-NMR (DMSO-d6) δ 3.84 (2H, br), 4.11 (2H, br), 4.23 (2H, br), 4.39 (2H, br), 5.16 (2H, br), 5.80 (1H, br), 5.91 (1H, br), 7.09–7.62 (11H, m)

Example 136

Synthesis of 4-(4-chlorobenzoyl)-1-[4-(2,5-dihydro-1H-pyrrol-1-ylcarbonyl)benzyl]-8-methoxy-1,3,4,5-tetrahydrobenzo[e][1,4]-diazepin-2-on Step 1: Synthesis of ethyl (4-methoxy-2-nitrobenzyl) aminoacetate 5.0 g (29 mmol) of 4-methoxy-1-methyl-2-nitrobenzene was added to a mixture of 50 ml of benzene, 50 ml of perbenzoic acid and 8 g (45 mmol) of N-bromosuccinimide, and they were stirred at 80° C. for one day. After the treatment with ethyl acetate as the extracting solvent by an ordinary method, the obtained crude product was dissolved in 50 ml of ethanol. 8.4 g (60 mmol) of glycine ethyl ester hydrochloride and 5.0 g (60 mmol) of sodium hydrogencarbonate were added to the obtained solution, and they were stirred at 70° C. overnight. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 3.6 g (13.7 mmol) (46%)

Step 2: Synthesis of 4-(4-chlorobenzoyl)-1-[4-(2,5-dihydro-1H-pyrrol-1-ylcarbonyl)benzyl]-6-methoxy-1,3,4,5-tetrahydrobenzo[e][1,4]diazepin-2-on 3.6 g (13.7 mmol) of ethyl (4-methoxy-2-nitrobenzyl)aminoacetate was dissolved in 50 ml of dichloromethane. 2.1 ml (16.4 mmol) of 4-chlorobenzoyl chloride and 2.9 ml (20.6 mmol) of triethylamine were added to the obtained solution under cooling with ice, and they were stirred under cooling with ice for 2 hours. After the treatment with dichloromethane as the extracting solvent by an ordinary method, the crude product was obtained. The crude product was dissolved in 50 ml of ethyl acetate. 360 mg of 10% palladium/carbon was added to the obtained solution and they were stirred in the presence of hydrogen at room temperature for 4 hours. The reaction solution was filtered through Celite. The solvent was evaporated to obtain the crude product. 243 mg (0.65 mmol) of the crude product was dissolved in 5 ml of dichloromethane. 156 mg (0.78 mmol) of 4-(2,5-dihydro-1H-pyrrol-1-ylcarbonyl)benzaldehyde and 0.074 ml (1.3 mmol) of acetic acid were added to the obtained solution, and they were stirred at room temperature for 30 minutes. 340 mg (1.6 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 2 ml of 1 N sodium hydroxide and 10 ml of ethanol, and the obtained solution was stirred at room temperature for 5 hours. After the treatment with ethyl acetate as the extracting solvent by an ordinary method, the obtained crude product was dissolved in 5 ml of dichloromethane. 131 mg (0.78 mmol) of 2-chloro-1,3-dimethylimidazonium chloride and 0.19 ml (1.3 mmol) of triethylamine were added to the obtained solution, and they were stirred overnight. The solvent was evaporated, and the obtained crude product was treated in the same manner as in step 3 in Example 1 to obtain the title compound.

Yield: 89 mg (0.17 mmol) (27%)
MS (ESI, m/z) 516(MH+)
H-NMR (DMSO-d6) δ 3.74 (3H, br), 3.94 (2H, br), 4.16 (2H, br), 4.24 (4H, br), 5.16 (2H, br), 5.80 (1H, br), 5.91 (1H, br), 7.22–7.62 (11H, m)

Example 137

Synthesis of 4-(4-chlorobenzoyl)-1-[4-(2,5-dihydro-1H-pyrrol-1-ylcarbonyl)benzyl]-8-hydroxy-1,3,4,5-tetrahydrobenzo[e][1,4]-diazepin-2-on 79 mg (0.15 mmol) of 4-(4-chlorobenzoyl)-1-[4-(2,5-dihydro-1H-pyrrol-1-ylcarbonyl)benzyl]-8-methoxy-1,3,4,5-tetrahydrobenzo[e][1,4]-diazepin-2-on was dissolved in 10 ml of dichloromethane. 1.0 ml of borane tribromide was added to the obtained solution, and they were stirred at room temperature for 6 hours. After the treatment with dichloromethane as the extracting solvent by an ordinary method, the obtained crude product was treated in the same manner as in step 3 in Example 1 to obtain the title compound.

Yield: 65 mg (0.13 mmol) (86%)
MS (ESI, m/z) 502(MH+)
H-NMR (DMSO-d6) δ 3.91 (2H, br), 4.17 (2H, br), 4.23 (4H, br), 5.06 (2H, br), 5.80 (1H, br), 5.91 (1H, br), 7.21–7.62 (11H, m)

Example 138

Synthesis of 4-(4-chlorobenzoyl)-1-[4-(2,5-dihydro-1H-pyrrol-1-ylcarbonyl)benzyl]-8-isopropoxy-1,3,4,5-tetrahydrobenzo[e][1,4]-diazepin-2-on 22 mg (0.044 mmol) of 4-(4-chlorobenzoyl)-1-[4-(2,5-dihydro-1H-pyrrol-1-ylcarbonyl)benzyl]-8-hydroxy-1,3,4,5-tetrahydrobenzo[e][1,4]-diazepin-2-on was dissolved in 5 ml of THF. 15 mg (0.05 mmol) of triphenylphosphine, 0.004 ml (0.05 mmol) of isopropyl alcohol and 25 mg (0.05 mmol) of diethylazo dicarboxylate were added to the obtained solution, and they were stirred at room temperature overnight. After the treatment with ethyl acetate as the extracting solvent, the obtained crude product was treated in the same manner as in step 3 in Example 1 to obtain the title compound.

Yield: 5.1 mg (0.009 mmol) (21%)
MS (ESI, m/z) 544(MH+)
H-NMR (DMSO-d6) δ 1.20 (3H, s), 1.22 (3H, br), 3.94 (2H, br), 4.12 (2H, br), 4.24 (2H, br), 4.47 (2H, br), 5.13 (2H, br), 5.80 (1H, br), 5.92 (1H, br), 7.23–7.63 (1H, m)

Example 139

Synthesis of N-[4-(4-chlorobenzoyl)-2-oxo-1-(4-(2,5-dihydro-1H-pyrrol-1-ylcarbonyl)benzyl)-2,3,4,5-tetrahydro-1H-benzo[e][1,4]diazepin-8-yl]acetamide 90 mg (0.17 mmol) of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-8-carboxylic acid was dissolved in 5 ml of t-butyl alcohol. 58 mg (0.21 mmol) of diphenylphosphoryl azide and 0.056 ml (0.30 mmol) of triethylamine were added to the obtained solution and they were stirred at 70° C. overnight. The crude product obtained by the treatment with ethyl acetate as the extracting solvent was dissolved in 5 ml of 4N solution of hydrogen chloride in dioxane and the obtained solution was stirred at room temperature for 2 hours. The solvent was evaporated and the obtained crude product was dissolved in 5 ml of dichloromethane. 0.056 ml (0.30 mmol) of triethylamine and 0.028 ml of acetyl chloride were added to the obtained solution, and they were stirred at room temperature overnight. The solvent was evaporated and the obtained crude product was treated in the same manner as in step 3 in Example 1 to obtain the title compound.

Yield: 5.5 mg (0.008 mmol) (5%)
MS (ESI, m/z) 543(MH+)
H-NMR (DMSO-d6) δ 2.00 (3H, br), 3.98 (2H, br), 4.14 (2H, br), 4.25 (2H, br), 4.41 (2H, br), 5.05 (2H, br), 5.80 (1H, br), 5.92 (1H, br), 7.21–7.62 (11H, m)

Example 140

Synthesis of 4-(4-chlorobenzoyl)-1-(4-piperidinylmethyl)-1,3,4,5-tetrahydrobenzo[e][1,4]diazepin-2-on trifluoroacetate 150 mg (0.50 mmol) of 4-(4-chlorobenzoyl)-1,3,4,5-tetrahydrobenzo[e][1,4]diazepin-2-on was dissolved in 10 ml of DMF. 24 mg (0.60 mmol) of sodium hydride was added to the obtained solution, and they were stirred at room temperature for 30 minutes. 147 mg (0.50 mmol) of t-butyl 4-((methanesulfonyloxy)methyl)piperidinecarboxylic acid was added to the obtained mixture, and they were stirred at 70° C. for 2 days. After the treatment with ethyl acetate as the extracting solvent by an ordinary method, the obtained crude product was dissolved in 8 ml of 4N solution of hydrogen chloride in dioxane, and the obtained solution was stirred overnight. The solvent was evaporated and the obtained crude product was treated in the same manner as in step 3 in Example 1 to obtain the title compound.

Yield: 56 mg (0.11 mmol) (22%)
MS (ESI, m/z) 398(MH+)
H-NMR (DMSO-d6) δ 1.24 (2H, br), 1.64 (2H, br), 1.80 (1H, br), 2.77 (2H, br), 3.18 (2H, br), 3.70–4.00 (4H, m), 4.40–4.66 (2H, br), 7.00–7.40 (1H, m), 7.45–7.68 (7H, m), 8.15 (1H, br), 8.48 (1H, br)

Example 141
Synthesis of 4-(4-chlorobenzoyl)-1-[(1-methyl-4-piperidinyl)methyl]-1,3,4,5-tetrahydrobenzo[e][1,4]diazepin-2-on trifluoroacetate 0.08 mmol of 4-(4-chlorobenzoyl)-1-(4-piperidinylmethyl)-1,3,4,5-tetrahydrobenzo[e][1,4]diazepin-2-on trifluoroacetate obtained in Example 140 and 5 mg (0.17 mmol) of paraformaldehyde were dissolved in 3 ml of dichloromethane. 12 mg (0.20 mmol) of acetic acid was added to the obtained solution. After stirring at room temperature for 30 minutes, 53 mg (0.25 mmol) of sodium triacetoxyborohydride was added to the obtained mixture, and they were stirred at room temperature overnight. After the treatment with dichloromethane as the extracting solvent by an ordinary method, the obtained crude product was treated in the same manner as in step 3 in Example 1 to obtain the title compound.

Yield: 17.7 mg (0.043 mmol) (54%)
MS (ESI, m/z) 412(MH+)
H-NMR (DMSO-d6) δ 1.28 (2H, br), 1.69 (3H, br), 2.68 (3H, s), 2.70–2.88 (2H, m), 3.32 (2H, br), 3.78–3.90 (4H, m), 4.38–4.70 (2H, br), 7.18–7.40 (1H, br), 7.43–7.68 (7H, m), 9.18 (1H, br)

Example 142
Synthesis of 4-(4-chlorobenzoyl)-1-[(1-isopropyl-4-piperidinyl)methyl]-1,3,4,5-tetrahydrobenzo[e][1,4]diazepin-2-on trifluoroacetate 0.08 mmol of 4-(4-chlorobenzoyl)-1-(4-piperidinylmethyl)-1,3,4,5-tetrahydrobenzo[e][1,4]diazepin-2-on trifluoroacetate obtained in Example 140 and 7 mg (0.12 mmol) of acetone were dissolved in 3 ml of dichloromethane. 12 mg (0.20 mmol) of acetic acid was added to the obtained solution. After stirring at room temperature for 30 minutes. 53 mg (0.25 mmol) of sodium triacetoxyborohydride was added to the obtained mixture, and they were stirred at room temperature overnight. After the treatment with dichloromethane as the extracting solvent by an ordinary method, the obtained crude product was treated in the same manner as in step 3 in Example 1 to obtain the title compound.

Yield: 1.0 mg (0.002 mmol) (3%)
MS (ESI, m/z) 440(MH+)
H-NMR (DMSO-d6) δ 1.16 (6H, d), 1.21 (1H, m), 1.35 (2H, br), 1.69–1.88 (3H, br), 2.86 (2H, br), 3.26 (2H, br), 3.75–3.92 (4H, m), 4.40–4.70 (2H, br), 7.18–7.40 (1H, br), 7.43–7.68 (7H, m), 8.82 (1H, br)

Example 143
Synthesis of 4-(4-chlorobenzoyl)-1-[(1-cyclohexyl-4-piperidinyl)methyl]-1,3,4,5-tetrahydrobenzo[e][1,4]diazepin-2-on mono(trifluoroacetate)

0.08 mmol of 4-(4-chlorobenzoyl)-1-(4-piperidinylmethyl)-1,3,4,5-tetrahydrobenzo[e][1,4]diazepin-2-on mono(trifluoroacetate) obtained in Example 140 and 12 ml (0.12 mmol) of cyclohexanone were dissolved in 3 ml of dichloromethane. 12 mg (0.20 mmol) of acetic acid was added to the obtained solution. After stirring at room temperature for 30 minutes. 53 mg (0.25 mmol) of sodium triacetoxyborohydride was added to the obtained mixture, and they were stirred at room temperature overnight. After the treatment with dichloromethane as the extracting solvent by an ordinary method, the obtained crude product was treated in the same manner as in step 3 in Example 1 to obtain the title compound.

Yield: 14.6 mg (0.030 mmol) (38%)
MS (ESI, m/z) 480(MH+)
H-NMR (DMSO-d6) δ 1.00–1.42 (7H, m), 1.58 (1H, br), 1.62–1.93 (7H, m), 2.89 (2H, br), 3.05 (1H, br), 3.31 (2H, br), 3.78–4.20 (4H, m), 4.40–4.70 (2H, br), 7.18–7.40 (1H, br), 7.43–7.68 (7H, m), 8.82 (1H, br)

Example 144
Synthesis of 4-(4-chlorobenzoyl)-1-[4-(1-methyl-4,5-dihydro-1H-imidazol-2-yl)benzyl]-8-[3-(4-morpholinyl)-3-oxopropyl]-1,3,4,5-tetrahydrobenzo[e][1,4]diazepin-2-on mono(trifluoroacetate)

Step 1: Synthesis of 3-[4-(4-chlorobenzoyl)-2-oxo-1-(4-(cyano)benzyl)-2,3,4,5-tetrahydro-1H-benzo[e][1,4]diazepin-8-yl]propionic acid 1.02 g (2.4 mmol) of methyl 3-[3-amino-4-(((4-chlorobenzoyl)ethoxycarbonylmethylamino)methyl)phenyl]propionate and 371 mg (2.8 mmol) of 4-cyanobenzaldehyde were dissolved in 100 ml of dichloromethane. 0.27 ml (4.8 mmol) of acetic acid was added to the obtained solution, and they were stirred at room temperature for 30 minutes. 1300 mg (6.0 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 10 ml of 1 N sodium hydroxide and 10 ml of ethanol, and the obtained solution was stirred at room temperature for 4 hours. After the treatment with ethyl acetate as the extracting solvent by an ordinary method, the obtained crude product was dissolved in 10 ml of dichloromethane. 470 mg (2.8 mmol) of 2-chloro-1,3-dimethylimidazonium chloride and 0.5 ml (3.6 mmol) of triethylamine were added to the obtained solution, and they were stirred overnight. The solvent was evaporated to obtain the title compound.

Yield: 750 mg (1.8 mmol) (75%)

Step 2: Synthesis of 4-(4-chlorobenzoyl)-1-[4-(1-methyl-4,5-dihydro-1H-imidazol-2-yl)benzyl]-8-[3-(4-morpholinyl)-3-oxopropyl]-1,3,4,5-tetrahydrobenzo[e][1,4]diazepin-2-on trifluoroacetate 40 mg (0.096 mmol) of 3-[4-(4-chlorobenzoyl)-2-oxo-1-(4-(cyano)benzyl)-2,3,4,5-tetrahydro-1H-benzo[e][1,4]diazepin-8-yl]-propionic acid was dissolved in 5 ml of dichloromethane. 20 mg (0.12 mmol) of 2-chloro-1,3-dimethylimidazonium chloride, 0.026 ml (0.19 mmol) of triethylamine and 12 mg (0.12 mmol) of morpholine were added to the obtained solution, and they were stirred overnight. The solvent was evaporated, and the obtained crude product was dissolved in a mixture of 5 ml of 4N solution of hydrogen chloride in dioxane and 1 ml of ethanol, and the obtained solution was stirred at room temperature for 2 days. The solvent was evaporated and the obtained crude product was dissolved in 5 ml of ethanol. 58 mg (0.79 mmol) of N-methylethylenediamine was added to the obtained solution, and they were stirred at 70° C. for 4 hours. The solvent was evaporated and the obtained crude product was treated in the same manner as in step 3 in Example 1 to obtain the title compound.

Yield: 3.6 mg (0.005 mmol) (5%)
MS (ESI, m/z) 614(MH+)
H-NMR (DMSO-d6) δ 2.61 (5H, br), 2.81 (2H, br), 3.07–3.44 (8H, m), 3.88–4.12 (6H, br), 4.42 (2H, br), 5.22 (2H, br), 7.37–7.62 (11H, m)

Example 145
Synthesis of 4-(4-chlorobenzoyl)-1-[4-(2,5-dihydro-1H-pyrrol-1-ylcarbonyl)benzyl]-7-methoxy-1,3,4,5-tetrahydrobenzo[e][1,4]-diazepin-2-on Step 1: Synthesis of ethyl [(5-methoxy-2-nitrobenzyl)-(4-chlorobenzoyl)-amino]acetate 3.0 g (15.2 mmol) of 5-methoxy-2-nitrobenzoic acid was dissolved in a mixture of 200 ml of THF and 2.7 ml (19.8 mmol) of triethylamine. 1.7 ml (17.6 mmol) of ethyl chloroformate was added to the obtained solution under cooling with ice, and they were stirred for 15 minutes. A piece of ice was added to the obtained filtrate, and then 1.1 g (30.4 mmol) of sodium borohydride was added thereto under cooling with ice. The temperature was elevated to room temperature, and the obtained mixture was stirred overnight. After the treatment with ethyl acetate as the extracting solvent by an ordinary method, the obtained crude product was dissolved in 100 ml of dichloromethane. 1.4 ml (18.2 mmol) of methanesulfonyl chloride and 3.2 ml (22.8 mmol) of triethylamine were added to the obtained solution, and they were stirred under cooling with ice for 2 hours. After the treatment with dichloromethane as the extracting solvent by an ordinary method, the obtained crude product was dissolved in 100 ml of ethanol. 3.2 g (22.8 mmol) of glycine ethyl ester hydrochloride and 2.6 g (30.4 mmol) of sodium hydrogencarbonate were added to the obtained solution, and they were stirred at 70° C. for 6 hours. The solvent was evaporated. After the extraction with ethyl acetate as the extracting solvent by an ordinary method, the obtained crude product was dissolved in 70 ml of dichloromethane. 0.63 ml (4.9 mmol) of 4-chlorobenzoyl chloride and 0.86 ml (6.2 mmol) of triethylamine were added to the obtained solution under cooling with ice, and they were stirred under cooling with ice for 2 hours. After the treatment with dichloromethane as the extracting solvent by an ordinary method, the obtained crude product was purified by the silica gel column chromatography to obtain the title compound.

Yield: 1.0 g (2.5 mmol) (16%)
H-NMR (CD3Cl) δ 1.23 (3H, t), 3.90 (5H, br), 4.12 (2H, br), 5.01–5.12 (2H, m), 7.01–7.47 (7H, m)
Step 2: Synthesis of ethyl [(2-amino-5-methoxybenzyl)-(4-chlorobenzoyl)amino]acetate 1.0 g (2.5 mmol) of ethyl [(5-methoxy-2-nitrobenzyl)-(4-chlorobenzoyl)amino]acetate was dissolved in a mixture of 10 ml of ethyl acetate and 10 ml of ethanol. 360 mg of 10% palladium/carbon was added to the obtained solution, and they were stirred in the presence of hydrogen at room temperature for 4 hours. The reaction mixture was filtered through Celite and the solvent was evaporated. The obtained crude product was purified by the silica gel column chromatography to obtain the title compound.

Yield: 320 mg (0.85 mmol) (34%)
H-NMR (CD3Cl) δ 1.24 (3H, t), 3.74 (5H, br), 4.18 (2H, br), 4.82 (2H, br) 6.61–6.78 (4H, m), 7.37 (5H, br)
Step 3 Synthesis of 4-(4-chlorobenzoyl)-1-[4-(2,5-dihydro-1H-pyrrol-1-ylcarbonyl)benzyl]-7-methoxy-1,3,4,5-tetrahydrobenzo[e][1,4]-diazepin-2-on 320 mg (0.85 mmol) of ethyl [(2-amino-5-methoxybenzyl)-(4-chlorobenzoyl)amino]acetate was dissolved in 5 ml of dichloromethane. 205 mg (1.0 mmol) of 4-(2,5-dihydro-1H-pyrrol-1-ylcarbonyl)benzaldehyde and 0.097 ml (1.7 mmol) of acetic acid were added to the obtained solution, and they were stirred at room temperature for 30 minutes. 440 mg (2.1 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 5 ml of dichloromethane. 169 mg (1.0 mmol) of 2-chloro-1,3-dimethylimidazonium chloride and 0.24 ml (1.7 mmol) of triethylamine were added to the obtained solution, and they were stirred overnight. The solvent was evaporated, and the obtained crude product was treated in the same manner as in step 3 in Example 1 to obtain the title compound.

Yield: 4.5 mg (0.087 mmol) (10%)
MS (ESI, m/z) 516(MH+)
H-NMR (DMSO-d6) δ 3.74 (5H, br), 4.11 (2H, br), 4.23 (4H, br), 5.06 (2H, br), 5.80 (1H, br), 5.91 (1H, br), 7.17–7.62 (11H, m)

Example 146
Synthesis of 4-(4-chlorobenzoyl)-1-[4-(2,5-dihydro-1H-pyrrol-1-ylcarbonyl)benzyl]-9-methoxy-1,3,4,5-tetrahydrobenzo[e][1,4]-diazepin-2-on
Step 1: Synthesis of ethyl [(3-methoxy-2-nitrobenzyl)-(4-chlorobenzoyl)amino]acetate 2.5 g (13.8 mmol) of 3-methoxy-2-nitrobenzaldehyde was dissolved in a mixture of 70 ml of ethanol and 70 ml of THF. 1.0 g (27.6 mmol) of sodium borohydride was added to the obtained solution. They were stirred at room temperature overnight. After the treatment with ethyl acetate as the extracting solvent by an ordinary method, the obtained crude product was dissolved in 100 ml of dichloromethane. 1.3 ml (16.6 mmol) of methanesulfonyl chloride and 2.9 ml (20.7 mmol) of triethylamine were added to the obtained solution, and they were stirred under cooling with ice for 2 hours. After the treatment with dichloromethane as the extracting solvent by an ordinary method, the obtained crude product was dissolved in 70 ml of ethanol. 2.9 g (20.7 mmol) of glycine ethyl ester hydrochloride and 2.3 g (27.6 mmol) of sodium hydrogencarbonate were added to the obtained solution, and they were stirred at 70° C. for 6 hours. The solvent was evaporated. After the extraction with ethyl acetate as the extracting solvent by an ordinary method, the obtained crude product was dissolved in 100 ml of dichloromethane. 2.0 ml (15.6 mmol) of 4-chlorobenzoyl chloride and 2.7 ml (19.5 mmol) of triethylamine were added to the obtained solution under cooling with ice, and they were stirred under cooling with ice for 2 hours. After the treatment with dichloromethane as the extracting solvent by an ordinary method, the obtained crude product was purified by the silica gel column chromatography to obtain the title compound.

Yield: 1.8 g (4.4 mmol) (32%)
H-NMR (CD3Cl) δ 1.23 (3H, t), 3.90 (5H, br), 4.12 (2H, br), 4.60–4.80 (2H, m), 7.01 (2H, br), 7.38 (5H, m)
Step 2: Synthesis of ethyl [(2-amino-3-methoxybenzyl)-(4-chlorobenzoyl)amino]acetate 1.8 g (4.4 mmol) of ethyl [(3-methoxy-2-nitrobenzyl)-(4-chlorobenzoyl)amino]acetate was dissolved in a mixture of 10 ml of ethyl acetate and 10 ml of ethanol. 180 mg of 10% palladium/carbon was added to the obtained solution, and they were stirred in the presence of hydrogen at room temperature for 4 hours. The reaction mixture was filtered through Celite and the solvent was evaporated. The obtained crude product was purified by the silica gel column chromatography to obtain the title compound.

Yield: 1.1 g (2.9 mmol) (66%)
H-NMR (CD3Cl) δ 1.24 (3H, t), 3.85 (5H, br), 4.18 (2H, q), 4.80 (2H, br), 6.63–6.80 (4H, m), 7.36 (5H, br)
Step 3 Synthesis of 4-(4-chlorobenzoyl)-1-[4-(2,5-dihydro-1H-pyrrol-1-ylcarbonyl)benzyl]-9-methoxy-1,3,4,5-tetrahydrobenzo[e][1,4]diazepin-2-on 320 mg (0.85 mmol) of ethyl [(2-amino-5-methoxybenzyl)-(4-chlorobenzoyl)amino]acetate was dissolved in 5 ml of dichloromethane. 205 mg (1.0 mmol) of 4-(2,5-dihydro-1H-pyrrol-1-ylcarbonyl)benz-aldehyde and 0.097 ml (1.7 mmol) of acetic acid were added to the obtained solution, and they were stirred at room temperature for 30 minutes. 440 mg (2.1 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 5 ml of dichloromethane. 169 mg (1.0 mmol) of 2-chloro-1,3-dimethylimidazonium chloride and 0.24 ml (1.7 mmol) of triethylamine were added to the obtained solution, and they were stirred overnight. The solvent was evaporated, and the obtained crude product was treated in the same manner as in step 3 in Example 1 to obtain the title compound.

Yield: 12 mg (0.023 mmol) (3%)
MS (ESI, m/z) 516(MH+)
H-NMR (DMSO-d6) δ 3.88 (5H, br), 4.08 (2H, br), 4.23 (4H, br), 5.06 (2H, br), 5.80 (1H, br), 5.91 (1H, br), 7.22–7.62 (11H, m)

Example 147

Synthesis of 4-(4-chlorobenzoyl)-1-[4-(2,5-dihydro-1H-pyrrol-1-ylcarbonyl)benzyl]-7-hydroxy-1,3,4,5-tetrahydrobenzo[e][1,4]-diazepin-2-on 35 mg (0.068 mmol) of 4-(4-chlorobenzoyl)-1-[4-(2,5-dihydro-1H-pyrrol-1-ylcarbonyl)benzyl]-7-methoxy-1,3,4,5-tetrahydrobenzo[e][1,4]-diazepin-2-on was dissolved in 10 ml of dichloromethane. 1.0 ml of borane tribromide was added to the obtained solution, and they were stirred at room temperature overnight. After the treatment with dichloromethane as the extracting solvent by an ordinary method, the obtained crude product was treated in the same manner as in step 3 in Example 1 to obtain the title compound.

Yield: 11 mg (0.022 mmol) (32%)
MS (ESI, m/z) 502(MH+)
H-NMR (DMSO-d6) δ 3.78 (2H, br), 4.14 (2H, br), 4.24 (4H, br), 5.04 (2H, br), 5.80 (1H, br), 5.91 (1H, br), 7.22–7.60 (11H, m)

Example 148

Synthesis of 4-(4-chlorobenzoyl)-1-[4-(2,5-dihydro-1H-pyrrol-1-ylcarbonyl)benzyl]-9-hydroxy-1,3,4,5-tetrahydrobenzo[e][1,4]-diazepin-2-on 7 mg (0.014 mmol) of 4-(4-chlorobenzoyl)-1-[4-(2,5-dihydro-1H-pyrrol-1-ylcarbonyl)benzyl]-9-methoxy-1,3,4,5-tetrahydrobenzo[e][1,4]-diazepin-2-on was dissolved in 10 ml of dichloromethane. 1.0 ml of borane tribromide was added to the obtained solution, and they were stirred at room temperature overnight. After the treatment with dichloromethane as the extracting solvent by an ordinary method, the obtained crude product was treated in the same manner as in step 3 in Example 1 to obtain the title compound.

Yield: 1.1 mg (0.002 mmol) (15%)
MS (ESI, m/z) 502(MH+)
H-NMR (DMSO-d6) δ 3.78 (2H, br), 4.08 (2H, br), 4.23 (4H, br), 5.19 (2H, br), 5.80 (1H, br), 5.91 (1H, br), 6.97–7.57 (11H, m)

Example 149

Synthesis of 4-(4-chlorobenzoyl)-1-[4-(2,5-dihydro-1H-pyrrol-1-ylcarbonyl)benzyl]-8-[3-(1-piperazinyl)propyl]-1,3,4,5-tetrahydrobenzo[e][1,4]diazepin-2-on bistrifluoroacetate 24 mg (0.04 mmol) of 8-(3-hydroxypropyl)-1-[4-(2,5-dihydro-1H-pyrrol-1-ylcarbonyl)benzyl]-4-(4-chlorobenzoyl)-1,3,4,5-tetrahydro-benzo[e][1,4]diazepin-2-on was dissolved in 5 ml of dichloromethane. 0.004 ml (0.05 mmol) of methanesulfonyl chloride and 0.008 ml (0.06 mmol) of triethylamine were added to the obtained solution, and they were stirred under cooling with ice for 2 hours. After the treatment with dichloromethane as the extracting solvent by an ordinary method, the obtained crude product was dissolved in 5 ml of acetonitrile. 8 mg (0.06 mmol) of potassium carbonate and 8 ml (0.06 mmol) of t-butylpiperazine carboxylate were added to the obtained solution, and they were stirred at 70° C. overnight. After the treatment with ethyl acetate by an ordinary method, the obtained crude product was dissolved in 5 ml of 4N solution of hydrogen chloride in dioxane and the solution was stirred at room temperature for 2 hours. The solvent was evaporated and the obtained crude product was treated in the same manner as in step 3 in Example 1 to obtain the title compound.

Yield: 2 mg (0.023 mmol) (6%)
MS (ESI, m/z) 612(MH+)
H-NMR (DMSO-d6) δ 2.42–2.63 (4H, br), 3.12–3.58 (10H, m), 3.91 (2H, br), 4.11 (2H, br), 4.23 (4H, br), 5.18 (2H, br), 5.80 (1H, br), 5.91 (1H, br), 7.24–7.62 (11H, m)

Example 150

Synthesis of ethyl 3-[4-(4-chlorobenzoyl)-2-oxo-1-(4-(1-methyl-4,5-dihydro-1H-imidazol-2-yl)benzyl)-2,3,4,5-tetrahydro-1H-benzo[e][1,4]diazepin-8-yl]propionate trifluoroacetate 150 mg of the crude product obtained in Step 1 in Example 130 was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 17 mg (0.24 mmol) of N-methylethylenediamine was added to the obtained solution, and they were stirred at 70° C. for 4 hours. The solvent was evaporated and the obtained crude product was treated in the same manner as in step 3 in Example 1 to obtain the title compound.

Yield: 5.8 mg (0.009 mmol) (4%)
MS (ESI, m/z) 572(MH+)
H-NMR (DMSO-d6) δ 1.13 (3H, t), 2.82 (2H, br), 3.01 (3H, s), 3.03 (2H, br), 3.78–4.04 (6H, m), 4.42 (4H, br), 5.12 (2H, br), 7.03–7.67 (11H, m)

Example 151

Synthesis of 4-(4-chlorobenzoyl)-1-[4-(2,5-dihydro-1H-pyrrol-1-ylcarbonyl)benzyl]-6-(trifluoromethanesulfonyloxy)-1,3,4,5-tetrahydrobenzo[e][1,4]diazepin-2-on 30 mg (0.06 mmol) of 4-(4-chlorobenzoyl)-1-[4-(2,5-dihydro-1H-pyrrol-1-ylcarbonyl)benzyl]-6-hydroxy-1,3,4,5-tetrahydrobenzo[e][1,4]-diazepin-2-on was dissolved in 5 ml of dichloromethane. 0.016 ml (0.12 mmol) of triethylamine and 0.012 ml (0.07 mmol) of trifluoromethanesulfonyl anhydride were added to the obtained solution, and they were stirred at room temperature overnight. The reaction mixture was treated with dichloromethane as the extracting solvent by an ordinary method, and the obtained crude product was dissolved in 5 ml of DMF. 3 mg (0.01 mmol) of palladium acetate, 8 mg (0.03 mmol) of triphenylphosphine, 0.010 ml (0.07 mmol) of triethylamine and 0.01 ml (0.07 mmol) of benzyl alcohol were added to the obtained solution, and they were stirred at 110° C. for 2 days. The solvent was evaporated and the obtained crude product was treated in the same manner as in Step 3 in Example 1 to obtain the title compound and benzyl 4-(4- chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-6-carboxylic acid. (No NMR data obtained.)
Yield: 3 mg (0.004 mmol) (7%)
MS (ESI, m/z) 634(MH+)
H-NMR (DMSO-d6) δ 3.89 (2H, br), 4.10 (2H, br), 4.24 (2H, br), 4.54 (2H, br), 5.17 (2H, br), 5.80 (1H, br), 5.91 (1H, br), 7.24–7.83 (11H, m)

Example 152

Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-6-carboxylic acid Benzyl 4-(4-chlorobenzoyl)-2-oxo-1-[4-(2,5-dihydro-1H-pyrrol-1-ylcarbonyl)benzyl]-2,3,4,5-tetrahydro-11H-benzo[e][1,4]-diazepine-6-carboxylate obtained in Example 151 was dissolved in a mixture of 1 ml of 1 N sodium hydroxide and 1 ml of ethanol, and the obtained solution was stirred at room temperature for 4 hours. The solvent was evaporated and the obtained crude product was treated in the same manner as in Step 3 in Example 1 to obtain the title compound.
Yield: 1.1 mg (0.002 mmol) (3%)
MS (ESI, m/z) 530(MH+)
H-NMR (DMSO-d6) δ 3.98 (2H, br), 4.12 (2H, br), 4.24 (2H, br), 4.83 (2H, br), 5.18 (2H, br), 5.81 (1H, br), 5.91 (1H, br), 7.22–7.65 (11H, m)

Example 153

Synthesis of 4-(4-chlorobenzoyl)-1-[4-(1-methyl-4,5-dihydro-1H-imidazol-2-ylcarbonyl)benzyl]-8-[3-oxo-3-(4-thiomorpholinyl)-propyl]-1,3,4,5-tetrahydrobenzo[e][1,4]-diazepin-2-on trifluoroacetate 80 mg (0.192 mmol) of 3-[4-(4-chlorobenzoyl)-2-oxo-1-(4-(cyano)-benzyl)-2,3,4,5-tetrahydro-1H-benzo[e][1,4]-diazepin-8-yl]propionic acid was dissolved in 5 ml of dichloromethane. 40 mg (0.24 mmol) of 2-chloro-1,3-dimethylimidazonium chloride, 0.052 ml (0.38 mmol) of triethylamine and 24 mg (0.24 mmol) of thiomorpholine were added to the obtained solution, and they were stirred overnight. The solvent was evaporated, and the obtained crude product was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 58 mg (0.79 mmol) of N-methylethylenediamine was added to the obtained solution, and they were stirred at 70° C. for 4 hours. The solvent was evaporated and the obtained crude product was treated in the same manner as in Step 3 in Example 1 to obtain the title compound.
Yield: 6.2 mg (0.008 mmol) (4%)
MS (ESI, m/z) 630(MH+)
H-NMR (DMSO-d6) 62.61–2.86 (4H, m), 3.01 (3H, s), 3.41–4.03 (14H, m), 4.42 (2H, br), 5.13 (2H, br), 7.00–7.62 (11H, m)

Example 154

Synthesis of 4-(4-chlorobenzoyl)-1-[4-(1-methyl-4,5-dihydro-1H-imidazol-2-yl)benzyl]-8-[3-oxo-3-(1-piperazinyl)propyl]-1,3,4,5-tetrahydrobenzo[e][1,4]-diazepin-2-on bistrifluoroacetate 120 mg (0.288 mmol) of 3-[4-(4-chlorobenzoyl)-2-oxo-1-(4-cyanobenzyl)-2,3,4,5-tetrahydro-1H-benzo[e][1,4]-diazepin-8-yl]propionic acid was dissolved in 5 ml of dichloromethane. 60 mg (0.36 mmol) of 2-chloro-1,3-dimethylimidazonium chloride, 0.078 ml (0.57 mmol) of triethylamine and 67 mg (0.36 mmol) of t-butylpiperazine carboxylate were added to the obtained solution, and they were stirred overnight. The solvent was evaporated, and the obtained crude product was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 58 mg (0.79 mmol) of N-methylethylenediamine was added to the obtained solution, and they were stirred at 70° C. for 4 hours. The solvent was evaporated and the obtained crude product was treated in the same manner as in Step 3 in Example 1 to obtain the title compound.
Yield: 11 mg (0.013 mmol) (5%)
MS (ESI, m/z) 613(MH+)
H-NMR (DMSO-d6) δ 2.61–2.86 (4H, m), 3.01 (3H, s), 3.12 (4H, br), 3.51–3.63 (6H, m), 3.83–4.09 (4H, br), 4.24 (2H, br), 5.13 (2H, br), 7.40–7.62 (11H, m)

Example 155

Synthesis of 4-(4-chlorobenzoyl)-1-[(1-acetimidoyl-4-piperidinyl)methyl]-1,3,4,5-tetrahydrobenzo[e][1,4]diazepin-2-on trifluoroacetate 15 mg (0.029 mmol) of 4-(4-chlorobenzoyl)-1-(4-piperidinyl-methyl)-1,3,4,5-tetrahydrobenzo[e][1,4]diazepin-2-on trifluoroacetate was dissolved in 5 ml of ethanol. 120 mg (1.7 mmol) of ethyl acetimidate hydrochloride and 0.50 ml (3.6 mmol) of triethylamine were added to the obtained solution, and they were stirred at 80° C. for 2 days. The solvent was evaporated, and the obtained crude product was treated in the same manner as in Step 3 in Example 1 to obtain the title compound.
Yield: 5.21 mg (0.009 mmol) (32%)
MS (ESI, m/z) 439(MH+)
H-NMR (DMSO-d6) δ 1.10–1.30 (2H, m), 1.62 (2H, br), 1.90 (1H, br), 2.20 (3H, s), 2.90–3.18 (2H, m), 3.85–4.00 (6H, m), 4.40–4.70 (2H, br), 7.18–7.38 (1H, br), 7.43–7.65 (7H, m), 8.40 (1H, s), 9.00 (1H, s)

Example 156

Synthesis of 4-(4-chlorobenzoyl)-1-[4-((4-cyclohexylpiperazin-1-yl)methyl)benzyl]-1,3,4,5-tetrahydrobenzo[e][1,4]diazepin-2-on bistrifluoroacetate 35 mg (0.078 mmol) of 4-(4-chlorobenzoyl)-1-(4-chloromethylbenzyl)-1,3,4,5-tetrahydrobenzo[e][1,4]diazepin-2-on obtained in Step 1 in Example 126 was dissolved in 5 ml of acetonitrile. 40 mg (0.30 mmol) of potassium carbonate and 37 mg (0.2 mmol) of t-butyl 1-piperazinecarboxylate were added to the obtained solution, and they were stirred at room temperature for 2 days. The reaction solution was filtered, and the obtained filtrate was concentrated to dryness. The obtained crude product was dissolved in 4N solution of hydrogen chloride in dioxane, and the obtained solution was stirred for 1 hour. The solvent was evaporated to obtain the crude product. 9 mg (0.015 mmol) of the crude product and 15 mg (0.15 mmol) of cyclohexanone were dissolved in 2 ml of dichloromethane. 10 mg (0.17 mmol) of acetic acid was added to the obtained solution, and they were stirred at room temperature for 30 minutes. 53 mg (0.25 mmol) of sodium triacetoxyborohydride was added to the obtained mixture, acid they were stirred at room temperature overnight. The reaction mixture was treated with dichloromethane as the extracting solvent by an ordinary method. The crude product thus obtained was treated in the same manner as in Step 3 in Example 1 to obtain the title compound.
Yield: 1.3 mg (0.0016 mmol) (11%)
MS (ESI, m/z) 571(MH+)
H-NMR (DMSO-d6) δ 1.00–1.40 (5H, m), 1.58 (1H, br), 1.78 (2H, br), 1.96 (2H, br), 2.30–2.42 (1H, m), 2.88–3.20

(6H, m), 3.30–3.70 (4H, m), 3.85–4.18 (2H, m), 4.40 (2H, m), 5.08 (2H, br), 7.15–7.62 (12H, m)

Example 157

Synthesis of 4-(4-chlorobenzoyl)-1-[4-((methyl(2-(1-pyrrolidinyl)ethyl)amino)methyl)benzyl]-1,3,4,5-tetrahydrobenzo[e][1,4]-diazepin-2-on bistrifluoroacetate 17 mg (0.039 mmol) of 4-(4-chlorobenzoyl)-1-(4-chloromethylbenzyl)-1,3,4,5-tetrahydrobenzo[e][1,4] diazepin-2-on obtained in Step 1 in Example 126 was dissolved in 4 ml of acetonitrile. 20 mg (0.15 mmol) of potassium carbonate and 7.5 mg (0.1 mmol) of 2-(methylamino)ethanol were added to the obtained solution, and they were stirred at room temperature for 2 days. The reaction solution was filtered, and the obtained filtrate was concentrated to dryness. The obtained crude product was dissolved in 5 ml of dichloromethane. 0.08 ml (0.58 mmol) of triethylamine and 0.03 ml (0.39 mmol) of methanesulfonyl chloride were added to the obtained solution under cooling with ice, and they were stirred overnight. After the treatment with dichloromethane as the extracting solvent by an ordinary method, the obtained crude product was dissolved in 5 ml of acetonitrile. 40 mg (0.30 mmol) of potassium carbonate and 20 mg (0.28 mmol) of pyrrolidine were added to the obtained solution, and they were stirred at room temperature overnight. The solvent was evaporated, and the crude product thus obtained was treated in the same manner as in Step 3 in Example 1 to obtain the title compound.

Yield: 5.6 mg (0.0073 mmol) (19%)

MS (ESI, m/z) 531(MH+)

H-NMR (DMSO-d6) δ 1.91 (4H, br), 2.49 (3H, s), 3.00–3.70, (10H, m), 3.83–4.15 (2H, br), 4.40 (2H, br), 5.11 (2H, br), 7.10–7.62 (12H, m)

Example 158

Synthesis of 4-(4-chlorobenzoyl)-1-[(1-cyclopentyl-4-piperidinyl)methyl]-1,3,4,5-tetrahydrobenzo[e][1,4] diazepin-2-on trifluoroacetate 4-(4-chlorobenzoyl)-1-(4-piperidinylmethyl)-1,3,4,5-tetrahydrobenzo[e][1,4]diazepin-2-on trifluoroacetate obtained 4 Example 140 was treated with an alkali to make it free from trifluoroacetic acid. 35 mg (0.088 mmol) of the obtained oily product and 22 mg (0.26 mmol) of cyclopentanone were dissolved in 5 ml of dichloromethane. 11 mg (0.18 mmol) of acetic acid was added to the obtained solution, and they were stirred at room temperature for 30 minutes. 53 mg (0.25 mmol) of sodium triacetoxyborohydride was added to the obtained mixture, and they were stirred at room temperature overnight. The reaction mixture was treated with dichloromethane as the extracting solvent by an ordinary method. The crude product thus obtained was treated in the same manner as in Step 3 in Example 1 to obtain the title compound.

Yield: 40 mg (0.069 mmol) (78%)

MS (ESI, m/z) 466(MH+)

H-NMR (DMSO-d6) δ 1.20–1.40 (1H, m), 1.43–2.03 (12H, m), 2.80 (2H, br), 3.18 (1H, br), 3.39 (2H, br), 3.78–4.70 (6H, br), 7.18–7.40 (1H, br), 7.43–7.68 (7H, m), 9.08 (1H, br)

Example 159

Synthesis of 4-(4-chlorobenzoyl)-1-[4-(1-ethyl-4,5-dihydro-1H-imidazol-2-yl)benzyl]-1,3,4,5-tetrahydrobenzo[e][1,4] diazepin-2-on trifluoroacetate 38 mg (0.091 mmol) of 4-(4-chlorobenzoyl)-1-(4-cyanobenzyl)-1,3,4,5-tetrahydrobenzo[e][1,4]diazepin-2-on obtained in Step 1 in Example 125 was dissolved in a mixture of 5 ml of 4 N dioxane hydrochloride solution and 1 ml of ethanol, and the obtained solution was stirred at room temperature for 2 days. The solvent was evaporated, and the obtained crude product was dissolved in 5 ml of ethanol. 20 mg (0.23 mmol) of N-ethylethylenediamine was added to the obtained solution, and they were stirred at 65° C. for 6 hours. The solvent was evaporated, and the crude product thus obtained was treated in the same manner as in Step 3 in Example 1 to obtain the title compound.

Yield: 55 mg (0.91 mmol) (100%)

MS (ESI, m/z) 487(MH+)

H-NMR (DMSO-d6) δ 1.16 (3H, t,), 3.33 (2H, q), 3.70–4.15 (6H, m), 4.50 (2H, br), 5.20 (2H, br), 7.13–7.77 (12H, m)

Example 160

Synthesis of 4-(4-chlorobenzoyl)-1-[(1'-methyl-1,4'-bipiperidin-4-yl)methyl]-1,3,4,5-tetrahydrobenzo[e][1,4] diazepin-2-on bistrifluoroacetate 4-(4-chlorobenzoyl)-1-(4-piperidinylmethyl)-1,3,4,5-tetrahydrobenzo[e][1,4]diazepin-2-on hydrochloride obtained in the same manner as in Example 140 and 20 mg (0.18 mmol) of 1-methyl-4-piperidone were dissolved in 3 ml of dichloromethane. 10 mg (0.17 mmol) of acetic acid was added to the obtained solution, and they were stirred at room temperature for 30 minutes. 53 mg (0.25 mmol) of sodium triacetoxyborohydride was added to the obtained mixture, and they were stirred at room temperature overnight. The reaction mixture was treated with dichloromethane as the extracting solvent by an ordinary method. The crude product thus obtained was treated in the same manner as in Step 3 in Example 1 to obtain the title compound.

Yield: 5.8 mg (0.008 mmol) (11%)

MS (ESI, m/z) 495(MH+)

H-NMR (DMSO-d6) δ 1.38 (2H, m), 1.60–1.90 (7H, m), 2.17 (2H, br), 2.73 (3H, s), 2.93 (2H, br), 3.13–3.60 (5H, m), 3.78–4.10 (4H, m), 4.40–4.70 (2H, br), 7.18–7.68 (8H, m)

Example 161

Synthesis of 1-(1,4'-bipiperidin-4-ylmethyl)-4-(4-chlorobenzoyl)-1,3,4,5-tetrahydrobenzo[e][1,4]diazepin-2-on bistrifluoroacetate 70 mg (0.16 mmol) of 4-(4-chlorobenzoyl)-1-(4-piperidinylmethyl)-1,3,4,5-tetrahydrobenzo[e][1,4] diazepin-2-on hydrochloride obtained in the same manner as in Example 140 and 113 mg (0.57 mmol) of t-butyl 4-oxo-1-piperidinecarboxylate were dissolved in 5 ml of dichloromethane. 20 mg (0.34 mmol) of acetic acid was added to the obtained solution, and they were stirred at room temperature for 30 minutes. 106 mg (0.50 mmol) of sodium triacetoxyborohydride was added to the reaction mixture, and they were stirred at room temperature overnight. After the treatment with dichloromethane as the extracting solvent by an ordinary method, the obtained crude product was dissolved in 4N solution of hydrogen chloride in dioxane. The obtained solution was stirred for 1 hour. The solvent was evaporated, and the crude product thus obtained was treated in the same manner as in Step 3 in Example 1 to obtain the title compound.

Yield: 4.5 mg (0.006 mmol) (4%)

MS (ESI, m/z) 481(MH+)

H-NMR (DMSO-d6) δ 1.38 (2H, m), 1.60–1.90 (7H, m), 2.15 (2H, br), 2.80–2.98 (5H, br), 3.08–3.40 (2H, br), 3.78–4.03 (4H, m), 4.38–4.70 (2H, br), 7.18–7.65 (8H, m),8.53 (1H, br), 8.81 (1H, br), 9.60 (1H, br)

Example 162
Synthesis of 4-(4-chlorobenzoyl)-1-[(1-(1-methyl-4,5-dihydro-1H-imidazol-2-yl)-4-piperidinyl)methyl]-1,3,4,5-tetrahydro-benzo[e][1,4]diazepin-2-on trifluoroacetate 70 mg (0.16 mmol) of 4-(4-chlorobenzoyl)-1-(4-piperidinylmethyl)-1,3,4,5-tetrahydrobenzo[e][1,4]diazepin-2-on hydrochloride obtained in the same manner as in Example 140 and 78 mg (0.32 mmol) of 2-methylthio-2-imidazoline were dissolved in 10 ml of methanol. 0.5 ml (3.6 mmol) of triethylamine was added to the obtained solution, and they were refluxed at 80° C. overnight. The solvent was evaporated, and the obtained crude product was treated in the same manner as in Step 3 in Example 1 to obtain 123 mg of a white solid. 70 mg of the solid was dissolved in 5 ml of DMF. 13 mg (0.33 mmol) of sodium hydride was added to the obtained solution, and they were stirred at room temperature for 30 minutes. 15 mg (0.11 mmol) of methyl iodide was added to the obtained mixture, and they were stirred at room temperature for 6 hours. The solvent was evaporated, and the crude product thus obtained was treated in the same manner as in Step 3 in Example 1 to obtain the title compound.

Yield: 2.2 mg (0.003 mmol) (3%)
MS (ESI, m/z) 480(MH+)
H-NMR (DMSO-d6) δ 1.22 (2H, br), 1.60 (2H, br), 1.91 (1H, br), 2.82–3.10 (5H, m), 3.30–3.75 (6H, m), 3.78–4.00 (4H, br), 4.58 (2H, br), 7.18–7.65 (8H, m),8.37 (1H, br)

Example 163
Synthesis of 4-(4-chlorobenzoyl)-1-[4-(1-methyl-1H-imidazol-2-yl)benzyl]-1,3,4,5-tetrahydrobenzo[e][1,4]diazepin-2-on trifluoroacetate 36 mg (0.16 mmol) of ethyl 4-(1-methyl-1H-imidazol-2-yl)benzoate was dissolved in 10 ml of dichloromethane. 0.49 ml (0.47 mmol) of 0.95 M solution of lithium diisobutylaluminum hydride in n-hexane was added to the obtained solution, and they were stirred for 30 minutes. 0.2 ml of methanol and 0.2 ml of water were added thereto, and they were stirred overnight. The reaction solution was filtered, and the filtrate was concentrated. The crude product thus obtained was dissolved in 5 ml of dichloromethane. 0.05 ml (0.36 mmol) of triethylamine and 0.02 ml (0.23 mmol) of methanesulfonyl chloride were added to the obtained solution under cooling with ice, and they were stirred for 5 hours. After the treatment with dichloromethane as the extracting solvent by an ordinary method, the crude product was obtained.

54 mg (0.18 mmol) of 4-(4-chlorobenzoyl)-1,3,4,5-tetrahydrobenzo[e][1,4]diazepin-2-on was dissolved in 5 ml of DMF. 7 mg (0.18 mmol) of sodium hydride was added to the obtained solution. After stirring at room temperature for 30 minutes, the crude product obtained as above was added thereto, and they were stirred at room temperature overnight. The solvent was evaporated and the obtained crude product was treated in the same manner as in step 3 in Example 1 to obtain the title compound.

Yield: 12 mg (0.021 mmol) (12%)
MS (ESI, m/z) 471(MH+)
H-NMR (DMSO-d6) δ 3.50–4.20 (5H, m), 4.51 (2H, br), 5.22 (2H, br), 7.18–7.65 (10H, m), 7.68–7.81 (4H, m)

Example 164
Synthesis of 4-(4-chlorobenzoyl)-1-[4-(2,5-dihydro-1H-pyrrol-1-ylcarbonyl)benzyl]-8-(3-(methanesulfonylamino)propyl)-1,3,4,5-tetrahydrobenzo[e][1,4]-diazepin-2-on 12 mg (0.018 mmol) of 8-(3-aminopropyl-4-(4-chlorobenzoyl)-1-[4-(4,5-dihydro-1H-pyrrol-1-ylcarbonyl)benzyl]1,3,4,5-tetrahydrobenzo[e][1,4]diazepin-2-on trifluoroacetate was dissolved in 5 ml of dichloromethane. 0.004 ml (0.05 mmol) of methanesulfonyl chloride and 0.008 ml (0.06 mmol) of triethylamine were added to the obtained solution, and they were stirred under cooling with ice for 2 hours. The solvent was evaporated and the obtained crude product was treated in the same manner as in step 3 in Example 1 to obtain the title compound.

Yield: 5.7 mg (0.009 mmol) (51%)
MS (ESI, m/z) 621(MH+)
H-NMR (DMSO-d6) 61.78 (2H, br), 2.54 (2H, br), 2.86 (3H, s), 2.89 (2H, br), 3.94 (2H, br), 4.17 (2H, br), 4.23 (2H, br), 4.41 (2H, br), 5.16 (2H, br), 5.80 (1H, br), 5.91 (1H, br), 6.98–7.62 (11H, m)

Example 165
Synthesis of 4-(4-chlorobenzoyl)-8-[3-(4-isopropyl-1-piperazinyl)-oxopropyl]-1-[4-(1-methyl-4,5-dihydro-1H-imidazol-2-yl)-benzyl]1,3,4,5-tetrahydrobenzo[e][1,4]diazepin-2-on bistrifluoroacetate 10 mg (0.012 mmol) of 4-(4-chlorobenzoyl)-1-[4-(1-methyl-4,5-dihydro-1H-imidazol-2-yl)benzyl]-8-[3-oxo-3-(1-piperazinyl)propyl]-1,3,4,5-tetrahydrobenzo[e][1,4]diazepin-2-on bistrifluoroacetate was dissolved in 5 ml of dichloromethane. 5 mg of isopropyl alcohol and 0.005 ml (0.09 mmol) of acetic acid were added to the obtained solution, and they were stirred at room temperature for 30 minutes. 24 mg (0.12 mmol) of sodium triacetoxyborohydride was added to the obtained mixture, and they were stirred at room temperature overnight. The solvent was evaporated and the obtained crude product was treated in the same manner as in step 3 in Example 1 to obtain the title compound.

Yield: 3.4 mg (0.004 mmol) (33%)
MS (ESI, m/z) 655(MH+)
H-NMR (DMSO-d6) δ 1.22 (3H, s), 1.24 (3H, s), 2.63–2.99 (4H, m), 3.01 (3H, s), 3.26–3,38 (4H, m), 3.81–4.16 (9H, m), 4.43 (4H, br), 5.11 (2H, br), 7.19–7.63 (11H, m)

Example 166
Synthesis of 3-[4-(4-chlorobenzoyl)-2-oxo-1-(4-(2,5-dihydro-1H-pyrrol-1-ylcarbonyl)benzyl)-2,3,4,5-tetrahydro-1H-benzo[e][1,4]diazepin-6-yl]propionic acid 5.0 g (23 mmol) of 6-bromo-2-methyl-1-nitrobenzene was added to a mixture of 50 ml of benzene, 100 ml of perbenzoic acid and 4.9 g (27.7 mmol) of N-bromosuccinimide, and they were stirred at 80° C. for 2 days. After the treatment with ethyl acetate at the extracting solvent by an ordinary method, the obtained crude product was dissolved in 50 ml of ethanol. 6.4 g (46 mmol) of glycine ethyl ester hydrochloride and 5.8 g (69 mmol) of sodium hydrogencarbonate were added to the obtained solution, and they were stirred at 70° C. for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 5.1 g (16.8 mmol) (73%)
Step 2: Synthesis of methyl 3-[2-((4-chlorobenzoyl)-(2-ethoxy-2-oxoethyl)aminomethyl)-3-nitrophenyl)-2-propenate 5.1 g (16.8 mmol) of ethyl (6-bromo-2-nitrobenzyl)aminoacetate was dissolved in 100 ml of dichloromethane. 2.4 ml (19.3 mmol) of 4-chlorobenzoyl chloride and 3.6 ml (25.2 mmol) of triethylamine were added to the obtained solution under cooling with ice, and they were stirred under cooling with ice for 2 hours. After the treatment with dichloromethane as the extracting solvent by an ordinary method, the crude product was obtained. The crude product was dissolved in 50 ml of DMF. 171 mg (0.75 mmol) of palladium acetate, 2.1 ml (22 mmol) of methyl acrylate, 292 mg (1.5 mmol) of triphenylphosphine and 3.0 ml (9.24 mmol) of triethylamine were added to the obtained solution and they were stirred at 100° C. overnight. After the treatment with ethyl acetate as the extracting solvent by an ordinary method, the crude product was obtained. The crude product was then purified by the silica gel column chromatography to obtain the title compound.

Yield: 3.0 g (6.5 mmol) (39%)

H-NMR (CDCl3) δ 1.25 (3H, t), 3.67 (3H, s), 3.79 (2H, br), 4.12 (2H, dd), 5.01 (2H, br), 6.38 (1H, br), 7.22–7.80 (8H, m)

Step 3 Synthesis of 3-[4-(4-chlorobenzoyl)-2-oxo-1-(4-(2,5-dihydro-1H-pyrrol-1-ylcarbonyl)benzyl)-2,3,4,5-tetrahydro-1H-benzo[e][1,4]diazepin-6-yl]propionic acid 3.0 g (6.5 mmol) of 3-[2-((4-chlorobenzoyl)-2-ethoxy-2-oxoethyl)aminomethyl)-3-nitrophenyl)-2-propenate was dissolved in 100 ml ethyl acetate. 300 mg of 10% palladium/carbon was added to the obtained solution and they were stirred in the presence of hydrogen at room temperature for 4 hours. The reaction solution was filtered through Celite. The solvent was evaporated and 432 mg (1.0 mmol) of the obtained crude product was dissolved in 10 ml of dichloromethane. 241 mg (1.2 mmol) of 4-(2,5-dihydro-1H-pyrrol-1-ylcarbonyl)benzaldehyde and 0.115 ml (2.0 mmol) of acetic acid were added to the obtained solution, and they were stirred at room temperature foil 30 minutes. 550 mg (2.5 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 10 ml of dichloromethane. 169 mg (1.0 mmol) of 2-chloro-1,3-dimethylimidazonium chloride and 0.28 ml (2.9 mmol) of triethylamine were added to the obtained solution, and they were stirred overnight. The solvent was evaporated, and the obtained crude product was treated in the same manner as in step 3 in Example 1 to obtain the title compound.

Yield: 49 mg (0.088 mmol) (9%)

MS (ESI, m/z) 558(MH+)

Example 167

Synthesis of 4-(4-chlorobenzoyl)-1-[4-((1-methyl-4,5-dihydro-1H-imidazol-2-yl)methyl)benzyl]-1,3,4,5-tetrahydrobenzo[e][1,4]diazepin-2-on trifluoroacetate Step 1: Synthesis of 4-(4-chlorobenzoyl)-1-(4-cyanomethylbenzyl)-1,3,4,5-tetrahydrobenzo[e][1,4]diazepin-2-on 60 mg (0.20 mmol) of 4-(4-chlorobenzoyl)-1,3,4,5-tetrahydrobenzo[e][1,4diazepin-2-on was dissolved in of DMF. 10 mg (0.25 mmol) of sodium hydride was added to the obtained solution, and they were stirred at room temperature for 30 minutes. 60 mg (0.29 mmol) of 4-cyanomethylbenzyl bromide was added to the reaction mixture, and they were stirred at room temperature overnight. After the treatment with ethyl acetate as the extracting solvent by an ordinary method, the crude product was obtained. The crude product was then purified by the silica gel column chromatography to obtain the title compound.

Yield: 32 mg (0.074 mmol) (37%)

MS (ESI, m/z) 430(MH+)

H-NMR (CDCl3) δ 3.98 (2H, br), 4.53 (2H, br), 5.09 (4H, br), 7.22–7.48 (12H, m)

Step 2: Synthesis of 4-(4-chlorobenzoyl)-[4-((1-methyl-4,5-dihydro-1H-imidazol-2-yl)methyl)benzyl]-1,3,4,5-tetrahydrobenzo[e][1,4]diazepin-2-on trifluoroacetate 32.4 mg (0.075 mmol) of 4-(4-chlorobenzoyl)-1-(4-cyanomethylbenzyl)-1,3,4,5-tetrahydrobenzo[e][1,4]diazepin-2-on obtained in step 1 was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 30 mg (0.40 mmol) of N-methylethylenediamine was added to the obtained solution, and they were stirred at 70° C. overnight. The solvent was evaporated, and the obtained crude product was treated in the same manner as in step 3 in Example 1 to obtain the title compound.

Yield: 10 mg (0.017 mmol) (23%)

MS (ESI, m/z) 487(MH+)

H-NMR (DMSO-d6) δ 2.99 (3H, s), 3.60–4.18 (8H, m), 4.43 (2H, br), 5.09 (2H, br), 7.10–7.66 (12H, m), 9.85 (1H, s)

Example 168

Synthesis of 4-(4-chlorobenzoyl)-1-[2-(1-methyl-4-piperidinyl)ethyl]-1,3,4,5-tetrahydrobenzo[e][1,4]diazepin-2-on trifluoroacetate Step 1: Synthesis of 4-(4-chlorobenzoyl)-1-[2-(4-piperidinyl)ethyl]-1,3,4,5-tetrahydrobenzo[e][1,4]diazepin-2-on 150 mg (0.50 mmol) of 4-(4-chlorobenzoyl)-1,3,4,5-tetrahydrobenzo[e][1,4]diazepin-2-on was dissolved in 10 ml of DMF. 24 mg (0.60 mmol) of sodium hydride was added to the obtained solution. After stirring at room temperature for 30 minutes, 184 g (0.60 mmol) of t-butyl 4-(2-((methylsulfonyl)oxy)ethyl)-1-piperidinecarboxylate was added to the obtained mixture, and they were stirred at 70° C. overnight. After the treatment with ethyl acetate as the extracting solvent by an ordinary method, the obtained crude product was dissolved in 10 ml of 4N solution of hydrogen chloride in dioxane, and the obtained solution was stirred overnight. After the treatment with ethyl acetate as the extracting solvent by an ordinary method, the title compound was obtained.

Yield: 179 mg (0.043 mmol) (86%)

MS (ESI, m/z) 412(MH+)

H-NMR (CDCl3) δ 1.08–73 (7H, m), 2.55 (2H, br), 3.06 (2H, br), 3.82–4.15 (4H, m), 4.30–4.78 (2H, br), 7.25–7.65 (9H, m)

Step 2: Synthesis of 4-(4-chlorobenzoyl)-1-[2-(1-methyl-4-piperidinyl)-ethyl]-1,3,4,5-tetrahydrobenzo[e][1,4] piperidinyl)-ethyl]-1,3,4,5-tetrahydrobenzo[e][1,4] diazepin-2-on trifluoroacetate 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 and 11 mg (0.37 mmol) of paraformaldehyde were dissolved in 2 ml of dichloromethane. 10 ml (0.17 mmol) of acetic acid was added to the obtained solution, and they were stirred at room temperature for 30 minutes. 50 mg (0.24 mmol) of sodium triacetoxyborohydride was added to the reaction mixture, and they were stirred at room temperature overnight. After the treatment with dichloromethane as the extracting solvent by an ordinary method, the obtained crude product was treated in the same manner as in step 3 in Example 1 to obtain the title compound.

Yield: 16.4 mg (0.030 mmol) (41%)

MS (ESI, m/z) 426(MH+)

H-NMR (DMSO-d6) δ 0.98–1.48 (4H, m), 1.59 (1H, m), 1.83 (2H, br), 2.70 (3H, s), 2.81 (2H, br), 3.35 (2H, br), 3.76–4.60 (6H, m), 7.18–7.64 (8H, m), 9.29 (1H, br)

Example 169

Synthesis of 4-(4-chlorobenzoyl)-1-[2-(1-isopropyl-4-piperidinyl)ethyl]-1,3,4,5-tetrahydrobenzo[e][1,4]diazepin-2-on trifluoroacetate 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 in Example 168 and 130 mg (4.6 mmol) of acetone were dissolved in 2 ml of dichloromethane. 10 ml (0.17 mmol) of acetic acid was added to the obtained solution, and they were stirred at room temperature for 30 minutes. 50 mg (0.24 mmol) of sodium triacetoxyborohydride was added to the reaction mixture, and they were stirred at room temperature overnight. After the treatment with dichloromethane as the extracting solvent by an ordinary method, the obtained crude product was treated in the same manner as in step 3 in Example 1 to obtain the title compound.

Yield: 18.7 mg (0.033 mmol) (45%)

MS (ESI, m/z) 454(MH+)

H-NMR (DMSO-d6) δ 1.20 (6H, d), 1.21–1.54 (5H, m), 1.86 (2H, m), 2.84 (2H, br), 3.32 (2H, br), 3.39 (1H, br), 3.60–4.00 (4H, m), 4.38–4.62 (2H, br), 7.18–7.62 (8H, m), 8.88 (1H, br)

Example 170

Synthesis of 4-(4-chlorobenzoyl)-1-[2-(1-cyclopentyl-4-piperidinyl)ethyl]-1,3,4,5-tetrahydrobenzo[e][1,4]diazepin-2-on trifluoroacetate 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 in Example 168 and 31 mg (0.37 mmol) of cyclopentanone were dissolved in 2 ml of dichloromethane. 10 ml (0.17 mmol) of acetic acid was added to the obtained solution, and they were stirred at room temperature for 30 minutes. 50 mg (0.24 mmol) of sodium triacetoxyborohydride was added to the reaction mixture, and they were stirred at room temperature overnight. After the treatment with dichloromethane as the extracting solvent by an ordinary method, the obtained crude product was treated in the same manner as in step 3 in Example 1 to obtain the title compound.

Yield: 18.7 mg (0.031 mmol) (42%)

MS (ESI, m/z) 480(MH+)

H-NMR (DMSO-d6) δ 1.20–2.05 (15H, m), 2.82 (2H, br), 3.43 (3H, m), 3.50–4.00 (4H, m), 4.38–4.62 (2H, br), 7.18–7.62 (8H, m), 9.08 (1H, br)

Example 171

Synthesis of 4-(4-chlorobenzoyl)-1-[2-(1-cyclohexyl-4-piperidinyl)ethyl]-1,3,4,5-tetrahydrobenzo[e][1,4]diazepin-2-on trifluoroacetate 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 in Example 168 and 36 mg (0.37 mmol) of cyclohexanone were dissolved in 2 ml of dichloromethane. 10 ml (0.17 mmol) of acetic acid was added to the obtained solution, and they were stirred at room temperature for 30 minutes. 50 mg (0.24 mmol) of sodium triacetoxyborohydride was added to the reaction mixture, and they were stirred at room temperature overnight. After the treatment with dichloromethane as the extracting solvent by an ordinary method, the obtained crude product was treated in the same manner as in step 3 in Example 1 to obtain the title compound.

Yield: 25.9 mg (0.042 mmol) (58%)

MS (ESI, m/z) 494(MH+)

H-NMR (DMSO-d6) δ 1.02–1.64 (9H, m), 1.73–2.03 (8H, m), 2.87 (2H, br), 3.08 (1H, m), 3.35 (2H, br), 3.50–4.00 (4H, m), 4.39–4.63 (2H, br), 7.18–7.63 (8H, m), 8.88 (1H, br)

Example 172

Synthesis of 4-(4-chlorobenzoyl)-1-[2-(1'-methyl-1,4'-bipiperidin-4-yl)ethyl]-1,3,4,5-tetrahydrobenzo[e][1,4]diazepin-2-on bistrifluoroacetate 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 in Example 168 and 42 mg (0.37 mmol) of 1-methyl-4-piperidinone were dissolved in 2 ml of dichloromethane. 10 mg (0.17 mmol) of acetic acid was added to the obtained solution, and they were stirred at room temperature for 30 minutes. 50 mg (0.24 mmol) of sodium triacetoxyborohydride was added to the reaction mixture, and they were stirred at room temperature overnight. After the treatment with dichloromethane as the extracting solvent by an ordinary method, the obtained crude product was treated in the same manner as in step 3 in Example 1 to obtain the title compound.

Yield: 15.9 mg (0.022 mmol) (30%)

MS (ESI, m/z) 509(MH+)

H-NMR (DMSO-d6) δ 1.20–1.60 (6H, m), 1.64–1.95 (5H, m), 2.24 (2H, br), 2.75 (3H, s), 2.78–3.05 (4H, br), 3.20–4.00 (7H, m), 4.39–4.61 (2H, br), 7.20–7.63 (8H, m), 9.53 (1H, br), 9.82 (1H, br)

Example 173

Synthesis of 4-(4-chlorobenzoyl)-1-[2-(4-(1-methyl-4,5-dihydro-1H-imidazol-2-yl)phenyl)ethyl]-1,3,4,5-tetrahydrobenzo[e][1,4]-diazepin-2-on trifluoroacetate 100 mg (0.33 mmol) of 4-(4-chlorobenzoyl)-1,3,4,5-tetrahydrobenzo[e][1,4]diazepin-2-on was dissolved in 5 ml of DMF. 14 mg (0.35 mmol) of sodium hydride was added to the obtained solution, and they were stirred at room temperature for 30 minutes. 153 mg (0.68 mmol)] of 4-(2-(methanesulfonyloxy)ethyl)benzonitrile was added to the obtained mixture, and they were stirred at 70° C. overnight. The solvent was evaporated, and the obtained crude product was treated in the same manner as in step 3 in Example 1 to obtain an oily substance. The oily substance was dissolved in a mixture of 3 ml of 4N solution of hydrogen chloride in dioxane and 0.7 ml of ethanol, and the obtained solution was stirred at room temperature for 2 days. The solvent was evaporated, and the obtained crude product was dissolved in 5 ml of ethanol. 20 mg (0.27 mmol) of N-methylethylenediamine was added to the obtained solution, and they were stirred at 70° C. overnight. The solvent was evaporated, and the obtained crude product was treated in the same manner as in step 3 in Example 1 to obtain the title compound.

Yield: 4.7 mg (0.078 mmol) (2%)

MS (ESI, m/z) 487(MH+)

H-NMR (DMSO-d6) δ 2.90–3.08 (5H, m), 3.30–3.60 (4H, m), 3.70–4.10 (4H m), 4.21 (2H, br), 7.12–7.60 (12H, m)

Example 174
Synthesis of 4-(4-chlorobenzoyl)-7-cyano-1-[4-(2,5-dihydro-1H-pyrrol-1-ylcarbonyl)benzyl]-1,3,4,5-tetrahydrobenzo[e][1,4]-diazepin-2-on Step 1: Synthesis of ethyl (5-cyano-2-nitrobenzyl) aminoacetate 4.0 g (24.6 mmol) of 3-methyl-4-nitrobenzonitrile was added to a mixture of 100 ml of benzene, 100 ml of perbenzoic acid and 5.3 g (29 mmol) of N-bromosuccinimide, and they were heated under reflux for 2 days. 100 mg of perbenzoic acid and 4.0 g (22.5 mmol) of N-bromosuccinimide were added to the reaction mixture, and they were heated under reflux for 2 days. Thereafter, 100 mg of perbenzoic acid and 4.0 g (22.5 mmol) of N-bromosuccinimide were added to the reaction mixture, and they were heated under reflux for 2 days. After the treatment with ethyl acetate as the extracting solvent by an ordinary method, the obtained crude product was dissolved in 50 ml of ethanol. 6.9 g (49.2 mmol) of glycine ethyl ester hydrochloride and 6.2 g (73.8 mmol) of sodium hydrogencarbonate were added to the obtained solution, and they were stirred at 70° C. for 6 hours. The solvent was evaporated. After the extraction with ethyl acetate, the extract was washed with 1 N hydrochloric acid. The obtained aqueous layer was made basic with 1 N sodium hydroxide. After the extraction with ethyl acetate, the obtained organic layer was washed with saturated aqueous sodium chloride solution and then dried. The solvent was evaporated to obtain the title compound.

Yield: 2.5 g (9.6 mmol) (38%)

H-NMR (CDCl3) δ 1.28 (3H, t), 3.42 (2H, s), 4.13 (2H, s), 4.21 (2H, q), 7.72 (1H, dd), 7.99 (1H, d), 8.12 (1H, s)

Step 2: Synthesis of ethyl 4-(4-chlorobenzoyl)-(5-cyano-2-((4-(2,5-dihydro-1H-pyrrol-1-ylcarbonyl)benzyl)amino)benzyl)amino]acetate 5.1 g (16.8 mmol) of ethyl (5-cyano-2-nitrobenzyl) aminoacetate was dissolved in 100 ml of dichloromethane. 2.4 ml (19.3 mmol) of 4-chlorobenzoyl chloride and 3.6 ml (25.2 mmol) of triethylamine were added to the obtained solution under cooling with ice, and they were stirred under cooling with ice for 2 hours. After the treatment with dichloromethane as the extracting solvent by an ordinary method, the crude product thus obtained was dissolved in a mixture of 30 ml of ethyl acetate and 30 ml of THF. 300 mg of 10% palladium/carbon was added to the obtained solution and they were stirred in the presence of hydrogen at room temperature for 6 hours. The reaction solution was filtered through Celite. The solvent was evaporated and 1.4 g (3.8 mmol) of the obtained crude product was dissolved in 50 ml of dichloromethane. 834 mg (4.2 mmol) of 4-(2,5-dihydro-1H-pyrrol-1-ylcarbonyl)benzaldehyde and 0.43 ml (7.6 mmol) of acetic acid were added to the obtained solution, and they were stirred at room temperature for 30 minutes. 2.0 g (9.5 mmol) of sodium triacetoxyborohydride was added to the reaction mixture, and they were stirred at room temperature overnight. After the treatment with dichloromethane as the extracting solvent by an ordinary method, the obtained crude product was purified by the silica gel column chromatography to obtain the title compound.

Yield: 600 mg (1.08 mmol) (28%)

H-NMR (CDCl3) δ 1.22 (3H, t), 3.50–3.87 (2H, m), 4.03–4.21 (6H, m), 4.48 (4H, br), 5.72 (1H, br), 5.91 (4H, br), 7.23–7.77 (11H, m)

Step 3: Synthesis of 4-(4-chlorobenzoyl)-7-cyano-1-[4-(2,5-dihydro-1H-pyrrol-1-ylcarbonyl)benzyl]-1,3,4,5-tetrahydrobenzo[e][1,4]-diazepin-2-on 600 mg (1.08 mmol) of ethyl 4-(4-chlorobenzoyl)-(5-cyano-2-((4-(2,5-dihydro-1H-pyrrol-1-ylcarbonyl)benzyl)amino)benzyl)amino]acetate was dissolved in a mixture of 5 ml of 1 N sodium hydroxide and 5 ml of ethanol, and the obtained solution was stirred at room temperature for 5 hours. After the treatment with ethyl acetate as the extracting solvent by an ordinary method, the obtained crude product was dissolved in 10 ml of dichloromethane. 220 mg (1.3 mmol) of 2-chloro-1,3-dimethyl-imidazonium chloride and 0.23 ml (1.6 mmol) of triethylamine were added to the obtained solution, and they were stirred overnight. The solvent was evaporated, and the obtained crude product was treated in the same manner as in step 3 in Example 1 to obtain the title compound.

Yield: 7.4 mg (0.015 mmol) (1%)

MS (ESI, m/z) 511(MH+)

H-NMR (DMSO-d6) δ 3.95 (2H, br), 4.12 (2H, br), 4.24 (2H, br), 4.48 (2H, br), 5.19 (2H, br), 5.80 (1H, br), 5.90 (1H, br), 7.26–8.08 (11H, m)

Example 175
Synthesis of 4-(4-chlorobenzoyl)-2-oxo-1-[4-(2,5-dihydro-1H-pyrrol-1-ylcarbonyl)benzyl]-2,3,4,5-tetrahydro-1H-benzo[e][1,4]-diazepine-7-carboxyamide 780 mg (1.47 mmol) of 4-(4-chlorobenzoyl)-2-oxo-1-[4-(2,5-dihydro-1 H-pyrrol-1-ylcarbonyl)benzyl]-2,3,4,5-tetrahydro-1H-benzo[e][1,4]-diazepine-7-carboxyl acid was dissolved in 10 ml of THF. 0.32 ml (2.2 mmol) of triethylamine and 0.17 ml (1.75 mmol) of ethyl chloroformate were added to the obtained solution, and they were stirred for 30 minutes. 10 ml of aqueous ammonia was added to the reaction mixture. The temperature was elevated to room temperature, and the obtained mixture was stirred overnight. After the treatment with ethyl acetate as the extracting solvent by an ordinary method, the solvent was evaporated and the obtained crude product was treated in the same manner as in step 3 in Example 1 to obtain the title compound.

Yield: 72 mg (0.136 mmol) (9%)

MS (ESI, m/z) 529(MH+)

H-NMR (DMSO-d6) δ 3.95 (2H, br), 4.12 (2H, br), 4.23 (2H, br), 4.48 (2H, br), 5.19 (2H, br), 5.80 (1H, br), 5.90 (1H, br), 7.26–8.08 (11H, m)

Example 176
Synthesis of 4-(4-chlorobenzoyl)-1-[3-(1-methyl-4,5-dihydro-1H-imidazol-2-yl)benzyl]-1,3,4,5-tetrahydrobenzo[e][1,4]-diazepin-2-on trifluoroacetate Step 1: Synthesis of 4-(4-chlorobenzoyl)-1-(3-cyanobenzyl)-1,3,4,5-tetrahydrobenzo[e][1,4]diazepin-2-on 150 mg (0.50 mmol) of 4-(4-chlorobenzoyl)-1,3,4,5-tetrahydrobenzo[e][1,4]diazepin-2-on was dissolved in 6 ml of DMF. 24 mg (0.60 mmol) of sodium hydride was added to the obtained solution, and they were stirred at room temperature for 30 minutes. 137 mg (0.70 mmol) of 3-cyanobenzyl bromide was added to the obtained mixture, and they were stirred at room temperature overnight. After the treatment with ethyl acetate as the extracting solvent by an ordinary method, the obtained crude product was purified by the silica gel column chromatography to obtain the title compound.

Yield: 204 mg (0.49 mmol) (98%)

MS (ESI, m/z) 416(MH+)

H-NMR (CDCl3) δ 4.01 (2H, br), 4.10–4.60 (2H, m), 5.09 (2H, s), 7.25–7.62 (12H, m)

Step 2 Synthesis of 4-(4-chlorobenzoyl)-1-[3-(1-methyl-4,5-dihydro-1H-imidazol-2-yl)benzyl]1,3,4,5-tetrahydrobenzo[e][1,4]diazepin2-on trifluoroacetate 82 mg (0.18 mmol) of 4-(4-chlorobenzoyl)-1-(3-cyanobenzyl)-1,3,4,5-tetrahydrobenzo[e][1,4]diazepin-2-on obtained in step 1 was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 6 ml of ethanol. 80 mg (1.08 mmol) of N-methylethylenediamine was added to the obtained solution, and they were stirred at 70° C. overnight. The solvent was evaporated and the obtained crude product was treated in the same manner as in step 3 in Example 1 to obtain the title compound.

Yield: 44 mg (0.074 mmol) (42%)
MS (ESI, m/z) 473(MH+)
H-NMR (DMSO-d6) δ 2.90 (3H, s), 3.70–4.10 (6H, m), 4.48 (2H, br), 5.18 (2H, br), 7.10–7.67 (12H, m)

Example 177

Synthesis of 4-(4-chlorobenzoyl)-1-[2-(1(1-methyl-4,5-dihydro-1H-imidazol-2-yl-4-piperidinyl)ethyl]-1,3,4,5-tetrahydrobenzo[e][1,4]diazepin-2-on trifluoroacetate Step 1: Synthesis of 4-(4-chlorobenzoyl)-1-[2-(1-(4,5-dihydro-1H-imidazol-2-yl)-4-piperidinyl)ethyl]-1,3,4,5-tetrahydrobenzo[e][1,4]-diazepin-2-on 30 mg (0.073 mmol) of 4-(4-chlorobenzoyl)-1-[2-(4-piperidinyl)-ethyl]-1,3,4,5-tetrahydrobenzo[e][1,4]diazepin-2-on obtained in step 1 in Example 168 and 178 mg (0.73 mmol) of 2-methylthio-2-imidazoline were dissolved in 7 ml of methanol. 0.2 mg (1.4 mmol) of triethylamine was added to the obtained solution, and they were stirred at 70° C. overnight. The solvent was evaporated, and the obtained crude product was treated by the reversed phase high-performance liquid chromatography with silica gel chemically bonded with octadodecyl group as the filler and then eluted with a solvent mixture of water and acetonitrile containing 0.1% (V/V) of trifluoroacetic acid. Acetonitrile was evaporated. After the extraction with dichloromethane, the title compound was obtained.

MS (ESI, m/z) 480(MH+)
H-NMR (CDCl3) δ 1.05–1.78 (7H, m), 2.40–2.88 (6H, m), 3.80–4.00 (6H, m) 4.38–4.72 (2H, br), 7.28–7.58 (9H, m)

Yield: 9.7 mg (0.020 mmol) (28%)

Step 2: Synthesis of 4-(4-chlorobenzoyl)-1-[2-(1-(1-methyl-4,5-dihydro-1H-imidazol-2-yl)-4-piperidinyl)ethyl]-1,3,4,5-tetrahydrobenzo[e][1,4]-diazepin-2-on trifluoroacetate 9.7 mg (0.02 mol) of 4-(4-chlorobenzoyl)-1-[2-(1-(4,5-dihydro-1H-imidazol-2-yl)-4-piperidinyl)ethyl]-1,3,4,5-tetrahydrobenzo[e][1,4]-diazepin-2-on obtained in Step 1 was dissolved in 5 ml of DMF. 2.8 mg (0.02 mmol) of methyl iodide was added to the obtained solution, and they were stirred at room temperature overnight. The solvent was evaporated and the obtained crude product was treated in the same manner as in step 3 in Example 1 to obtain the title compound.

Yield: 0.72 mg (0.0012 mmol) (58%)
MS (ESI, m/z) 494(MH+)
H-NMR (DMSO-d6) δ 1.08–1.25 (2H, m), 1.30–1.50 (5H, m), 1.70 (2H, br), 2.82–3.08 (5H, m), 3.10–3.72 (4H, m), 3.78–4.00 (4H, br), 4.40–4.60 (2H, br), 7.18–7.63 (8H, m), 8.38 (1H, s)

Example 178

Synthesis of 4-(4-chlorobenzoyl)-1-[2-(1-(1,3-dimethyl-4,5-dihydro-1H-imidazo-3-ium-2-yl)-4-piperidinyl)ethyl]-1,3,4,5-tetra-hydrobenzo[e][1,4]diazepin-2-on trifluoroacetate The title compound was obtained by the same process as in Example 177.

Yield: 0.72 mg(0.0012 mmol) (58%)
MS (ESI, m/z) 508(MH+)

H-NMR (DMSO-d6) δ 1.18 (2H, m), 1.44 (3H, m), 1.72 (2H, br), 2.91 (6H, s), 3.14 (4H, br), 3.62 (4H, s), 3.70–4.00 (4H, m), 4.38–4.60 (2H, br), 7.18–7.63 (8H, m)

Example 179

Synthesis of 4-(4-chlorobenzoyl)-1-[4-(methyl-2-(4-pyridinyl)-1,3-thiazol-5-yl)methyl]-1,3,4,5-tetrahydrobenzo[e][1,4]-diazepin-2-on trifluoroacetate 111 mg (0.5 mmol) of 4-methyl-2-(4-pyridinyl)-1,3-thiazole-5-carboxylic acid was dissolved in 8 ml of THF. 0.2 ml (1.4 mmol) of triethylamine and 0.1 ml (1.0 mmol) of ethyl chloroformate were added to the obtained solution under cooling with ice, and they were stirred for 30 minutes. A piece of ice and 50 mg (1.4 mmol) of sodium borohydride were added to the obtained mixture. The temperature was elevated to room temperature, and the obtained mixture was stirred overnight. The solvent was evaporated, and the obtained crude product was dissolved in 8 ml of dichloromethane. 0.03 ml (0.22 mmol)) of triethylamine and 0.01 ml (0.13 mmol) of methanesulfonyl chloride were added to the obtained solution under cooling with ice, and they were stirred overnight. After the treatment with dichloromethane as the extracting solvent by an ordinary method, the crude product was obtained.

15 mg (0.05 mmol) of 4-(4-chlorobenzoyl)-1,3,4,5-tetrahydrobenzo[e][1,4]diazepin-2-on was dissolved in 3 ml of DMF. 2 mg (0.05 mmol) of sodium hydride was added to the obtained solutions and they were stirred at room temperature for 30 minutes. The crude product obtained as described above was added thereto, and they were stirred at room temperature overnight. The solvent was evaporated, and the obtained crude product was treated in the same manner as in step 3 in Example 1 to obtain the title compound.

Yield: 1.2 mg (0.002 mmol) (4%)
MS (ESI, m/z) 489(MH+)
H-NMR (DMSO-d6) δ 2.30 (3H, s), 3.80–4.08 (2H, br), 4.20–4.40 (2H, br), 5.32 (2H, br), 7.10–7.62 (7H, m), 7.70 (1H, d), 7.83 (2H, d), 8.67 (2H, d)

Example 180

Synthesis of 4-(4-chlorobenzoyl)-1-[4-(4-pyridinyl)benzyl]-1,3,4,5,-tetrahydrobenzo[e][1,4]diazepin-2-on trifluoroacetate 100 mg (0.5 mmol) of 4-(4-pyridinyl)benzoic acid was dissolved in 8 ml of THF. 0.2 ml (1.4 mmol) of triethylamine and 0.1 ml (1.0 mmol) of ethyl chloroformate were added to the obtained solution under cooling with ice, and they were stirred for 30 minutes. A piece of ice and 50 mg (1.4 mmol) of sodium borohydride were added to the obtained mixture. The temperature was elevated to room temperature, and the obtained mixture was stirred overnight. The solvent was evaporated, and the obtained crude product was dissolved in 8 ml of dichloromethane. 0.03 ml (0.22 mmol)) of triethylamine and 0.01 ml (0.13 mmol) of methanesulfonyl chloride were added to the obtained solution under cooling with ice, and they were stirred overnight. After the treatment with dichloromethane as the extracting solvent by an ordinary method, the crude product was obtained.

30 mg (0.10 mmol) of 4-(4-chlorobenzoyl)-1,3,4,5-tetrahydrobenzo[e][1,4]diazepin-2-on was dissolved in 3 ml of DMF. 4 mg (0.10 mmol) of sodium hydride was added to the obtained solution, and they were stirred at room temperature for 30 minutes. The crude product obtained as described above was added thereto, and they were stirred at room temperature overnight. The solvent was evaporated, and the obtained crude product was treated in the same manner as in step 3 in Example 1 to obtain the title compound.

Yield: 8.3 mg (0.016 mmol) (16%)

MS (ESI, m/z) 468(MH+)

H-NMR (DMSO-d6) δ 3.80–4.15 (2H, br), 4.49 (2H, br), 5.19 (2H, br), 7.08–7.62 (10H, m), 7.87 (2H, d), 8.08 (2H, d), 8.79 (2H, d)

Example 181

Synthesis of 4-(4-chlorobenzoyl)-1-[(5-(2,5-dihydro-1H-pyrrol-1-ylcarbonyl)-2-pyridinyl)methyl]-1,3,4,5-tetrahydrobenzo[e][1,4]-diazepin-2-on trifluoroacetate Step 1: Synthesis of 2-bromomethyl-5-cyanopyridine 0.3 g (2.5 mmol) of 5-cyano-2-methylpyridine was dissolved in 15 ml of benzene. 10 mg of perbenzoic acid and 0.49 g (2.8 mmol) of N-bromosuccinimide were added to the obtained solution, and they were stirred at 75° C. for 2 days. The solvent was evaporated and the crude product was purified by the silica gel column chromatography.

Yield: 0.21 g (1.07 mmol) (43%)

H-NMR (CDCl3) δ 4.56 (2H, s), 7.59 (1H, d), 7.97 (1H, dd), 8.84 (1H, d)

Step 2: Synthesis of 4-(4-chlorobenzoyl)-1-[(5-(2,5-dihydro-1H-pyrrol-1-ylcarbonyl)-2-pyridinyl)methyl]-1,3,4,5-tetrahydrobenzo[e][1,4]diazepin-2-on trifluoroacetate 100 mg (0.33 mmol) of 4-(4-chlorobenzoyl)-1,3,4,5-tetrahydro-benzo[e][1,4]diazepin-2-on was dissolved in 8 ml of DMF. 14 mg (0.35 mmol) of sodium hydride was added to the obtained solution, and they were stirred at room temperature for 30 minutes. 100 mg (0.51 mmol) of 2-bromomethyl-5-cyanopyridine obtained in step 1 was added to the obtained mixture, and they were stirred at room temperature overnight. After the treatment with ethyl acetate as the extracting solvent by an ordinary method, the obtained crude product was dissolved in a mixture of 6 ml of 4N solution of hydrogen chloride in dioxane and 1.5 ml of ethanol. The obtained solution was stirred at room temperature overnight. The solvent was evaporated, and the obtained crude product was treated in the same manner as in Step 3 in Example 1 to obtain a solid. The solid was dissolved in 2 ml of THF. 0.2 ml of 1 M aqueous lithium hydroxide solution was added to the obtained solution, and they were stirred for 2 days. After the treatment th ethyl acetate as the extracting solvent by an ordinary method, the obtained crude product was dissolved in 5 ml of dichloromethane. 5 mg (0.072 mmol) of 3-pyrroline, 60 mg (0.31 mmol) of 1-ethyl-3-(3-dimethylaminopropyl)carbodiimide (WSC) hydrochloride and 0.15 ml (1.08 mmol) of triethylamine were added to the obtained solution, and they were stirred overnight. The solvent was evaporated, and the obtained crude product was treated in the same manner as in step 3 in Example 1 to obtain the title compound.

Yield: 5.6 mg (0.009 mmol) (3%)

MS ESI, m/z) 487(MH+)

H-NMR (DMSO-d6) δ 3.83–4.12 (2H, m), 4.19 (2H, br), 4.26 (2H, br), 4.57–4.77 (2H, m), 5.20 (2H, br), 5.83 (1H, br), 5.92 (1H, br), 7.18–7.64 (10H, m), 7.94 (1H, dd), 8.65 (1H, s)

Example 182

Synthesis of 4-(4-chlorobenzoyl)-1-[4-(1,3-dimethyl-4,5-dihydro-1H-imidazol-3-ium-2-yl)benzyl]-1,3,4,5-tetrahydrobenzo[e][1,4]-diazepin-2-on trifluoroacetate 20 mg (0.034 mmol) of 4-(4-chlorobenzoyl)-1-[4-(1-methyl-4,5-dihydro-1H-imidazol-2-yl)benzyl]-1,3,4,5-tetrahydrobenzo[e][1,4]diazepin2on trifluoroacetate obtained in Example 125 was dissolved in 3 ml of DMF. 3 mg (0.075 mmol) of sodium hydride was added to the obtained solution, and they were stirred at room temperature for 30 minutes. 30 mg (0.21 mmol) of methyl iodide was added to the reaction mixture, and they were stirred at room temperature for 5 hours. The solvent evaporated, and the obtained crude product was treated in the same manner as in step 3 in Example 1 to obtain the title compound.

Yield: 13.2 mg (0.022 mmol) (64%)

MS (ESI, m/z) 487(MH+)

H-NMR (DMSO-d6) δ 2.83 (6H, s), 3.86–4.13 (6H, m), 4.38–4.59 (2H, br), 4.18 (2H, br), 7.15–7.64 (12H, m)

Example 183

Synthesis of 4-(4-chlorobenzoyl)-1-[3-(1-pyrrolidinylmethyl)benzyl]-1,3,4,5-tetrahydrobenzo[e][1,4]diazepin-2-on trifluoroacetate Step 1: Synthesis of 4-(4-chlorobenzoyl)-1-(3-methoxycarbonylbenzyl)-1,3,4,5-tetrahydrobenzo[e][1,4]diazepin-2-on 150 mg (0.50 mmol) of 4-(4-chlorobenzoyl)-1,3,4,5-tetrahydrobenzo[e][1,4]diazepin-2-on was dissolved in 10 ml of DMF. 24 mg (0.60 mmol) of sodium hydride was added to the obtained solution, and they were stirred at room temperature for 30 minutes. 160 mg (0.70 mmol) of methyl 3-(bromomethyl)benzoate was added to the reaction mixture, and they were stirred at room temperature overnight. After the treatment with ethyl acetate as the extracting solvent by an ordinary method, the obtained crude product was purified by the silica gel column chromatography.

Yield: 210 mg (0.47 mmol) (94%)

MS (ESI, m/z) 449(MH+)

H-NMR (CDCl3) δ 3,89 (3H, s), 3.98–4.62 (4H, m), 5.14 (2H, s), 7.25–7.50 (10H, m), 7.83–7.95 (2H, m)

Step 2: Synthesis of 4-(4-chlorobenzoyl)-1-(3-chloromethylbenzyl)-1,3,4,5-tetrahydrobenzo[e][1,4]diazepin-2-on 145 mg (0.32 mmol) of 4-(4-chlorobenzoyl)-1-(3-methoxycarbonylbenzyl)-1,3,4,5-tetrahydrobenzo[e][1,4]diazepin-2-on obtained in step 1 was dissolved in 3 ml of THF. 1.6 ml of 1 M aqueous lithium hydroxide solution was added to the obtained solution, and they were stirred overnight. After the treatment with ethyl acetate as the extracting solvent by an ordinary method, the obtained crude product was dissolved in 5 ml of THF. 0.1 ml (0.7 mmol) of triethylamine and 0.05 ml (0.5 mmol) of ethyl chloroformate were added to the obtained solution under cooling with ice, and they were stirred for 30 minutes. A piece of ice and 50 mg (1.4 mmol) of sodium borohydride were added to the obtained mixture. The temperature was elevated to room temperature, and the obtained mixture was stirred overnight. The solvent was evaporated, and the obtained crude product was dissolved in 8 ml of dichloromethane. 0.03 ml (0.22 mmol)) of triethylamine and 0.01 ml (0.13 mmol) of methanesulfonyl chloride were added to the obtained solution under cooling with ice, and they were stirred overnight. After the treatment with ethyl acetate as the extracting solvent by an ordinary method, the crude product was obtained. After the purification by the silica gel column chromatography, the title compound was obtained.

Yield: 47.1 mg (0.11 mmol) (34%)

MS (ESI, m/z) 439(MH+)

H-NMR (CDC13) δ 3,99 (2H, br), 4.21 (1H, m), 4.52 (2H, s), 4.56 (1H, br), 5.09 (2 H, s), 7.18–7.50 (12H, m)

Step 3 Synthesis of 4-(4-chlorobenzoyl)-1-[3-(1-pyrrolidinylmethyl)benzyl]-1,3,4,5-tetrahydrobenzo[e][1,4]diazepin-2-on trifluoroacetate 23 mg (0.052 mmol) of 4-(4-chlorobenzoyl)-1-(3-chloromethyl-benzyl)-1,3,4,5-tetrahydrobenzo[e][1,4]diazepin-2-on obtained in step 2 was dissolved in 4 ml of acetonitrile. 20 mg (0.15 mmol) of potassium carbonate and 7.0 mg (0.1 mmol) of pyrrolidine were added to the obtained solution, and they were stirred at room temperature overnight. The solvent was evaporated, and the obtained crude product was treated in the same manner as in step 3 in Example 1 to obtain the title compound.

Yield: 20.8 mg (0.035 mmol) (68%)

MS (ESI, m/z) 474(MH+)

H-NMR (DMSO-d6) δ 1.82 (2H, br), 1.98 (2H, br), 3.00 (2H, br), 3.20 (2H, br), 3.86–4.12 (2H, br), 4.22–4.50 (4H, m), 5.13 (2H, br), 7.10–7.72 (12H, m), 9.93 (1H, br)

Example 184

Synthesis of 4-(4-chlorobenzoyl)-1-[3-(((2-dimethylaminoethyl)(methyl)amino)methyl)benzyl]-1,3,4,5-tetrahydrobenzo[e][1,4]diazepin-2-on bistrifluoroacetate 23 mg (0.052 mmol) of 4-(4-chlorobenzoyl)-1-(3-chloromethyl-benzyl)-1,3,4,5-tetrahydrobenzo[e][1,4]diazepin-2-on obtained in step 2 in Example 183 was dissolved in 4 ml of acetonitrile. 20 mg (0.15 mmol) of potassium carbonate and 10 mg (0.098 mmol) of N,N,N'-trimethylethylenediamine were added to the obtained solution, and the obtained mixture was stirred at room temperature overnight. The solvent was evaporated, and the obtained crude product was treated in the same manner as in step 3 in Example 1 to obtain the title compound.

Yield: 9.2 mg(0.013 mmol)(25%)

MS (ESI, m/z) 505(MH+)

H-NMR (DMSO-d6) δ 2.38 (2H, br), 2.48 (6H, s), 2.76 (3H, s), 3.38 (2H, br), 3.50–4.20 (4H, m), 4.40 (2H, br), 5.12 (2H, br), 7.08–7.62 (12H, m)

Example 185

Synthesis of 4-(4-chlorobenzoyl)-1-(1H-pyrrolo[3,2-c]pyridin-2-ylmethyl)-1,3,4,5-tetrahydrobenzo[e][1,4]diazepin-2-on trifluoroacetate Step 1: Synthesis of 4-(4-chlorobenzoyl)-1-(2-propynyl)-1,3,4,5-tetrahydrobenzo[e][1,4]diazepin-2-on 50 mg (0.17 mmol) of 4-(4-chlorobenzoyl)-1,3,4,5-tetrahydrobenzo[e][1,4]diazepin-2-on was dissolved in 4 ml of DMF. 7 mg (0.18 mmol) of sodium hydride was added, to the obtained solution, and they were stirred at room temperature for 30 minutes. 30 mg (0.25 mmol) of 3-bromopropyne was added to the obtained solution, and they were stirred at room temperature overnight. After the treatment with ethyl acetate as the extracting solvent by an ordinary method, the obtained crude product was purified by the silica gel column chromatography.

Yield: 57 mg (0.13 mmol) (76%)

MS (ESI, m/z) 339(MH+)

H-NMR (CDCl3) δ 2.23 (1H, t), 3.85–4.23 (2H, m), 4.40–4.80 (4H, m), 6.95–7.58 (8H, m)

Step 2: Synthesis of 4-(4-chlorobenzoyl)-1-(1H-pyrrolo[3,2-c]pyridin-2-ylmethyl)-1,3,4,5-tetrahydrobenzo[e][1,4]diazepin-2-on trifluoroacetate 57 mg (0.13 mmol) of 4-(4-chlorobenzoyl)-1-(2-propynyl)-1,3,4,5-tetrahydrobenzo[e][1,4]diazepin-2-on obtained in step 1 and 50 mg (0.16 mmol) of t-butyl (3-iodopyridin-4-yl)carbamate were dissolved in 5 ml of DMF. 5.6 mg (0.08 mmol) of bis(triphenylphosphine) palladium (II), 1 mg (0.005 mmol) of copper iodide and 0.09 ml (0.64 mmol) of triethylamine were added to the obtained solution, and they were stirred at 100° C. for 1–5 hours. The reaction solution was cooled to 50° C. 0.05 ml (0.32 mmol) of DBU was added thereto, and they were stirred at 50° C. for 30 minutes and then at room temperature overnight. After the treatment with ethyl acetate as the extracting solvent by an ordinary method, the obtained crude product was dissolved in 10 ml of dichloromethane. 1.5 ml of trifluoroacetic acid was added to the obtained solution, and they were stirred overnight. The solvent was evaporated, and the obtained crude product was treated in the same manner as in step 3 in Example 1 to obtain the title compound.

Yield: 15.5 mg (0.028 mmol) (22%)

MS (ESI, m/z) 431(MH+)

H-NMR ((DMSO-d6) δ 3.80–4.20 (2H, m), 4.30–4.65 (2H, m), 5.37 (2H, br), 6.87 (1H, s), 7.10–7.70 (9H, m), 7.86 (1H, d), 8.35 (1H, d), 9.11 (1H, s)

Example 188

Synthesis of 4-(4-chlorobenzoyl)-1-[4-(2,5-dihydro-1H-pyrrol-1-ylcarbonyl)benzyl]-7-(1H-tetrazol-5-yl)-1,3,4,5-tetrahydrobenzo[e][1,4]diazepin-2-on 26 mg (0.051 mmol) of 4-(4-chlorobenzoyl)-7-cyano-1-[4-(2,5-dihydro-1H-pyrrol-1-ylcarbonyl)benzyl]-1,3,4,5-tetrahydrobenzo[e][1,4]-diazepin-2-on was dissolved in 10 ml of toluene. 0.032 ml (0.11 mmol) of tributyltin azide was added to the obtained solution, and they were stirred at 100° C. overnight. After the treatment with ethyl acetate as the extracting solvent by an ordinary method, the solvent was evaporated and the obtained crude product was treated in the same manner as in Step 3 in Example 1 to obtain the title compound.

Yield: 1.8 mg (0.003 mmol) (6%)

MS (ESI, m/z) 553(MH+)

H-NMR (DMSO-d6) δ 3.98 (2H, br), 4.12 (2H, br), 4.22 (2H, br), 4.58 (2H, br), 5.19 (2H, br), 5.80 (1H, br), 5.90 (1H, br), 7.26–8.16 (11H, m)

Example 189

Synthesis of 4-(4-chlorobenzoyl)-7-(4,5-dihydro-1H-imidazol-2-yl)-1-[4-(2,5-dihydro-1H-pyrrol-1-ylcarbonyl)benzyl]-1,3,4,5-tetrahydrobenzo[e][1,4]diazepin-2-on trifluoroacetate 26 mg (0.051 mmol) of 4-(4-chlorobenzoyl)-7-cyano-1-[4-(2,5-dihydro1 1H-pyrrol-1-ylcarbonyl)benzyl]-1,3,4,5-tetrahydrobenzo[e][1,4]-diazepin-2-on was dissolved in a mixture of 5 ml of 4N solution of hydrogen chloride in dioxane and 1 ml of ethanol, and the obtained solution was stirred at room temperature or 2 days. The solvent was evaporated, and the obtained crude product was dissolved in 5 ml of ethanol. 0.050 ml of ethylenediamine was added to the obtained solution, and they were stirred at 70° C. for 4 hours. The solvent was evaporated and the obtained crude product was treated in the same manner as in Step 3 in Example 1 to obtain the title compound.

Yield: 2.1 mg (0.003 mmol) (6%)

MS (ESI, m/z) 553(MH+)

H-NMR (DMSO-d6) δ 3.23 (4H, br), 3.96 (2H, br), 4.11 (2H, br), 4.22 (2H, br), 4.58 (2H, br), 5.22 (2H, br), 5.80 (1H, br), 5.95 (1H, br), 7.26–8.12 (12H, m)

Example 190

Synthesis of 4-(4-chlorobenzoyl)-1-[4-(2,5-dihydro-1H-pyrrol-1-ylcarbonyl)benzyl]-7-(1-methyl-4,5-dihydro-1H-imidazol-2-yl)-1,3,4,5-tetrahydrobenzo[e][1,4]diazepin-2-on trifluoroacetate 26 mg (0.051 mmol) of 4-(4-chlorobenzoyl)-7-cyano-1-[4-(4,5-dihydro-1H-pyrrol-1-ylcarbonyl)benzyl]-1,3,4,5-tetrahydrobenzo[e][1,4]-diazepin-2-on was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 0.050 ml of ethylenediamine was added to the obtained solution, and they were stirred at 70° C. for 4 hours. The solvent was evaporated and the obtained crude product was treated in the same manner as in Step 3 in Example 1 to obtain the title compound.

Yield: 4.4 mg (0.006 mmol) (13%)

MS (ESI, m/z) 567(MH+)

H-NMR (DMSO-d6) δ 3.08 (4H, br), 3.80–4.24 (9H, m), 4.59 (2H, br), 5.22 (2H, br), 5.81 (1H, br), 5.96 (1H, br), 7.26–8.12 (11H, m)

Example 191

Synthesis of 4-(4-chlorobenzoyl)-1-[(5-(1-methyl-4,5-dihydro-1H-imidazol-2-yl)-2-pyridinyl)methyl]-1,3,4,5-tetrahydrobenzo[e][1,4]diazepin-2-on bistrifluoroacetate 100 mg (0.33 mmol) of 4-(4-chlorobenzoyl)-1,3,4,5-tetrahydrobenzo[e][1,4]diazepin-2-on was dissolved in 8 ml of DMF. 14 mg (0.35 mmol) of sodium hydride was added to the obtained solution, and they were stirred at room temperature for 30 minutes. 100 mg (0.51 mmol) of 2-bromomethyl-5-cyanopyridine obtained in step 1 in Example 181 was added to the reaction mixture, and they were stirred at room temperature overnight. After the treatment with ethyl acetate as the extracting solvent by an ordinary method, 160 mg of the crude product was obtained. A part (31 mg) of the crude product was dissolved in a mixture of 3 ml of 4N solution of hydrogen chloride in dioxane and 0.6 ml of ethanol, and the obtained solution was stirred at room temperature overnight. The solvent was evaporated, and the obtained crude product was dissolved in 5 ml of ethanol. 40 mg (0.54 mmol) of N-methylethylenediamine was added to the obtained solution, and they were stirred at 65° C. overnight. The solvent was evaporated and the obtained crude product was treated in the same manner as in Step 3 in Example 1 to obtain the title compound.

Yield: 1.8 mg (0.0031 mmol) (5%)

MS (ESI, m/z) 474(MH+)

H-NMR (DMSO-d6) δ 3.03 (3H, s), 3.84–4.14 (6H, m), 4.60–4.80 (2H, br), 5.29 (2H, br), 7.15–7.78 (9H, m), 8.06 (1H, dd), 8.75 (1H, s)

Example 192

Synthesis of 4-(4-chlorobenzoyl)-8-cyano-1-[4-(1-pyrrolidinylcarbonyl)benzyl]-1,3,4,5-tetrahydrobenzo[e][1,4]diazepin-2-on 1.8 g (3.5 mmol) of 4-(4-chlorobenzoyl)-2-oxo-1-[4(2,5-dihydro-1H-pyrrol-1-ylcarbonyl)benzyl]-2,3,4,5-tetrahydro-1H-benzo[e][1,4]-diazepine-8-carboxylic acid was dissolved in 10 ml of THF. 0.73 ml (5.3 mmol) of triethylamine and 0.40 ml (4.1 mmol) of ethyl chloroformate were added to the obtained solution, and they were stirred or 30 minutes. 10 ml of aqueous ammonia was added to the reaction mixture. The temperature was elevated to room temperature, and the obtained mixture was stirred overnight. After the treatment with ethyl acetate as the extracting solvent by ah ordinary method, the solvent was evaporated and 1.35 g (2.63 mmol) of the obtained elide product was dissolved in 20 ml of dichloromethane. 760 mg (3.19 mmol) of (methoxycarbonylsulfamoyl)-triethylammonium hydroxide was added to the obtained solution, and the obtained mixture was stirred overnight. After the treatment with dichloromethane as the extracting solvent by an ordinary method, the solvent was evaporated, and the obtained crude product was treated in the same manner as in step 3 in Example 1 to obtain the title compound.

Yield: 380 mg (0.74 mmol) (28%)

MS (ESI, m/z) 513(MH+)

H-NMR (DMSO-d6) δ 1.68–1.91 (4H, m), 3.22–3.42 (4H, m), 3.96 (2H, br), 4.44 (2H, br), 5.17 (2H, br), 7.22–8.06 (11H, m)

Example 193

Synthesis of 4-(4-chlorobenzoyl)-1-[4-(1-pyrrolidinylcarbonyl)benzyl]-8-(1H-tetrazol-5-yl)-1,3,4,5-tetrahydrobenzo[e][1,4]diazepin-2-on 30 mg (0.059 mmol) of 4-(4-chlorobenzoyl)-8-cyano-1-[4-(pyrrolidinylcarbonyl)benzyl]-1,3,4,5-tetrahydrobenzo[e][1,4]diazepin-2-on was dissolved in 2 ml of toluene. 0.032 ml (0.11 mmol) of tributyltin azide was added to the obtained solution, and they were stirred at 120° C. for 6 hours. After the treatment with ethyl acetate as the extracting solvent by an ordinary method, the solvent was evaporated and the obtained crude product was treated in the same manner as in Step 3 in Example 1 to obtain the title compound.

Yield: 6.5 mg (0.012 mmol) (20%)

MS (ESI, m/z) 555(MH+)

H-NMR (DMSO-d6) δ 1.68–1.91 (4H, m), 3.22–3.36 (4H, m), 3.92 (2H, br), 4.44 (2H, br), 5.15 (2H, br), 7.22–7.80 (11H, m)

Example 194

Synthesis of 4-(4-chlorobenzoyl)-8-(4,5-dihydro-1H-imidazol-2-yl)-1-[4-(1-pyrrolidinylcarbonyl)benzyl]-1,3,4,5-tetrahydro-benzo[e][1,4]diazepin-2-on trifluoroacetate 60 mg (0.118 mmol) of 4-(4-chlorobenzoyl)-8-cyano-1-[4-(1-pyrrolidinylcarbonyl)benzyl]1,3,4,5-tetrahydrobenzo[e][1,4]diazepin-2-on was dissolved in a mixture of 5 ml of 4N solution of hydrogen chloride in dioxane and 1 ml of ethanol, and they were stirred at room temperature for 2 days. The solvent was evaporated, and the obtained crude product was dissolved in 5 ml of ethanol. 0.050 ml of ethylenediamine was added to the obtained solution, and they were stirred at 70° C. for 4 hours. The solvent was evaporated and the obtained crude product as treated in the same manner as in Step 3 in Example 1 to obtain the title compound.

Yield: 4.5 mg (0.006 mmol) (6%)

MS (ESI, m/z) 556(MH+)

H-NMR (DMSO-d6) δ 1.68–1.91 (4H, m), 3.22–3.36 (4H, m), 4.03 (2H, br), 4.48 (2H, br), 5.18 (2H, br), 7.26–8.12 (11H, m)

Example 195

Synthesis of 4-(4-chlorobenzoyl)-8-hydroxyamidino-2-oxo-1-[4-(1-pyrrolidinylcarbonyl)benzyl]2,3,4,5-tetrahydro-1H-benzo[e][1,4]-diazepine trifluoroacetate 50 mg (0.098 mmol) of 4-(4-chlorobenzoyl)-8-cyano-1-[4-(1-pyrrolidinylcarbonyl)benzyl]-1,3,4,5-tetrahydrobenzo[e][1,4]diazepin-2-on was dissolved in 5 ml of ethanol. 0.040 ml (0.294 mmol) of triethylamine and 8 mg (0.196 mmol) of hydroxylamine were added to the obtained solution, and they were stirred at 70° C. for 2 hours. The solvent was evaporated and the obtained crude product was treated in the same manner as in Step 3 in Example 1 to obtain the title compound.

Yield: 4.1 mg (0.006 mmol) (6%)

MS (ESI, m/z) 546(MH+)

H-NMR (DMSO-d6) δ 1.68–1.91 (4H, m), 3.22–3.36 (4H, m), 3.92 (2H, br), 4.44 (2H, br), 5.15 (2H, br), 7.22–7.80 (11H, m)

Example 196

Synthesis of 4-(4-chlorobenzoyl)-1-[4-(2,5-dihydro-1H-pyrrol-1-ylcarbonyl)benzyl]-1,3,4,5-tetrahydro-2H-pyrido[4,3e][1,4]-diazepin-2-on trifluoroacetate Step 1: Synthesis of t-butyl (3-ethoxycarbonyl-4-yl) carbamate 0.5 g (1.55 mmol) of t-butyl (3-iodo-pyridin-4-yl) carbamate was dissolved in 10 ml of DMF. 0.7 ml (5.1 mmol) of triethylamine, 0.7 ml of ethanol and 55 mg (0.8 mmol) of bis(triphenylphosphine)palladium (II) chloride were added to the obtained solution, and they were stirred in the presence of carbon monoxide at 70° C. overnight. The solvent was evaporated, and the residue was purified by the silica gel column chromatography to obtain the title compound.

Yield: 0.41 g (1.54 mmol) (99%)
MS (ESI, m/z) 267 (MH+)
H-NMR (CD3Cl) δ 1.40 (3H, t), 1.51 (9H, s), 4.39 (2H, q), 8.31 (1H, d), 8.51 (1H, d), 9.08 (1H, d)

Step 2: Synthesis of t-butyl (3-hydroxymethyl-4-yl) carbamate 0.26 g (0.98 mmol) of t-butyl (3-ethoxycarbonyl-4-yl) carbamate obtained in step 1 was dissolved in 20 ml of diethyl ether. 110 mg (2.9 mmol) of lithium aluminum hydride was added to the obtained solution at −10° C., and they were stirred for 30 minutes. A small amount of water and sodium sulfate was added to the obtained mixture, and they were stirred for 1 hour. The reaction solution was filtered, and the filtrate was concentrated to dryness to obtain the title compound.

Yield: 0.21 g (0.94 mmol) (96%)
H-NMR (CD3Cl) δ 1.52 (9H, s), 4.66 (2H, s), 7.94 (1H, s), 8.07 (1H, d), 8.29 (1H, d)

Step 3 Synthesis of 4-(4-chlorobenzoyl)-1,3,4,5-tetrahydro-2H-pyrido[4,3e][1,4]diazepin-2-on 0.21 g (0.94 mmol) of t-butyl (3-hydroxymethyl-4-yl) carbamate obtained in step 2 was dissolved in 20 ml of dichloromethane. 0.2 ml (1.4 mmol) of triethyl 1amino and 0.1 ml (1.3 mmol) of methanesulfonyl chloride were added to the obtained solution under cooling with ice, and they were stirred for 2 hours. After the treatment with dichloromethane as the extracting solvent by an ordinary method, the obtained crude product and 252 mg (1.8 mmol) of glycine ethyl ester hydrochloride were dissolved in 15 ml of ethanol. 190 mg (2.3 mmol) of sodium hydrogencarbonate was added to the obtained solution, and they were stirred at 80° C. overnight. The solvent was evaporated, and dichloromethane was added to the residue. After the filtration, 0.2 ml (1.5 mmol) of 4-chlorobenzoyl chloride and 0.4 ml (2.9 mmol) of triethylamine were added to the filtrate, and they were stirred at room temperature for 5 hours. The solvent was evaporated, and the residue was roughly purified by the silica gel column chromatography. The obtained crude product was dissolved in 1 ml of THF. 0.4 ml of 1 M aqueous lithium hydroxide solution was added to the obtained solution, and they were stirred overnight. The solvent was evaporated 5 ml of 4N solution of hydrogen chloride in dioxane was added to the residue, and they were stirred at room temperature for 6 hours. The solvent was evaporated and the obtained crude product was dissolved in 8 ml of dichloromethane. 100 mg (0.5 mmol) of 2-chloro-1,3-dimethylimidazoniu in chloride and 0.2 ml (1.4 mmol) of triethylamine were added to the obtained solution, and they were stirred overnight. The solvent was evaporated, and the obtained crude product was treated in the same manner as in Step 3 in Example 1 to obtain the title compound.

Yield: 28 mg (0.093 mmol) (27%)
MS (ESI, m/z) 302 (MH+)
H-NMR (CD3OD) δ 3.16–3.27 (2H, m), 4.72 (2H, br), 7.30–7.52 (5H, m), 8.52 (2H, br), 8.78 (1H, br)

Step 4 Synthesis of 4-(4-chlorobenzoyl)-1-[4-(2,5-dihydro-1H-pyrrol-1-ylcarbonyl)benzyl]-1,3,4,5-tetrahydro-2H-pyrido[4,3-el][1,4] diazepin-2-on trifluoroacetate 14 mg (0.047 mmol) of 4-(4-chlorobenzoyl)-1,3,4,5-tetrahydro-2H-pyrido[4,3-e][1,4]diazepin-2-on obtained in step 3 was dissolved in 3 ml of DMF. 4 mg (0.1 mmol) of sodium hydride was added to the obtained solution, and they were stirred at room temperature for 30 minutes. 13 mg (0.059) of (2.5-dihydro-1H-pyrrol-1-ylcarbonyl)benzyl chloride was added to the obtained mixture, and they were stirred at room temperature overnight. The solvent was evaporated, and the obtained crude product was treated in the same manner as 4 Step 3 in Example 1 to obtain the title compound.

Yield: 4.3 mg (0.007 mmol) (15%)
MS (ESI, m/z) 487 (MH+)
H-NMR (DMSO-d6) δ 3.98–4.80 (8H, m), 5.19 (2H, br), 5.81 (1H, br), 5.91 (1H, br), 7.24–7.70 (10H, m), 8.63 (1H, br)

Example 197

Synthesis of 1-[4-(2,5-dihydro-1H-pyrrol-1-ylcarbonyl)benzyl4-(4-piperidinylcarbonyl)1,3,4,5-tetrahydrobenzo[e][1,4]diazepin-2-on trifluoroacetate 80 mg (0.21 mmol) of 1-[4-(2,5-dihydro-1H-pyrrol-1-ylcarbonyl)-benzyl]-1,3,4,5-tetrahydrobenzo[e][1,4]diazepin-2-on hydrochloride was dissolved in 10 ml of dichloromethane. 56 mg (0.32 mmol) of 2-chloro-1,3-dimethylimidazonium chloride and 51 mg (0.24 mmol) of 1-(t-butoxycarbonyl)-4-piperidinecarboxylic acid and then 0.061 ml (0.44 mmol) of triethylamine were added to the obtained solution, and they were stirred overnight. The solvent was evaporated, and the obtained crude product was dissolved in 5 ml of 4N solution of hydrogen chloride in dioxane. The obtained solution was stirred at room temperature for 2 hours. The solvent evaporated, and the obtained crude product was treated in the same manner as in Step 3 in Example 1 to obtain the title compound.

Yield: 12 mg (0.021 mmol) (10%)
MS (ESI, m/z) 459 (MH+)
H-NMR (DMSO-d6) δ 1.65–1.91 (4H, m), 2.83–3.37 (7H, m), 4.02 (2H, br), 4.14 (2H, br), 4.23 (2H, br), 4.44 (2H, br), 5.13 (2H, br), 5.82 (1H, br), 5.91 (1H, br), 7.22-7.57 (8H, m)

Example 198

Synthesis of 1[4-(2,5-dihydro-1H-pyrrol-1-ylcarbonyl)benzyl]-4-[(1-methyl-4-piperidinyl)carbonyl]-1,3,4,5-tetrahydrobenzo[e][4]diazepin-2-on trifluoroacetate 8 mg (0.014 mmol) of 1-[4-(2,5-dihydro-1H-pyrrol-1-ylcarbonyl)benzyl]-4-(4-piperidinylcarbonyl)-1,3,4,5-tetrahydrobenzo-[e][1,4]diazepin-2-on trifluoroacetate was dissolved in 5 ml of dichloromethane. 5 mg of paraformaldehyde and 0.005 ml (0.09 mmol) of acetic acid were added to the obtained solution, and they were stirred at room temperature for 30 minutes. 24 mg (0.12 mmol) of sodium triacetoxyborohydride was added to the obtained mixture, and they were stirred at room temperature overnight. The solvent was evaporated, and the obtained crude product was treated in the same manner as in Step 3 in Example 1 to obtain the title compound.

Yield: 4 mg (0.007 mmol) (49%)
MS (ESI, m/z) 473 (MH+)
H-NMR (DMSO-d6) δ 1.68–2.03 (4H, m), 2.66–3.03 (8H, m), 4.02 (2H, br), 4.12 (2H, br), 4.23 (2H, br), 4.42 (2H, br), 5.13 (2H, br), 5.82 (1H, br), 5.91(1H, br), 7.22-7.57 (8H, m)

Example 199

Synthesis of 7-(4-chlorobenzoyl)-4-[4-(1-pyrrolidinylcarbonyl)benzyl]-2,6,7,8-tetrahydropyrazolo[4,3,e][1,4]-diazepin-5(4H)-on trifluoroacetate Step 1: Synthesis of Methyl 1-benzyl-4-nitro-1H-pyrazole-3-carboxylate 10 g (63.7 mmol) of 4-nitro-3-pyrazolecarboxylic acid was dissolved in 100 ml of methanol. 5.7 ml (76.4 mmol) of thionyl chloride was added dropwise to the obtained solution under cooling with ice. The temperature was elevated to room temperature and the obtained mixture was stirred for 2 days. After the treatment with ethyl acetate as the extracting solvent by an ordinary method, the solvent was evaporated. The obtained crude product was dissolved in 150 ml of DMF. 9.5 g (68.8 mmol) of potassium carbonate and 7.5 ml (65.0 mmol) of benzyl chloride were added to the obtained solution, and they were stirred at room temperature overnight. After the treatment with ethyl acetate as the extracting solvent by an ordinary method, the obtained crude product was purified by the silica gel column chromatography to obtain the title compound.

Yield: 10.5 g (40.2 mmol) (63%)

H-NMR (CDCl3) δ 3.99 (3H, s), 5.34 (2H, s), 7.28–7.33 (2H, m), 7.39–7.45 (3H, m), 8.00 (1H, s)

Step 2: Synthesis of (1-benzyl-4-nitro-1H-pyrazol-3-yl)methanol 2.04 g (7.8 mmol) of methyl 1-benzyl-4-nitro-1H-pyrazole-3-carboxylate was dissolved in a mixture of 10 ml of ethanol, 10 ml of THF and 5 ml of 1 N sodium hydroxide, and the obtained solution was stirred at room temperature for 4 hours. After the treatment with ethyl acetate as the extracting solvent by an ordinary method, the solvent was evaporated, and the obtained crude product was dissolved in 100 ml of THF. 1.5 ml (10.1 mmol) of triethylamine and 0.81 ml (8.5 mmol) of ethyl chloroformate were added to the obtained solution under cooling with ice, and they were stirred at room temperature for 30 minutes. A piece of ice and 600 mg (15.6 mmol) of sodium borohydride were added to the obtained mixture. The temperature was elevated to room temperature, and the obtained mixture was stirred overnight. After the treatment with ethyl acetate as the extracting solvent by an ordinary method, the crude product was obtained. After the purification by the silica gel column chromatography, the title compound was obtained.

Yield: 1.4 g (5.6 mmol) (73%)

H-NMR (CDCl3) δ 4.92 (2H, s), 5.27 (2H, s), 7.27–7.37 (2H, m), 7.39–7.45 (3H, m), 8.04 (1H, s)

Step 3 Synthesis of Ethyl [((1-benzyl-4-nitro-1H-pyrazol-3-yl)methyl)amino]acetate 1.4 g (5.6 mmol) of (1-benzyl-4-nitro-1H-pyrazol-3-yl)methanol was dissolved in 20 ml of dichloromethane. 0.53 ml (6.7 mmol) of methanesulfonyl chloride and 1.0 ml (7.3 mmol) of triethylamine were added to the obtained solution, and they were stirred at room temperature for 2 hours. After the treatment with dichloromethane as the extracting solvent by an ordinary method, the obtained crude product was dissolved in 50 ml of ethanol. 1.6 g (11.2 mmol) of glycine ethyl ester hydrochloride and 1.4 g (16.8 mmol) of sodium hydrogencarbonate were added to the obtained solution, and they were stirred at 70° C. overnight. The insoluble matter was filtered. The solvent was evaporated and the residue was treated with ethyl acetate as the extracting solvent by an ordinary method, which was purified by the silica gel column chromatography to obtain the title compound.

Yield: 1.5 g (4.7 mmol) (84%)

H-NMR (CDCl3) δ 1.25 (3H, t), 3.55 (2H, d), 4.07–4.26 (4H, m), 5.26 (2H, s), 7.28–7.37 (2H, m), 7.39–7.45 (3H, m), 7.98 (1H, d)

Step 4 Synthesis of Ethyl [((4-amino-1-benzyl-1H-pyrazol-3-yl)methyl)(4-chlorobenzoyl)amino]acetate 1.5 g (4.7 mol) of ethyl[((1-benzyl-4-nitro-1H-pyrazol-3-yl)methyl)amino]acetate was dissolved in 50 ml of dichloromethane: 0.71 ml (5.6 mmol) of 4-chlorobenzoyl chloride and 0.85 ml (6.1 mmol) of triethylamine were added to the obtained solution under cooling with ice, and they were stirred under cooling with ice for 2 hours. After the treatment with dichloromethane as the extracting solvent by an ordinary method, the obtained crude product was dissolved in 100 ml of ethanol. 5.3 g (23.5 mmol) of tin chloride was added to the obtained solution, and they were stirred at 70° C. overnight. The solvent was evaporated. Sodium carbonate and ethyl acetate were added to the residue, and they were vigorously stirred at room temperature. After the treatment with ethyl acetate as the extracting solvent by an ordinary method, the obtained crude product was purified by the silica gel column chromatography to obtain the title compound.

Yield: 600 mg (1.4 mmol) (30%)

Step 5: Synthesis of 2-benzyl-7-(4-chlorobenzoyl)-4-(4-(1-pyrrolidinylcarbonyl)benzyl]-2,6,7,8-tetrahydropyrazolo[4,3,e][1,4]-diazepin-5(4H)-on trifluoroacetate 600 mg (1.4 mmol) of ethyl [((4-amino-1-benzyl-1H-pyrazol-3-yl)methyl)(4-chlorobenzoyl)amino]acetate and 343 mg (1.7 mmol) of 4-(pyrrolidinylcarbonyl)benzaldehyde were dissolved in 10 ml of dichloromethane. 0.16 ml (2.8 mmol) of acetic acid was added to the obtained solution, and they were stirred at room temperature for 30 minutes. 770 mg (3.5 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 5 ml of 1 N sodium hydroxide, 5 ml of ethanol and 5 ml of THF, and the obtained solution was stirred at room temperature for 5 hours. After the treatment with ethyl acetate as the extracting solvent by an ordinary method, the obtained crude product was dissolved in 10 ml of dichloromethane. 237 mg (1.4 mmol) of 2-chloro-1,3-dimethylimidazonium chloride and 0.59 ml (2.8 mmol) of triethylamine were added to the obtained solution, and they were stirred overnight. The solvent was evaporated, and the obtained crude product was treated in the same manner as in Step 3 in Example 1 to obtain the title compound.

Yield: 25 mg (0.037 mmol) (3%)

MS (ESI, m/z) 568 (MH+)

H-NMR (DMSO-d6) δ 1.81 (4H, br), 3.32 (2H, br), 3.42 (2H, br), 4.43 (2H, br), 4.63 (2H, br), 4.98 (2H, br), 5.09 (2H, br), 7.03–7.83 (14H, m)

Step 6 Synthesis of 7-(4-chlorobenzoyl)-4-[4-(1-pyrrolidinylcarbonyl)-benzyl]-2,6,7,8-tetrahydropyrazolo[4,3,e][1,4]-diazepin-5(4H)-on trio) trifluroacetate 60 mg (0.1 mmol) of 2-benzyl-7-(4-chlorobenzoyl)-4-[4-(1-pyrrolidinylcarbonyl)benzyl]-2,6,7,8-tetrahydropyrazolo[4,3,e][1,4]-diazepin-5(4H)-on trifluoroacetate was dissolved in 5 ml of benzene. 70 mg (0.5 mmol) of aluminum chloride was added to the obtained solution, and they were heated under reflux for 6 hours. The solvent was evaporated, and the obtained crude product was treated in the same manner as in Step 3 in Example 1 to obtain the title compound.

Yield: 17 mg (0.029 mmol) (29%)

MS (ESI, m/z) 478 (MH+)

H-NMR (DMSO-d6) δ 1.81 (4H, br), 3.32 (2H, br), 3.42 (2H, br), 4.43 (2H, br), 4.63 (2H, br), 5.01 (2H, br), 7.18–7.66 (10H, m)

Example 200

Synthesis of 7-amidino-4-(4-chlorobenzoyl)-1-[4-(2,5-dihydro-1-pyrrol-1-ylcarbonyl)benzyl]-1,3,4,5-tetrahydrobenzo[e][1,4]-diazepin-2-on trifluoroacetate 30 mg (0.059 mmol) of 4-(4-chlorobenzoyl)-7-cyano4-(4-chloro-benzoyl)-1-[4-(2,5-dihydro-1H-pyrrol-1-ylcarbonyl)benzyl]-1,3,4,5-tetra-hydrobenzo[e][1,4]diazepin-2-on was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 30 mg of ammonium carbonate was added to the obtained solution, and they were stirred overnight. The solvent was evaporated, and the obtained crude product was treated in the same manner as in step 3 in Example 1 to obtain the title compound.

Yield: 6.9 mg (0.010 mmol) (17%)

MS (ESI, m/z) 528 (MH+)

H-NMR (DMSO-d6) δ 3.97 (2H, br), 4.12 (2H, br), 4.23 (2H, br), 4.57 (2H, br), 5.24 (2H, br), 5.81 (1H, br), 5.91 (1H, br), 7.18–8.04 (11H, m), 9.05 (2H, br), 9.23 (2H, br)

Example 201

Synthesis of 8-amidino-4-(4-chlorobenzoyl)-1-[4-(1-pyrrolidinylcarbonyl)benzyl]-1,3,4,5-tetrahydrobenzo[e][1,4]diazepin-2-on trifluoroacetate 30 mg (0.059 mmol) of 4-(4-chlorobenzoyl)-8-cyano-1-[4-(1-pyrrolidinylcarbonyl)benzyl]-1,3,4,5-tetrahydrobenzo[e][1,4]diazepin-2-on was dissolved in a mixture of 5 ml of 4N solution of hydrogen chloride in dioxane and 1 ml of ethanol, and the obtained solution was stirred at room temperature for 2 days. The solvent was evaporated, and the obtained crude product was dissolved in 5 ml of ethanol. 30 mg of ammonium carbonate was added to the obtained solution, and they were stirred overnight. The solvent was evaporated, and the obtained crude product was treated in the same manner as in step 3 in Example 1 to obtain the title compound.

Yield: 7.3 mg (0.011 mmol) (18%)

MS (ESI, m/z) 530 (MH+)

H-NMR (DMSO-d6) δ 1.80 (4H, br), 3.29 (2H, br), 3.38 (2H, br), 3.86 (2H, br), 4.43 (2H, br), 5.23 (2H, br), 7.21–8.03 (11H, m), 9.38 (2H, br), 9.57 (2H, br).

Example 202

Synthesis of 4-(4-chlorobenzoyl)-1-[4-(1-methyl-4,5-dihydro-1H-imidazol-2-yl)benzyl]-1,3,4,5-tetrahydro-2H-pyrido[4,3-e][1,4]diazepin-2-on bistrifluoroacetate Step 1: Synthesis of 4-(4-chlorobenzoyl)-1-(4-cyanobenzyl)-1,3,4,5-tetrahydro-2H-pyrido[4,3-e][1,4]diazepin-2-on trifluoroacetate 14 mg (0.047 mmol of 4-(4-chlorobenzoyl)-1,3,4,5-tetrahydro-2H-pyrido[4,3-e][1,4]diazepin-2-on obtained in Step 3 in Example 196 was dissolved in 3 ml of DMF. 4 mg (0.1 mmol) of sodium hydride was added to the obtained solution, and they were stirred at room temperature for 30 minutes. 19 mg (0.1 mmol) of 4-cyanobenzyl bromide was added to the reaction mixture, and they were stirred at room temperature overnight. The solvent was evaporated, and the obtained crude product was treated in the same manner as in step 3 in Example 1 to obtain the title compound.

Yield: 4.7 mg (0.009 mmol) (19%)

MS (ESI, m/z) 417 (MH+)

H-NMR (CDCl3) δ 4.21 (2H, br), 4.70 (2H, br), 5.23 (2H, s), 7.30–7.50 (8H, m), 7.64 (2H, d), 8.75 (2H, m)

Step 2 Synthesis of 4-(4-chlorobenzoyl)-1-[4-(1-methyl-4,5-dihydro-1H-imidazol-2-yl)benzyl]-1,3,4,5-tetrahydro-2H-pyrido[4,3-e][1,4]-diazepin-2-on bistrifluoroacetate 4.7 mg (0.009 mmol) of 4-(4-chlorobenzoyl)-1-(4-cyanobenzyl)-1,3,4,5-tetrahydro-2H-pyrido[4,3-e][1,4]-diazepin-2-on trifluoroacetate obtained in Step 1 was dissolved in a mixture of 3 ml of 4N solution of hydrogen chloride in dioxane and 0.6 ml of ethanol, and the obtained solution was stirred at room temperature for 2 days. The solvent was evaporated, and the obtained crude product was dissolved in 5 ml of ethanol. 20 mg (0.26 mmol) of N-methylethylenedime was added to the obtained solution, and they were stirred overnight. The solvent was evaporated, and the obtained crude product was treated in the same manner as in step 3 in Example 1 to obtain the title compound.

Yield: 1.3 mg (0.0018 mmol) (20%)

MS (ESI, m/z) 474 (MH+)

H-NMR (DMSO-d6) δ 3.01 (3H, s), 3.80–4.25 (6H, m), 4.61 (2H, br), 5.25 (2H, br), 7.20–7.85 (10H, m), 8.55–8.68 (2H, m)

Example 203

Synthesis of 4-(4-chlorobenzoyl)-2-oxo-1-[4-(1-methyl-4,5-dihydro-1H-imidazol-2-yl)benzyl]-2,3,4,5-tetrahydro-1H-benzoyl[e][1,4]-diazepine-8-carboxylic acid trifluoroacetate Step 1: Synthesis of methyl 4-[((4-chlorobenzoyl)-(2-ethoxy-2-oxyethyl)amino)methyl]-3-[(4-cyanobenzyl)amino]benzoate 1.86 g (4.6 mmol) of methyl 4-[((4-chlorobenzoyl)ethoxycarbonylmethylamino)methyl]-3-aminobenzoate and 0.73 g (5.6 mmol) of 4-cyanobenzaldehyde were dissolved in 30 ml of dichloromethane. 0.3 ml (5.0 mmol) of acetic acid was added to the obtained solution, and they were stirred at room temperature for 30 minutes. 1.46 g (6.9 mmol) of sodium triacetoxyborohydride was added to the reaction mixture, and they were stirred at room temperature overnight. After the treatment with dichloromethane as the extracting solvent by an ordinary method, the obtained crude product was purified by the silica gel column chromatography to obtain the title compound.

Yield: 1.6 g (3.1 mmol) (67%)

MS (ESI, m/z) 520 (MH+)

H-NMR (CDCl3) δ 1.23 (3H, t), 3.82–3.92 (5H, m), 4.14 (2H, q), 4.55 (2H, br), 4.77 (2H, s), 7.08–7.40 (5H, m), 7.48 (3H, m), 7.60–7.70 (3H, m)

Step 2 Synthesis of 4-(4-chlorobenzoyl)-2-oxo-1-[4-(1-methyl-4,5-dihydro-1H-imidazol-2-yl)benzyl]-2,3,4,5-tetrahydro-1H-benzoyl[e][1,4]-diazepine-8-carboxylic acid trifluoroacetate 1.6 g (3.1 mmol) of methyl 4-[((4-chlorobenzoyl)-(2-ethoxy-2-oxyethyl)amino)methyl]-3-[(4-cyanobenzyl)amino]benzoate obtained in step 1 was dissolved in 14 ml of THF. 6 ml of 1 M lithium hydroxide was added to the obtained solution, and they were stirred at room temperature for 8 hours. The reaction solution was washed with ethyl acetate. 1 M hydrochloric acid was added to the aqueous layer, and the crude product in the form of crystals thus precipitated was taken by the filtration. The crude product was dissolved in 30 ml of dichloromethane. 0.64 g (3.8 mmol) of 2-chloro-1,3-dimethylimidazonium chloride and 0.7 ml (5.1 mmol) of triethylamine were added to the obtained solution, and they were stirred overnight. The solvent was evaporated, and the obtained crude product was treated in the same manner as in Step 3 in Example 1. A white solid thus obtained was dissolved in a mixture of 10 ml of 4N solution of hydrogen chloride in dioxane and 2 ml of ethanol, and the obtained solution was stirred at room temperature for 1 day. The solvent was evaporated, and the obtained crude product was dissolved in 10 ml of ethanol. 80 mg (1.08 mmol) of N-methylethylenediamine was added to the obtained solution, and they were stirred at 70□ overnight. The solvent was evaporated, and the obtained crude product was treated in the same manner as in step 3 in Example 1 to obtain the title compound.

Yield: 26 mg (0.05 mmol) (2%)
MS (ESI, m/z) 517 (MH+)
H-NMR (DMSO-d6) δ 3.02 (3H, s), 3.70–4.18 (6H, m), 4.59 (2H, br), 5.22 (2H, br), 7.30–7.92 (11H, m)

Example 204
Synthesis of ethyl 4-(4-chlorobenzoyl)-2-oxo-1-[4-(1-methyl-4,5-dihydro-1H-imidazol-2-yl)benzyl]-2,3,4,5-tetrahydro-1H-benzoyl[e][1,4]diazepine-8-carboxylate trifluoroacetate The title compound was obtained in the same manner as in Example 203.

Yield: 86 mg(0.13 mmol)(4%)
MS (ESI, m/z) 545 (MH+)
H-NMR (DMSO-d6) δ 1.27 (3H, t), 3.02 (3H, s), 3.82–4.33 (8H, m), 4.59 (2H, br), 5.22 (2H, br), 7.30–7.92 (11H, m)

Example 205
Synthesis of 4-(4-chlorobenzoyl)-1-(7-isoquinolinylmethyl)-1,3,4,5-tetrahydrobenzo[e][1,4]diazepin-2-on (trifluoroacetate) trifluoroacetate 0.89 g (6.1 mmol) of 7-hydroxyisoquinoline was dissolved in 15 ml of dichloromethane. 1.1 ml of pyridine and 1.3 ml (7.7 mmol) of trifluoromethanesulfonyl anhydride were added to the obtained solution under cooling with ice, and they were stirred at 0° C. for 1 hour. After the treatment with dichloromethane as the extracting solvent by an ordinary method, the obtained crude product was purified by the silica gel column chromatography to obtain an oily product. This oily product was dissolved in 10 ml of DMF. 0.4 ml (2.9 mmol) of triethylamine, 50 mg (0.04 mmol) of (tetrakistriphenylphosphine) palladium, 16 mg (0.04 mmol) of 1,3-bis(diphenylphosphino)propane and 5 ml of ethanol were added to the obtained solution, and they were stirred in the presence of carbon monoxide at 70° C. overnight. The solvent was evaporated, and the residue was purified by the silica gel column chromatography to obtain the title compound.

Yield: 196 mg (0.97 mmol) (16%)
MS (ESI, m/z) 202 (MH+)
H-NMR (CD3Cl) δ 1.48 (3H, t), 4.47 (2H, q), 7.70 (1H, d), 7.88 (1H, d), 8.30(1H, dd), 8.62 (1H, d), 8.74 (1H, s), 9.37 (1H, s)

Step 2 Synthesis of 7-chloromethy-lisoquinoline
196 mg (0.97 mmol) of 7-ethoxycarbonylisoquinoline obtained in step 1 was dissolved in 15 ml of ethanol. 110 mg (2.9 mmol) of lithium aluminum hydride was added to the solution under cooling with ice, and they were stirred at room temperature for 2 hours. Water was added to the reaction mixture and they were stirred for 2 hours. The reaction solution was filtered, and the filtrate was concentrated. The obtained oily product was dissolved in 10 ml of dichloromethane. 0.26 ml (1.9 mmol) of triethylamine and 0.1 ml (1.3 mmol) of methanesulfonyl chloride were added to the obtained solution, and they were stirred overnight. After the treatment with dichloromethane as the extracting solvent by an ordinary method, the crude product was obtained.

Yield: 84 mg (0.47 mmol) (49%)
H-NMR (CD3Cl) δ 4.77 (2H, s), 7.63 (1H, d), 7.73 (1H, dd), 7.82 (1H, d), 7.96 (1H, s), 8.55 (1H, d), 9.25 (1H, s)

Step 3: Synthesis of 4-(4-chlorobenzoyl)-1-(7-isoquinolinylmethyl)-1,3,4,5-tetrahydrobenzo[e][1,4]diazepin-2-on trifluoroacetate 90 mg (0.3 mmol) of 4-(4-chlorobenzoyl)-1,3,4,5-tetrahydrobenzo[e][1,4]diazepin-2-on was dissolved in 8 ml of DMF. 14 mg (0.35 mmol) of sodium hydride was added to the obtained solution, and they were stirred at room temperature for 30 minutes. 50 mg (0.28 mmol) of 7-chloromethy-lisoquinolinne obtained in step 2 was added to the reaction mixture, and they were stirred at room temperature overnight. The solvent was evaporated, and the obtained crude product was treated in the same manner as in step 3 in Example 1 to obtain the title compound.

Yield: 5.4 mg (0.01 mmol) (3%)
MS (ESI, m/z) 442 (MH+)
H-NMR (DMSO-d6) δ 3.90–4.18 (2H, m), 4.40–4.58 (2H, br), 5.36 (2H, br), 7.08–7.65 (8H, m), 7.95 (1H, br), 8.12–8.30 (3H, m), 8.57 (1H, d), 9.60 (1H, s)

Example 206
Synthesis of 2-[4-((4-(4-chlorobenzoyl)-8-(ethoxycarbonyl)-2-oxo-2,3,4,5-tetrahydro-1H-1,4-benzodiazepin-1-yl)methyl)phenyl]-1,3-dimethyl-4,5-dihydro-1H-imidazol-3-ium trifluoroacetate 11 mg (0.017 mmol) of ethyl 4-(4-chlorobenzoyl)-2-oxo-1-[4-(1-methyl-4,5-dihydro-1H-imidazol-2-yl)benzyl]-2,3,4,5-tetrahydro-1H-benzo[e][1,4]diazepine-8-carboxylate trifluoroacetate obtained in Example 204 was dissolved in 3 ml of acetonitrile. 10 mg (0.08 mmol) of potassium carbonate and 0.05 ml (0.32 1) of methyl iodide were added to the obtained solution, and they were stirred at room temperature for 5 hours. The solvent was evaporated, and the obtained crude product was treated in the same manner as in step 3 in Example 1 to obtain the title compound.

Yield: 5.6 mg (0.008 mmol) (49%)
MS (ESI, m/z) 559 (MH+)
H-NMR (DMSO-d6) δ 1.24 (3H, t), 2.83 (6H, s), 3.96 (6H, m), 4.10–4.69 (4H, m), 5.20 (2H, br), 7.30–7.88 (11H, m)

Example 207
Synthesis of 6-chloro-4-(4-chlorobenzoyl)-1-[4-(1,3-dimethyl-4,5-dihydro-1H-imidazol-3-ium-2-yl)benzyl]-1,3,4,5-tetrahydro-benzo[e][1,4]diazepin-2-on trifluoroacetate 12 mg (0.019 mmol) of 6-chloro-4-(4-chlorobenzoyl)-1-[4-(1-methyl-4,5-dihydro-1H-imidazol-2-yl)benzyl]-1,3,4,5-tetrahydrobenzo[e][1,4]-diazepin-2-on trifluoroacetate was dissolved in 5 ml of acetonitrile. 5 mg (0.036 mmol) of potassium carbonate and 0.010 ml of methyl iodide were added to the obtained solution, and they were stirred at room temperature for 4 hours. The solvent was evaporated, and the obtained crude product was treated in the same manner as in step 3 in Example 1 to obtain the title compound.

Yield: 4.1 mg (0.006 mmol) (32%)
MS (ESI, m/z) 523 (MH+)
H-NMR (DMSO-d6) δ 2.84 (6H, s), 3.95 (4H, s), 4.03 (2H, br), 4.62 (2H, br), 5.21 (2H, br), 7.17–7.66 (11H, m)

Example 208
Synthesis of (5aS,9aS)-4-(4-chlorobenzoyl)1-[4-(2,5-dihydro-1H-pyrrol-1-ylcarbonyl)benzyl]decahydro-2H-1,4-benzo-diazepin-2-on Step 1: Synthesis of (cis)-(1R,2S)-2-(benzyloxycarbonylamino)cyclo-hexane methanol 4.0 g (18.3 mmol) of (cis)-(1R,2S)-(+)-2-(benzylamino) cyclohexane methanol was dissolved in 20 ml of ethyl acetate. 400 mg of 10% palladium/carbon was added to the obtained solution, and they were stirred in the presence of hydrogen at room temperature overnight. The reaction solution was filtered through Celite and then the solvent was evaporated. The obtained crude product was dissolved in 100 ml of dichloromethane. 3.4 ml (23.8 mmol) of triethylamine and 3.2 ml (21.9 mmol) of benzyl chloroformate were added to the obtained solution under cooling with ice. The temperature was elevated to room temperature, and the reaction mixture was stirred overnight. After the treatment with ethyl acetate as the extracting solvent by an ordinary method, the obtained crude product was purified by the silica gel column chromatography to obtain the title compound.

Yield: 4.1 g (15.6 mmol) (85%)

H-NMR (CDCl3) δ 0.84–1.03 (2H, m), 1.17–1.41 (2H, m), 1.58–1.84 (4H, m), 3.20–3.42 (2H, m), 3.79–3.85 (1H, m), 4.70 (1H, d), 5.12 (2H, s), 7.37 (5H, br)

Step 2: Synthesis of ethyl [(((1S,2S)-2-(((benzyloxy)carbonyl)amino)-cyclohexyl)methyl)amino]acetate 1.7 g (6.5 mmol) of (cis)-(1R,2S)-2-(benzyloxycarbonylamino)cyclo-hexane methanol was dissolved in 100 ml of dichloromethane. 1.7 g of pyridinium dichromate and 1.7 g of silica gel were added to the obtained solution, and they were stirred overnight. After the filtration through Celite, the solvent was evaporated. The obtained crude product was dissolved in 100 ml of dichloromethane. 1.1 g (7.8 mmol) of glycine ethyl ester hydrochloride and 0.74 ml (13 mmol) of acetic acid were added to the obtained solution, and they were stirred at room temperature for 30 minutes. 3.4 g (16 mmol) of sodium triacetoxyborohydride was added to the reaction mixture, and they were stirred at room temperature overnight. After the treatment with dichloromethane as the extracting solvent by an ordinary method, the obtained crude product was purified by the silica gel column chromatography to obtain the title compound.

Yield: 1.0 g (15.6 mmol) (45%)

H-NMR (CDCl3) δ 0.85–1.83 (11H, m), 3.20–3.42 (2H, m), 3.79 (4H, br), 4.18 (2H, q), 5.12 (2H, s), 7.36 (5H, br)

Step 3: Synthesis of ethyl [(((1S,2S)-2-(((benzyloxy)carbonyl)amino)-cyclohexyl)methyl)(t-butoxycarbonyl)amino]acetate 1.0 g (15.6 mmol) of ethyl [(((1S,2S)-2-(((benzyloxy)carbonyl)amino)cyclohexyl)methyl)amino]acetate was dissolved in 20 ml of dichloromethane. 0.75 g (3.4 mmol) of di-t-butyl dicarbonate and 0.6 ml (4.3 mmol) of triethylamine were added to the obtained solution, and they were stirred at room temperature for 2 hours. After the treatment with dichloromethane as the extracting solvent by an ordinary method, the obtained crude product was purified by the silica gel column chromatography to obtain the title compound.

Yield: 450 mg (1.0 mmol) (35%)

Step 4: Synthesis of (5aS,9aS)-4-(4-chlorobenzoyl)-1-[4-(2,5-dihydro-1H-pyrrol-1-ylcarbonyl)benzyl]decahydro-2H-1,4-benzo-diazepin-2-on 225 mg (0.5 mmol) of ethyl [(((1S,2S)-2-(((benzyloxy)carbonyl)amino)cyclohexyl)methyl)(t-butoxycarbonyl)-amino]acetate was dissolved in 10 ml of ethyl acetate. 30 mg of 10% palladium/carbon was added to the obtained solution, and they were stirred in the presence of hydrogen at room temperature overnight. The reaction solution was filtered through Celite. The solvent was evaporated, and the obtained crude product was dissolved in 10 ml of dichloromethane. 121 mg (0.67 mmol) of 4-(2,5-dihydro-1H-pyrrol-1-ylcarbonyl)benzaldehyde and 0.065 ml (1.14 mmol) of acetic acid were added to the obtained solution, and they were stirred at room temperature for 30 minutes. 310 mg (1.4 mmol) of sodium triacetoxyborohydride was added to the reaction mixture, and they were stirred at room temperature overnight. After the treatment with dichloromethane as the extracting solvent by an ordinary method, the obtained crude product was dissolved in a mixture of 2 ml of ethanol and 2 ml of 1 N sodium hydroxide, and the obtained solution was stirred at room temperature for 4 hours. After the treatment with ethyl acetate as the extracting solvent by an ordinary method, the obtained crude product was dissolved in 5 ml of dichloromethane. 84 mg (0.5 mmol) of 2-chloro-1,3-dimethylimidazonium chloride and 0.14 ml (1.0 mmol) of triethylamine were added to the obtained solution, and they were stirred overnight. After the treatment with dichloromethane as the extracting solvent by an ordinary method, the obtained crude product was dissolved in 5 ml of 4N solution of hydrogen chloride in dioxane and the obtained solution was stirred at room temperature for 2 hours. The solvent was evaporated, and the obtained crude product was dissolved in 5 ml of dichloromethane. 0.062 ml (0.5 mmol) of 4-chlorobenzoyl chloride and 0.14 ml (1.0 mmol) of triethylamine were added to the obtained solution, and they were stirred at room temperature for 4 hours. The solvent was evaporated, and the obtained crude product was treated in the same manner as in step 3 in Example 1 to obtain the title compound.

Yield: 6.3 mg (0.013 mmol) (3%)

MS (ESI, m/z) 492 (MH+)

H-NMR (DMSO-d6) δ 0.98–1.83 (8H, m), 2.07–2.42 (2H, m), 3.21–3.48 (3H, m), 4.17 (2H, br), 4.27 (2H, br), 4.81 (1H, d), 5.83 (1H, br), 5.93 (1H, br), 7.20–7.64 (11H, m)

Example 209

Determination of Activity of inhibiting the Activated Blood-coagulation Factor X 130 μl of 100 mM tris hydrochloride buffer adjusted to pH 8.4 was added to 10 μl of an aqueous solution of a compound to be tested. Then 10 μl of a 0.5 unit/ml solution of activated human blood coagulation factor X (a product of Enzyme Research Co.) in tris hydrochloride buffer of pH 8.4 was added to the resultant mixture. After the incubation at room temperature for 10 minutes, 50 μl of a solution of N-benzoyl-L-isoleucyl-L-glutamyl-glycyl-L-arginyl-P-nitroanilide hydrochloride (a product of Peptide Institute Inc.) adjusted to 0.8 mM with tris hydrochloride (pH 8.4) was added thereto. The a absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC$_{50}$) of a concentration of the test compound which inhibits 50% of the activity (initial rate) of the activated blood coagulation factor X in the absence of the test compound was determined, and employed as the index of the activity of inhibiting activated blood coagulation factor X. The activities, of inhibiting activated blood coagulation factor X, of typical compounds are shown in Table 1 given below.

Example 210

Determination of Thrombin-inhibiting Activity

130 μL of 100 mM tris hydrochloride buffer adjusted to pH 8.4 was added to 10 μl of an aqueous solution of a test compound. Then 10 μl of a solution of human thrombin (a product of SIGMA Co.) adjusted to 2 units/ml with tris hydrochloride buffer of pH 8.4 was added to the resultant mixture. After the incubation at room temperature for 10 minutes, 50 μl of a solution of D-phenylalanine-L-pipecolyl-L-arginine-P-nitroanilide dihydrochloride (S-2238; a product of Daiichi Kagaku Yakuhin Co.) adjusted to 0.4 mM with tris hydrochloride buffer of pH 8.4 was added thereto. The absorbance was determined and then the initial reaction rate was determined. A control was prepared in the same manner as that described above except that the solution of the compound to be tested was replaced with 10 μl of tris hydrochloride buffer adjusted to pH 8.4. The absorbance was determined with MICROPLATE READER Model 3550-UV (a product of BIO RAD) at a wave length of 405 nm at intervals of 15 seconds for 16 minutes. The negative logarithm (pIC$_{50}$) of a concentration of the test compound which inhibits 50% of the activity (initial rate) of the thrombin in the absence of the test compound was determined, and employed as the index of the activity of inhibiting thrombin. The activities, of inhibiting thrombin, of typical compounds are shown in Table 1 given below.

Example 211

Determination of Blood Anticoagulating Activity

The blood anticoagulating activity was determined by a prothrombin time (PT) determination method. The PT was determined as follows: The blood was taken from healthy people. 3.8% aqueous trisodium citrate solution was added to the blood in a volume ratio of 1:10. The blood plasma was separated by the centrifugation. 5 μl of DMSO solution containing a test compound was added to 45 μl of the blood plasma. After the incubation apt room temperature for 2 minutes, a test tube containing the blood plasma solution was placed in Sysmex CA-3000 fully automatic blood coagulation determination device (a product of Toa Medical Electronics Co., Ltd), and incubated at 37° C. for 3 minutes. 100 μl of Sysmex PT II (rabbit brain tissue thromboplastin, 13.2 mM calcium chloride; a product of Toa Medical Electronics Co., Ltd) was fed into the test tube. PT was automatically determined with the device. A sample containing 5 μl of DMSO in place of the solution of the test compound was used as the control. The negative logarithm (pPT2) of the concentration of the test compound which elongated PT of the control to the twice as long was determined, and employed as the index of the blood anticoagulating activity.

TABLE 1

|  | Activity of inhibiting activated blood coagulation factor X (pIC$_{50}$) | Thrombin-inhibiting activity (pIC$_{50}$) | Human blood coagulating activity (pPT2) |
| --- | --- | --- | --- |
| Compd. of Ex. 2 | 6.4 | <4.0 | 4.9 |
| Compd. of Ex. 9 | 6.3 | <4.0 | 4.9 |
| Compd. of Ex. 24 | 6.1 | <4.0 | — |
| Compd. of Ex. 25 | 6.4 | <4.0 | 4.9 |
| Compd. of Ex. 27 | 6.4 | <4.0 | 4.8 |
| Compd. of Ex. 39 | 6.7 | <4.0 | 4.8 |
| Compd. of Ex. 43 | 6.9 | <4.0 | 5.2 |
| Compd. of Ex. 49 | 7.5 | 4.3 | 5.0 |
| Compd. of Ex. 65 | 7.4 | 4.0 | 4.7 |
| Compd. of Ex. 68 | 7.4 | 4.2 | 5.2 |
| Compd. of Ex. 71-1 | 7.6 | 4.5 | 5.0 |
| Compd. of Ex. 73 | 8.1 | 4.4 | 4.9 |
| Compd. of Ex. 90 | 7.4 | 4.1 | 5.0 |
| Compd. of Ex. 93 | 7.1 | 4.2 | 5.5 |
| Compd. of Ex. 107 | 7.3 | <4.0 | 5.5 |
| Compd. of Ex. 115 | 7.2 | 4.4 | 5.4 |
| Compd. of Ex. 122 | 7.3 | <4.0 | 5.6 |
| Compd. of Ex. 125 | 6.6 | <4.0 | 5.6 |
| Compd. of Ex. 142 | 6.1 | 4.4 | 5.5 |
| Compd. of Ex. 143 | 6.5 | 4.2 | 5.4 |
| Compd. of Ex. 144 | 6.7 | 4.1 | 5.6 |
| Compd. of Ex. 169 | 6.5 | <4.0 | 5.4 |
| Compd. of Ex. 178 | 7.1 | <4.0 | 5.8 |
| Compd. of Ex. 181 | 7.1 | <4.0 | 5.3 |
| Compd. of Ex. 187 | 6.5 | 4.1 | 5.5 |
| Compd. of Ex. 203 | 7.1 | <4.0 | 5.5 |
| Compd. of Ex. 204 | 6.5 | <4.0 | 5.2 |
| Compd. of Ex. 206 | 6.7 | <4.0 | 5.5 |
| Compd. of Ex. 207 | 7.5 | <4.0 | 5.7 |

From the results, it is understood that the benzodiazepine derivatives of the present invention exhibit a high activity of specifically inhibiting activated blood coagulation factor X, and they exhibit a high anticoagulating activity based on this inhibiting activity.

The structural formulae of the compounds of the present invention described in the Examples are given below.

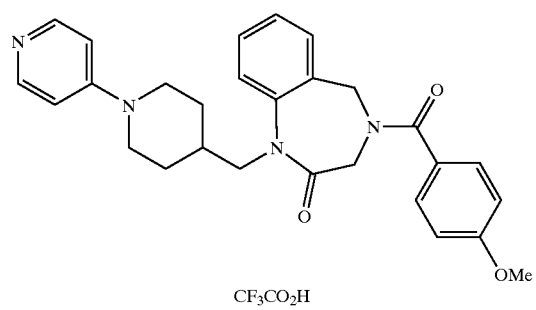

Compound of Example 1

Compound of Example 2
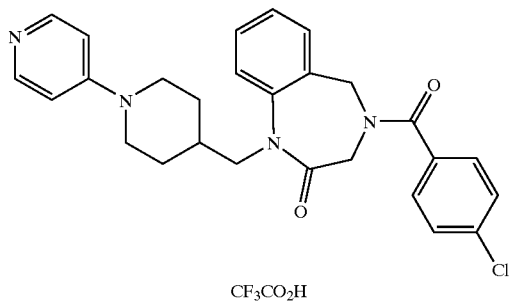
CF₃CO₂H
Compound of Example 3
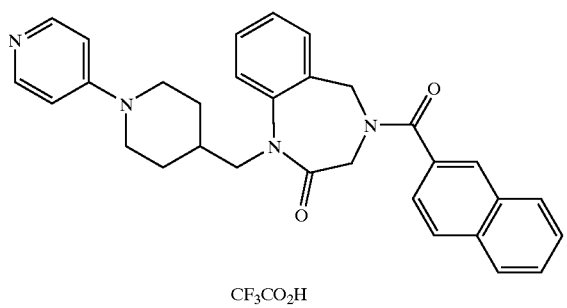
CF₃CO₂H
Compound of Example 4
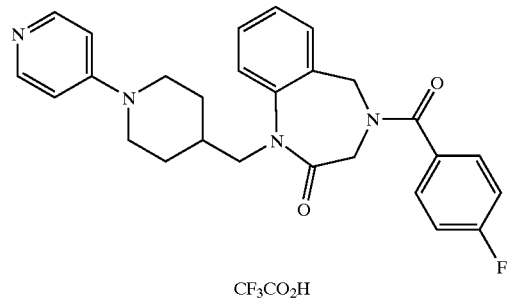
CF₃CO₂H
Compound of Example 5
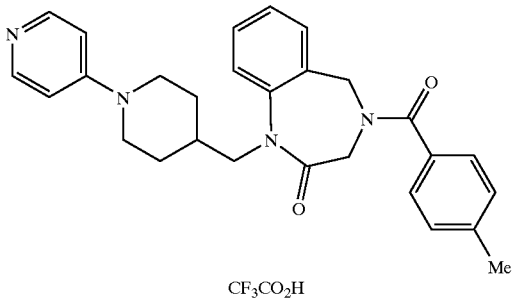
CF₃CO₂H
Compound of Example 6
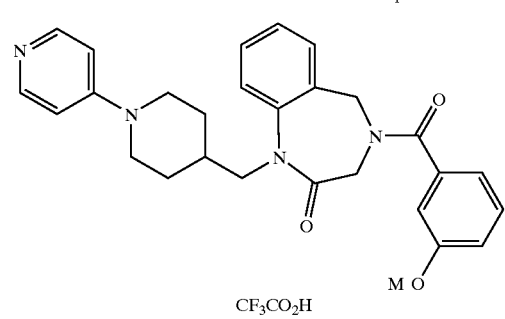
CF₃CO₂H
Compound of Example 7
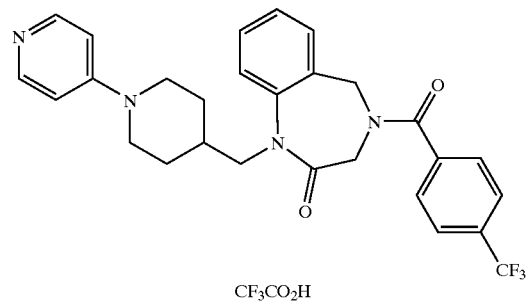
CF₃CO₂H
Compound of Example 8
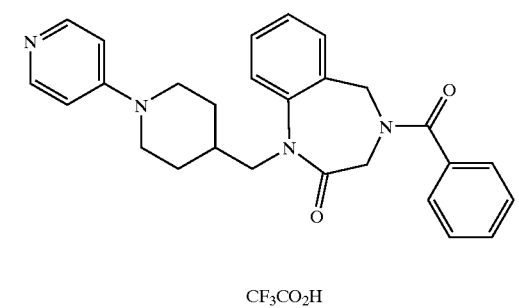
CF₃CO₂H
Compound of Example 9
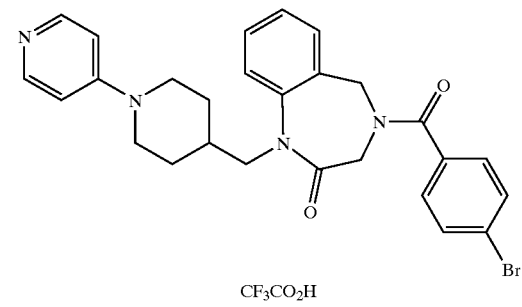
CF₃CO₂H
Compound of Example 10
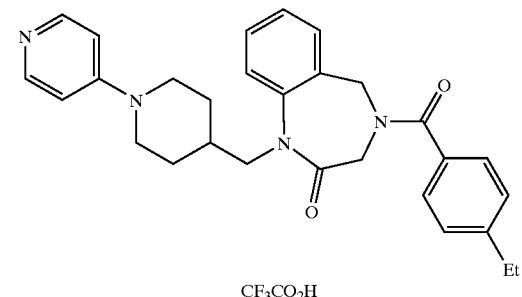
CF₃CO₂H
Compound of Example 11
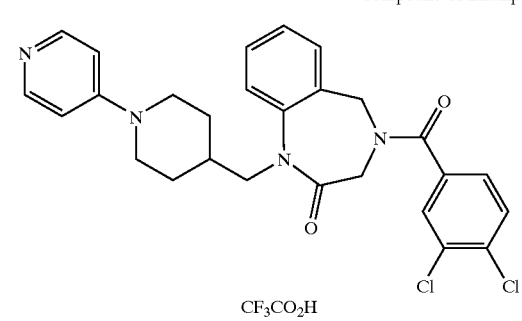
CF₃CO₂H Compound of Example 12
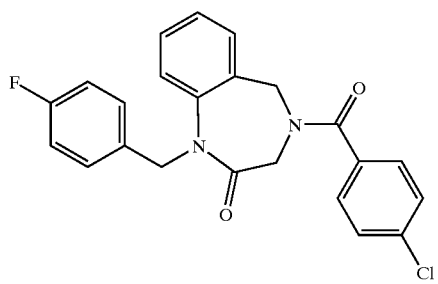
Compound of Example 13
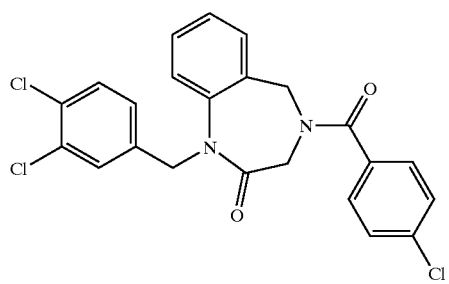
Compound of Example 14
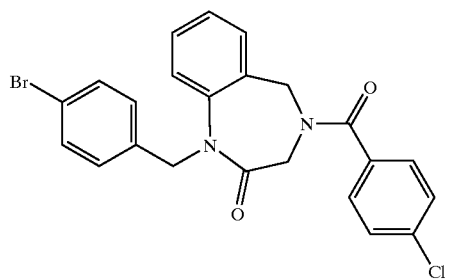
Compound of Example 15
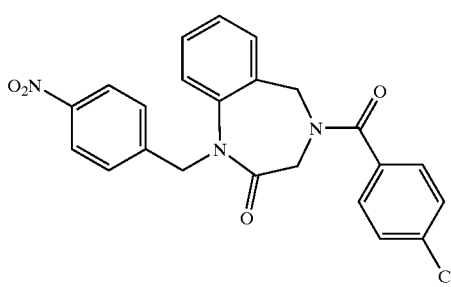
Compound of Example 16
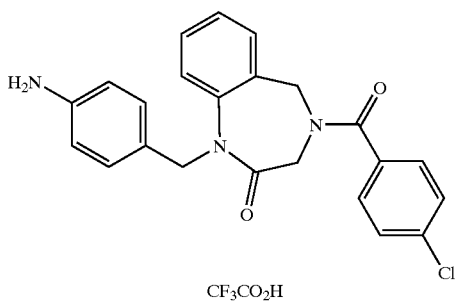
CF₃CO₂H
Compound of Example 17
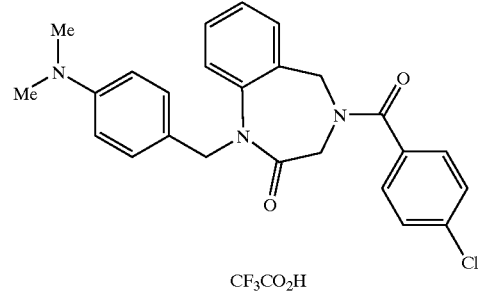
CF₃CO₂H
Compound of Example 18
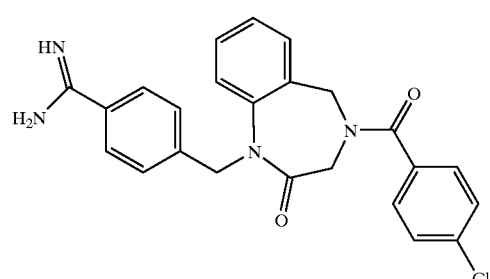
CF₃CO₂H
Compound of Example 19
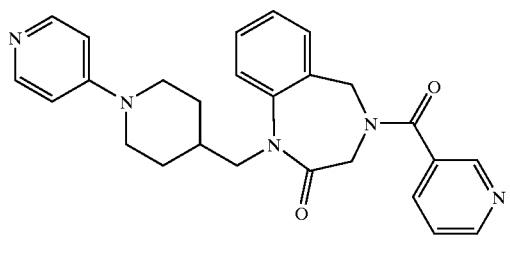
2 CF₃CO₂H
Compound of Example 20
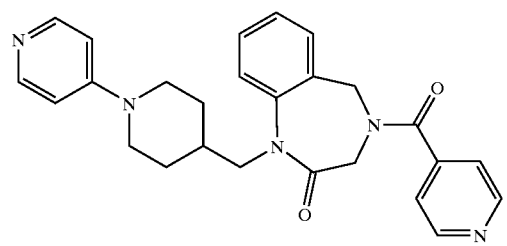
2 CF₃CO₂H
Compound of Example 21
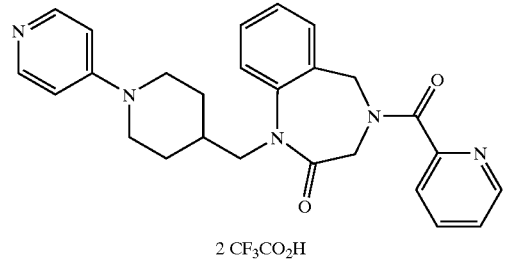
2 CF₃CO₂H Compound of Example 22

2 CF₃CO₂H

Compound of Example 23

CF₃CO₂H

Compound of Example 24

CF₃CO₂H

Compound of Example 25

CF₃CO₂H

Compound of Example 26

CF₃CO₂H

Compound of Example 27

CF₃CO₂H

Compound of Example 28

CF₃CO₂H

Compound of Example 29

2 CF₃CO₂H

Compound of Example 30

2 CF₃CO₂H

Compound of Example 31

CF₃CO₂H

Compound of Example 32
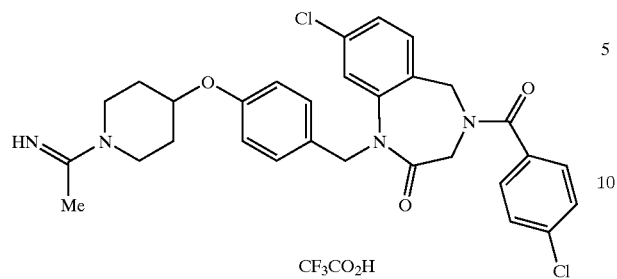
CF₃CO₂H
Compound of Example 33
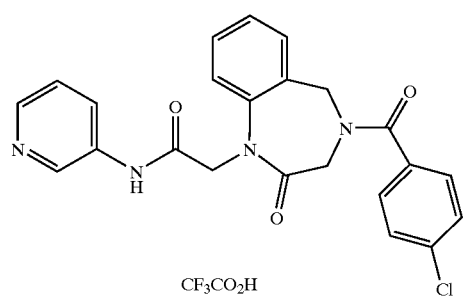
CF₃CO₂H
Compound of Example 34
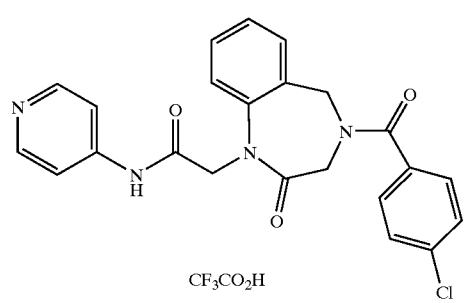
CF₃CO₂H
Compound of Example 35
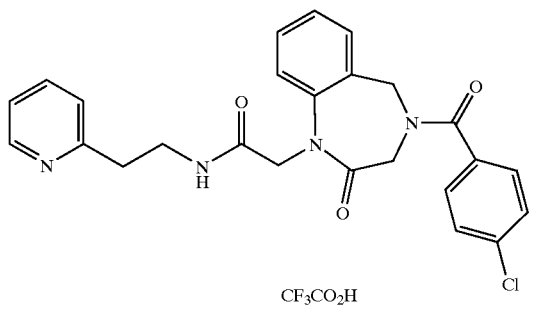
CF₃CO₂H
Compound of Example 36
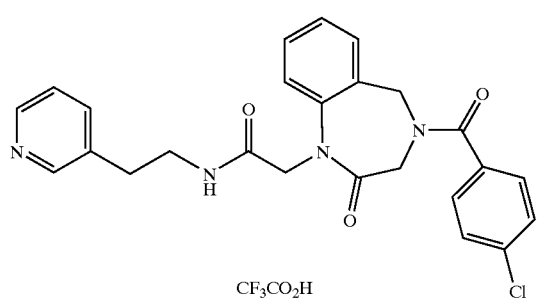
CF₃CO₂H
Compound of Example 37
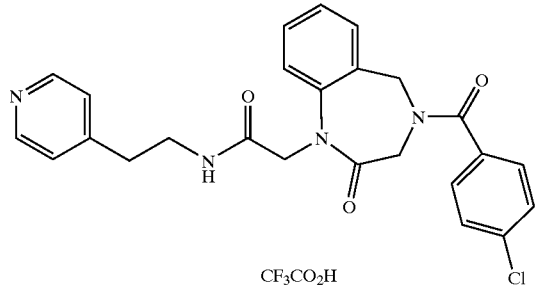
CF₃CO₂H
Compound of Example 38
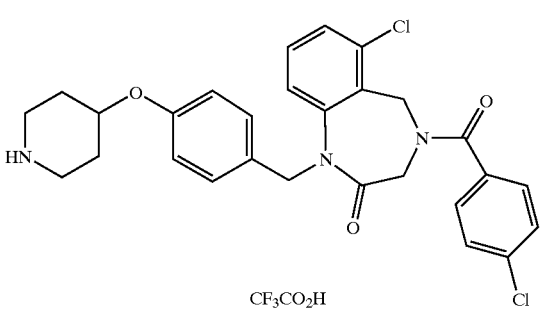
CF₃CO₂H
Compound of Example 39
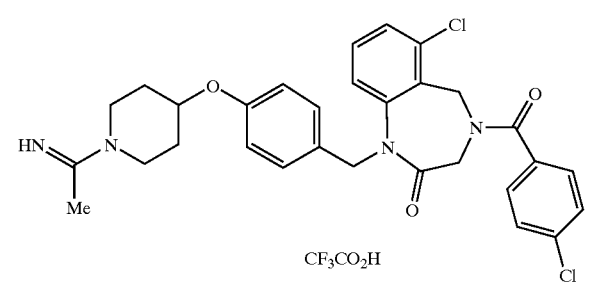
CF₃CO₂H
Compound of Example 40
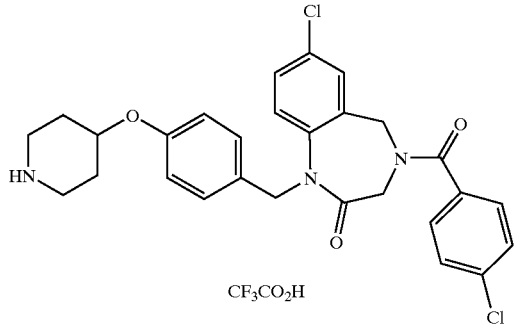
CF₃CO₂H
Compound of Example 41
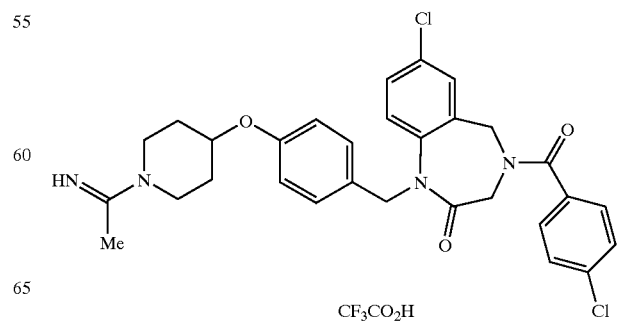
CF₃CO₂H Compound of Example 42
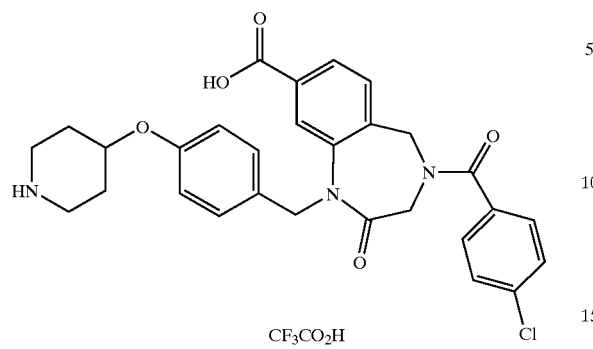
CF₃CO₂H
Compound of Example 43
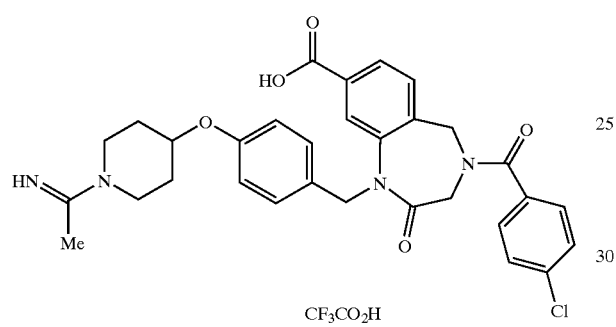
CF₃CO₂H
Compound of Example 44
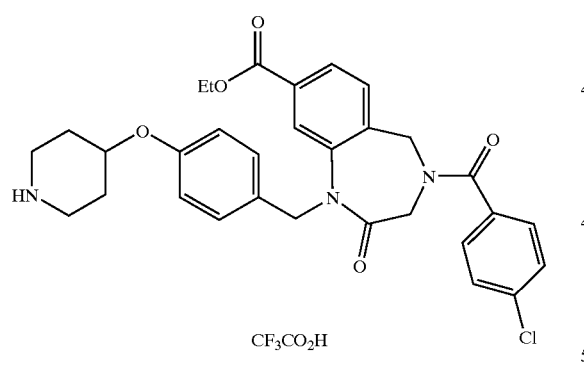
CF₃CO₂H
Compound of Example 45
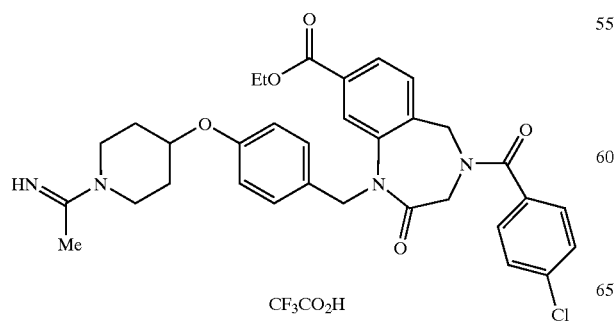
CF₃CO₂H
Compound of Example 46
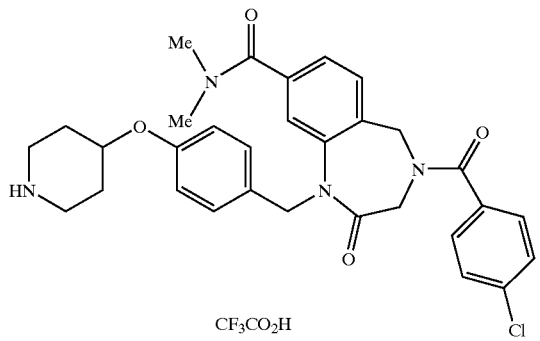
CF₃CO₂H
Compound of Example 47
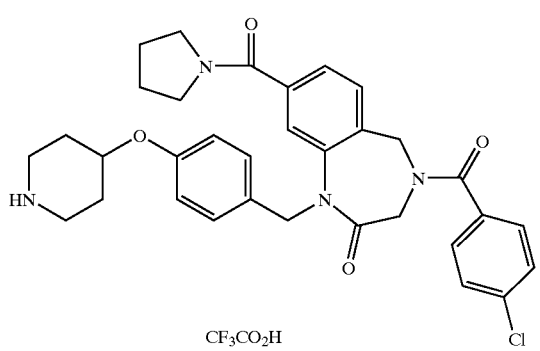
CF₃CO₂H
Compound of Example 48
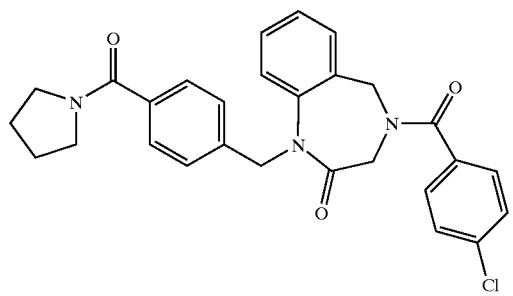
Compound of Example 49
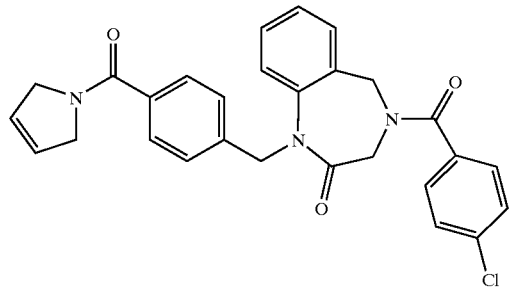

-continued
Compound of Example 50
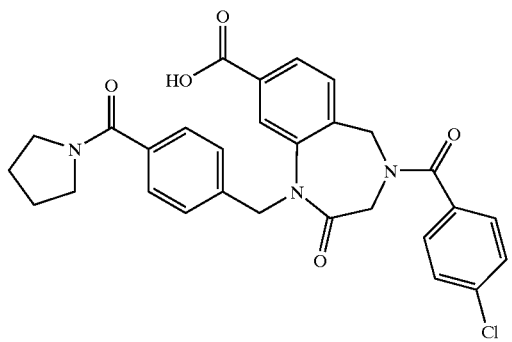
Compound of Example 51
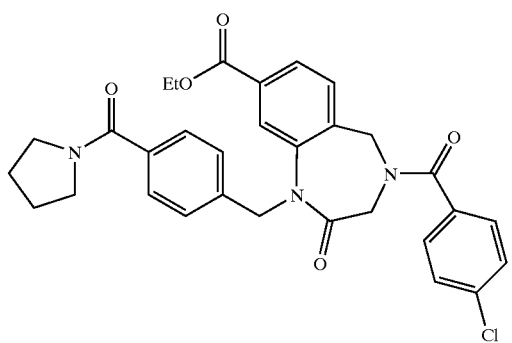
Compound of Example 52
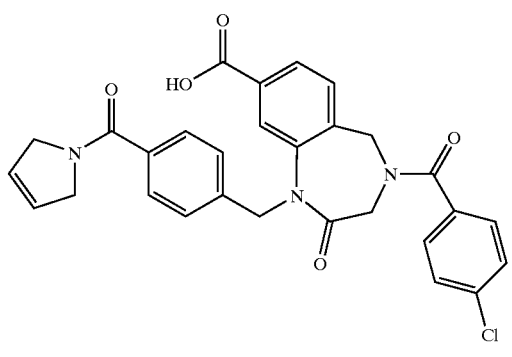
Compound of Example 53
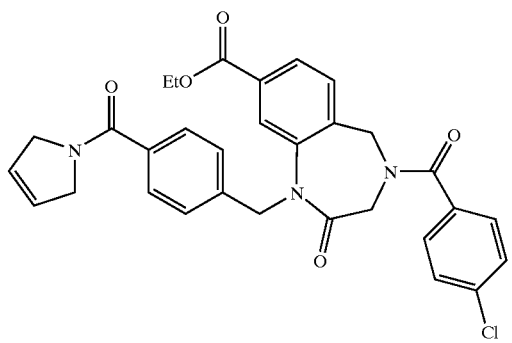
-continued
Compound of Example 54
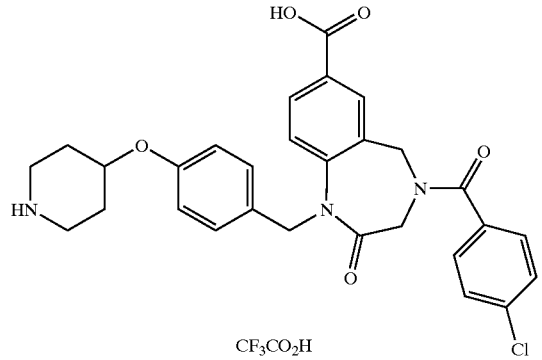
$CF_3CO_2H$
Compound of Example 55
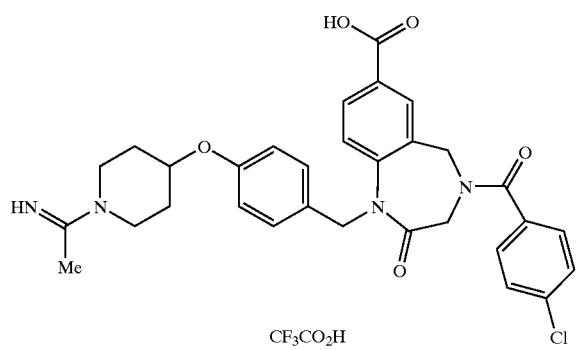
$CF_3CO_2H$
Compound of Example 56
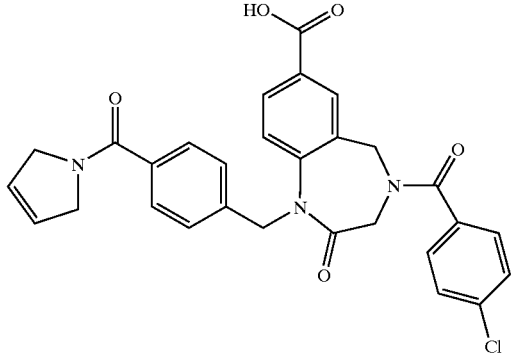
Compound of Example 57
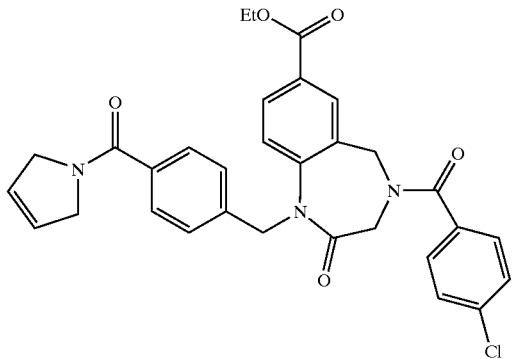

Compound of Example 58
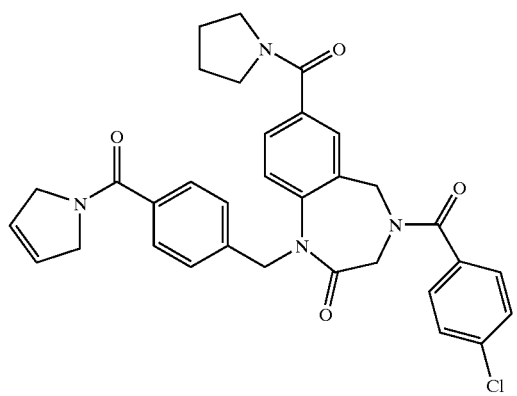
Compound of Example 59
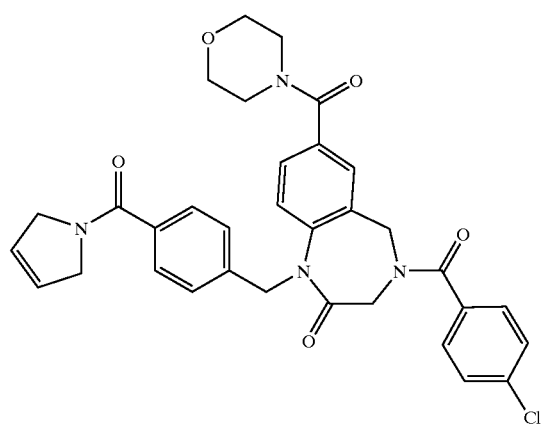
Compound of Example 60
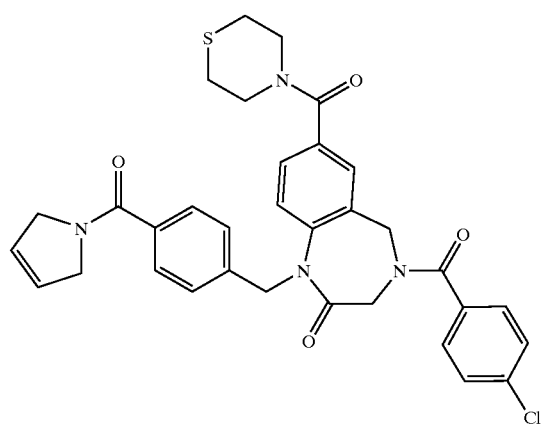
Compound of Example 61
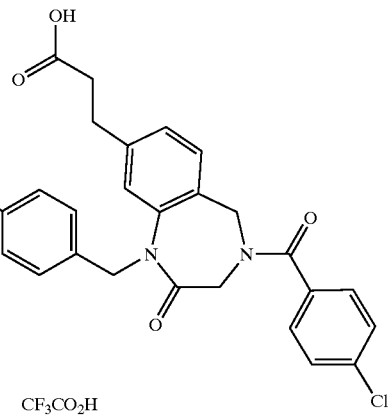
$CF_3CO_2H$
Compound of Example 62
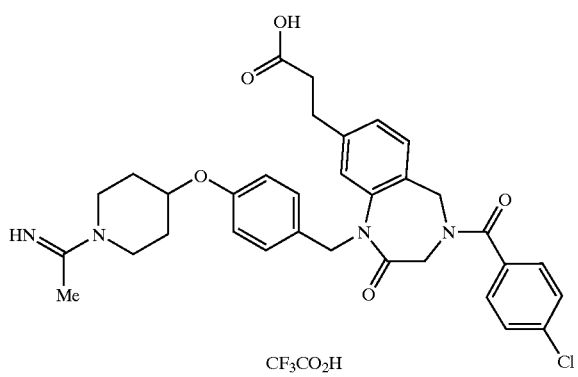
$CF_3CO_2H$
Compound of Example 63
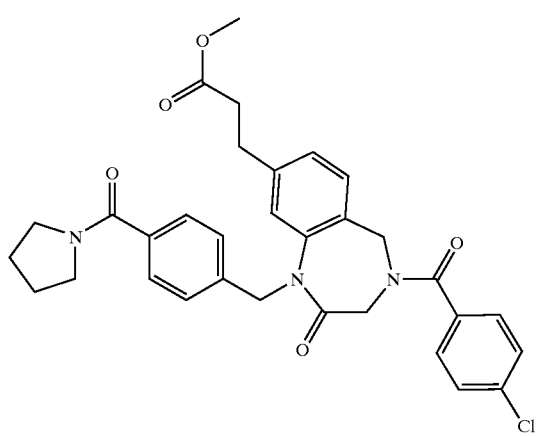

Compound of Example 64
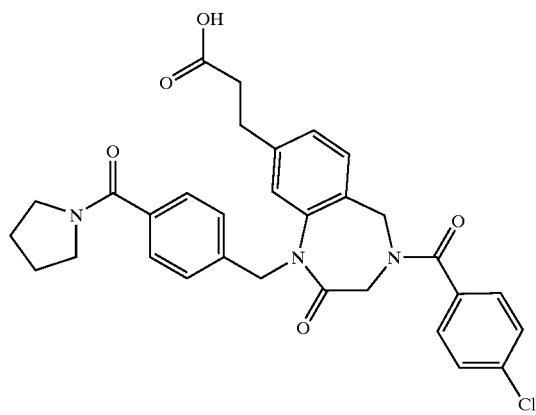
Compound of Example 65
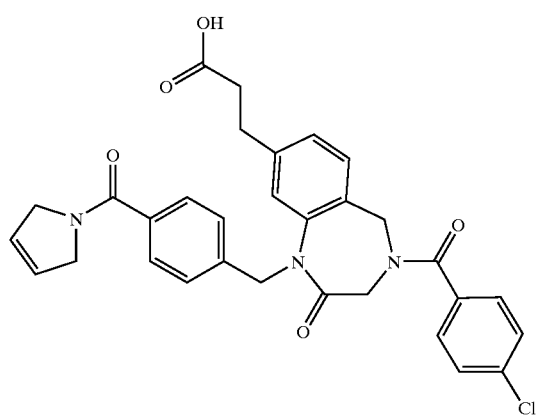
Compound of Example 66
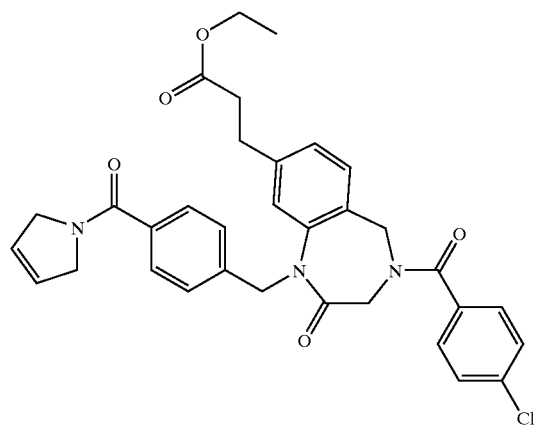
Compound of Example 67
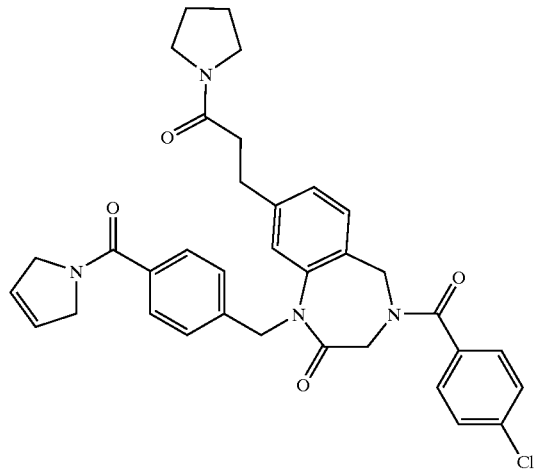
Compound of Example 68
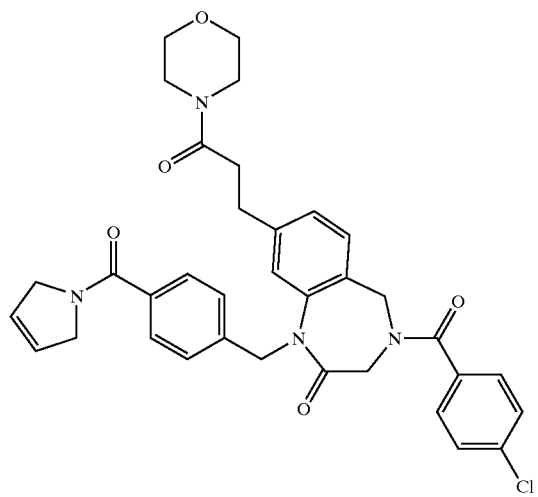
Compound of Example 69
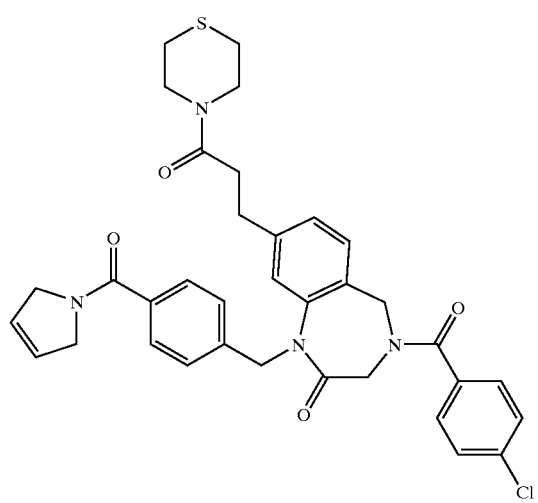

Compound of Example 70
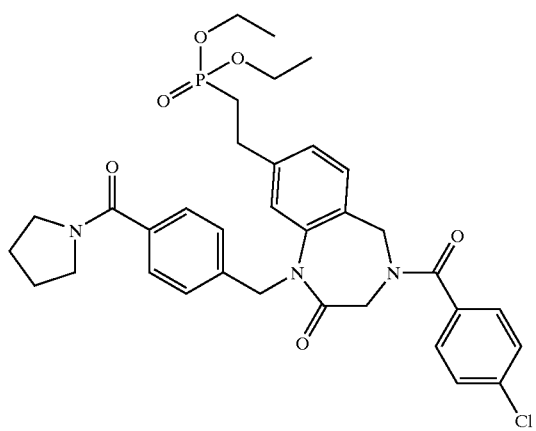
Compound of Example 71-1
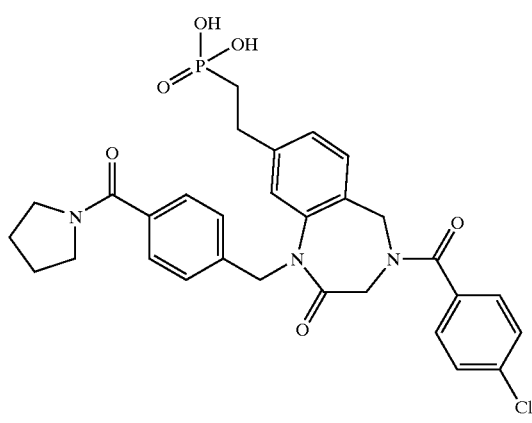
Compound of Example 71-2
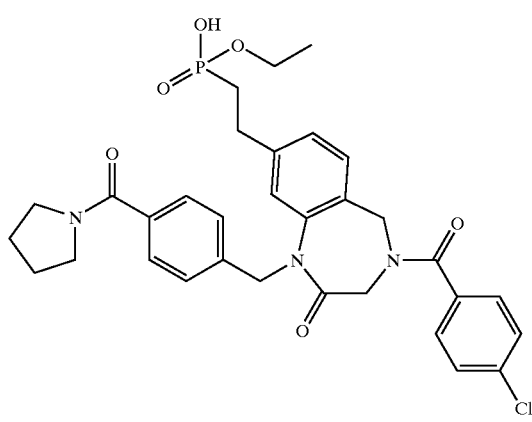
Compound of Example 72
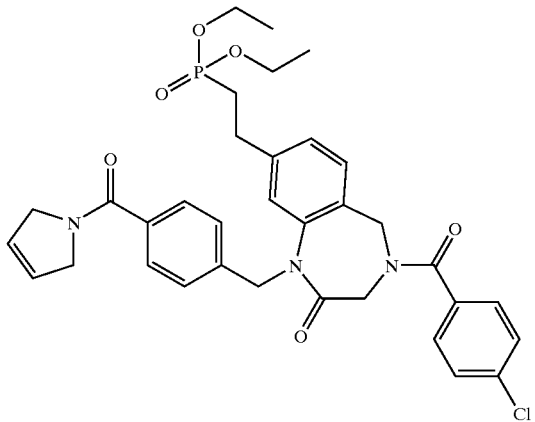
Compound of Example 73
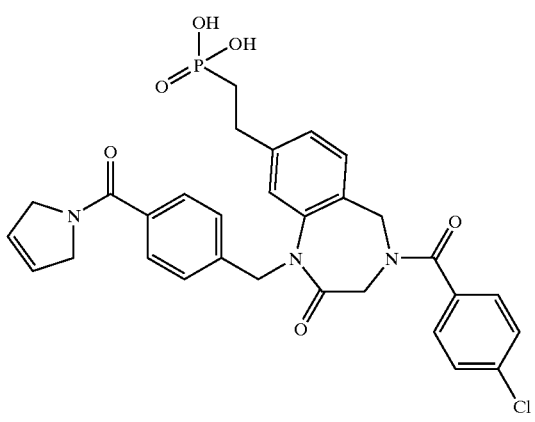
Compound of Example 74
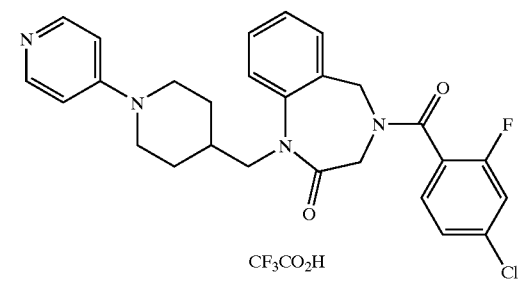
CF$_3$CO$_2$H
Compound of Example 75
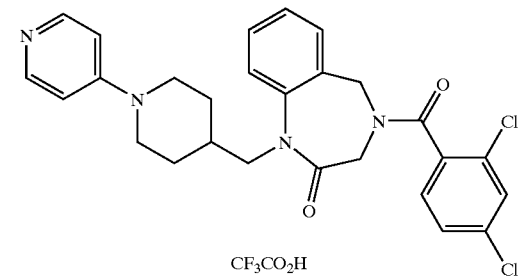
CF$_3$CO$_2$H Compound of Example 76
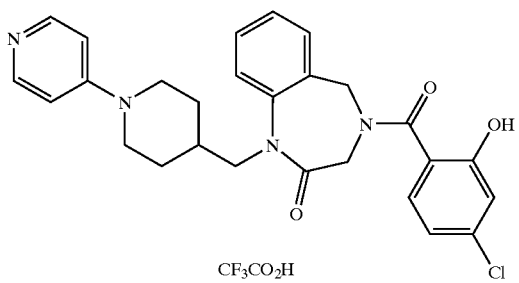
Compound of Example 77
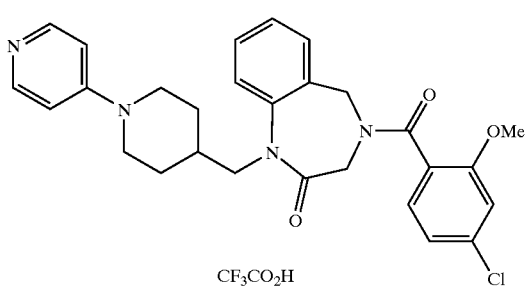
Compound of Example 78
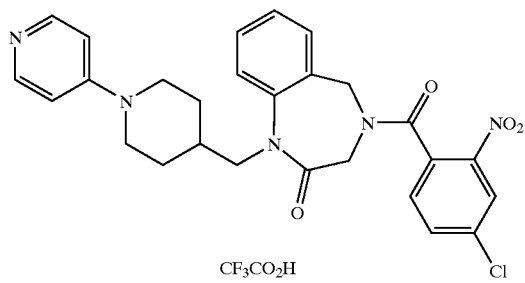
Compound of Example 79
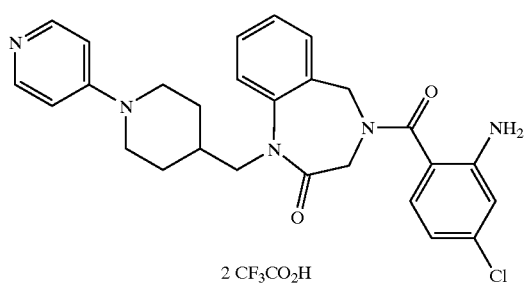
Compound of Example 80
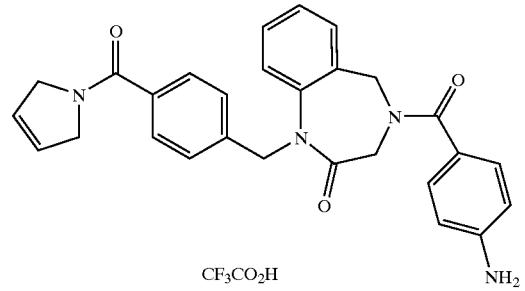
Compound of Example 81
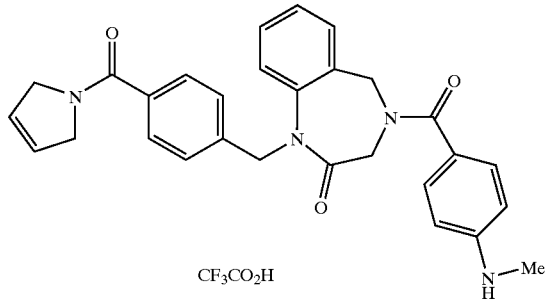
Compound of Example 82
Compound of Example 83
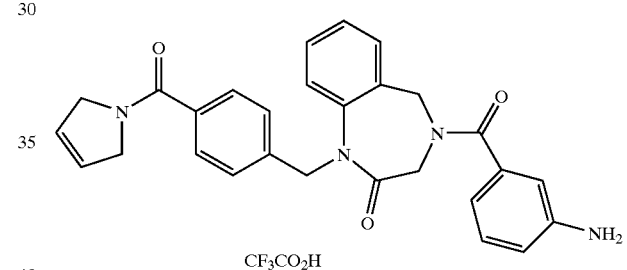
Compound of Example 84
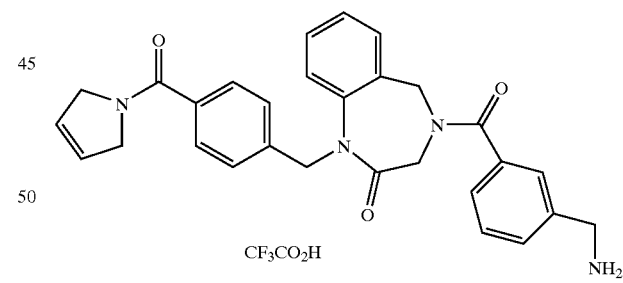
Compound of Example 85
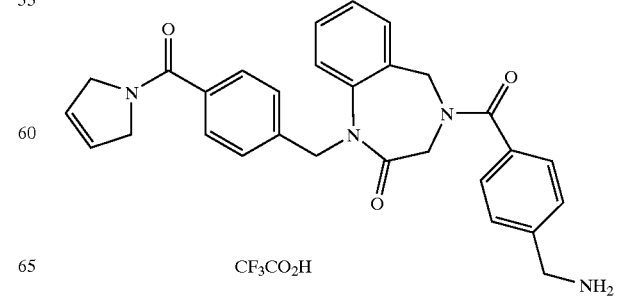

Compound of Example 86
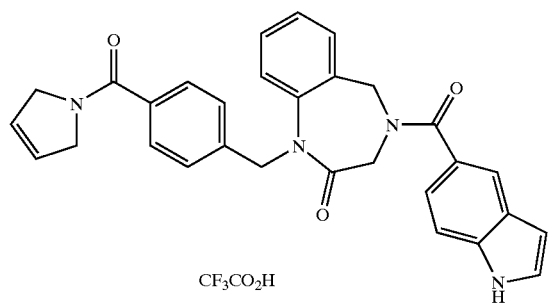
Compound of Example 87
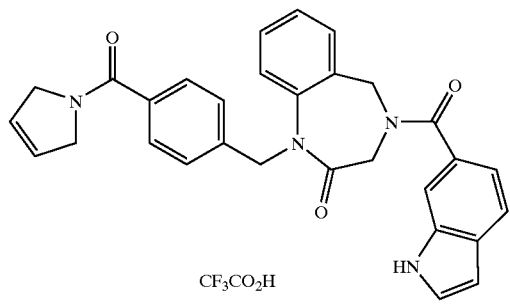
Compound of Example 88
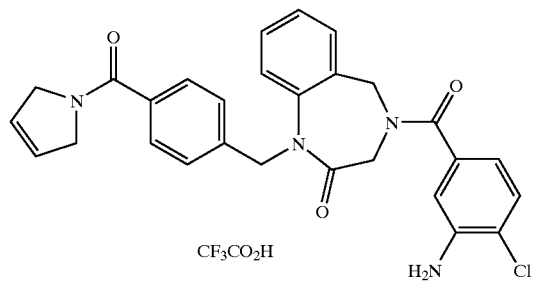
Compound of Example 89
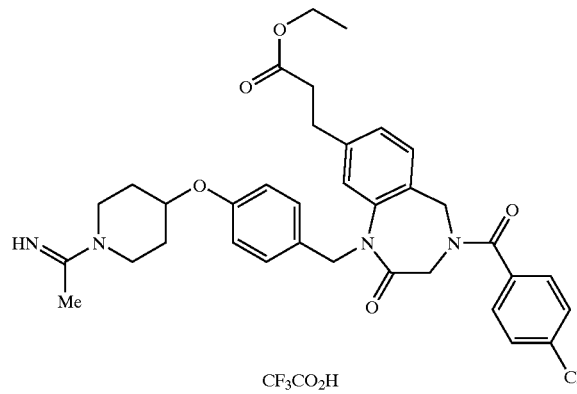
Compound of Example 90
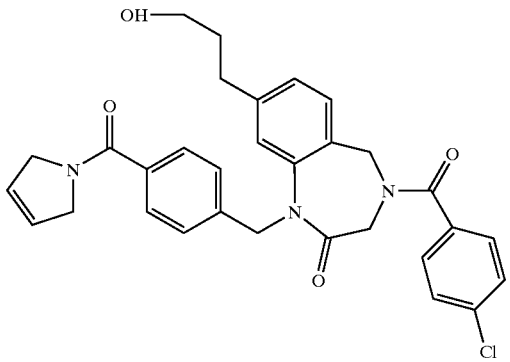
Compound of Example 91
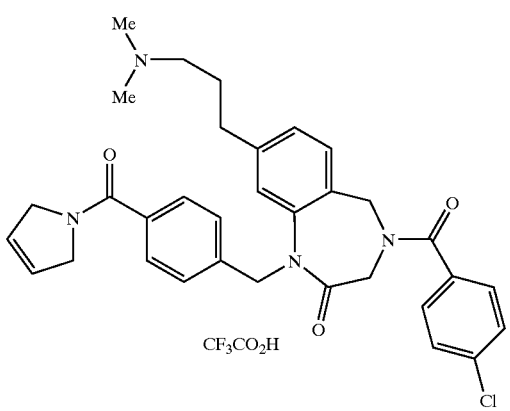
Compound of Example 92
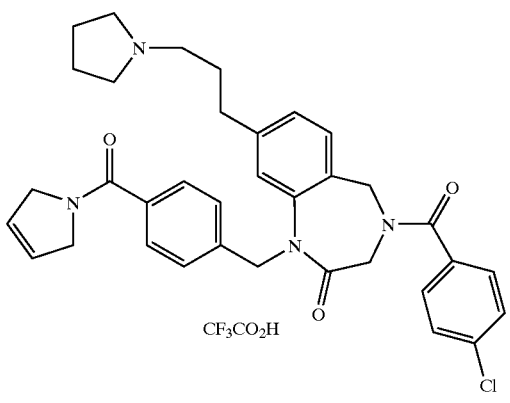
Compound of Example 93
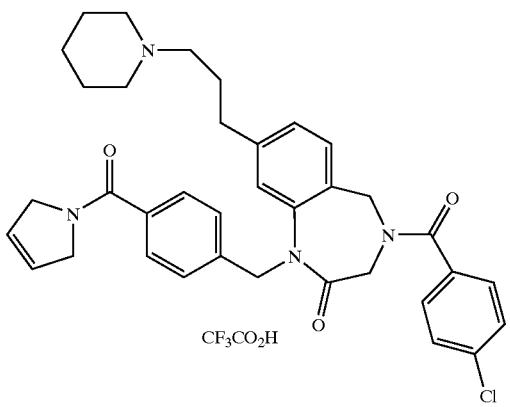

Compound of Example 94
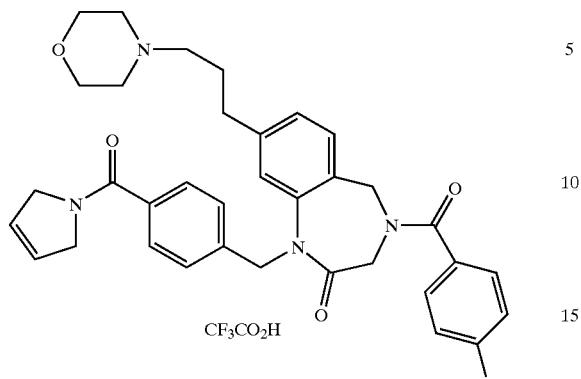
CF$_3$CO$_2$H
Compound of Example 95
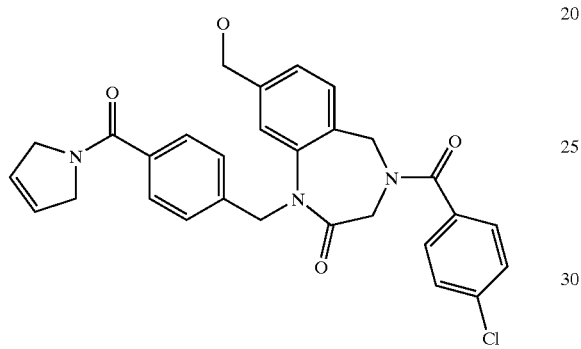
Compound of Example 96
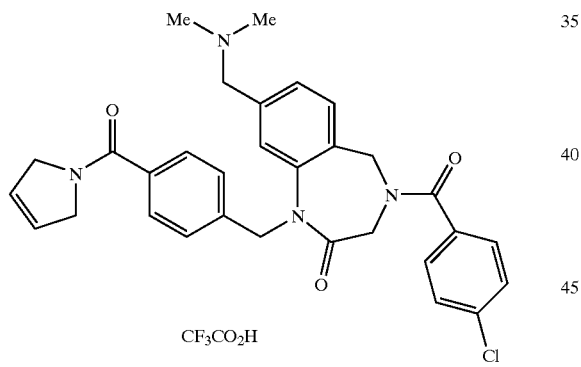
CF$_3$CO$_2$H
Compound of Example 97
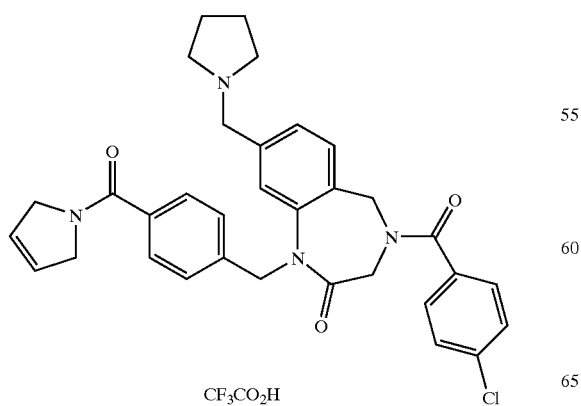
CF$_3$CO$_2$H
Compound of Example 98
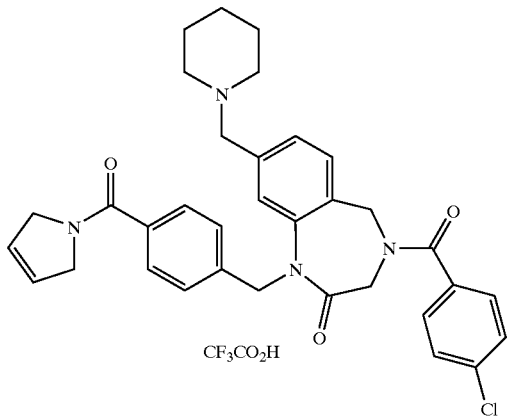
CF$_3$CO$_2$H
Compound of Example 99
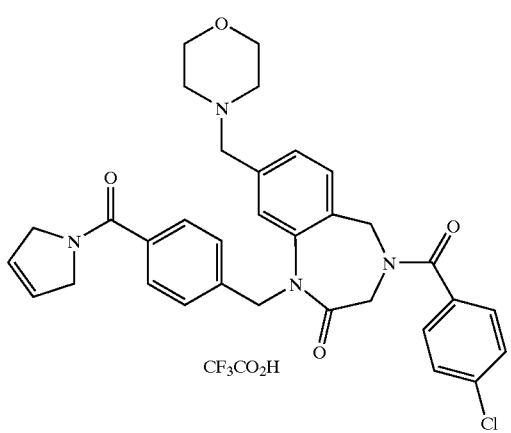
CF$_3$CO$_2$H
Compound of Example 100
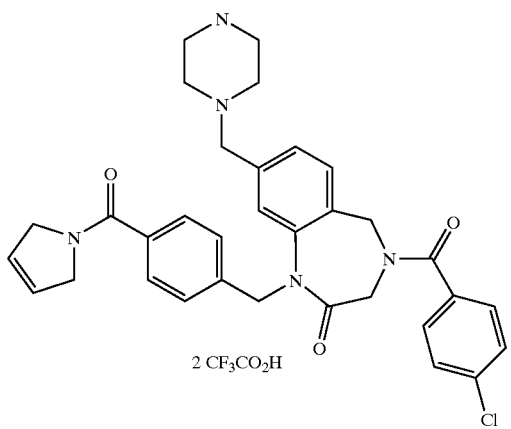
2 CF$_3$CO$_2$H -continued
Compound of Example 101
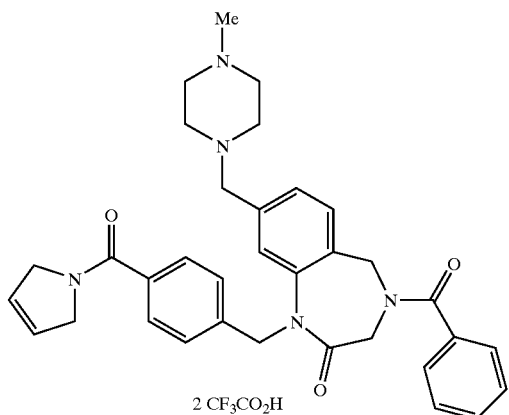
2 CF₃CO₂H
Compound of Example 102
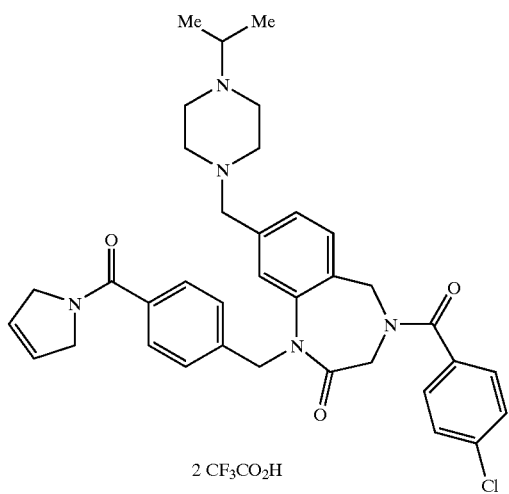
2 CF₃CO₂H
Compound of Example 104
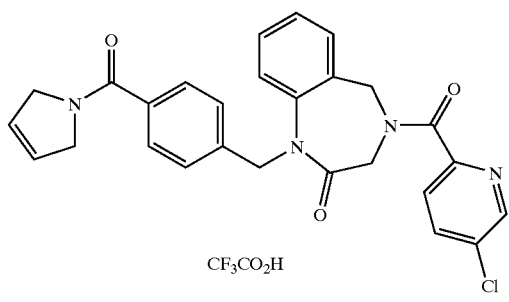
CF₃CO₂H
Compound of Example 105
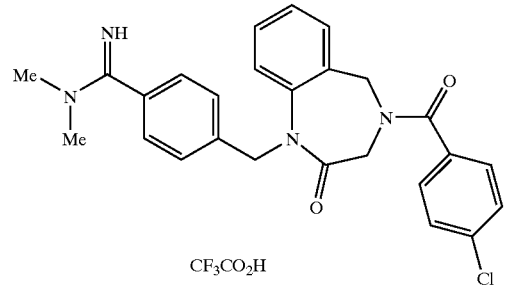
CF₃CO₂H
-continued
Compound of Example 106
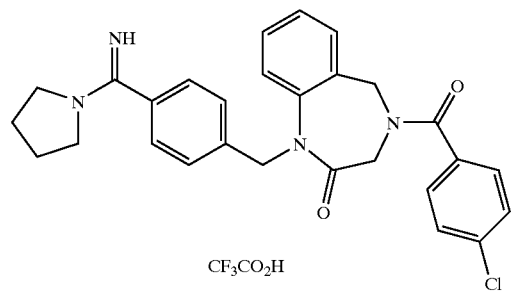
CF₃CO₂H
Compound of Example 107
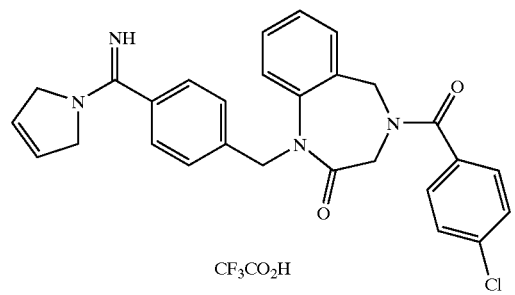
CF₃CO₂H
Compound of Example 108
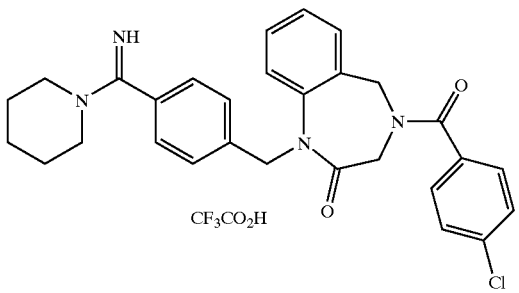
CF₃CO₂H
Compound of Example 109
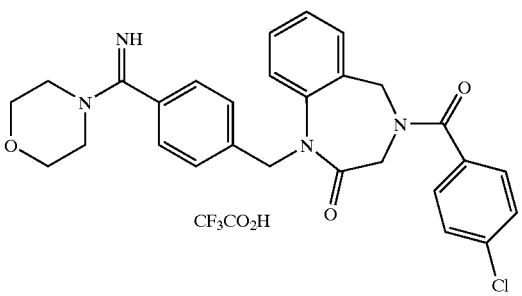
CF₃CO₂H
Compound of Example 110
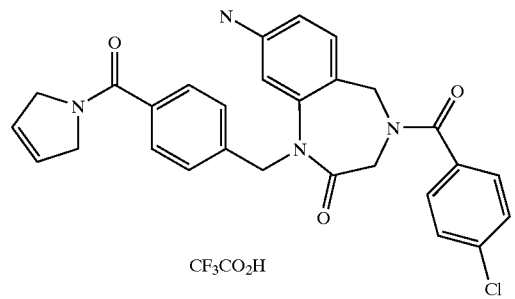
CF₃CO₂H Compound of Examble 111
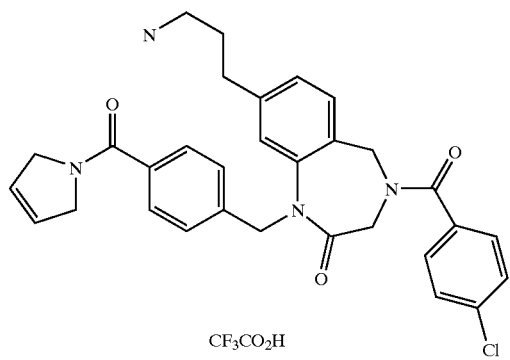
CF₃CO₂H
Compound of Examble 112
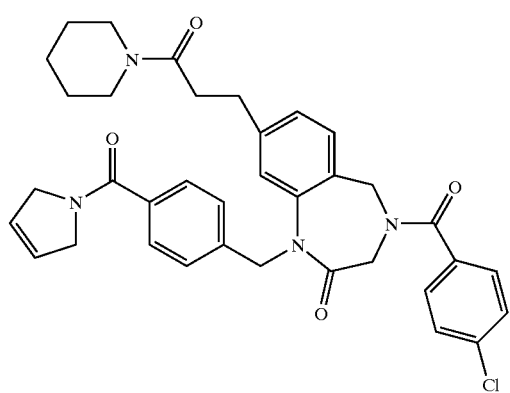
Compound of Examble 113
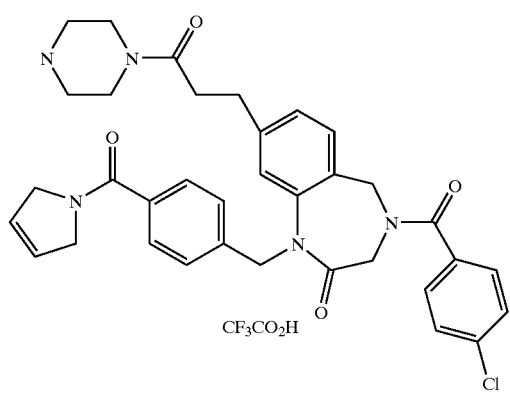
CF₃CO₂H
Compound of Examble 114
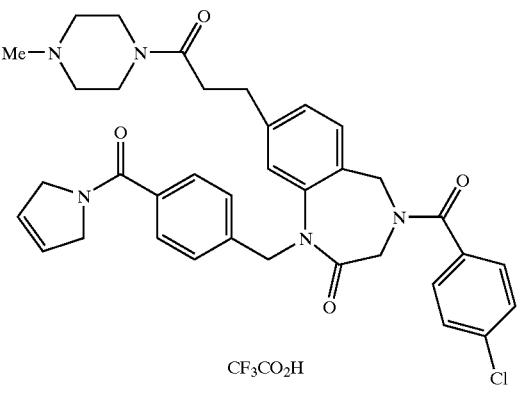
CF₃CO₂H
Compound of Example 115
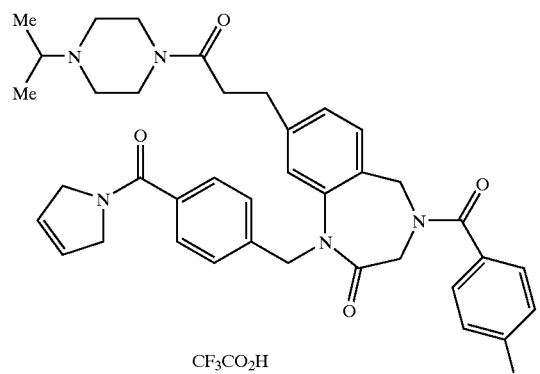
CF₃CO₂H
Compound of Example 116
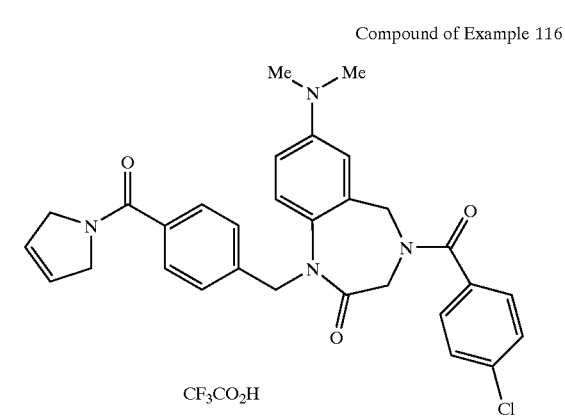
CF₃CO₂H
Compound of Example 117
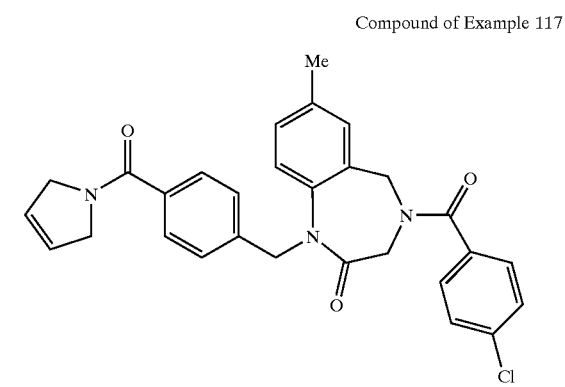
Compound of Example 118
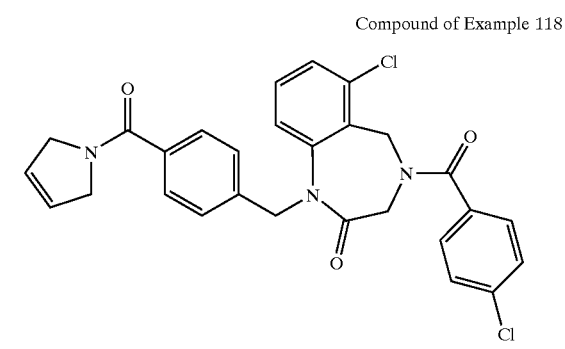

-continued
Compound of Example 119
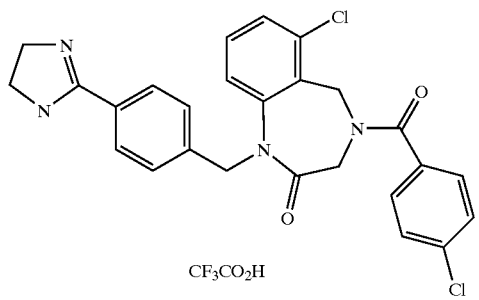
CF₃CO₂H
Compound of Example 120
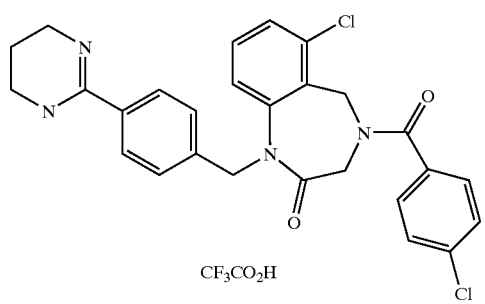
CF₃CO₂H
Compound of Example 121
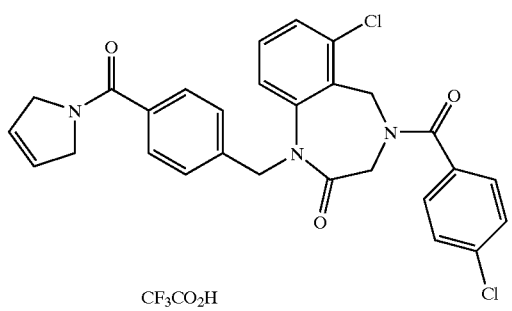
CF₃CO₂H
Compound of Example 122
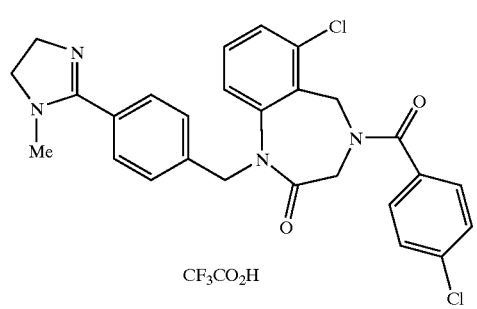
CF₃CO₂H
Compound of Example 123
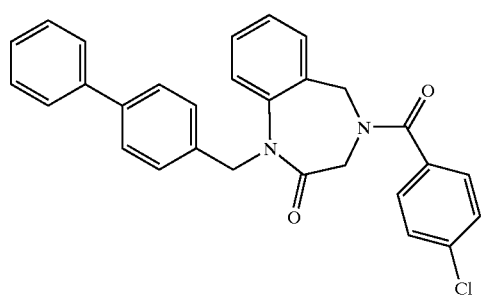
-continued
Compound of Example 124
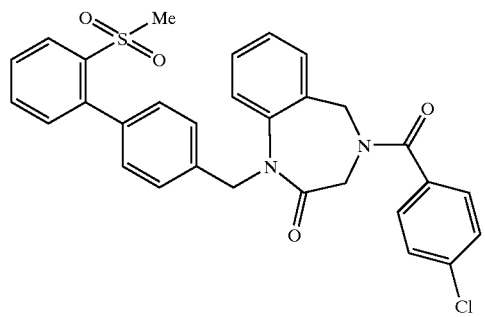
Compound of Example 125
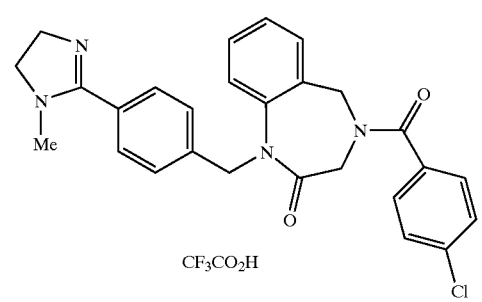
CF₃CO₂H
Compound of Example 126
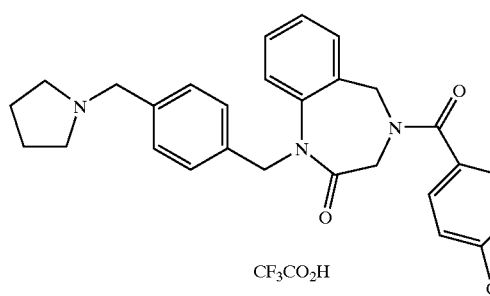
CF₃CO₂H
Compound of Example 127
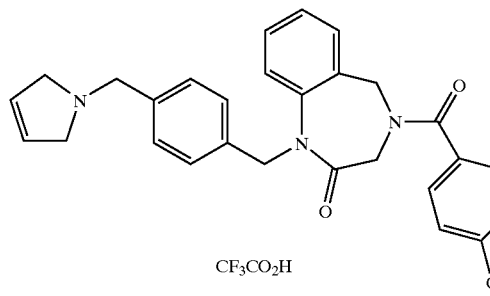
CF₃CO₂H
Compound of Example 128
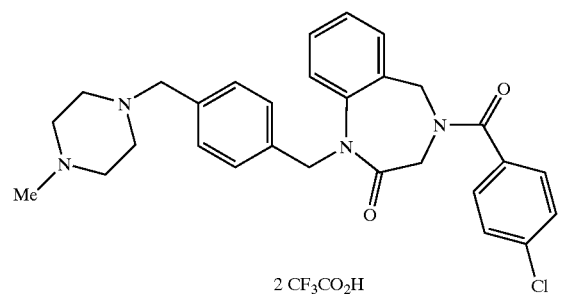
2 CF₃CO₂H Compound of Example 129
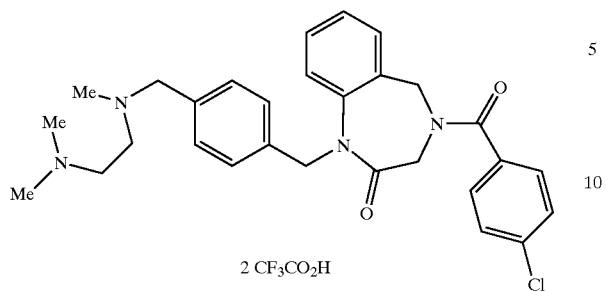
2 CF₃CO₂H
Compound of Example 130
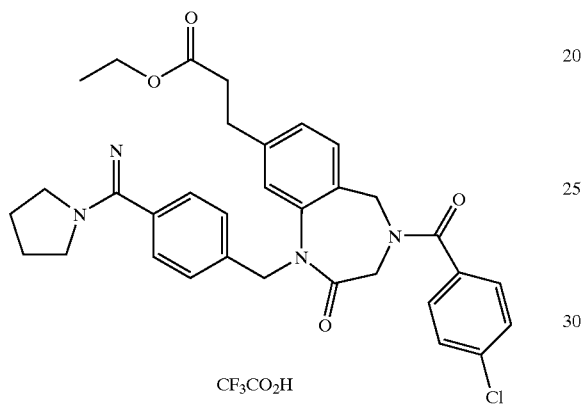
CF₃CO₂H
Compound of Example 131
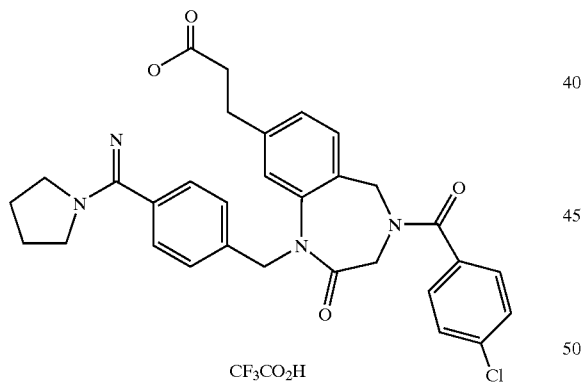
CF₃CO₂H
Compound of Example 132
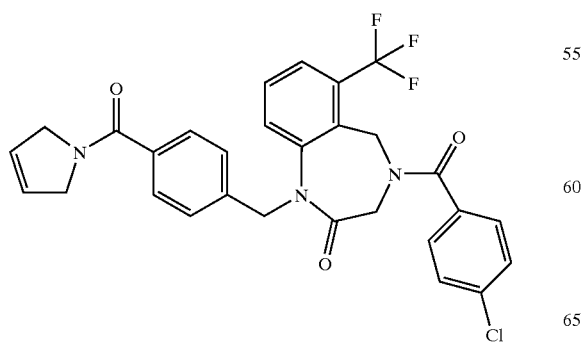
Compound of Example 133
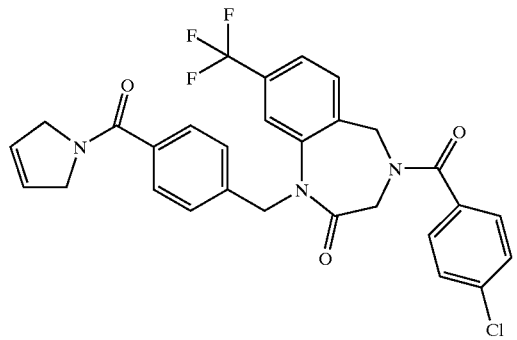
Compound of Example of 134
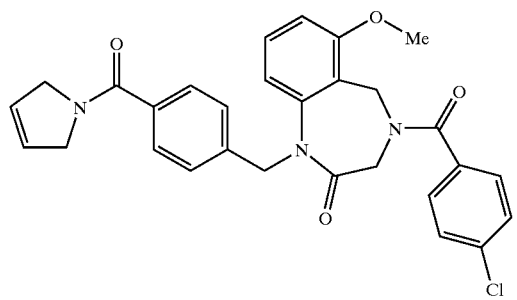
Compound of Example 135
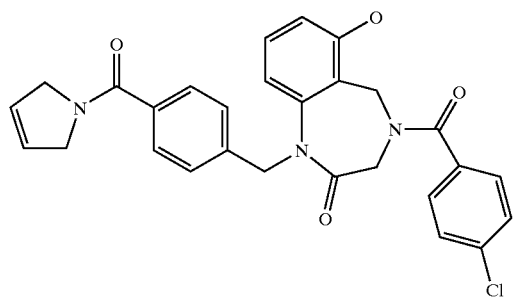
Compound of Example 136
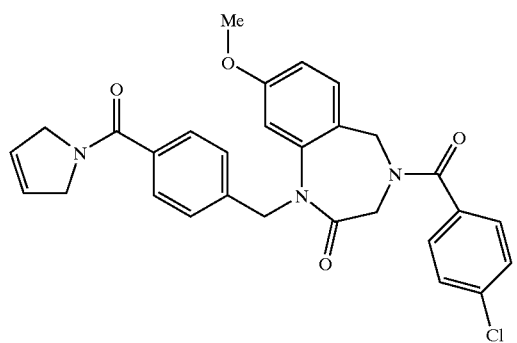

Compound of Example 137
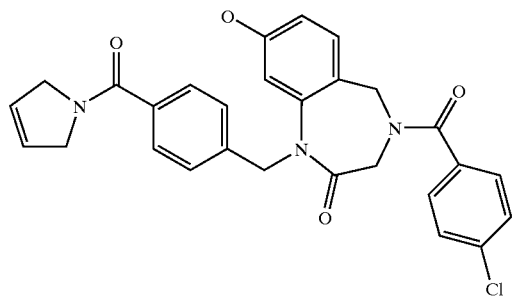
Compound of Example 138
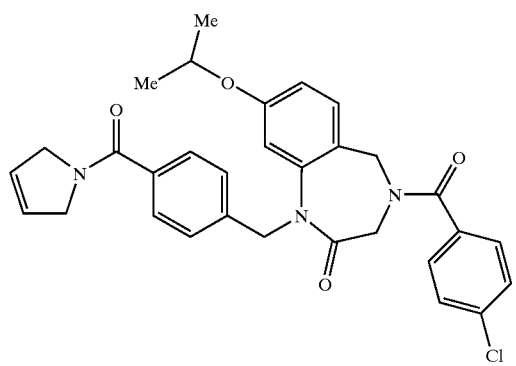
Compound of Example 139
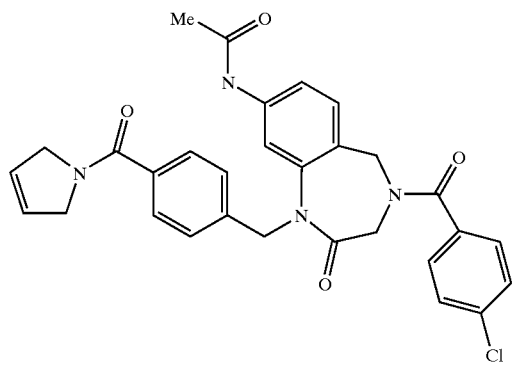
Compound of Example 140
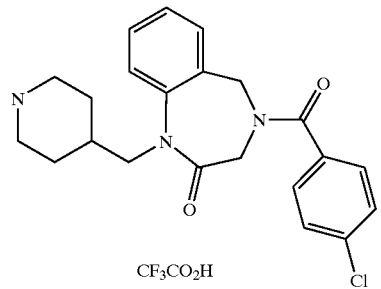
CF$_3$CO$_2$H
Compound of Example 141
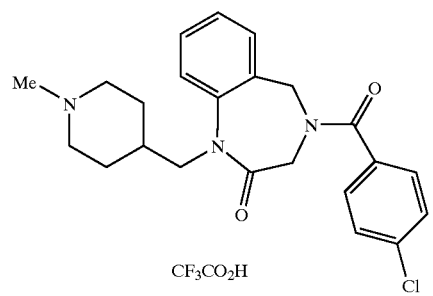
CF$_3$CO$_2$H
Compound of Example 142
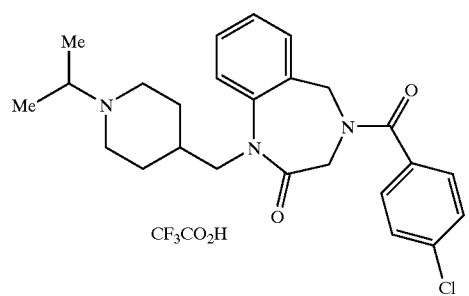
CF$_3$CO$_2$H
Compound of Example 143
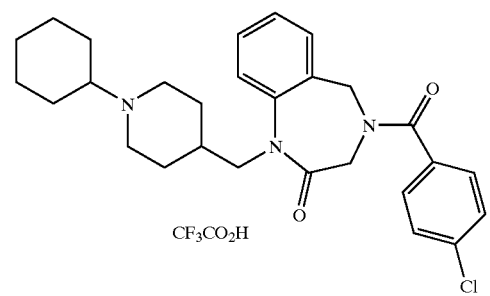
CF$_3$CO$_2$H
Compound of Example 144
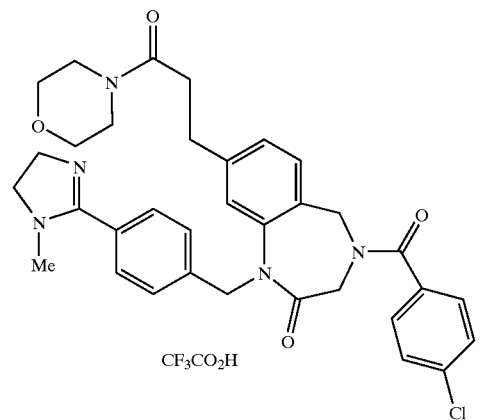
CF$_3$CO$_2$H -continued
Compound of Example 145
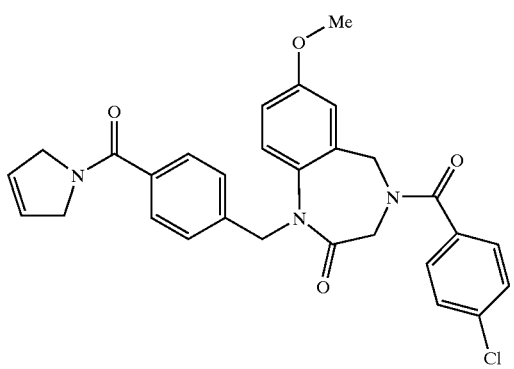
Compound of Example 146
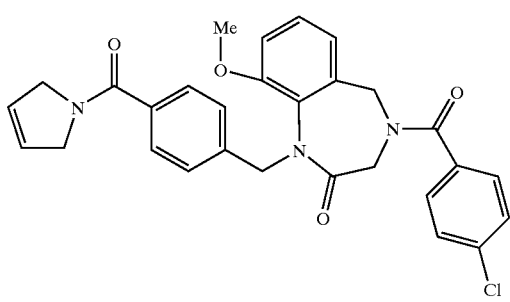
Compound of Example 147
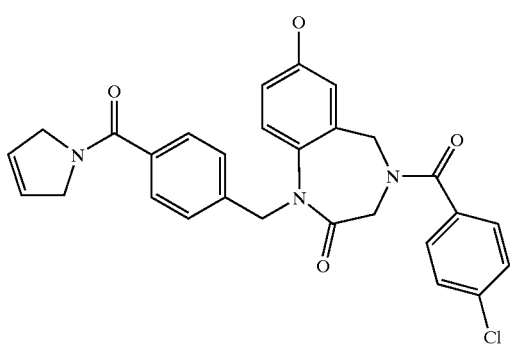
Compound of Example 148
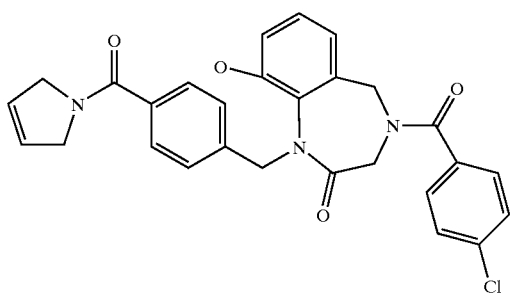
-continued
Compound of Example 149
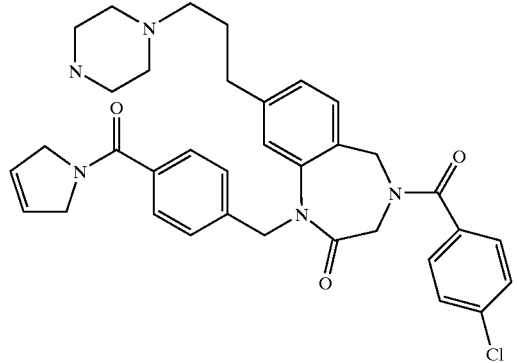
2 CF$_3$CO$_2$H
Compound of Example 150
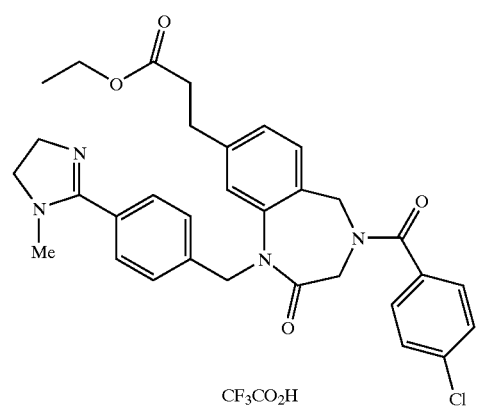
CF$_3$CO$_2$H
Compound of Example 151
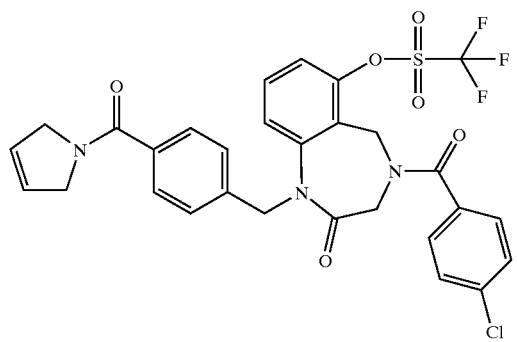
Compound of Example 152
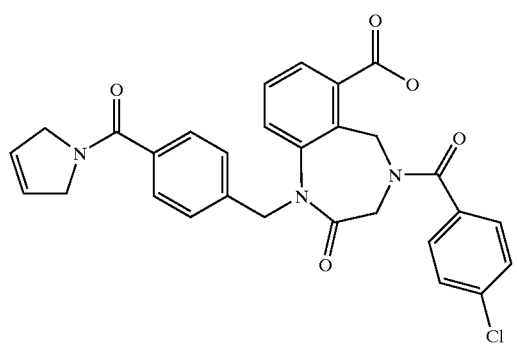

Compound of Example 153
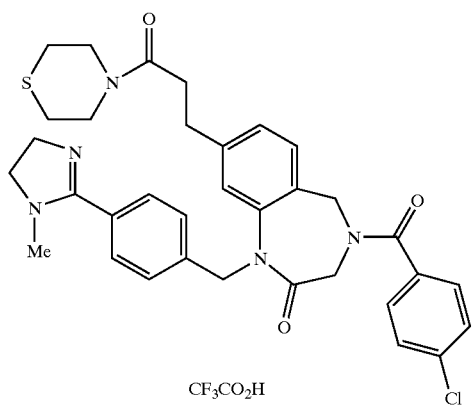
CF₃CO₂H
Compound of Example 154
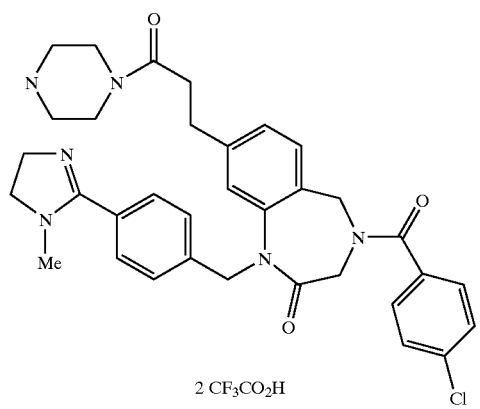
2 CF₃CO₂H
Compound of Example 155
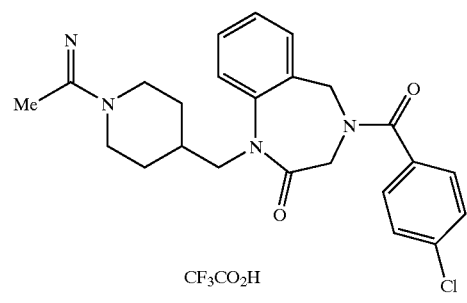
CF₃CO₂H
Compound of Example 156
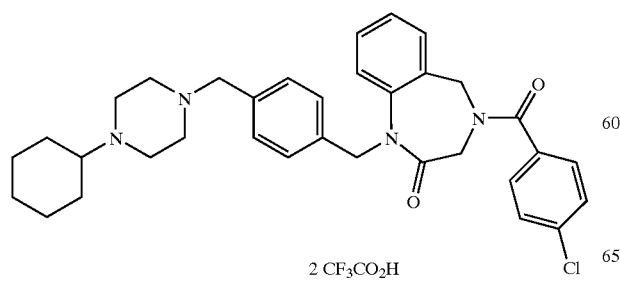
2 CF₃CO₂H
Compound of Example 157
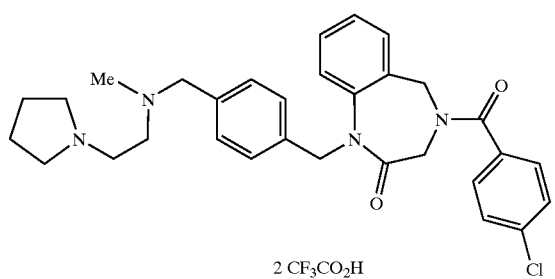
2 CF₃CO₂H
Compound of Example 158
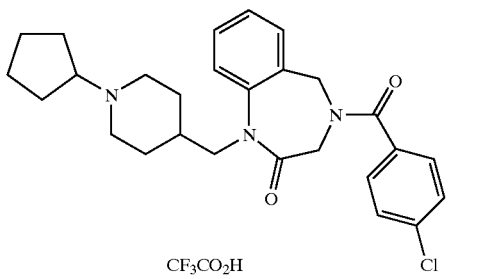
CF₃CO₂H
Compound of Example 159
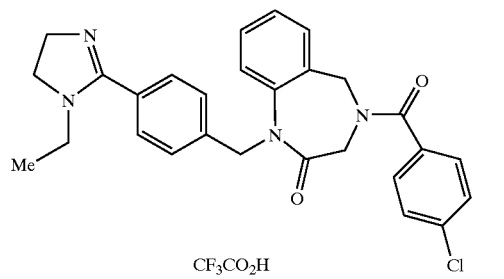
CF₃CO₂H
Compound of Example 160
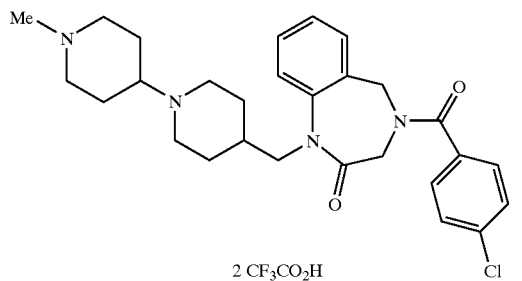
2 CF₃CO₂H
Compound of Example 161
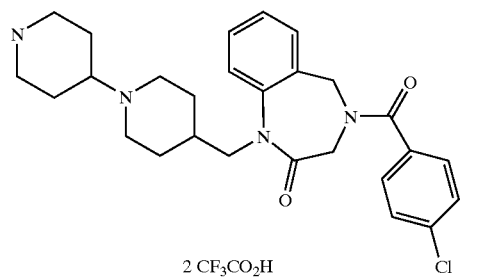
2 CF₃CO₂H Compound of Example 162
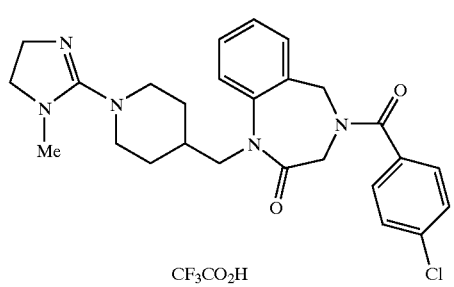
Compound of Example 163
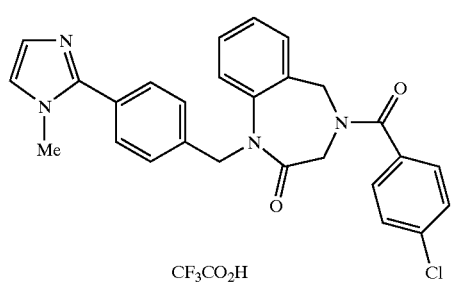
Compound of Example 164
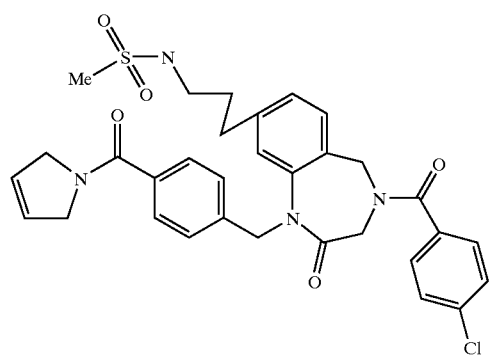
Compound of Example 165
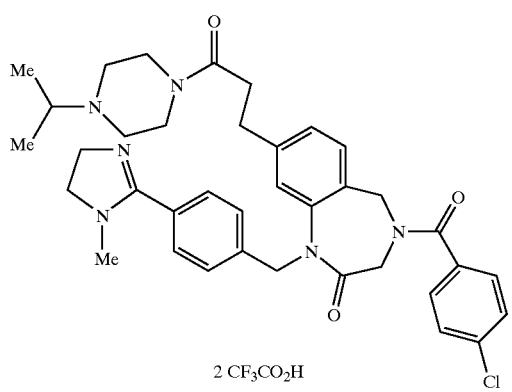
Compound of Example 166
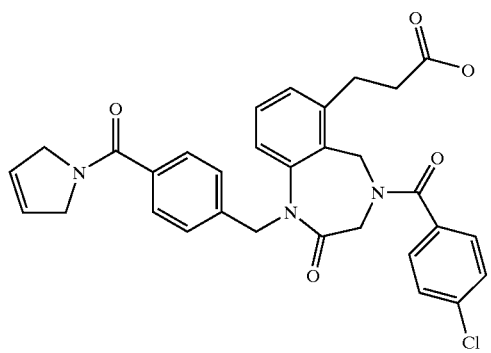
Compound of Example 167
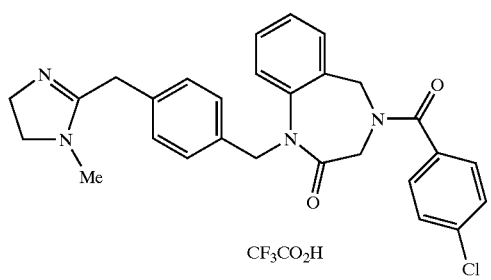
Compound of Example 168
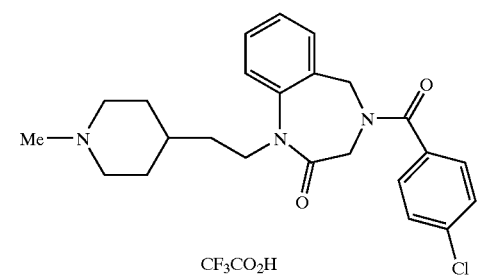
Compound of Example 169
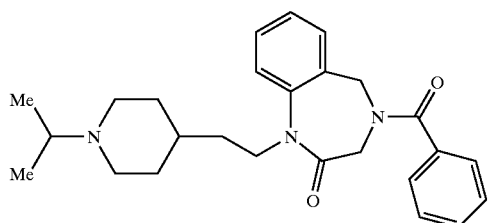
Compound of Example 170
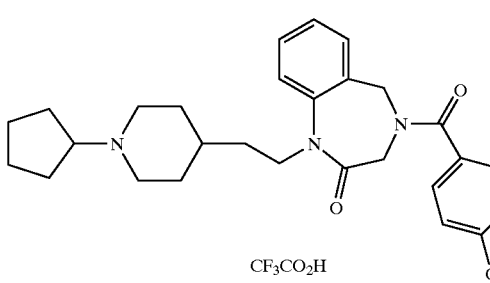

Compound of Example 171
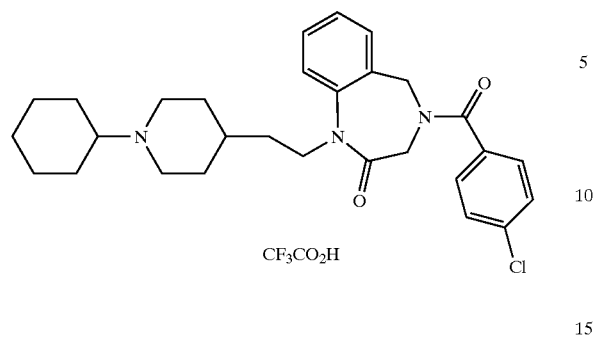
Compound of Example 175
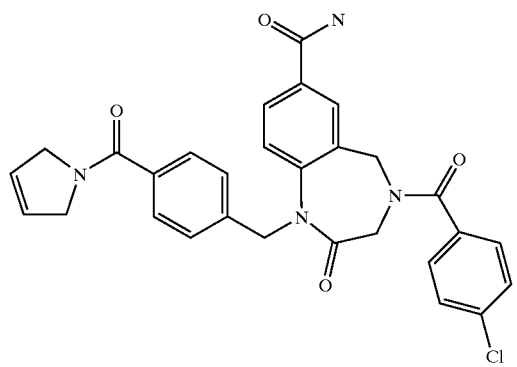
Compound of Example 172
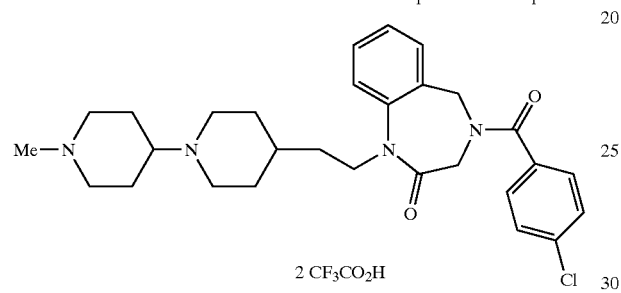
Compound of Example 176
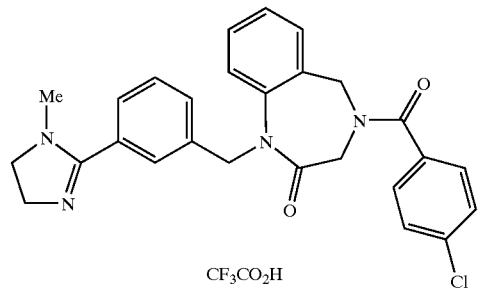
Compound of Example 173
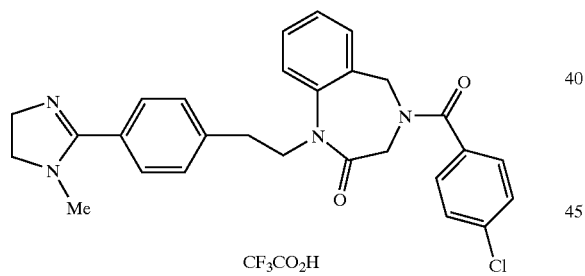
Compound of Example 177
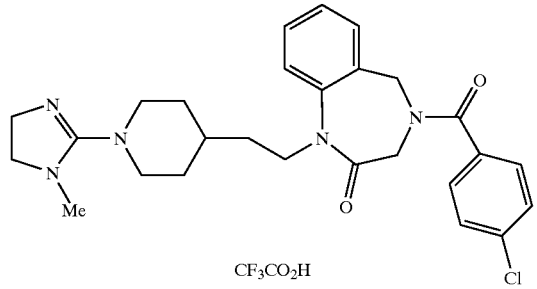
Compound of Example 174
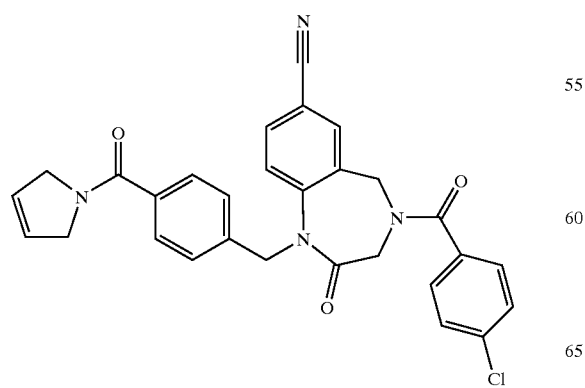
Compound of Example 178
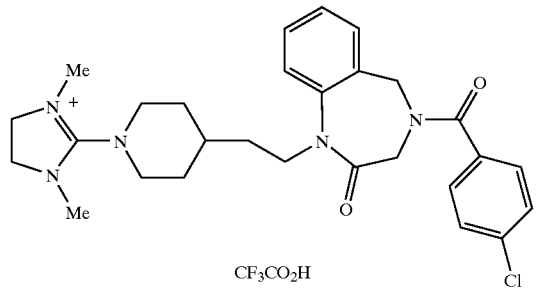

-continued
Compound of Example 179
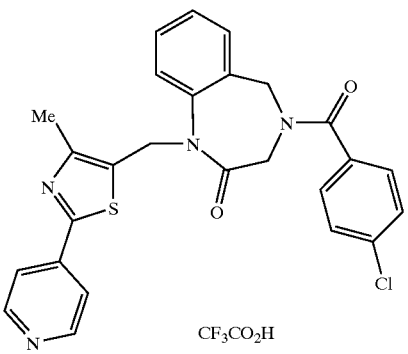
CF₃CO₂H
Compound of Example 180
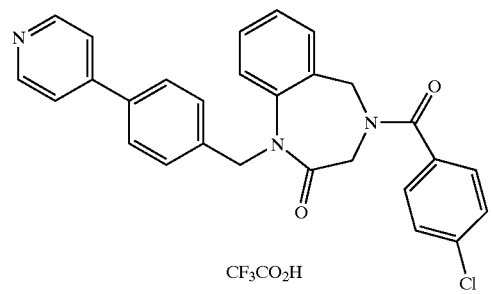
CF₃CO₂H
Compound of Example 181
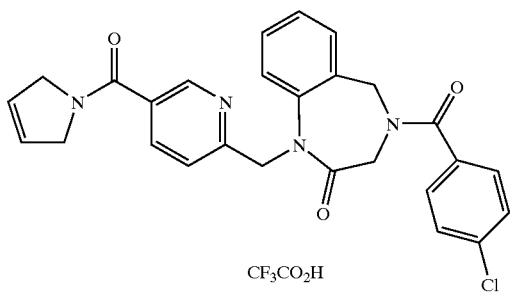
CF₃CO₂H
Compound of Example 182
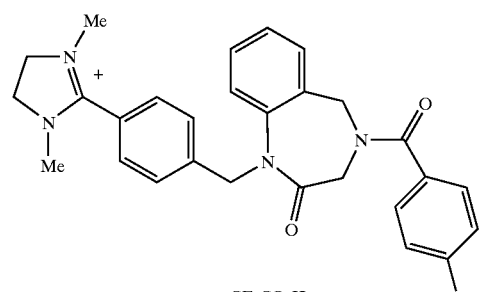
CF₃CO₂H
Compound of Example 183
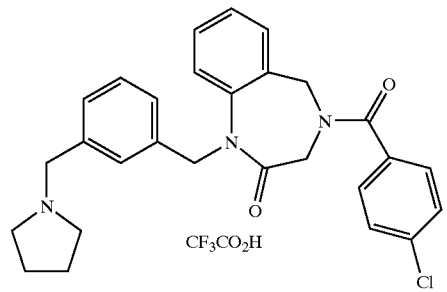
CF₃CO₂H
-continued
Compound of Example 184
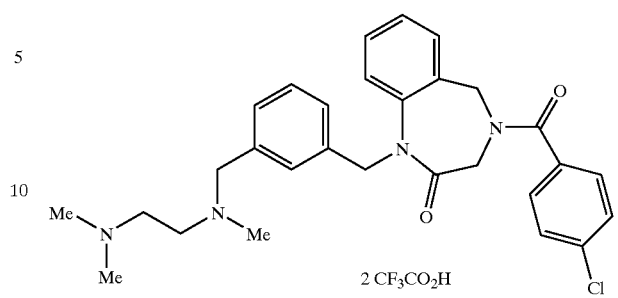
2 CF₃CO₂H
Compound of Example 185
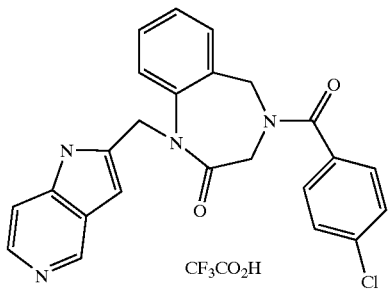
CF₃CO₂H
Compound of Example 186
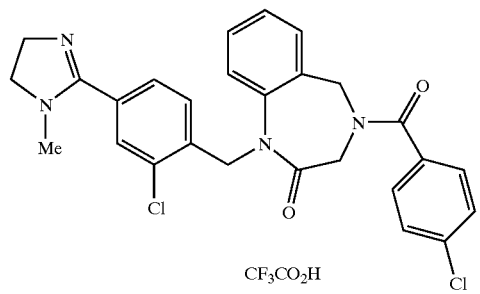
CF₃CO₂H
Compound of Example 187
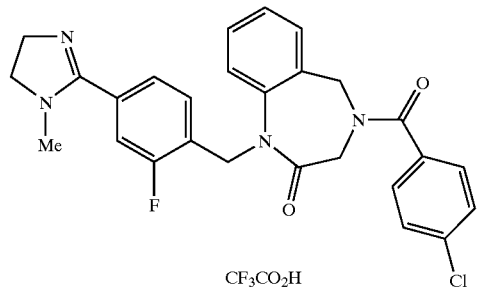
CF₃CO₂H Compound of Example 188
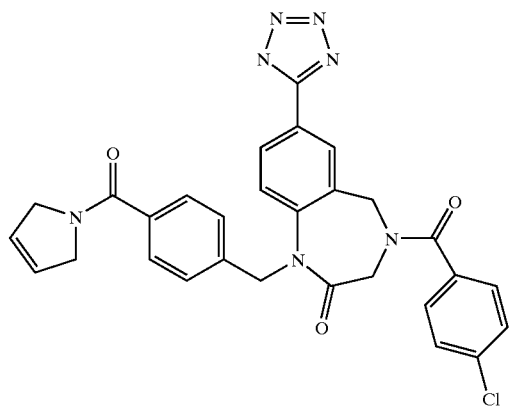
Compound of Example 189
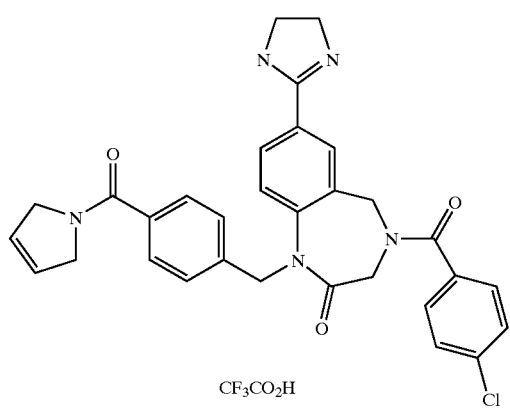
CF₃CO₂H
Compound of Example 190
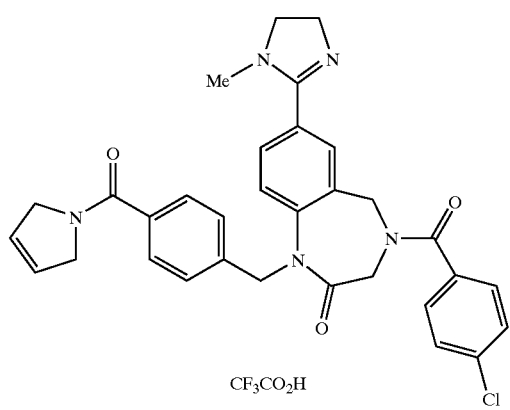
CF₃CO₂H
Compound of Example 191
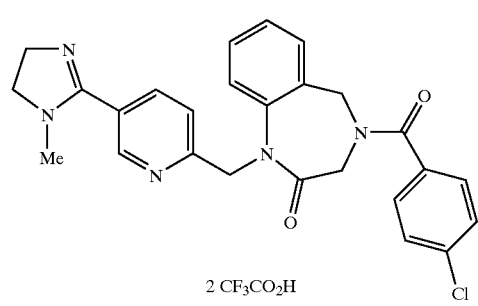
2 CF₃CO₂H
Compound of Example 192
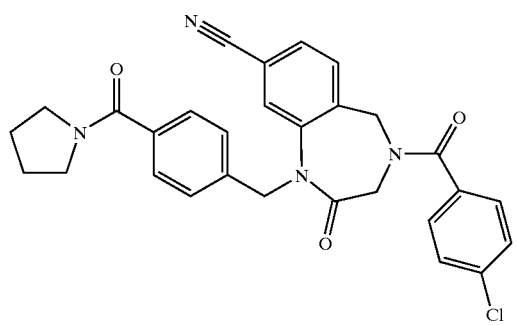
Compound of Example 193
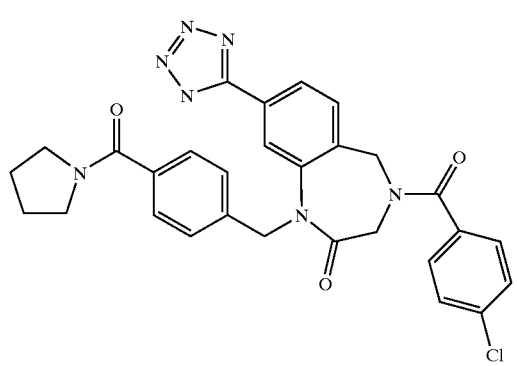
Compound of Example 194
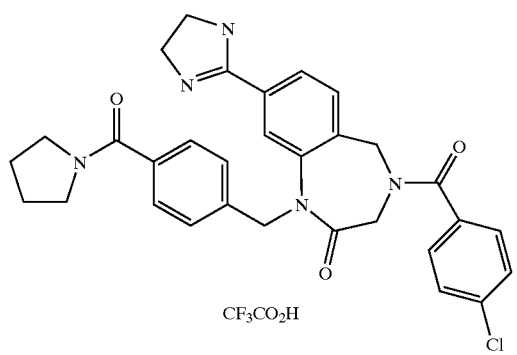
CF₃CO₂H
Compound of Example 195
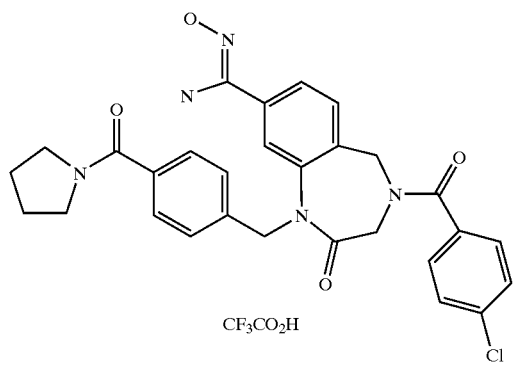
CF₃CO₂H Compound of Example 196
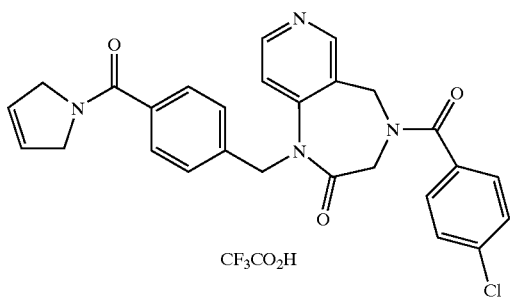
CF₃CO₂H
Compound of Example 197
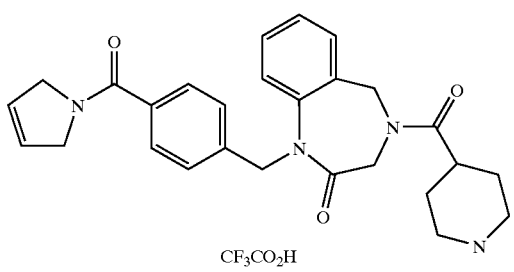
CF₃CO₂H
Compound of Example 198
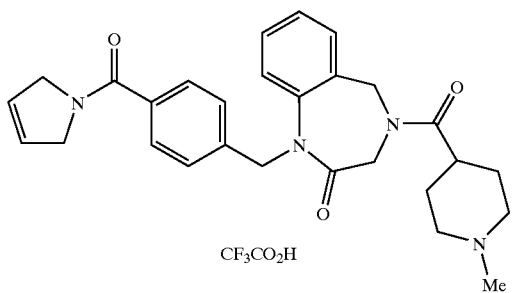
CF₃CO₂H
Compound of Example 199
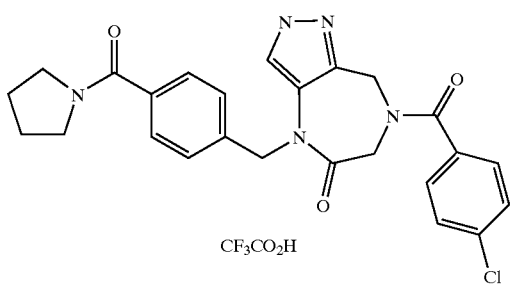
CF₃CO₂H
Compound of Example 200
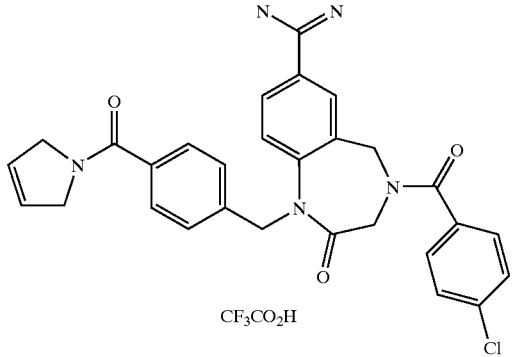
CF₃CO₂H
Compound of Example 201
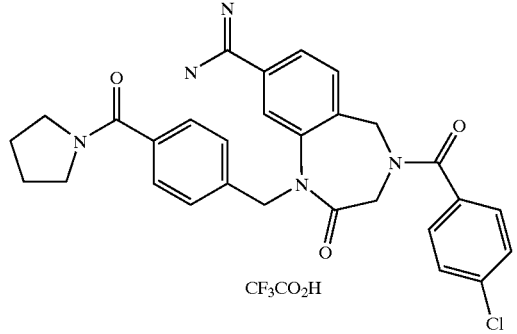
CF₃CO₂H
Compound of Example 202
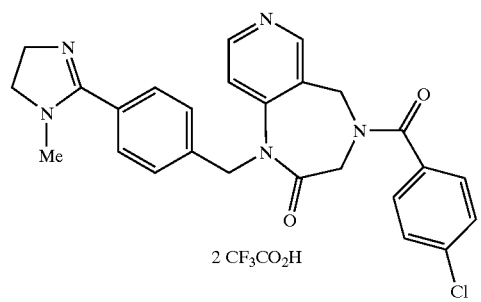
2 CF₃CO₂H
Compound of Example 203
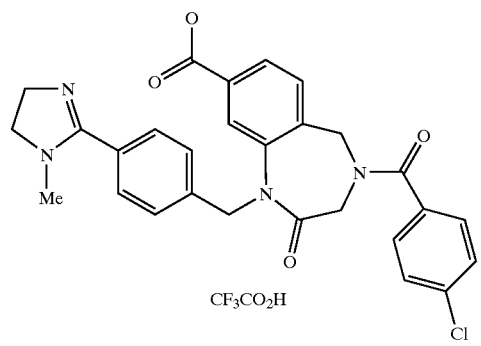
CF₃CO₂H
Compound of Example 204
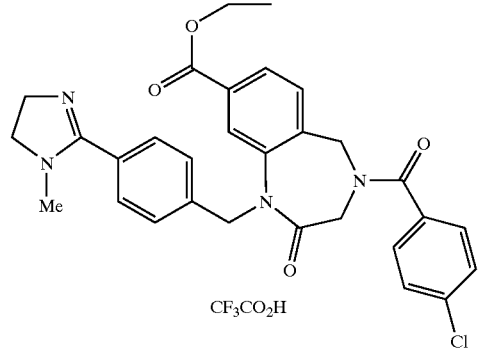
CF₃CO₂H -continued Compound of Example 205

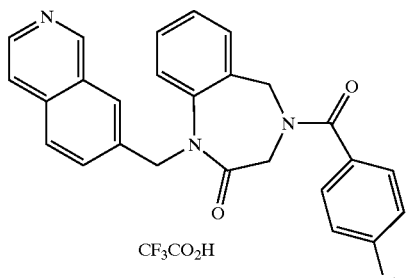

CF₃CO₂H

Compound of Example 206

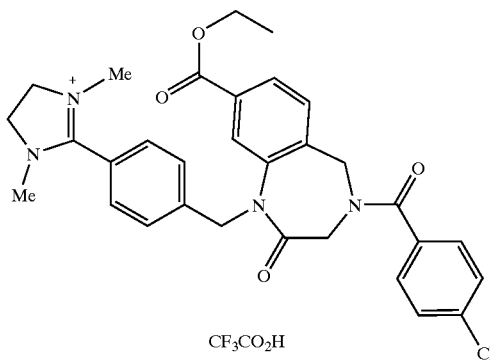

CF₃CO₂H

Compound of Example 207

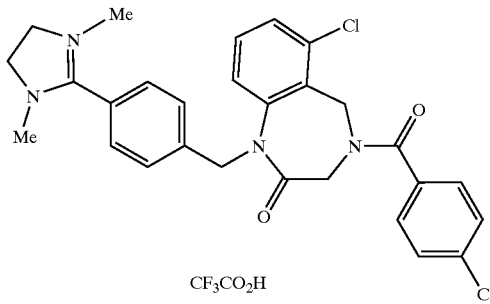

CF₃CO₂H

Compound of Example 208

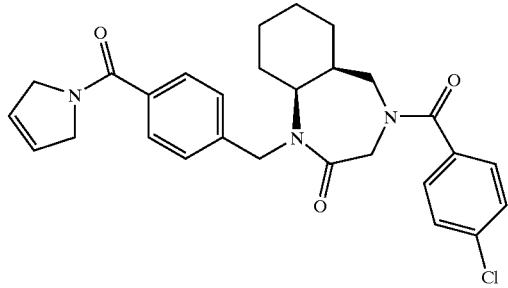

The blood coagulation inhibitor containing a compound of the present invention or a salt thereof as the active ingredient has a blood-coagulation inhibiting effect based on the excellent effect of inhibiting activated blood-coagulation factor X. In addition, the blood coagulation inhibitor containing a compound of the present invention or a salt thereof as the active ingredient also has a high oral absorbability. Therefore, the compounds of the present invention are usable as agents for preventing or treating diseases, for example, cerebrovascular disorders such as cerebral infarction, cerebral thrombosis, cerebral embolism, transient ischemic attack (TIA) and subarachnoidal hemorrhage (vasospasm); ischemic heart diseases such as acute and chronic myocardial infarction, unstable angina and coronary thrombolysis; pulmonary vascular disorders such as pulmonary infarction and pulmonary embolism; peripheral arterial occlusive disease; deep vein thrombosis; disseminated intravascular coagulation; thrombus formation after an artificial blood vessel-forming operation or artificial valve substitution; reocclusion and restenosis after a coronary artery bypass grafting; reocclusion and restenosis after reconstructive operation for the blood circulation such as percutaneous transluminal coronary angioplasty (PTCA) or percutaneous transluminal coronary recanalization (PTCR); and thrombus formation in the course of the extracorporeal circulation.

What is claimed is:

1. A compound of formula (1) or pharmaceutically acceptable salts thereof:

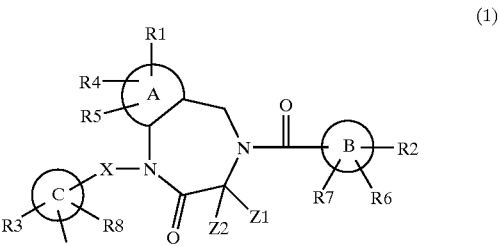

(1)

wherein ring A represents an aryl group having 6 to 10 carbon atoms, a heteroaryl group having 3 to 10 carbon atoms wherein said heteroaryl group is an aromatic cyclic hydrocarbon group having 1 to 3 hetero atoms selected from the group consisting of O, N and S or a cycloalkyl group having 4 to 10 carbon atoms, R1 represents hydrogen atom, a halogen group, hydroxyl group, an alkoxyl group having 1 to 10 carbon atoms, nitro group, formyl group, trifluoromethyl group, trifluoromethoxyl group, trifluoromethanesulfonyloxyl group, methylenedioxyl group, carbamoyl group, thiocarbamoyl group, a mono- or dialkylcarbamoyl group having 2 to 7 carbon atoms, cyano group, a mono- or dialkylamino group having 1 to 6 carbon atoms, carboxyl group, an alkoxycarbonyl group having 2 to 7 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms, a monoalkoxyhydroxyphosphoryl group having 1 to 4 carbon atoms, an alkylsulfonyl group having 1 to 6 carbon atoms, an aminosulfonyl group, a mono- or dialkylaminosulfonyl group having 2 to 8 carbon atoms, an alkyl group having 1 to 6 carbon atoms, which may have a substituent(s), an aryl group having 6 to 10 carbon atoms, which may have a substituent(s), a heteroaryl group having 1 to 10 carbon atoms wherein said heteroaryl group is an aromatic cyclic hydrocarbon group having 1 to 3 hetero atoms selected from the group consisting of O, N and S, which may have a substituent(s), arylsulfonyl group having 6 to 10 carbon atoms, which may have a substituent(s), a heteroarysulfonyl group having 4 to 10 carbon atoms, which may have a substituent(s), an acyl group having 1 to 8 carbon atoms, which may have a substituent(s), an alkyl group having 1 to 6 carbon atoms substituted with an aryl group(s) having 6 to 10 carbon atoms, which may have a substituent(s), an alkyl group having 1 to 6 carbon atoms substituted with a heteroaryl group(s) having 5 to 10 carbon atoms wherein said heteroaryl group is an aromatic cyclic hydrocarbon group having 1 to 3 hetero atoms selected from the group consisting of O, N and S, which may have a substituent(s), an aryl group having 6 to 10 carbon atoms substituted with an alkyl group(s) having 1 to 6 carbon atoms, which may have a substituent(s), a heteroaryl group having 5 to 10 carbon atoms substituted with an alkyl group(s) having 1 to 6 carbon atoms wherein said heteroaryl group is an aromatic cyclic hydrocarbon group having 1 to 3 hetero atoms selected from the group consisting of O, N and S, which may have a substituent(s), an amino group, which may have a substituent(s), an aminoalkyl group having 1 to 7 carbon atoms, which may have a substituent(s), pyrrolidine group, which may have a substituent(s), pyrrolidyloxyl group, which may have a substituent(s), piperidine group, which may have a substituent(s), piperidyloxy group, which may have a substituent(s), piperazine group, which may have a substituent(s), piperazinecarbonyl group, which may have a substituent(s), amidino group, which may have a substituent(s) or guanidino group, which may have a substituent(s), when R1 has a substituent(s), the substituent is any of alkyl groups having 1 to 6 carbon atoms, halogeno groups, hydroxyl group, alkoxyl groups having 1 to 10 carbon atoms, trifluoromethyl group, trifluoromethoxyl group, carbamoyl group, mono- or dialkylcarbamoyl groups having 2 to 7 carbon atoms, amino group, aminoalkyl groups having 1 to 7 carbon atoms, mono- or dialkylamino groups having 1 to 6 carbon atoms, amidino group, mono- or dialkylamidino groups having 2 to 7 carbon atoms, trialkylamidino groups having 4 to 7 carbon atoms, tetraalkylamidino groups having 5 to 8 carbon atoms, guanidino group, dialkylguanidino groups having 3 to 8 carbon atoms, trialkylguanidino groups having 4 to 9 carbon atoms, aryl groups having 6 to 10 carbon atoms, heteroaryl groups having 1 to 10 carbon atoms wherein said heteroaryl group is an aromatic cyclic hydrocarbon group having 1 to 3 hetero atoms selected from the group consisting of O, N and S, alkyl groups having 1 to 6 carbon atoms substituted with an aryl group(s) having 6 to 10 carbon atoms, alkyl groups having 1 to 6 carbon atoms substituted with a heteroaryl group(s) having 5 to 10 carbon atoms wherein said heteroaryl group is an aromatic cyclic hydrocarbon group having 1 to 3 hetero atoms selected from the group consisting of O, N and S, aryl groups having 6 to 10 carbon atoms substituted with an alkyl group(s) having 1 to 6 carbon atoms, heteroaryl groups having 5 to 10 carbon atoms substituted with an alkyl group(s) having to 6 carbon atoms wherein said heteroaryl group is an aromatic cyclic hydrocarbon group having 1 to 3 hetero atoms selected from the group consisting of O, N and S arylsulfonyl groups having 6 to 10 carbon atoms, heteroarylsulfonyl groups having 4 to 10 carbon atoms, carboxyl group, alkoxycarbonyl groups having 2 to 7 carbon atoms, pyrrolidine group, piperidine group, piperazine group, piperazinecarbonyl group, alkylpiperazinecarbonyl groups having 6 to 10 carbon atoms, iminoalkylpiperazinecarbonyl groups having 7 to 10 carbon atoms, piperidyloxyl group, alkylpiperidyloxyl groups having 6 to 10 carbon atoms, iminoalkylpiperidyloxyl groups having 7 to 10 carbon atoms, pyrrolidyloxy group, alkylpyrrolidyloxyl groups having 6 to 10 carbon atoms, iminoalkylpyrrodidyloxyl groups having 7 to 10 carbon atoms, methylenedioxyl group, cyano group, iminoalkyl groups having 2 to 7 carbon atoms, acyl groups having 1 to 8 carbon atoms, phosphono group, dialkoxyphosphoryl groups having 2 to 9 carbon atoms, monoalkoxyhydroxyphosphoryl groups having 1 to 4 carbon atoms, alkylsulfonyl groups having 1 to 6 carbon atoms, aminosulfonyl group and dialkylaminosulfonyl groups having 2 to 8 carbon atoms, rings B and C may be the same or different from each other, and they each represent an aryl group having 6 to 10 carbon atoms, a heteroaryl group having 3 to 10 carbon atoms wherein said heteroaryl group is an aromatic cyclic hydrocarbon group having 1 to 3 hetero atoms selected from the group consisting of O, N and S, pyrrolidyl group, piperidyl group or piperazinyl group, R2 represents hydrogen atom, an alkyl group having 1 to 6 carbon atoms, a halogeno group, hydroxyl group, a hydroxyalkyl group having 1 to 10 carbon atoms, an alkoxyl group having 1 to 10 carbon atoms, an alkoxyalkyl group having 1 to 10 carbon atoms, nitro group, formyl group, trifluoromethoxyl group, trifluoromethyl group, carbamoyl group, thiocarbamoyl group, a mono- or dialkylcarbamoyl group having 2 to 7 carbon atoms, amino group, a mono- or dialkylamino group having 1 to 6 carbon atoms, an aminoalkyl group having 1 to 9 carbon atoms, a mono- or dialkylaminoalkyl group having 2 to 9 carbon atoms, amidino group, a mono- or dialkylamidino group having 2 to 7 carbon atoms,a trialkylamidino group having 4 to 7 carbon atoms, a tetraalkylamidino group having 5 to 8 carbon atoms, guanidino group, a dialkylguanidino group having 3 to 8 carbon atoms, a trialkylguanidino group having 4 to 9 carbon atoms, methylenedioxyl group, cyano group, an iminoalkyl group having 2 to 7 carbon atoms, an acyl group having 1 to 8 carbon atoms, piperidyloxyl group, an alkylpiperidyloxyl group having 6 to 10 carbon atoms, an iminoalkylpiperidyloxyl group having 6 to 10 carbon atoms, an alkoxycarbonylpiperidyloxyl group having 8 to 14 carbon atoms, pyrrolidyloxyl group, an alkylpyrrolidyloxyl group having 5 to 9 carbon atoms, an iminoalkylpyrrolidyloxyl group having 5 to 9 carbon atoms, an alkoxycarbonylpyrrolidyloxyl group having 7 to 13 carbon atoms, pyrrolidine group, an alkylpyrrolidine group having 5 to 9 carbon atoms, an iminoalkylpyrrolidine group having 5 to 9 carbon atoms, piperidine group, an alkylpiperidine group having 6 to 10 carbon atoms, an iminoalkylpiperidine group having 6 to 10 carbon atoms, piperazine group,an alkylpiperazine group having 5 to 13 carbon atoms, an iminoalkylpiperazine group having 6 to 9 carbon atoms, an aryl group having 6 to 10 carbon atoms, a heteroaryl group having 1 to 10 carbon atoms wherein said heteroaryl group is an aromatic cyclic hydrocarbon group having 1 to 3 hetero atoms selected from the group consisting of O, N and S, arylsulfonyl group having 6 to 10 carbon atoms, a heteroarylsulfonyl group having 4 to 10 carbon atoms, an iminoalkylpiperazinecarbonyl group having 7 to 10 carbon atoms, an alkylpiperazinecarbonyl group having 6 to 10 carbon atoms, piperazinesulfonyl group, an alkylpiperazinesulfonyl group having 5 to 9 carbon atoms, an iminoalkylpiperazinesulfonyl group having 6 to 9 carbon atoms, an alkylsulfonyl group having 1 to 8 carbon atoms, aminosulfonyl group, a mono- or dialkylaminosulfonyl group having 2 to 8 carbon atoms, a piperidylalkyl group having 6 to 9 carbon atoms or an iminoalkylpiperidylalkyl group having 8 to 12 carbon atoms, R3 represents hydrogen atom, a halogeno group, hydroxyl group, an alkoxyl group having 1 to 10 carbon atoms, nitro group, formyl group, trifluoromethyl group, trifluoromethoxyl group, carbamoyl group, thiocarbaxnoyl group, a mono- or dialkylcarbamoyl group having 2 to 7 carbon atoms, methylenedioxyl group, cyano group, an iminoalkyl group having 2 to 7 carbon atoms, an acyl group having 1 to 8 carbon atoms, piperidyloxyl group, an iminoalkylpiperidyloxyl group having 6 to 10 carbon atoms, an alkylpiperidyloxyl group having 5 to 10 carbon atoms, an alkoxycarbonylpiperidyloxyl group having 8 to 14 carbon atoms, pyrrolidyloxyl group, an iminoalkylpyrrolidyloxyl group having 5 to 9 carbon atoms, an alkylpyrrolidyloxyl group having 5 to 10 carbon atoms, an alkoxycarbonylpyrrolidyloxyl group having 7 to 13 carbon atoms, an arylsulfonyl group having 6 to 10 carbon atoms, a heteroarylsulfonyl group having 4 to 10 carbon atoms, an iminoalkylpiperazinecarbonyl group having 7 to 10 carbon atoms, piperazinesulfonyl group, an iminoalkylpiperazinesulfonyl group having 6 to 9 carbon atoms, an alkyl group having 1 to 6 carbon atoms, which may have a substituent(s), an amino group, which may have a substituent(s), an aminoalkyl group having 1 to 9 carbon atoms, which may have a substituent(s), pyrrolidine group, which may have a substituent(s), piperidyl group, which may have a substituent(s), piperazine group, which may have a substituent(s), an aryl group having 6 to 10 carbon atoms, which may have a substituent(s), a heteroaryl group having 1 to 10 carbon atoms wherein said heteroaryl group is an aromatic cyclic hydrocarbon group having 1 to 3 hetero atoms selected from the group consisting of O, N and S, which may have a substituent(s), an aryl group having 6 to 10 carbon atoms, which is substituted with an alkyl group (s) having 1 to 6 carbon atoms, which may have a substituent(s), a heteroaryl group having 5 to 10 carbon atoms wherein said heteroaryl group is an aromatic cyclic hydrocarbon group having 1 to 3 hetero atoms selected from the group consisting of O, N and S, which is substituted with an alkyl group(s) having 1 to 6 carbon atoms, which may have a substituent(s), an alkyl group having 1 to 6 carbon atoms substituted with an aryl group(s) having 6 to 10 carbon atoms, which may have a substituent(s), an alkyl group having 1 to 6 carbon atoms substituted with a heteroaryl group(s) having 5 to 10 carbon atoms wherein said heteroaryl group is an aromatic cyclic hydrocarbon group having 1 to 3 hetero atoms selected from the group consisting of O, N and S, which may have a substituent(s), an amidino group, which may have a substituent(s), a guanidino group, which may have a substituent(s), a piperidylalkyl group having 6 to 9 carbon atoms or an iminoalkylpiperidylalkyl group having 8 to 12 carbon atoms, when R3 has a substituent(s), the substituent is any of hydrogen atom, alkyl groups having 1 to 6 carbon atoms, halogeno groups, hydroxyl group, hydroxyalkyl groups having 1 to 10 carbon atoms, alkoxyl groups having 1 to 10 carbon atoms, alkoxyalkyl groups having 1 to 10 carbon atoms, nitro group, formyl group, trifluoromethoxyl group, trifluoromethyl group, carbamoyl group, thiocarbamoyl group, mono- or dialkylcarbamoyl groups having 2 to 7 carbon atoms, amino group, mono- or dialkylamino groups having 1 to 6 carbon atoms, aminoalkyl groups having 1 to 9 carbon atoms, mono- or dialkylaminoalkyl groups having 2 to 9 carbon atoms, amidino group, mono- or dialkylamidino groups having 2 to 7 carbon atoms, trialkylamidino groups having 4 to 7 carbon atoms, tetraalkylamidino groups having 5 to 8 carbon atoms, guanidino group, dialkylguanidino groups having 3 to 8 carbon atoms, trialkylguanidino groups having 4 to 9 carbon atoms, methylenedioxyl group, cyano group, iminoalkyl groups having 2 to 7 carbon atoms, acyl groups having 1 to 8 carbon atoms, piperidyloxyl group, alkylpiperidyloxyl groups having 6 to 10 carbon atoms, iminoalkylpiperidyloxyl groups having 6 to 10 carbon atoms, alkoxycarbonylpiperidyloxyl groups having 8 to 14 carbon atoms, pyrrolidyloxyl group, alkylpyrrolidyloxyl groups having 5 to 9 carbon atoms, iminoalkylpyrrolidyloxyl groups having 5 to 9 carbon atoms, alkoxycarbonylpyrrolidyloxyl groups having 7 to 13 carbon atoms, pyrrolidine group, alkylpyrrolidine groups having 5 to 9 carbon atoms, iminoalkylpyrrolidine groups having 5 to 9 carbon atoms, piperidine group, alkylpiperidine groups having 6 to 10 carbon atoms, iminoalkylpiperidine groups having 6 to 10 carbon atoms, piperazine group, alkylpiperazine groups having 5 to 13 carbon atoms, iminoalkylpiperazine groups having 6 to 9 carbon atoms, aryl groups having 6 to 10 carbon atoms, heteroaryl groups having 1 to 10 carbon atoms wherein said heteroaryl group is an aromatic cyclic hydrocarbon group having 1 to 3 hetero atoms selected from the group consisting of O, N and S, arylsulfonyl groups having 6 to 10 carbon atoms, heteroarylsulfonyl groups having 4 to 10 carbon atoms, iminoalkylpiperazinecarbonyl groups having 7 to 10 carbon atoms, alkylpiperazinecarbonyl groups having 6 to 10 carbon atoms, piperazinesulfonyl group, alkylpiperazinesulfonyl groups having 5 to 9 carbon atoms, iminoalkylpiperazinesulfonyl groups having 6 to 9 carbon atoms, alkylsulfonyl groups having 1 to 8 carbon atoms, aminosulfonyl group and mono- or dialkylaminosulfonyl groups having 2 to 8 carbon atoms, R4, R5, R6, R7, R8 and R9 may be the same or different from one another, and they each represent hydrogen atom, an alkyl group having 1 to 6 carbon atoms, a halogeno group, hydroxyl group, a hydroxyalkyl group having 1 to 10 carbon atoms, an alkoxyl group having 1 to 10 carbon atoms, an alkoxyalkyl group having 1 to 10 carbon atoms, nitro group, trifluoromethoxyl group, trifluoromethyl group, amino group, a mono- or dialkylamino group having 1 to 6 carbon atoms, an aminoalkyl group having 1 to 9 carbon atoms, a mono- or dialkylaminoalkyl group having 2 to 9 carbon atoms, methylenedioxyl group, cyano group, formyl group, carboxyl group, an alkoxycarbonyl group having 2 to 7 carbon atoms, an alkoxycarbonylalkyl group having 3 to 9 carbon atoms, a hydroxycarbonylalkyl group having 3 to 9 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms, a monoalkoxyhydroxyphosphoryl group having 1 to 4 carbon atoms, a phosphorylalkyl group having 1 to 9 carbon atoms, a dialkoxyphosphorylalkyl group having 3 to 9 carbon atoms, a monoalkoxyhydroxyphosphorylalkyl group having 2 to 9 carbon atoms, 2-carboxy-2-oxoethyl group or a heteroaryl group having 1 to 1 carbon atoms wherein said heteroaryl group is an aromatic cyclic hydrocarbon group having 1 to 3 hetero atoms selected from the group consisting of O, N and S, X represents an alkylene group having 1 to 6 carbon atoms, which may contain —NH—, —C(=O), —NHC(=O)—, —C(=O)NH— or —NHC(=O)NH— in its chain, and Z1 and Z2 may be the same or different from each other, and they each represent hydrogen atom, a halogeno group, an alkyl group having 1 to 6 carbon atoms, hydroxyl group, a hydroxyalkyl group having 1 to 6 carbon atoms, an alkoxyalkyl group having 2 to 6 carbon atoms, a thioalkyl group having 1 to 6 carbon atoms, an alkylthioalkyl group having 2 to 8 carbon atoms, a carbamoylalkyl group having 1 to 6 carbon atoms, an aryl group having 6 to 10 carbon atoms, a heteroaryl group having 1 to 10 carbon atoms wherein said heteroaryl group is an aromatic cyclic hydrocarbon group having 1 to 3 hetero atoms selected from the group consisting of O, N and S, an aryl group having 6 to 10 carbon atoms, which is substituted with an alkyl group(s) having 1 to 6 carbon atoms, a heteroaryl group having 4 to 10 carbon atoms wherein said heteroaryl group is an aromatic cyclic hydrocarbon group having 1 to 3 hetero atoms selected from the group consisting of O, N and S, which is substituted with an alkyl group(s) having 1 to 6 carbon atoms, an aminoalkyl group having 1 to 6 carbon atoms, carboxyl group, an alkoxycarbonyl group having 2 to 6 carbon atoms, a hydroxycarbonylalkyl group having 2 to 8 carbon atoms, an alkoxycarbonylalkyl group having 3 to 8 carbon atoms, an aminoalkyl group having 1 to 6 carbon atoms or a mono- or dialkylaminoalkyl group having 2 to 10 carbon atoms, or Z1 and Z2 together from a ring and in such a case, -Z1-Z2-represents ethylene group, trimethylene group or tetramthylene group.

2. The compound of formula (1) or pharmaceutically acceptable salts thereof according to claim 1, wherein ring A represents an aryl group having 6 to 10 carbon atoms, a heteroaryl group having 3 to 10 carbon atoms wherein said heteroaryl group is an aromatic cyclic hydrocarbon group having 1 to 3 hetero atoms selected from the group consisting of O, N S or a cycloalkyl group having 5 or 6 carbon atoms, R1 represents hydrogen atom, a halogeno group, hydroxyl group, an alkoxyl group having 1 to 10 carbon atoms, trifluoromethyl group, trifluoromethanesulfonyloxyl group, carbamoyl group, a mono- or dialkylcarbamoyl group having 2 to 7 carbon atoms, cyano group, a mono- or dialkylamino group having 1 to 6 carbon atoms, carboxyl group, an alkoxycarbonyl group having 2 to 7 carbon atoms, an alkyl group having 1 to 6 carbon atoms, which may have a substituent(s), an aminoalkyl group having 2 to 7 carbon atoms, which may have a substituent(s), piperazinecarbonyl group, which may have a substituent(s) or amidino group, which may have a substituent(s), when R1 has a substituent(s), the substituent is any of alkyl groups having 1 to 6 carbon atoms, hydroxyl group, mono- or dialkylamino groups having 1 to 6 carbon atoms, heteroaryl groups having 1 to 10 carbon atoms wherein said heteroaryl group is an aromatic cyclic hydrocarbon group having 1 to 3 hetero atoms selected from the group consisting of O, N and S, carboxyl group, alkoxycarbonyl groups having 2 to 7 carbon atoms, pyrrolidine group, piperidine group, piperazine group, piperazinecarbonyl group, alkylpiperazinecarbonyl groups having 6 to 10 carbon atoms, phosphono group dialkoxyphosphoryl groups having 2 to 9 carbon atoms, monoalkoxyhydroxyphosphoryl groups having 1 to 4 carbon atoms, alkylsulfonyl groups having 1 to 6 carbon atoms and dialkylamidino groups having 1 to 6 carbon atoms, and R4 and R5 are both hydrogen atoms.

3. The compound of formula (1) or pharmaceutically acceptable salts thereof according to claim 1, wherein ring A represents phenyl group, R1 represents hydrogen atom, chloro group, carboxyl group, an alkoxycarbonyl group having 2 to 7 carbon atoms, an amino group, which may have a substituent (s), hydroxyl group, which may have a substituent or an alkyl group having 1 to 6 carbon atoms, which may have a substituent(s), when R1 has a substituent(s), the substituent is hydroxyl group, phosphono group, carboxyl group, an alkoxycarbonyl group having 2 to 7 carbon atoms, a mono- or dialkylcarbamoyl group having 2 to 7 carbon atoms, a mono- or dialkylamino group having 1 to 6 carbon atoms, piperazinecarbonyl group, an alkylpiperazinecarbonyl group having 6 to 10 carbon atoms or an alkylsulfonyl group having 1 to 6 carbon atoms, and R4 and R5 may be the same or different from each other and they each represent hydrogen atom, a halogeno group, trifluoromethyl group, methoxyl group or hydroxyl group.

4. The compound of formula (1) or pharmaceutically acceptable salts thereof according to claim 1, wherein ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents chloro group or bromo group, and R6 and R7 may be the same or different from each other and they each represent hydrogen atom, a halogeno group, trifluoromethyl group, methoxyl group or hydroxyl group.

5. The compound of formula (1) or pharmaceutically acceptable salts thereof according to claim 1, wherein ring C represents an aryl group having 6 to 10 carbon atoms or piperidyl group, R3 represents a halogeno group, nitro group, an iminoalkyl group having 2 to 7 carbon atoms, a mono- or dialkylcarbamoyl group having 2 to 7 carbon atoms, piperidyloxy group, an iminoalkylpiperidyloxy group having 6 to 10 carbon atoms, an alkylpiperidyloxy group having 5 to 10 carbon atoms, an amino group, which may have a substituent(s), an aminoalkyl group having 2 to 9 carbon atoms, which may have a substituent(s), an alkyl group having 1 to 6 carbon atoms, which may have a substituent(s), pyrrolidine group, which may have a substituent(s), piperazine group, which may have a substituent(s), a heteroaryl group having 1 to 10 carbon atoms wherein said heteroaryl group is an aromatic cyclic hydrocarbon group having 1 to 3 hetero atoms selected from the group consisting of O, N and S, which may have a substituent(s), or an amidino group, which may have a substituent(s), when R3 has a substituent(s), the substituent is hydrogen atom, an alkyl group having 1 to 6 carbon atoms, a mono- or dialkylcarbamoyl group having 2 to 7 carbon atoms, a mono- or dialkylaminoalkyl group having 2 to 9 carbon atoms, a mono- or dialkylamidino group having 2 to 7 carbon atoms, a trialkylamidino group having 4 to 7 carbon atoms, pyrrolidine group, piperidine group, an alkylsulfonyl group having 1 to 8 carbon atoms or pyridyl group, R8 and R9 may be the same or different from each other and each represent hydrogen atom, a halogeno group or pyridyl group, and X represents an alkylene group having 1 to 3 carbon atoms, which may contain —C(=O)NH— in the chain thereof.

6. The compound of formula (1) or pharmaceutically acceptable salts thereof according to claim 1, wherein ring C represents phenyl group or piperidyl group, X represents an alkylene group having 1 to 6 carbon atoms, R3 represents a mono- or dialkylcarbamoyl group having 2 to 7 carbon atoms, an alkyl group having 1 to 6 carbon atoms, which may have a substituent(s) or amidino group, which may have a substituent(s), when R3 has a substituent(s), the substituent is an alkyl group having 1 to 6 carbon atoms or pyridyl group, and R8 and R9 may be the same or different from each other and they each represent hydrogen atom, a halogeno group, trifluoromethyl group, methoxyl group or hydroxyl group.

7. The compound of formula (1) or pharmaceutically acceptable salts thereof according to claim 1, wherein A represents phenyl group, R1 represents hydrogen atom, chloro group, carboxyl group, an alkoxycarbonyl group having 2 to 7 carbon atoms, amino group, which may have a substituent(s), hydroxyl group, which may have a substituent(s) or an alkyl group having 1 to 6 carbon atoms, which may have a substituent(s), when R1 has a substituent(s), the substituent is hydroxyl group, phosphono group, carboxyl group, an alkoxycarbonyl group having 2 to 7 carbon atoms, a mono- or dialkylcarbamoyl group having 2 to 7 carbon atoms, a mono- or dialkylamino group having 1 to 6 carbon atoms, piperazinecarbonyl group, an alkylpiperazinecarbonyl group having 6 to 10 carbon atoms or an alkylsulfonyl group having 1 to 6 carbon atoms, ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents chloro group or bromo group, ring C represents phenyl group or piperidyl group, R3 represents a mono- or dialkylcarbamoyl group having 2 to 7 carbon atoms, an alkyl group having 1 to 6 carbon atoms, which may have a substituent(s), or amidino group, which may have a substituent(s), when R3 has a substituent(s), the substituent is an alkyl group having 1 to 6 carbon atoms or pyridyl group, R4, R5, R6, R7, R8 and R9 may be the same or different from one another and they each represent hydrogen atom, a halogeno group, trifluoromethyl group, methoxyl group or hydroxyl group, and X represents an alkylene group having 1 to 6 carbon atoms.

8. The compound of formula (1) or pharmaceutically acceptable salts thereof according to claim 1, wherein in ring A represents phenyl group, R1 represents hydrogen atom, chloro group, amino group, carboxyl group, ethoxycarbonyl group, carboxyethyl group, ethoxycarbonylethyl group, a morpholinealkyl group, hydroxyl group, methyl group, phosphonoethyl group, morpholinecarbonylethyl group, piperazinecarbonylethyl group, isopropylpiperazinecarbonylethyl group, methanesulfonylaminopropyl group or hydroxypropyl group, ring B represents phenyl group or thiophene group, R2 represents chloro group or bromo group, ring C represents phenyl group or piperidyl group, R3 represents isopropyl group, cyclohexyl group, pyridyl group, 1-methyl-1H-imidazol-2-yl group, 1,3-dimethyl-4,5-dihydro-1H-imidazol-3-ium-2-yl group 2,5-dihydro-1H-pyrrol-1-ylcarbonyl group, 1-pyrrolidinylcarbonyl group, 2,5-dihydro-1H-pyrrol-1-yl(imino)methyl group or 1-iminoethyl-piperidin-4-yloxy group, R4, R5, R6, R7, R8 and R9 may be the same or different from one another and they each represent hydrogen atom or a halogeno group, X represents methylene group or ethylene group, and Z1 and Z2 each represent hydrogen atom.

9. The compound of formula (1) or pharmaceutically acceptable salts thereof according to claim 1, wherein ring A represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R1 represents hydrogen atom, a halogeno group, an alkyl group having 1 to 6 carbon atoms, hydroxyl group, a hydroxyalkyl group having 1 to 6 carbon atoms, an alkoxyl group having 1 to 10 carbon atoms, nitro group, trifluoromethyl group, trifluoromethoxyl group, carbamoyl group, a mono- or dialkylcarbamoyl group having 2 to 7 carbon atoms, amino group, an aminoalkyl group having 1 to 3 carbon atoms, a mono- or dialkylamino group having 1 to 6 carbon atoms, a mono- or dialkylaminoalkyl group having 2 to 7 carbon atoms, an aryl group having 6 to 10 carbon atoms, a heteroaryl group having 4 to 10 carbon atoms wherein said heteroaryl group is an aromatic cyclic hydrocarbon group having 1 to 3 hetero atoms selected from the group consisting of O, N and S, carboxyl group, an alkoxycarbonyl group having 2 to 7 carbon atoms, a hydroxycarbonylalkyl group having 2 to 7 carbon atoms, an alkoxycarbonylalkyl group having 3 to 8 carbon atoms, a hydroxycarbonylalkenyl group having 3 to 7 carbon atoms, an alkoxycarbonylalkenyl group having 4 to 8 carbon atoms, phosphono group, a dialkoxyphosphoryl group having 2 to 9 carbon atoms or a monoalkoxyhydroxyphosphoryl group having 1 to 4 carbon atoms, ring B represents an aryl group having 6 to 10 carbon atoms, a heteroaryl group having 4 to 10 carbon atoms wherein said heteroaryl group is an aromatic cyclic hydrocarbon group having 1 to 3 hetero atoms selected from the group consisting of O, N and S, piperidyl group or piperazine group, R2 and R3 may be the same or different from each other, and they each represent hydrogen atom (only for R2), a halogeno group, an alkyl group having 1 to 6 carbon atoms, hydroxyl group, a hydroxyalkyl group having 1 to 6 carbon atoms, an alkoxyl up having 1 to 10 carbon atoms, nitro group, trifluoromethyl group, trifluoromethoxyl group, carbamoyl group, a mono- or dialkylcarbamoyl group having 2 to 7 carbon atoms, amino group, an aminoalkyl group having 1 to 3 carbon atoms, a mono- or dialkylamino group having 1 to 6 carbon atoms, a mono- or dialkylaminoalkyl group having 2 to 7 carbon atoms, an aryl group having 6 to 10 carbon atoms, a heteroaryl group having 4 to 10 carbon atoms wherein said heteroaryl group is an aromatic cyclic hydrocarbon group having 1 to 3 hetero atoms selected from the group consisting of O, N and S, amidino group, a mono- or dialkylamidino group having 2 to 7 carbon atoms, guanidino group, a dialkylguanidino group having 3 to 8 carbon atoms, methylenedioxyl group, cyano group, an iminoalkyl group having 2 to 7 carbon atoms, acetyl group, piperidyloxy group, an iminoalkylpiperidyloxy group having 6 to 10 carbon atoms, an alkoxycarbonylpiperidyloxy group having 8 to 14 carbon atoms, pyrrolidyloxy group, an iminoalkylpyrrolidyloxy group having 5 to 9 carbon atoms, an alkoxycarbonylpyrrolidyloxy group having 7 to 13 carbon atoms, an arylsulfonyl group having 6 to 10 carbon atoms, a heteroarylsulfonyl group having 4 to 10 carbon atoms, an arylalkyl group having 5 to 12 carbon atoms, a heteroarylalkyl group having 5 to 12 carbon atoms, an iminoalkylpiperazinecarbonyl group having 7 to 10 carbon atoms, piperazinesulfonyl group, an iminoalkylpiperazinesulfonyl group having 6 to carbon atoms, piperidylalkyl group having 6 to 9 carbon atoms or an iminoalkylpiperidylalkyl group having 8 to 12 carbon atoms, ring C represents an aryl group having 6 to 10 carbon atoms, a heteroaryl group having 4 to 10 carbon atoms wherein said heteroaryl group is an aromatic cyclic hydrocarbon group having 1 to 3 hetero atoms selected from the group consisting of O, N and S, piperidyl group or piperazine group, R4, R5, R6, R7, R8 and R9 each represent hydrogen atom, X represents an alkyl group having 1 to 6 carbon atoms, which may co am —NH—, —C(=O), —NHC(=O)—, —C(=O)NH— or —NHC(=O)NH— in its chain, and Z1 and Z2 each represent hydrogen atom.

10. The compound of formula (I) or pharmaceutically acceptable salts thereof according to claim 9, wherein X represents an alkyl group having 1 to 6 carbon atoms.

11. The compound of formula (1) or pharmaceutically acceptable salts thereof according to claim 1, wherein ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents a halogeno group, an alkyl group having 1 to 6 carbon atoms, trifluoromethyl group or an alkoxyl group having 1 to 10 carbon atoms, and R6 and R7 each represent hydrogen atom.

12. The compound of formula (1) or pharmaceutically acceptable salts thereof according to claim 1, wherein ring B represents an aryl group having 6 to 10 carbon atoms and a substituent or a heteroaryl group having 4 to 10 carbon atoms wherein said heteroaryl group is an aromatic cyclic hydrocarbon group having 1 to 3 hetero atoms selected from the group consisting of O, N and S, R2 represents a halogeno group, an alkyl group having 1 or 2 carbon atoms, trifluoromethyl group or an alkoxyl group having 1 to 3 carbon atoms, and R6 and R7 each represent hydrogen atom.

13. The compound of formula (1) or pharmaceutically acceptable salts thereof according to claim 1, wherein ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents a chloro group or bromo group, and R8 and R9 are each hydrogen atoms.

14. The compound of formula (1) or pharmaceutically acceptable salts thereof according to claim 13, wherein ring B represents phenyl group, naphthyl group, pyridyl group or thiophene group.

15. The compound of formula (1) or pharmaceutically acceptable salts thereof according to claim 1, wherein ring C represents an aryl group having 6 to 10 carbon atoms or piperidyl group, R3 represents a mono- or dialkylcarbamoyl group having 2 to 7 carbon atoms, a halogeno group, an alkyl group having 1 to 6 carbon atoms, which may have a substituent(s), pyridyl group, nitro group, amino group, a dialkylamino group, amidino group which may have a substituent(s) or piperidyloxy group, which may have a substituent(s), and R8 and R9 are each hydrogen atoms.

16. The compound of formula (1) or pharmaceutically acceptable salts thereof according to claim 1, wherein ring C represents phenyl group or 4-piperidyl group, R3 represents a mono- or dialkylcarbamoyl group having 2 to 7 carbon atoms, a halogeno group, an alkyl group having 1 to 6 carbon atoms, which may have substituent(s), 4-pyridyl group, nitro group, amino group, dimethylamino group, amidino group, which may have a substituent(s) or a piperidyloxyl group, which may have a substituent(s), and R8 and R9 are each hydrogen atoms.

17. The compound of formula (1) or pharmaceutically acceptable salts thereof according to claim 1, wherein ring A represents phenyl group, ring B represents phenyl group or thiophene group, R2 represents chloro group or bromo group, ring C represents phenyl group or piperidyl group, R3 represents pyridyl group, and X represents methylene group.

18. The compound of formula (1) or pharmaceutically acceptable salts thereof according to claim 1, wherein ring A represents phenyl group, ring B represents phenyl group, pyridyl group, thiophene group or naphthyl group, R2 represents a halogeno group, an alkyl group having 1 to 6 carbon atoms, trifluoromethyl group or an alkoxyl group having 1 to 10 carbon atoms, ring C represents phenyl group or piperidyl group, R3 represents a mono- or dialkylcarbamoyl group having 2 to 7 carbon atoms, a halogeno group, pyridyl group, nitro group, amino group, an alkyl group having 1 to 6 carbon atoms, which may have a substituent(s), a dialkylamino group, amidino group, which may have a substituent(s) or piperidyloxyl group, which may have a substituent(s), and X represents methylene group.

19. The compound of formula (1) or pharmaceutically acceptable salts thereof according to claim 1, wherein ring A represents phenyl group, ring B represents phenyl group or thiophene group, R2 represents chloro group or bromo group, ring C represents phenyl group or piperidyl group, R3 represents pyridyl group, and X represents methylene group.

20. A method for inhibiting activated blood coagulation factor X, which comprises administering the compound of formula (1) or pharmaceutically acceptable salt thereof according to claim 1 as an active ingredient to a patient in need thereof.

21. A pharmaceutical composition comprising one or more compounds of formula (1) or pharmaceutically acceptable salts thereof according to claim 1 as an active ingredient and a pharmaceutically acceptable carrier.

22. A method for inhibiting blood-coagulation or for preventing or treating thrombosis or embolism, which comprises administering the compound of formula (1) or pharmaceutically acceptable salt thereof according to claim 1 as an active ingredient to a patient in need thereof.

23. The compound of formula (1) or pharmaceutically acceptable salts thereof according to claim 9, wherein ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents a halogeno group, an alkyl group having 1 to 6 carbon atoms, trifluoromethyl group or an alkoxyl group having 1 to 10 carbon atoms, and R6 and R7 each represent hydrogen atom.

24. The compound of formula (1) or pharmaceutically acceptable salts thereof according to claim 9, wherein ring B represents an aryl group having 6 to 10 carbon atoms and a substituent or a heteroaryl group having 4 to 10 carbon atoms wherein said heteroaryl group is an aromatic cyclic hydrocarbon group having 1 to 3 hetero atoms selected from the group consisting of O, N and S, R2 represents a halogeno group, an alkyl group having 1 or 2 carbon atoms, trifluoromethyl group or an alkoxyl group having 1 to 3 carbon atoms, and R6 and R7 each represent hydrogen atom.

25. The compound of formula (1) or pharmaceutically acceptable salts thereof according to claim 9, wherein ring B represents an aryl group having 6 to 10 carbon atoms or a heteroaryl group having 4 to 10 carbon atoms wherein said heteroaryl group is an aromatic cyclic hydrocarbon group having 1 to 3 hetero atoms selected from the group consisting of O, N and S, R2 represents a chloro group or bromo group, and R8 and R9 are each hydrogen atoms.

26. The compound of formula (1) or pharmaceutically acceptable salts thereof according to claim 25, wherein ring B represents phenyl group, naphthyl group, pyridyl group or thiophene group.

27. The compound of formula (1) or pharmaceutically acceptable salts thereof according to claim 9, wherein ring C represents an aryl group having 6 to 10 carbon atoms or piperidyl group, R3 represents a mono- or dialkylcarbamoyl group having 2 to 7 carbon atoms, a halogeno group, an alkyl group having 1 to 6 carbon atoms, which may have a substituent(s), pyridyl group, nitro group, amino group, a dialkylamino group, amidino group which may have a substituent(s) or piperidyloxy group, which may have a substituent(s), and R8 and R9 are each hydrogen atoms.

28. The compound of formula (1) or pharmaceutically acceptable salts thereof according to claim 9, wherein ring C represents phenyl group or 4-piperidyl group, R3 represents a mono- or dialkylcarbamoyl group having 2 to 7 carbon atoms, a halogeno group, an alkyl group having 1 to 6 carbon atoms, which may have a substituent(s), 4-pyridyl group, nitro group, amino group, dimethylamino group, amidino group, which may have a substituent(s) or a piperidyloxyl group, which may have a substituent(s), and R8 and R9 are each hydrogen atoms.

29. The compound of formula (1) or pharmaceutically acceptable salts thereof according to claim 9, wherein ring A represents phenyl group, ring B represents phenyl group or thiophene group, R2 represents chloro group or bromo group, ring C represents phenyl group or piperidyl group, R3 represents pyridyl group, and X represents methylene group.

30. The compound of formula (I) or pharmaceutically acceptable salts thereof according to claim 9, ring A represents phenyl group, ring B represents phenyl group, pyridyl group, thiophene group or naphthyl group, R2 represents a halogeno group, an alkyl group having 1 to 6 carbon atoms, trifluoromethyl group or an alkoxyl group having 1 to 10 carbon atoms, ring C represents phenyl group or piperidyl group, R3 represents a mono- or dialkylcarbamoyl group having 2 to 7 carbon atoms, a halogeno group, pyridyl group, nitro group, amino group, an alkyl group having 1 to 6 carbon atoms, which may have a substituent(s), a dialkylamino group, amidino group, which may have a substituent(s) or piperidyloxyl group, which may have a substituent(s), and X represents methylene group.

31. A method for inhibiting activated blood coagulation factor X, which comprises administering the compound of formula (1) or pharmaceutically acceptable salt thereof according to claim 9 as an active ingredient to a patient in need thereof.

32. A pharmaceutical composition comprising one or more compounds of formula (1) or pharmaceutically acceptable salts thereof according to claim 9 as an active ingredient and a pharmaceutically acceptable carrier.

33. A method for inhibiting blood-coagulation or for preventing or treating thrombosis or embolism, which comprises administering the compound of formula (1) or pharmaceutically acceptable salt thereof according to claim 9 as an active ingredient to a patient in need thereof.

* * * * *

UNITED STATES PATENT AND TRADEMARK OFFICE
CERTIFICATE OF CORRECTION

PATENT NO.    : 6,825,191 B2                                        Page 1 of 2
DATED         : November 30, 2004
INVENTOR(S)   : Tadakiyo Nakagawa et al.

It is certified that error appears in the above-identified patent and that said Letters Patent is hereby corrected as shown below:

Column 173,
Line 30, Example 207,
"
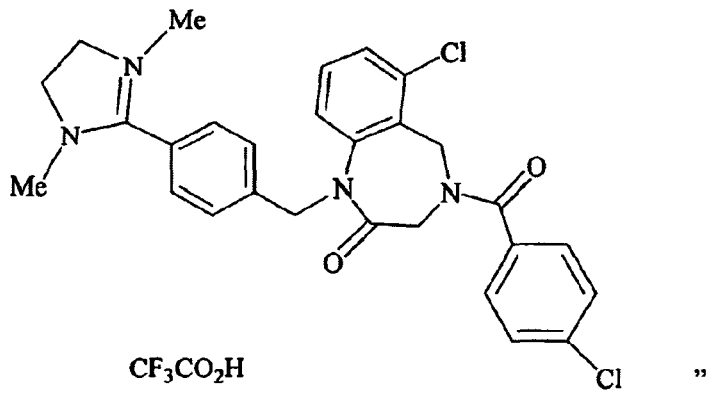
"

should read

--
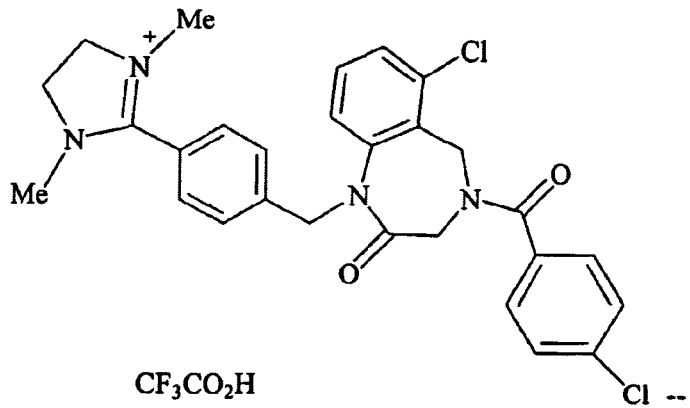
--

Column 177,
Line 4, "thiocarbaxnoyl" should read -- thiocarbamoyl --.

Column 179,
Line 32, "from" should read -- form --.

UNITED STATES PATENT AND TRADEMARK OFFICE
CERTIFICATE OF CORRECTION

PATENT NO. : 6,825,191 B2
DATED : November 30, 2004
INVENTOR(S) : Tadakiyo Nakagawa et al.

It is certified that error appears in the above-identified patent and that said Letters Patent is hereby corrected as shown below:

Column 183,
Line 42, "(I)" should read -- 1 --.

Column 186,
Line 28, "(I)" should read -- 1 --.

Signed and Sealed this

Fifteenth Day of November, 2005

JON W. DUDAS
*Director of the United States Patent and Trademark Office*